US006958236B2

(12) United States Patent
Pascal et al.

(10) Patent No.: US 6,958,236 B2
(45) Date of Patent: Oct. 25, 2005

(54) CONTROL OF GENE EXPRESSION IN PLANTS

(75) Inventors: Erica J. Pascal, San Diego, CA (US); Scott A. Valentine, Wake Forest, NC (US); Jeffrey A. Brown, Durham, NC (US); Adam S. Cockrell, Durham, NC (US); Brian D. Johnson, Cary, NC (US)

(73) Assignee: Syngenta Participations AG, Basel (CH)

( * ) Notice: Subject to any disclaimer, the term of this patent is extended or adjusted under 35 U.S.C. 154(b) by 272 days.

(21) Appl. No.: 10/087,167

(22) Filed: Oct. 24, 2001

(65) Prior Publication Data
US 2003/0154509 A1 Aug. 14, 2003

Related U.S. Application Data
(60) Provisional application No. 60/242,969, filed on Oct. 24, 2000.

(51) Int. Cl.⁷ .................. C12N 15/00; C12P 23/00; H01R 11/20; A01H 1/00; C07K 1/00
(52) U.S. Cl. ................... 435/320.1; 435/69.1; 435/419; 800/278; 530/350
(58) Field of Search .................. 435/69.1, 320.1, 435/468, 455, 419; 530/350; 800/278

(56) References Cited

U.S. PATENT DOCUMENTS

| | | | |
|---|---|---|---|
| 4,833,080 A | 5/1989 | Brent et al. | 435/172.3 |
| 4,981,784 A | 1/1991 | Evans et al. | 435/6 |
| 5,171,671 A | 12/1992 | Evans et al. | 435/69.1 |
| 5,262,300 A | 11/1993 | Evans et al. | 435/6 |
| 5,534,418 A | 7/1996 | Evans et al. | 435/69.1 |
| 5,614,395 A | 3/1997 | Ryals et al. | 435/172.3 |
| 5,641,652 A | 6/1997 | Oro et al. | 435/69.1 |
| 5,688,691 A | 11/1997 | Oro et al. | 455/348 |
| 5,707,800 A | 1/1998 | Mangelsdorf et al. | 435/6 |
| 5,710,004 A | 1/1998 | Evans et al. | 435/6 |
| 5,874,534 A | 2/1999 | Vegeto et al. | 530/350 |
| 5,880,333 A | 3/1999 | Goff et al. | 800/288 |
| 6,379,945 B1 * | 4/2002 | Jepson et al. | 435/243 |
| 6,504,082 B1 * | 1/2003 | Albertsen et al. | 800/278 |
| 2002/0119521 A1 * | 8/2002 | Palli et al. | 435/69.1 |

FOREIGN PATENT DOCUMENTS

| | | |
|---|---|---|
| EP | 0 332 104 | 6/1989 |
| WO | WO 90 11273 | 10/1990 |
| WO | WO 91 13167 | 9/1991 |
| WO | WO 91 14695 A | 10/1991 |
| WO | WO 93 03162 | 2/1993 |
| WO | WO 93 06215 | 4/1993 |
| WO | WO 93 21334 A | 10/1993 |
| WO | WO 93 23431 | 11/1993 |
| WO | WO 91 12258 | 1/1994 |
| WO | WO 94 01558 A | 1/1994 |
| WO | WO 96 27673 A | 9/1996 |
| WO | WO 96 37609 | 11/1996 |
| WO | WO 97 38117 | 10/1997 |
| WO | WO 99 02683 | 1/1999 ........... C12N/15/12 |

OTHER PUBLICATIONS

Martinez et al, *Creation of ecdysone receptor chimeras in plants for controlled regulation of gene expression* Molecular & General Genetics, vol. 261 (1999), pp. 546–552.

Wang et al, *Molecular Deteriminants of Differential Ligand Sensitivities of Insect Ecdysteroid Receptors* Molecular and Celluar Biology, vol. 20, No. 11 (Jun. 2000), pp. 3870–3879.

Beato, M., *Gene Regulation by Steroid*, Cell, vol. 56 (Feb. 10, 1989) pp. 335–344.

Brent, R. and Ptashne, M., *A Eukaryotic Transcriptional Activator Bearing the DNA Specificity of a Prokaryotic Repressor* Cell, vol. 43 (1985) pp. 729–736.

Christianson, A. and Kafatos, F., *Binding Affinity of the Drosophila melanogaster CF1/USP Protein to the Chorion s15 Promoter* Biochemical and Biophysical Research Communications, vol. 193, No. 3 (Jun. 30, 1993) pp. 1318–1323.

Christopherson, et al., *Ecdysteroid–dependent regulation of genes in mammalian cells by a Drosophila ecdysone receptor and chimeric transactivators*, Proceedings of the National Acedmy of Sciences, vol. 89 (1992) pp. 6314–6318.

Desjarlais, J. R. and Berg, J. M., *Use of a zinc–finger consensus sequence framework and specificity rules to design specific DNA binding proteins* Proceedings of the National Academy of Science, USA, vol. 90 (Mar. 1993), pp. 2256–2260.

Dhadialla et al., *New Insecticides with Ecdysteroidal and Juvenile Hormone Activity* Annual Review of Entomology, vol. 43 (1998) pp. 545–569.

Evans, R., *The Steriod and Thyroid Hormone Receptor Superfamily* Science, vol. 240 (May 13, 1988) pp. 889–895.

Fujiwara et al., *Cloning of an Ecdysone Receptor Homolog from Manduca Sexta and the Development Profile of its mRNA in Wings* Insect Biochemistry and Molecular Biology, vol. 25, No. 7 (1995) pp. 845–856.

(Continued)

Primary Examiner— Gerry Leffers
Assistant Examiner—Maria Marvich
(74) Attorney, Agent, or Firm—Mary Kakefuda

(57) ABSTRACT

Chimeric insect hormone receptors and receptor cassettes are provided as well as methods for their use in regulating expression of target polypeptides in plants in the presence of appropriate chemical ligands. In particular, each receptor cassette encodes a receptor polypeptide that comprises a DNA binding domain, a hinge region, a ligand binding domain and an activation domain. According to one embodiment, the hinge and ligand binding domains are from two different insect ecdysone receptors. According to another embodiment, the receptor cassettes are chimeric in that one or more of the DNA binding or activation domains are obtained from a source heterologous with respect to the other domains present in the chimeric receptor cassette.

26 Claims, No Drawings

OTHER PUBLICATIONS

Gaffney et al., *Requirement of Salicyliuc Acid for the Induction of Systemic Acquired Resistance Science*, vol. 261 (Aug. 6, 1993) pp. 754–756.

Goff, et al., *Identification of functional domains in the maize transcriptional activator C1: comparison of wild–type and dominant inhibitor proteins Genes & Development*, vol. 5 (1991) 298–309.

Harmon et al., *Activation of mammalian retinoid X receptors by the insert growth receptor methoprene Proceedings of the National Academy of Sciences*, vol. 92 (Jun. 1995) p. 6157–6160.

Henrich, et al., *A steriod/thyroid hormone receptor superfamily member in Drosophila melanogaster that shares extensive sequence similarity with a mammalian homologue Nucleic Acids Research*, vol. 18, No. 14 (1990) pp. 4143–4148.

Jones, G. and Sharp, Phillip, *Ultraspiracle: An invertebrate nuclear receptor for juvenile hormones Proceeedings of the National Academy of Sciences*, vol. 94 (Dec. 1997), pp. 13499–13503.

Koelle, et al., *The Drosophila EcR Gene Encodes an Ecdysone Receptor, a New Memeber of the Steroid Receptor Superfamily Cell*, vol. 67 (1991) pp. 59–77.

Kothapalli, et al., Cloning and development expression of the ecdysone receptor gene from th spruce budworm, *Choristoneura fumiferana Development Genetics*, vol. 17 (1995) pp. 319–330.

Liu, et al., *Design of polydactyl zinc–finger proteins for unique addressing within complex genomes Proceedings of the National Academy of Science, USA*, vol. 94 (May 1997) pp. 5525–5530.

Llyod et al., *Epidermal Cell Fate Determination in Arabidopsis: Patterns Defined by a Steroid–Inducible Regulator Science*, vol. 266 (Oct. 21, 1994) pp. 436–439.

Martinez et al., *A chemically inducible gene expression system for plants based on the ecdysteroid receptor from Heliothis virescens Plant Physiology*, (Supp.) vol. 114, No. 3 (Jul. 1997), pp. 258.

Meijer, et al. *HD–Zip proteins of families I and II from rice: interactions and functional properties Molecular and General Genetics*, vol. 263 (2000) pp. 12–21.

Meshi, T. and Iwabuchi M., *Plant Transcription Factors Plant Cell Physiology*, vol. 36(8) (1995) pp. 1405–1420.

Ng, H. and Bird, A., *Histone deacetylases: silencers for hire Trends in Biochemical Sciences*, vol.25 (Mar. 2000) pp. 121–126.

Oro, et al., *Relationship between the product of the Drosophila ultraspiracle locus and the vertebrate retinoid X receptor Nature*, vol. 347 (Sep. 20, 1990), pp. 298–301.

Oro, et al., *The Drosophila nuclear receptors: new insight into the actions of nuclear receptors in development Current Opinion in Genetics and Development*, vol. 2 (1992), pp. 269–274.

Palli, et al., *A nuclear juvenile hormone–binding protein from larvae of Manduca Sexta: A putative receptor for the metamorphic action of juvenile hormone Proceedings of the National Academy of Sciences*, vol. 91 (Jun. 1994), pp. 6191–6195.

Parker et al., *Structure and function of nuclear hormone receptors Seminars in Cancer Biology*, vol. 1 (1990) p. 81–87.

Picard et al., A Movable and Regulable Inactivation Function within the Steroid Binding Domain of the Glucocorticoid Receptor *Cell*, vol. 54 (Sep. 23, 1988) pp. 1073–1080.

Ptashne M., *How eukaryotic transcriptional activators work Nature*, vol. 335 (1988) pp. 683–689.

Riddiford, L., *Hormone Receptors and the Regulation of Insect Metamorphosis Receptor*, vol. 3 (1993) pp. 203–209.

Sadowski, et al., *GAL4–VP16 is an unusually potent transcriptional activator Nature*, vol. 335 (1988) 563–564.

Saleh, D., et al., *Cloning and characterization of an ecdysone receptor cDNA from Locus migratoria Molecular And Cellular. Endocrinology*, vol. 143 (1998) pp. 91–99.

Schene, M., et al., *A steroid–inducible gene expression system for plant cells Proceedings of the National Academy of Sciences*, vol. 88 (Dec. 1991) pp. 10421–10425.

Segraves, A., *Something Old, Some Things New: The Steriod Receptor Superfamily in Drosophila Cell*, vol. 67 (Oct. 18, 1991) pp. 225–228.

Sutherland, et al., *Drosophila hormone receptor 38: A second partner for Drosophila USP suggests an unexpected role for nuclear receptors of the nerve growth factor–induced protein B type Proceedings of the National Academy of Sciences*, vol. 92 (Aug. 1995) pp. 7966–7970.

Swevers et al., *The Silkmoth Homolog of the Drosophila Ecdysone Receptor (B1 Isoform): Cloning and Analysis of Expression During Follicullar Cell Differentiation Insect Biochemistry and Molecular Biology*, vol. 25, No. 7 (1995) pp. 857–866.

Thomas, et al., *Heterodimerization of the Drosophila ecdysone receptor with retinoid X receptor and ultraspiracle Nature*, vol. 362 (Apr. 1993) pp. 471–475.

Triezenberg, et al., *Functional dissection of VP16, the transactivator of herpes simplex virus immediate early gene expression Genes & Development*, vol. 2 (1988) pp. 718–729.

Wing K.D., *RH 5849, a Nonsteroidal Ecdysone Agonist: Effects on a Drosophila Cell Line Science*, 241 (1988) 467–469.

Wu, et al., *Functional analysis of HD2 histone deacetylase homologues in Arabidopsis thaliana The Plant Journal*, vol. 22(1) (2000) pp. 19–27.

* cited by examiner

SEQUENCE LISTING

<160> NUMBER OF SEQ ID NOS: 148

<210> SEQ ID NO 1
<211> LENGTH: 2840
<212> TYPE: DNA
<213> ORGANISM: Manduca sexta
<220> FEATURE:
<221> NAME/KEY: CDS
<222> LOCATION: (361)..(2031)
<223> OTHER INFORMATION: Manduca sexta Ecdysone Receptor
<300> PUBLICATION INFORMATION:
<301> AUTHORS: Fujiwara, et al.
<302> TITLE: Cloning of an ecdysone receptor homolog from Manduca sexta
       and the developmental profile of its mRNA in wings
<303> JOURNAL: Insect Biochem. Mol. Biol.
<304> VOLUME: 25
<305> ISSUE: 7
<306> PAGES: 845-856
<307> DATE: 1995
<308> DATABASE ACCESSION NUMBER: Genbank/U19812
<309> DATABASE ENTRY DATE: 1996-02-03

<400> SEQUENCE: 1
tccgttgacg acggtcgcac gcgtgcaacg tgctcgtttt tacggctcaa gcgaacgcgt      60
aacctccgtc tccacatcac cgagcgaact ctagaactcg cgtactcttc tcacctgttg     120
cttcggattg tgttgtgact gaaaagcgac gcgtatcgtg gtcgaagatt ctctataagt     180
gcataatata ttcgagacag tggatagcga ttcgtttcgg tttcatcgcg cggatgagtg     240
gttcatgccc gtagagacgc gtttagatag ttatggcgag gaaaaagtga agtgaaagcc     300
tacgtcagag gatgtccctc ggtggtcacg gaagccgggg cgtgtgacgc gctcttcgac     360 atg aga cgc cgc tgg tca aac aac gga tgt ttc cct ctg cga atg ttt      408
Met Arg Arg Arg Trp Ser Asn Asn Gly Cys Phe Pro Leu Arg Met Phe
1               5                   10                  15 gag gag agc tcc tct gaa gtg act tct tcc tcg gcg ttc ggg atg ccg      456
Glu Glu Ser Ser Ser Glu Val Thr Ser Ser Ser Ala Phe Gly Met Pro
            20                  25                  30 gcg gcc atg gta atg tca ccg gag tcg ctg gcg tcg cca gag tac ggc      504
Ala Ala Met Val Met Ser Pro Glu Ser Leu Ala Ser Pro Glu Tyr Gly
        35                  40                  45 ggc ctc gag ctc tgg agc tac gat gag acc atg aca aac tat ccg gcg      552
Gly Leu Glu Leu Trp Ser Tyr Asp Glu Thr Met Thr Asn Tyr Pro Ala
    50                  55                  60 cag tca ctg ctc ggc gcg tgt aat gcg ccg cag cag cag cag caa cag      600
Gln Ser Leu Leu Gly Ala Cys Asn Ala Pro Gln Gln Gln Gln Gln Gln
65                  70                  75                  80 caa caa cag cag ccg tcc gct cag ccg ctg ccg tct atg ccg ctg ccg      648
Gln Gln Gln Gln Pro Ser Ala Gln Pro Leu Pro Ser Met Pro Leu Pro
                85                  90                  95 atg cct cct aca act cct aaa tca gag aac gag tcc atg tcg tca ggt      696
Met Pro Pro Thr Thr Pro Lys Ser Glu Asn Glu Ser Met Ser Ser Gly
            100                 105                 110 cga gaa gaa tta tca ccg gcc tca agt ata aat gga tgt agt act gat      744
Arg Glu Glu Leu Ser Pro Ala Ser Ser Ile Asn Gly Cys Ser Thr Asp
        115                 120                 125 ggg gaa cca aga cga cag aag aaa ggg cca gcg ccg cgc cag cag gag      792
Gly Glu Pro Arg Arg Gln Lys Lys Gly Pro Ala Pro Arg Gln Gln Glu
    130                 135                 140 gaa ctg tgc ctt gtt tgc ggc gac agg gct tcg gga tat cac tat aac      840
Glu Leu Cys Leu Val Cys Gly Asp Arg Ala Ser Gly Tyr His Tyr Asn
145                 150                 155                 160

```
gcg ctt acg tgc gaa gga tgt aaa ggg ttc ttc agg cgg agt gtg acc      888
Ala Leu Thr Cys Glu Gly Cys Lys Gly Phe Phe Arg Arg Ser Val Thr
                165                 170                 175 aag aat gcg gta tat att tgt aaa ttt gga cac gcc tgc gag atg gac      936
Lys Asn Ala Val Tyr Ile Cys Lys Phe Gly His Ala Cys Glu Met Asp
            180                 185                 190 atg tac atg agg aga aaa tgc caa gag tgt cgg ttg aag aaa tgc ctc      984
Met Tyr Met Arg Arg Lys Cys Gln Glu Cys Arg Leu Lys Lys Cys Leu
        195                 200                 205 gcg gtg ggc atg agg ccc gag tgc gtc gtc cca gag tcc acg tgc aag     1032
Ala Val Gly Met Arg Pro Glu Cys Val Val Pro Glu Ser Thr Cys Lys
    210                 215                 220 aac aaa aga aga gaa aag gaa gca cag aga gaa aaa gac aaa ctg cca     1080
Asn Lys Arg Arg Glu Lys Glu Ala Gln Arg Glu Lys Asp Lys Leu Pro
225                 230                 235                 240 gtc agt acg acg aca gtg gac gat cat atg cct gcc ata atg caa tgt     1128
Val Ser Thr Thr Thr Val Asp Asp His Met Pro Ala Ile Met Gln Cys
            245                 250                 255 gac cct ccg ccc cca gag gcg gca agg att cac gaa gtg gtc ccg agg     1176
Asp Pro Pro Pro Pro Glu Ala Ala Arg Ile His Glu Val Val Pro Arg
        260                 265                 270 ttc cta acg gag aag cta atg gag cag aac aga ctg aag aat gtg acg     1224
Phe Leu Thr Glu Lys Leu Met Glu Gln Asn Arg Leu Lys Asn Val Thr
    275                 280                 285 ccg ctg tcg gcg aac cag aag tcc ctg atc gcg agg ctc gtg tgg tac     1272
Pro Leu Ser Ala Asn Gln Lys Ser Leu Ile Ala Arg Leu Val Trp Tyr
290                 295                 300 cag gag ggg tac gag cag ccg tcg gag gaa gat ctc aag aga gtt aca     1320
Gln Glu Gly Tyr Glu Gln Pro Ser Glu Glu Asp Leu Lys Arg Val Thr
305                 310                 315                 320 cag aca tgg cag tta gaa gaa gaa gaa gag gag gaa act gac atg ccc     1368
Gln Thr Trp Gln Leu Glu Glu Glu Glu Glu Glu Thr Asp Met Pro
            325                 330                 335 ttc cgt cag atc aca gag atg acg atc tta aca gtg cag ctt att gta     1416
Phe Arg Gln Ile Thr Glu Met Thr Ile Leu Thr Val Gln Leu Ile Val
        340                 345                 350 gaa ttc gca aag gga cta ccg gga ttc tcc aag ata tct cag tcc gat     1464
Glu Phe Ala Lys Gly Leu Pro Gly Phe Ser Lys Ile Ser Gln Ser Asp
    355                 360                 365 caa att aca tta tta aag gcg tca tca agc gaa gtg atg atg ctg cga     1512
Gln Ile Thr Leu Leu Lys Ala Ser Ser Ser Glu Val Met Met Leu Arg
370                 375                 380 gtg gcg cga cgg tac gac gcg gcg acg gac agc gtg ctg ttc gcg aac     1560
Val Ala Arg Arg Tyr Asp Ala Ala Thr Asp Ser Val Leu Phe Ala Asn
385                 390                 395                 400 aac cag gcg tac acg cgc gac aac tac cgc aag gcg ggc atg tcc tac     1608
Asn Gln Ala Tyr Thr Arg Asp Asn Tyr Arg Lys Ala Gly Met Ser Tyr
            405                 410                 415 gtc atc gag gac ctg ctg cac ttc tgt cgg tgt atg tac tcc atg agc     1656
Val Ile Glu Asp Leu Leu His Phe Cys Arg Cys Met Tyr Ser Met Ser
        420                 425                 430 atg gac aat gtg cac tac gcg ctg ctc acc gcc atc gtt ata ttc tca     1704
Met Asp Asn Val His Tyr Ala Leu Leu Thr Ala Ile Val Ile Phe Ser
    435                 440                 445 gac cgg cca ggc ctc gag caa ccc ctt tta gtg gag gaa atc cag aga     1752
Asp Arg Pro Gly Leu Glu Gln Pro Leu Leu Val Glu Glu Ile Gln Arg
450                 455                 460 tac tac ttg aag acg ctg cgg gtt tac att tta aat cag cac agc gcg     1800
Tyr Tyr Leu Lys Thr Leu Arg Val Tyr Ile Leu Asn Gln His Ser Ala
465                 470                 475                 480
```

| | | |
|---|---|---|
| tcg cct cgc tgc gcc gtg ctg ttc ggc aag atc ctc ggc gtg ctg acg<br>Ser Pro Arg Cys Ala Val Leu Phe Gly Lys Ile Leu Gly Val Leu Thr<br>485 490 495 | | 1848 |
| gaa ctg cgc acg ctc ggc acg cag aac tcc aac atg tgc atc tcg ctg<br>Glu Leu Arg Thr Leu Gly Thr Gln Asn Ser Asn Met Cys Ile Ser Leu<br>500 505 510 | | 1896 |
| aag ctg aag aac agg aaa ctt ccg cca ttc ctc gag gag atc tgg gac<br>Lys Leu Lys Asn Arg Lys Leu Pro Pro Phe Leu Glu Glu Ile Trp Asp<br>515 520 525 | | 1944 |
| gtg gcc gaa gtg tcg acg acg cag ccg acg ccg ggg gtg gcg gcg cag<br>Val Ala Glu Val Ser Thr Thr Gln Pro Thr Pro Gly Val Ala Ala Gln<br>530 535 540 | | 1992 |
| gtg acc ccc atc gtg gtg gac aac ccc gcg gcg ctc tag ctggcgcgcc<br>Val Thr Pro Ile Val Val Asp Asn Pro Ala Ala Leu<br>545 550 555 | | 2041 |
| ggcgccgcgc cccgccgccc cgccgccgcc cgctcccccg cgccgccgcc gcgcgccccc | | 2101 |
| gcggcctgcg ctgagtgcgg gacccgcccc gaggagagaa cgctcataga ctggctagtt | | 2161 |
| ttagtgaagt gcacggacgc gatcgtggga ccgcatcgac gcgtccgtga ggacagtgca | | 2221 |
| aatattaccg ctagggccgg ttcgtacgtg tccggtgacc gacgacgatg atgcgcgtga | | 2281 |
| gattagtgaa tatatgtgtt gttgaacgtt tggagagtat atttagtgtt gatcgtcggg | | 2341 |
| agcgcgcggc cggcgcgtgt cggcgagctg tccgccgcgc gccggccgcg gcgactccgc | | 2401 |
| gttttttcg tttgcgaccg gaaaccgagt cggtcactcg gatacgcccg tatgataaga | | 2461 |
| cttctttcga taaataagtt cacctgtatt gcgcgtacat acgagaatta taagaaaaa | | 2521 |
| aagtaatata tgaagagatg tttctattgg gtgaaaagtt taaacttatg tttatttacc | | 2581 |
| aaaattaact atacgttgat cgacctttg actataaat tgtgctgggt cgttggcagc | | 2641 |
| ggccgacgaa cgcgcgccga ccatatttgt ttatatatag tttatgtgag acgttatcgt | | 2701 |
| gtcgtgtcca cttagttccg attcatgttc caccaggtcg gtgtagtgat cagggcgggc | | 2761 |
| cagggtgacg gccaccacgg ataacaggca aagagcgacg aatgttttca tgttgagact | | 2821 |
| ttgggagacg ttattcctc | | 2840 |

<210> SEQ ID NO 2
<211> LENGTH: 556
<212> TYPE: PRT
<213> ORGANISM: Manduca sexta

<400> SEQUENCE: 2

Met Arg Arg Arg Trp Ser Asn Asn Gly Cys Phe Pro Leu Arg Met Phe
1               5                  10                  15

Glu Glu Ser Ser Glu Val Thr Ser Ser Ala Phe Gly Met Pro
            20                  25                  30

Ala Ala Met Val Met Ser Pro Glu Ser Leu Ala Ser Pro Glu Tyr Gly
        35                  40                  45

Gly Leu Glu Leu Trp Ser Tyr Asp Glu Thr Met Thr Asn Tyr Pro Ala
    50                  55                  60

Gln Ser Leu Leu Gly Ala Cys Asn Ala Pro Gln Gln Gln Gln Gln Gln
65                  70                  75                  80

Gln Gln Gln Gln Pro Ser Ala Gln Pro Leu Pro Ser Met Pro Leu Pro
                85                  90                  95

Met Pro Pro Thr Thr Pro Lys Ser Glu Asn Glu Ser Met Ser Ser Gly
            100                 105                 110

Arg Glu Glu Leu Ser Pro Ala Ser Ser Ile Asn Gly Cys Ser Thr Asp

```
                115                 120                 125
Gly Glu Pro Arg Arg Gln Lys Lys Gly Pro Ala Pro Arg Gln Gln Glu
            130                 135                 140
Glu Leu Cys Leu Val Cys Gly Asp Arg Ala Ser Gly Tyr His Tyr Asn
145                 150                 155                 160
Ala Leu Thr Cys Glu Gly Cys Lys Gly Phe Phe Arg Arg Ser Val Thr
                165                 170                 175
Lys Asn Ala Val Tyr Ile Cys Lys Phe Gly His Ala Cys Glu Met Asp
                180                 185                 190
Met Tyr Met Arg Arg Lys Cys Gln Glu Cys Arg Leu Lys Lys Cys Leu
                195                 200                 205
Ala Val Gly Met Arg Pro Glu Cys Val Val Pro Glu Ser Thr Cys Lys
            210                 215                 220
Asn Lys Arg Arg Glu Lys Glu Ala Gln Arg Glu Lys Asp Lys Leu Pro
225                 230                 235                 240
Val Ser Thr Thr Thr Val Asp Asp His Met Pro Ala Ile Met Gln Cys
                245                 250                 255
Asp Pro Pro Pro Glu Ala Ala Arg Ile His Glu Val Val Pro Arg
            260                 265                 270
Phe Leu Thr Glu Lys Leu Met Glu Gln Asn Arg Leu Lys Asn Val Thr
                275                 280                 285
Pro Leu Ser Ala Asn Gln Lys Ser Leu Ile Ala Arg Leu Val Trp Tyr
            290                 295                 300
Gln Glu Gly Tyr Glu Gln Pro Ser Glu Glu Asp Leu Lys Arg Val Thr
305                 310                 315                 320
Gln Thr Trp Gln Leu Glu Glu Glu Glu Glu Thr Asp Met Pro
                325                 330                 335
Phe Arg Gln Ile Thr Glu Met Thr Ile Leu Thr Val Gln Leu Ile Val
                340                 345                 350
Glu Phe Ala Lys Gly Leu Pro Gly Phe Ser Lys Ile Ser Gln Ser Asp
            355                 360                 365
Gln Ile Thr Leu Leu Lys Ala Ser Ser Ser Glu Val Met Met Leu Arg
            370                 375                 380
Val Ala Arg Arg Tyr Asp Ala Ala Thr Asp Ser Val Leu Phe Ala Asn
385                 390                 395                 400
Asn Gln Ala Tyr Thr Arg Asp Asn Tyr Arg Lys Ala Gly Met Ser Tyr
                405                 410                 415
Val Ile Glu Asp Leu Leu His Phe Cys Arg Cys Met Tyr Ser Met Ser
                420                 425                 430
Met Asp Asn Val His Tyr Ala Leu Leu Thr Ala Ile Val Ile Phe Ser
            435                 440                 445
Asp Arg Pro Gly Leu Glu Gln Pro Leu Leu Val Glu Glu Ile Gln Arg
            450                 455                 460
Tyr Tyr Leu Lys Thr Leu Arg Val Tyr Ile Leu Asn Gln His Ser Ala
465                 470                 475                 480
Ser Pro Arg Cys Ala Val Leu Phe Gly Lys Ile Leu Gly Val Leu Thr
                485                 490                 495
Glu Leu Arg Thr Leu Gly Thr Gln Asn Ser Asn Met Cys Ile Ser Leu
            500                 505                 510
Lys Leu Lys Asn Arg Lys Leu Pro Pro Phe Leu Glu Glu Ile Trp Asp
            515                 520                 525
Val Ala Glu Val Ser Thr Thr Gln Pro Thr Pro Gly Val Ala Ala Gln
530                 535                 540
```

```
Val Thr Pro Ile Val Val Asp Asn Pro Ala Ala Leu
545                 550                 555

<210> SEQ ID NO 3
<211> LENGTH: 1003
<212> TYPE: DNA
<213> ORGANISM: Ostrinia nubilalis
<220> FEATURE:
<221> NAME/KEY: CDS
<222> LOCATION: (3)..(1001)
<223> OTHER INFORMATION: 5' end of gene encoding Ostrinia nubilalis
      Ecdysone Receptor

<400> SEQUENCE: 3 gt gaa gtg aaa gcc tac gtc gga gga tgt ccg tcg gcg att gtg gat        47
   Glu Val Lys Ala Tyr Val Gly Gly Cys Pro Ser

```
                240                 245                 250                 255
aaa cta cca gtg agc aca acg aca gta gac gat cat atg ccc cca atc              815
Lys Leu Pro Val Ser Thr Thr Thr Val Asp Asp His Met Pro Pro Ile
                260                 265                 270 atg cag tgt gat cca cca ccc ccg gag gca gcg agg att ctg gaa tgt              863
Met Gln Cys Asp Pro Pro Pro Pro Glu Ala Ala Arg Ile Leu Glu Cys
            275                 280                 285 ttg cag cat gaa gtg gtc ccg cgg ttc ctc tcg gag aag ctg atg gag              911
Leu Gln His Glu Val Val Pro Arg Phe Leu Ser Glu Lys Leu Met Glu
        290                 295                 300 cag aat cgg ctg aag aac ata ccc ccc ctc acc gcc aac cag cag ttc              959
Gln Asn Arg Leu Lys Asn Ile Pro Pro Leu Thr Ala Asn Gln Gln Phe
    305                 310                 315 ctg atc gcg agg ctg gtg tgg tac cag gac ggc tac gaa cag cc                  1003
Leu Ile Ala Arg Leu Val Trp Tyr Gln Asp Gly Tyr Glu Gln
320                 325                 330

<210> SEQ ID NO 4
<211> LENGTH: 333
<212> TYPE: PRT
<213> ORGANISM: Ostrinia nubilalis

<400> SEQUENCE: 4

Glu Val Lys Ala Tyr Val Gly Gly Cys Pro Ser Ala Ile Val Asp Ser
1               5                   10                  15

Gly Ala Tyr Asp Thr Leu Ala Val Met Arg Arg Trp Ser Asn Asn
            20                  25                  30

Gly Gly Phe Gln Thr Leu Arg Met Leu Glu Glu Ser Ser Ser Glu Val
        35                  40                  45

Thr Ser Ser Ser Ala Leu Gly Leu Pro Pro Ala Met Val Met Ser Pro
    50                  55                  60

Glu Ser Leu Ala Ser Pro Glu Tyr Ser Asn Leu Glu Leu Trp Ala Tyr
65                  70                  75                  80

Glu Asp Gly Ile Ser Tyr Asn Thr Ala Gln Ser Leu Leu Gly Asn Ala
                85                  90                  95

Cys Thr Met Gln Gln Pro Pro Thr Gln Pro Leu Pro Ser Met Pro
            100                 105                 110

Leu Pro Met Pro Pro Thr Thr Pro Lys Ser Glu Asn Glu Ser Met Ser
        115                 120                 125

Ser Gly Arg Glu Glu Leu Ser Pro Ala Ser Ser Val Asn Gly Cys Ser
    130                 135                 140

Thr Asp Gly Glu Ala Arg Arg Gln Lys Lys Gly Pro Ala Pro Arg Gln
145                 150                 155                 160

Gln Glu Glu Leu Cys Leu Val Cys Gly Asp Arg Ala Ser Gly Tyr His
                165                 170                 175

Tyr Asn Ala Leu Thr Cys Glu Gly Cys Lys Gly Phe Phe Arg Arg Ser
            180                 185                 190

Val Thr Lys Asn Ala Val Tyr Ile Cys Lys Phe Gly His Ala Cys Glu
        195                 200                 205

Met Asp Met Tyr Met Arg Arg Lys Cys Gln Glu Cys Arg Leu Lys Lys
    210                 215                 220

Cys Leu Ala Val Gly Met Arg Pro Glu Cys Val Val Pro Glu Thr Gln
225                 230                 235                 240

Cys Ala Gln Lys Arg Lys Glu Lys Lys Ala Gln Arg Glu Lys Asp Lys
                245                 250                 255

Leu Pro Val Ser Thr Thr Thr Val Asp Asp His Met Pro Pro Ile Met
```

```
                     260                 265                 270
Gln Cys Asp Pro Pro Pro Glu Ala Ala Arg Ile Leu Glu Cys Leu
                275                 280                 285

Gln His Glu Val Val Pro Arg Phe Leu Ser Glu Lys Leu Met Glu Gln
            290                 295                 300

Asn Arg Leu Lys Asn Ile Pro Pro Leu Thr Ala Asn Gln Gln Phe Leu
305                 310                 315                 320

Ile Ala Arg Leu Val Trp Tyr Gln Asp Gly Tyr Glu Gln
                325                 330

<210> SEQ ID NO 5
<211> LENGTH: 763
<212> TYPE: DNA
<213> ORGANISM: Ostrinia nubilalis
<220> FEATURE:
<221> NAME/KEY: CDS
<222> LOCATION: (2)..(763)
<223> OTHER INFORMATION: 3' end of gene encoding Ostrinia nubilalis
      Ecdysone Receptor

<400> SEQUENCE: 5 g aat cgg ctg aag aac ata ccc ccc ctc acc gcc aac cag cag ttc ctg        49
  Asn Arg Leu Lys Asn Ile Pro Pro Leu Thr Ala Asn Gln Gln Phe Leu
  1               5                  10                  15 atc gcg agg ctg gtg tgg tac cag gac gga tac gag cag cct tcg gaa          97
Ile Ala Arg Leu Val Trp Tyr Gln Asp Gly Tyr Glu Gln Pro Ser Glu
             20                  25                  30 gag gat ctc aaa agg gtg acg cag act tgg caa tca gca gat gaa gaa         145
Glu Asp Leu Lys Arg Val Thr Gln Thr Trp Gln Ser Ala Asp Glu Glu
         35                  40                  45 gac gaa gac tca gac atg cca ttc cgc cag atc aca gaa atg acc atc         193
Asp Glu Asp Ser Asp Met Pro Phe Arg Gln Ile Thr Glu Met Thr Ile
     50                  55                  60 ctc aca gta cag cta ata gtc gag ttt gcc aaa ggc cta cct ggt ttt         241
Leu Thr Val Gln Leu Ile Val Glu Phe Ala Lys Gly Leu Pro Gly Phe
 65                  70                  75                  80 tca aag atc tca caa cct gac cag atc aca tta tta aag gca tgc tca         289
Ser Lys Ile Ser Gln Pro Asp Gln Ile Thr Leu Leu Lys Ala Cys Ser
                 85                  90                  95 agc gaa gtg atg atg ctg cga gta gcg agg cgg tac gac gcg gtg tcg         337
Ser Glu Val Met Met Leu Arg Val Ala Arg Arg Tyr Asp Ala Val Ser
            100                 105                 110 gat agc gtt ctg ttc gcc aac aac cag gcg tac act cgc gac aac tac         385
Asp Ser Val Leu Phe Ala Asn Asn Gln Ala Tyr Thr Arg Asp Asn Tyr
        115                 120                 125 cgc aag gcg ggc atg gcc tac gtc atc gaa gac ctg ctg cac ttc tgc         433
Arg Lys Ala Gly Met Ala Tyr Val Ile Glu Asp Leu Leu His Phe Cys
    130                 135                 140 cgc tgc atg tac tcg atg tcg atg gac aac gtg cat tac gcg ctc ctc         481
Arg Cys Met Tyr Ser Met Ser Met Asp Asn Val His Tyr Ala Leu Leu
145                 150                 155                 160 act gcc atc gtt ata ttc tcg gat cgg ccg ggc cta gag cag cca cag         529
Thr Ala Ile Val Ile Phe Ser Asp Arg Pro Gly Leu Glu Gln Pro Gln
                165                 170                 175 cta gta gaa gag atc cag cgg tat tac ctg aac acg ctg cgg gtg tac         577
Leu Val Glu Glu Ile Gln Arg Tyr Tyr Leu Asn Thr Leu Arg Val Tyr
            180                 185                 190 atc atg aac cag cac agc gcg tcg ccg cgt tgc gcc gtc atc tac gcg         625
Ile Met Asn Gln His Ser Ala Ser Pro Arg Cys Ala Val Ile Tyr Ala
        195                 200                 205
```

```
aag att ctg tcg gtg ctt acc gag ttg cgg acg ctg ggc atg cag aat      673
Lys Ile Leu Ser Val Leu Thr Glu Leu Arg Thr Leu Gly Met Gln Asn
    210                 215                 220 tcg aac atg tgc atc tcg ctg aag ctc aag aac agg aag ctg ccg ccg      721
Ser Asn Met Cys Ile Ser Leu Lys Leu Lys Asn Arg Lys Leu Pro Pro
225                 230                 235                 240 ttc ctg gag gag atc tgg gac gtg gaa tca cta gtg cgg ccg              763
Phe Leu Glu Glu Ile Trp Asp Val Glu Ser Leu Val Arg Pro
                245                 250

<210> SEQ ID NO 6
<211> LENGTH: 254
<212> TYPE: PRT
<213> ORGANISM: Ostrinia nubilalis

<400> SEQUENCE: 6

Asn Arg Leu Lys Asn Ile Pro Pro Leu Thr Ala Asn Gln Gln Phe Leu
1               5                   10                  15

Ile Ala Arg Leu Val Trp Tyr Gln Asp Gly Tyr Glu Gln Pro Ser Glu
            20                  25                  30

Glu Asp Leu Lys Arg Val Thr Gln Thr Trp Gln Ser Ala Asp Glu Glu
        35                  40                  45

Asp Glu Asp Ser Asp Met Pro Phe Arg Gln Ile Thr Glu Met Thr Ile
    50                  55                  60

Leu Thr Val Gln Leu Ile Val Glu Phe Ala Lys Gly Leu Pro Gly Phe
65                  70                  75                  80

Ser Lys Ile Ser Gln Pro Asp Gln Ile Thr Leu Leu Lys Ala Cys Ser
                85                  90                  95

Ser Glu Val Met Met Leu Arg Val Ala Arg Arg Tyr Asp Ala Val Ser
            100                 105                 110

Asp Ser Val Leu Phe Ala Asn Asn Gln Ala Tyr Thr Arg Asp Asn Tyr
        115                 120                 125

Arg Lys Ala Gly Met Ala Tyr Val Ile Glu Asp Leu Leu His Phe Cys
    130                 135                 140

Arg Cys Met Tyr Ser Met Ser Met Asp Asn Val His Tyr Ala Leu Leu
145                 150                 155                 160

Thr Ala Ile Val Ile Phe Ser Asp Arg Pro Gly Leu Glu Gln Pro Gln
                165                 170                 175

Leu Val Glu Glu Ile Gln Arg Tyr Tyr Leu Asn Thr Leu Arg Val Tyr
            180                 185                 190

Ile Met Asn Gln His Ser Ala Ser Pro Arg Cys Ala Val Ile Tyr Ala
        195                 200                 205

Lys Ile Leu Ser Val Leu Thr Glu Leu Arg Thr Leu Gly Met Gln Asn
    210                 215                 220

Ser Asn Met Cys Ile Ser Leu Lys Leu Lys Asn Arg Lys Leu Pro Pro
225                 230                 235                 240

Phe Leu Glu Glu Ile Trp Asp Val Glu Ser Leu Val Arg Pro
                245                 250

<210> SEQ ID NO 7
<211> LENGTH: 838
<212> TYPE: DNA
<213> ORGANISM: Spodoptera frugiperda
<220> FEATURE:
<221> NAME/KEY: CDS
<222> LOCATION: (1)..(837)
<223> OTHER INFORMATION: 3' end of gene encoding FAW EcR

<400> SEQUENCE: 7
```

```
ccg gcc atc atg caa tgt gac cct ccg ccc cca gag gcg gca agg att        48
Pro Ala Ile Met Gln Cys Asp Pro Pro Pro Glu Ala Ala Arg Ile
1               5                  10                  15 cac gaa gtg gtc ccg agg ttc cta acg gag aag cta atg gag cag aac        96
His Glu Val Val Pro Arg Phe Leu Thr Glu Lys Leu Met Glu Gln Asn
                20                  25                  30 aga ctg aag aat gtg acg ccg ctg tcg gcg aac cag aag tcc ctg atc       144
Arg Leu Lys Asn Val Thr Pro Leu Ser Ala Asn Gln Lys Ser Leu Ile
        35                  40                  45 gcg agg ctc gtg tgg tac cag gag ggg tac gag cag ccg tcg gag gaa       192
Ala Arg Leu Val Trp Tyr Gln Glu Gly Tyr Glu Gln Pro Ser Glu Glu
50                  55                  60 gat ctc aag aga gtt aca cag aca tgg cag tta gaa gaa gaa gaa gag       240
Asp Leu Lys Arg Val Thr Gln Thr Trp Gln Leu Glu Glu Glu Glu Glu
65                  70                  75                  80 gag gaa act gac atg ccc ttc cgt cag atc aca gag atg acg atc tta       288
Glu Glu Thr Asp Met Pro Phe Arg Gln Ile Thr Glu Met Thr Ile Leu
                85                  90                  95 aca gtg cag ctt att gta gaa ttc gca aag gga cta ccg gga ttc tcc       336
Thr Val Gln Leu Ile Val Glu Phe Ala Lys Gly Leu Pro Gly Phe Ser
            100                 105                 110 aag ata tct cag tcc gat caa att aca tta tta aag gcg tca tca agc       384
Lys Ile Ser Gln Ser Asp Gln Ile Thr Leu Leu Lys Ala Ser Ser Ser
        115                 120                 125 gaa gtg atg atg ctg cga gtg gcg cga cgg tac gac gcg gcg acg gac       432
Glu Val Met Met Leu Arg Val Ala Arg Arg Tyr Asp Ala Ala Thr Asp
130                 135                 140 agc gtg ctg ttc gcg aac aac cag gcg tac acg cgc gac aac tac cgc       480
Ser Val Leu Phe Ala Asn Asn Gln Ala Tyr Thr Arg Asp Asn Tyr Arg
145                 150                 155                 160 aag gcg ggc atg tcc tac gtc atc ggg gac ctg ctg cac ttc tgt cgg       528
Lys Ala Gly Met Ser Tyr Val Ile Gly Asp Leu Leu His Phe Cys Arg
                165                 170                 175 tgt atg tac tcc atg agc atg gac aat gtg cac tac gcg ctg ctc acc       576
Cys Met Tyr Ser Met Ser Met Asp Asn Val His Tyr Ala Leu Leu Thr
            180                 185                 190 gcc atc gtt ata ttc tca gac cgg cca ggc ctc gag caa ccc ctt tta       624
Ala Ile Val Ile Phe Ser Asp Arg Pro Gly Leu Glu Gln Pro Leu Leu
        195                 200                 205 gtg gag gaa atc cag aga tac tac ttg aag acg ctg cgg gtt tac att       672
Val Glu Glu Ile Gln Arg Tyr Tyr Leu Lys Thr Leu Arg Val Tyr Ile
210                 215                 220 tta aat cag tac agc gcg tcg cct cgc tgc gcc gtg ctg ttc ggc aag       720
Leu Asn Gln Tyr Ser Ala Ser Pro Arg Cys Ala Val Leu Phe Gly Lys
225                 230                 235                 240 atc ctc ggc gtg ctg acg gaa ctg cgc acg ctc ggc acg cag aac tcc       768
Ile Leu Gly Val Leu Thr Glu Leu Arg Thr Leu Gly Thr Gln Asn Ser
                245                 250                 255 aac atg tgc atc tcg ctg aag ctg aag aac agg aaa ctt ccg cca ttc       816
Asn Met Cys Ile Ser Leu Lys Leu Lys Asn Arg Lys Leu Pro Pro Phe
            260                 265                 270 ctc gag gag atc tgg gac gtg g                                         838
Leu Glu Glu Ile Trp Asp Val
        275
```

<210> SEQ ID NO 8
<211> LENGTH: 279
<212> TYPE: PRT
<213> ORGANISM: Spodoptera frugiperda -continued

```
<400> SEQUENCE: 8

Pro Ala Ile Met Gln Cys Asp Pro Pro Pro Glu Ala Ala Arg Ile
1               5                   10                  15

His Glu Val Val Pro Arg Phe Leu Thr Glu Lys Leu Met Glu Gln Asn
            20                  25                  30

Arg Leu Lys Asn Val Thr Pro Leu Ser Ala Asn Gln Lys Ser Leu Ile
        35                  40                  45

Ala Arg Leu Val Trp Tyr Gln Glu Gly Tyr Glu Gln Pro Ser Glu Glu
    50                  55                  60

Asp Leu Lys Arg Val Thr Gln Thr Trp Gln Leu Glu Glu Glu Glu
65                  70                  75                  80

Glu Glu Thr Asp Met Pro Phe Arg Gln Ile Thr Glu Met Thr Ile Leu
                85                  90                  95

Thr Val Gln Leu Ile Val Glu Phe Ala Lys Gly Leu Pro Gly Phe Ser
            100                 105                 110

Lys Ile Ser Gln Ser Asp Gln Ile Thr Leu Leu Lys Ala Ser Ser Ser
        115                 120                 125

Glu Val Met Met Leu Arg Val Ala Arg Arg Tyr Asp Ala Ala Thr Asp
130                 135                 140

Ser Val Leu Phe Ala Asn Asn Gln Ala Tyr Thr Arg Asp Asn Tyr Arg
145                 150                 155                 160

Lys Ala Gly Met Ser Tyr Val Ile Gly Asp Leu Leu His Phe Cys Arg
                165                 170                 175

Cys Met Tyr Ser Met Ser Met Asp Asn Val His Tyr Ala Leu Leu Thr
            180                 185                 190

Ala Ile Val Ile Phe Ser Asp Arg Pro Gly Leu Glu Gln Pro Leu Leu
        195                 200                 205

Val Glu Glu Ile Gln Arg Tyr Tyr Leu Lys Thr Leu Arg Val Tyr Ile
210                 215                 220

Leu Asn Gln Tyr Ser Ala Ser Pro Arg Cys Ala Val Leu Phe Gly Lys
225                 230                 235                 240

Ile Leu Gly Val Leu Thr Glu Leu Arg Thr Leu Gly Thr Gln Asn Ser
                245                 250                 255

Asn Met Cys Ile Ser Leu Lys Leu Lys Asn Arg Lys Leu Pro Pro Phe
            260                 265                 270

Leu Glu Glu Ile Trp Asp Val
        275

<210> SEQ ID NO 9
<211> LENGTH: 850
<212> TYPE: DNA
<213> ORGANISM: Agrotis ipsilon
<220> FEATURE:
<221> NAME/KEY: CDS
<222> LOCATION: (1)..(849)
<223> OTHER INFORMATION: 3' end of gene encoding BCW EcR

<400> SEQUENCE: 9 cct ccc atc atg caa tgt gat cct cca ccc cca gag gcc gct aga att      48
Pro Pro Ile Met Gln Cys Asp Pro Pro Pro Glu Ala Ala Arg Ile
1               5                   10                  15 ctg gaa tgt ttg cag cac gag gtg gtg cca cgg ttc ctc aat gag aag      96
Leu Glu Cys Leu Gln His Glu Val Val Pro Arg Phe Leu Asn Glu Lys
            20                  25                  30 ctg atg gag cag aat cgg ctg aaa aac gtg ccc ccc ctc act gcc aac     144
Leu Met Glu Gln Asn Arg Leu Lys Asn Val Pro Pro Leu Thr Ala Asn
        35                  40                  45
```

| | | | | | | | | | | | | | | | | |
|---|---|---|---|---|---|---|---|---|---|---|---|---|---|---|---|---|
| cag | aag | tcc | ctg | ata | gcg | agg | ctc | gtg | tgg | tac | cag | gaa | ggc | tat | gaa | 192 |
| Gln | Lys | Ser | Leu | Ile | Ala | Arg | Leu | Val | Trp | Tyr | Gln | Glu | Gly | Tyr | Glu | |
| | 50 | | | | 55 | | | | | 60 | | | | | | |
| caa | cct | tca | gag | gaa | gac | ctc | aag | agg | gtg | acg | cag | acc | tgg | cag | tcg | 240 |
| Gln | Pro | Ser | Glu | Glu | Asp | Leu | Lys | Arg | Val | Thr | Gln | Thr | Trp | Gln | Ser | |
| 65 | | | | | 70 | | | | | 75 | | | | | 80 | |
| gac | gag | gat | gaa | gag | gag | tca | gat | atg | ccg | ttc | cgc | cag | atc | acc | gag | 288 |
| Asp | Glu | Asp | Glu | Glu | Glu | Ser | Asp | Met | Pro | Phe | Arg | Gln | Ile | Thr | Glu | |
| | | | | 85 | | | | | 90 | | | | | 95 | | |
| atg | acg | atc | ctg | aca | gtt | caa | ctc | atc | gta | gaa | ttc | gca | aaa | ggc | ctg | 336 |
| Met | Thr | Ile | Leu | Thr | Val | Gln | Leu | Ile | Val | Glu | Phe | Ala | Lys | Gly | Leu | |
| | | | 100 | | | | | 105 | | | | | 110 | | | |
| cca | ggc | ttc | gcc | aag | atc | tcg | cag | tcg | gat | caa | atc | acg | tta | cta | aag | 384 |
| Pro | Gly | Phe | Ala | Lys | Ile | Ser | Gln | Ser | Asp | Gln | Ile | Thr | Leu | Leu | Lys | |
| | | | 115 | | | | | 120 | | | | | 125 | | | |
| gcg | tgt | tca | agt | gag | gtg | atg | atg | ctc | cga | gtg | gcc | cgg | cgg | tac | gac | 432 |
| Ala | Cys | Ser | Ser | Glu | Val | Met | Met | Leu | Arg | Val | Ala | Arg | Arg | Tyr | Asp | |
| 130 | | | | | 135 | | | | | 140 | | | | | | |
| gcg | gcc | acc | gac | agc | gta | ctg | ttc | gcc | aac | aac | cag | gcg | tac | tcc | cgc | 480 |
| Ala | Ala | Thr | Asp | Ser | Val | Leu | Phe | Ala | Asn | Asn | Gln | Ala | Tyr | Ser | Arg | |
| 145 | | | | | 150 | | | | | 155 | | | | | 160 | |
| gac | aac | tac | cgc | aag | gca | ggc | atg | tcc | tac | gtc | atc | gag | gat | ctc | ttg | 528 |
| Asp | Asn | Tyr | Arg | Lys | Ala | Gly | Met | Ser | Tyr | Val | Ile | Glu | Asp | Leu | Leu | |
| | | | | 165 | | | | | 170 | | | | | 175 | | |
| cac | ttc | tgt | cgg | tgc | atg | tac | tcc | atg | atg | atg | gat | aac | gtg | cac | tac | 576 |
| His | Phe | Cys | Arg | Cys | Met | Tyr | Ser | Met | Met | Met | Asp | Asn | Val | His | Tyr | |
| | | | 180 | | | | | 185 | | | | | 190 | | | |
| gcg | ctg | ctt | acg | gcc | att | gtc | att | ttc | tca | gac | cgg | cct | ggg | ctc | gag | 624 |
| Ala | Leu | Leu | Thr | Ala | Ile | Val | Ile | Phe | Ser | Asp | Arg | Pro | Gly | Leu | Glu | |
| | | | 195 | | | | | 200 | | | | | 205 | | | |
| caa | ccc | tta | ttg | gtg | gaa | gaa | atc | cag | cgg | tat | tac | ctg | aac | acg | ctg | 672 |
| Gln | Pro | Leu | Leu | Val | Glu | Glu | Ile | Gln | Arg | Tyr | Tyr | Leu | Asn | Thr | Leu | |
| | | 210 | | | | | 215 | | | | | 220 | | | | |
| cgg | gtg | tac | atc | ttg | aac | caa | aac | agt | gcg | tcg | ccg | cgc | tgc | ccc | gta | 720 |
| Arg | Val | Tyr | Ile | Leu | Asn | Gln | Asn | Ser | Ala | Ser | Pro | Arg | Cys | Pro | Val | |
| 225 | | | | | 230 | | | | | 235 | | | | | 240 | |
| gtc | ttc | gcc | aag | atc | ctg | ggg | ata | ttg | acg | gag | ctg | cgg | acc | ctc | ggc | 768 |
| Val | Phe | Ala | Lys | Ile | Leu | Gly | Ile | Leu | Thr | Glu | Leu | Arg | Thr | Leu | Gly | |
| | | | | 245 | | | | | 250 | | | | | 255 | | |
| atg | cag | aac | tcc | aac | atg | tgc | atc | tcg | ttg | aag | ctg | aag | aat | agg | aag | 816 |
| Met | Gln | Asn | Ser | Asn | Met | Cys | Ile | Ser | Leu | Lys | Leu | Lys | Asn | Arg | Lys | |
| | | | 260 | | | | | 265 | | | | | 270 | | | |
| ctg | ccg | ccg | ttc | ctc | gag | gag | atc | tgg | gac | gtg | g | | | | | 850 |
| Leu | Pro | Pro | Phe | Leu | Glu | Glu | Ile | Trp | Asp | Val | | | | | | |
| | | | 275 | | | | | 280 | | | | | | | | |

<210> SEQ ID NO 10
<211> LENGTH: 283
<212> TYPE: PRT
<213> ORGANISM: Agrotis ipsilon

<400> SEQUENCE: 10

Pro Pro Ile Met Gln Cys Asp Pro Pro Pro Glu Ala Ala Arg Ile
1               5                   10                  15

Leu Glu Cys Leu Gln His Glu Val Val Pro Arg Phe Leu Asn Glu Lys
                20                  25                  30

Leu Met Glu Gln Asn Arg Leu Lys Asn Val Pro Pro Leu Thr Ala Asn
            35                  40                  45

Gln Lys Ser Leu Ile Ala Arg Leu Val Trp Tyr Gln Glu Gly Tyr Glu

```
                    50                  55                  60
Gln Pro Ser Glu Glu Asp Leu Lys Arg Val Thr Gln Thr Trp Gln Ser
 65                  70                  75                  80
Asp Glu Asp Glu Glu Ser Asp Met Pro Phe Arg Gln Ile Thr Glu
                 85                  90                  95
Met Thr Ile Leu Thr Val Gln Leu Ile Val Glu Phe Ala Lys Gly Leu
                100                 105                 110
Pro Gly Phe Ala Lys Ile Ser Gln Ser Asp Gln Ile Thr Leu Leu Lys
                115                 120                 125
Ala Cys Ser Ser Glu Val Met Met Leu Arg Val Ala Arg Arg Tyr Asp
130                 135                 140
Ala Ala Thr Asp Ser Val Leu Phe Ala Asn Asn Gln Ala Tyr Ser Arg
145                 150                 155                 160
Asp Asn Tyr Arg Lys Ala Gly Met Ser Tyr Val Ile Glu Asp Leu Leu
                165                 170                 175
His Phe Cys Arg Cys Met Tyr Ser Met Met Met Asp Asn Val His Tyr
                180                 185                 190
Ala Leu Leu Thr Ala Ile Val Ile Phe Ser Asp Arg Pro Gly Leu Glu
                195                 200                 205
Gln Pro Leu Leu Val Glu Glu Ile Gln Arg Tyr Tyr Leu Asn Thr Leu
                210                 215                 220
Arg Val Tyr Ile Leu Asn Gln Asn Ser Ala Ser Pro Arg Cys Pro Val
225                 230                 235                 240
Val Phe Ala Lys Ile Leu Gly Ile Leu Thr Glu Leu Arg Thr Leu Gly
                245                 250                 255
Met Gln Asn Ser Asn Met Cys Ile Ser Leu Lys Leu Lys Asn Arg Lys
                260                 265                 270
Leu Pro Pro Phe Leu Glu Glu Ile Trp Asp Val
                275                 280

<210> SEQ ID NO 11
<211> LENGTH: 2401
<212> TYPE: DNA
<213> ORGANISM: Locusta migratoria
<220> FEATURE:
<221> NAME/KEY: CDS
<222> LOCATION: (541)..(2166)
<223> OTHER INFORMATION:
<221> NAME/KEY: misc_feature
<222> LOCATION: (1)..(2401)
<223> OTHER INFORMATION: n = a, t, c, or g
<300> PUBLICATION INFORMATION:
<301> AUTHORS: Saleh, et al.
<302> TITLE: Cloning and characterization of an ecdysone receptor cDNA
       from Locustamigratoria
<303> JOURNAL: Mol. Cell. Endocrinol.
<304> VOLUME: 143
<305> ISSUE: 1
<306> PAGES: 91-99
<307> DATE: 1998
<308> DATABASE ACCESSION NUMBER: Genbank/AF049136
<309> DATABASE ENTRY DATE: 2000-05-05

<400> SEQUENCE: 11
ggaattcggc acgaggtccg acaggagcta ttcccgtgca gctgcgcggc tccgctgtgt      60
cccgcgaacg cgccgttgcg ttttgtcaac agtgctccgc attccgccaa cagtgctacc     120
gacggctctc agtgcgacgg tgccaaagat aatcgcagtg ttggattaca gtgccccttt     180
ttaccgccga cgccacgcag ctttctgagt gcctctgang ccggctgtat tttccggcgc     240
cgagtttgga ggcgtggttg ggtgtacaag ggacgactgc ggaccttcga gtgttagttc     300
```

-continued

```
atcggtgact ggnacctgca gaggactgcg acaggtgtca gcggcagtgc gcgtgcgcag    360
accccgtgca gtggcggcgc gtctggtcgg cggccggcga gcccacagcg actggcggtc    420
gcccgcggcc tgttacaact cccgcaccag ctcttcccgc gcccgcttca cagtcgcatg    480
gcatgaggcg gtggcggtaa ccatggcggg cgcaggtcgg cgcctgggt cgcgctagcg     540
```

| | | | | | | | | | | | | | | | | |
|---|---|---|---|---|---|---|---|---|---|---|---|---|---|---|---|---|
| atg | gag | ctg | ttc | cgc | ggc | gcg | gac | ggc | gcg | ctg | ccg | tcg | gcg | tcg | gcg | 588 |
| Met | Glu | Leu | Phe | Arg | Gly | Ala | Asp | Gly | Ala | Leu | Pro | Ser | Ala | Ser | Ala | |
| 1 | | | | 5 | | | | | 10 | | | | | 15 | | |

| tcg | gct | tcg | gcg | tcc | gcg | tcg | ggc | gcg | ccg | gcg | gcg | tcg | ccg | ctg | gcg | 636 |
|---|---|---|---|---|---|---|---|---|---|---|---|---|---|---|---|---|
| Ser | Ala | Ser | Ala | Ser | Ala | Ser | Gly | Ala | Pro | Ala | Ala | Ser | Pro | Leu | Ala | |
| | | | 20 | | | | | 25 | | | | | 30 | | | |

| gtg | tcg | gtg | ccg | ctg | gcg | ctg | ccg | ctg | ccg | ggg | cac | gcg | tcg | ccc | gct | 684 |
|---|---|---|---|---|---|---|---|---|---|---|---|---|---|---|---|---|
| Val | Ser | Val | Pro | Leu | Ala | Leu | Pro | Leu | Pro | Gly | His | Ala | Ser | Pro | Ala | |
| | | 35 | | | | | 40 | | | | | 45 | | | | |

| tcc | gcg | gcg | gac | gcg | ctc | gtc | gtc | aag | acg | gag | ccg | cgg | gag | gcg | ggc | 732 |
|---|---|---|---|---|---|---|---|---|---|---|---|---|---|---|---|---|
| Ser | Ala | Ala | Asp | Ala | Leu | Val | Val | Lys | Thr | Glu | Pro | Arg | Glu | Ala | Gly | |
| 50 | | | | | 55 | | | | | 60 | | | | | | |

| gcg | ctg | ttc | gcc | gcc | atc | agc | tcg | ccc | ggc | cag | ggc | ccg | ggg | ccc | gcc | 780 |
|---|---|---|---|---|---|---|---|---|---|---|---|---|---|---|---|---|
| Ala | Leu | Phe | Ala | Ala | Ile | Ser | Ser | Pro | Gly | Gln | Gly | Pro | Gly | Pro | Ala | |
| 65 | | | | 70 | | | | | 75 | | | | | 80 | | |

| aag | cgc | gcg | cgc | ctc | gac | tcg | gac | tgg | ctg | tcg | tcg | ccg | ggc | agc | aac | 828 |
|---|---|---|---|---|---|---|---|---|---|---|---|---|---|---|---|---|
| Lys | Arg | Ala | Arg | Leu | Asp | Ser | Asp | Trp | Leu | Ser | Ser | Pro | Gly | Ser | Asn | |
| | | | | 85 | | | | | 90 | | | | | 95 | | |

| gcc | gca | ccc | tcg | ccg | ccc | ccg | cac | cac | ctg | ttc | ggc | gcc | gcc | gcc | tcc | 876 |
|---|---|---|---|---|---|---|---|---|---|---|---|---|---|---|---|---|
| Ala | Ala | Pro | Ser | Pro | Pro | Pro | His | His | Leu | Phe | Gly | Ala | Ala | Ala | Ser | |
| | | | 100 | | | | | 105 | | | | | 110 | | | |

| gcc | tcc | gcc | ggc | gcg | ccc | gcc | gcc | ctg | ccc | aac | ggc | tac | gcc | tcg | ccc | 924 |
|---|---|---|---|---|---|---|---|---|---|---|---|---|---|---|---|---|
| Ala | Ser | Ala | Gly | Ala | Pro | Ala | Ala | Leu | Pro | Asn | Gly | Tyr | Ala | Ser | Pro | |
| | | 115 | | | | | 120 | | | | | 125 | | | | |

| ctc | tcc | tcc | ggc | ggc | agc | tac | gac | ccc | tac | agc | ccg | ggc | ggc | aaa | atc | 972 |
|---|---|---|---|---|---|---|---|---|---|---|---|---|---|---|---|---|
| Leu | Ser | Ser | Gly | Gly | Ser | Tyr | Asp | Pro | Tyr | Ser | Pro | Gly | Gly | Lys | Ile | |
| | 130 | | | | | 135 | | | | | 140 | | | | | |

| ggc | cgg | gag | gac | ctc | tcg | ccg | cta | agc | agt | ctg | aac | ggt | tac | agc | gcg | 1020 |
|---|---|---|---|---|---|---|---|---|---|---|---|---|---|---|---|---|
| Gly | Arg | Glu | Asp | Leu | Ser | Pro | Leu | Ser | Ser | Leu | Asn | Gly | Tyr | Ser | Ala | |
| 145 | | | | | 150 | | | | | 155 | | | | | 160 | |

| gac | agc | tgt | gac | gcc | aaa | aag | aag | aag | ggc | gct | gca | ccg | cgc | cag | cag | 1068 |
|---|---|---|---|---|---|---|---|---|---|---|---|---|---|---|---|---|
| Asp | Ser | Cys | Asp | Ala | Lys | Lys | Lys | Lys | Gly | Ala | Ala | Pro | Arg | Gln | Gln | |
| | | | | 165 | | | | | 170 | | | | | 175 | | |

| gag | gag | ctg | tgc | ctc | gtc | tgt | gga | gac | cgc | gcc | tcc | gga | tac | cac | tac | 1116 |
|---|---|---|---|---|---|---|---|---|---|---|---|---|---|---|---|---|
| Glu | Glu | Leu | Cys | Leu | Val | Cys | Gly | Asp | Arg | Ala | Ser | Gly | Tyr | His | Tyr | |
| | | | 180 | | | | | 185 | | | | | 190 | | | |

| aat | gct | ctc | acc | tgc | gag | ggc | tgc | aaa | ggt | ttc | ttc | agg | agg | agc | ata | 1164 |
|---|---|---|---|---|---|---|---|---|---|---|---|---|---|---|---|---|
| Asn | Ala | Leu | Thr | Cys | Glu | Gly | Cys | Lys | Gly | Phe | Phe | Arg | Arg | Ser | Ile | |
| | | 195 | | | | | 200 | | | | | 205 | | | | |

| aca | aaa | aat | gcc | gtg | tac | cag | tgc | aaa | tat | ggc | aat | aat | tgt | gaa | att | 1212 |
|---|---|---|---|---|---|---|---|---|---|---|---|---|---|---|---|---|
| Thr | Lys | Asn | Ala | Val | Tyr | Gln | Cys | Lys | Tyr | Gly | Asn | Asn | Cys | Glu | Ile | |
| | 210 | | | | | 215 | | | | | 220 | | | | | |

| gat | atg | tat | atg | agg | aga | aag | tgc | cag | gag | tgc | cga | ctg | aag | aag | tgc | 1260 |
|---|---|---|---|---|---|---|---|---|---|---|---|---|---|---|---|---|
| Asp | Met | Tyr | Met | Arg | Arg | Lys | Cys | Gln | Glu | Cys | Arg | Leu | Lys | Lys | Cys | |
| 225 | | | | | 230 | | | | | 235 | | | | | 240 | |

| ctc | aca | gtg | ggc | atg | agg | cca | gag | tgt | gta | gta | cct | gaa | tac | caa | tgt | 1308 |
|---|---|---|---|---|---|---|---|---|---|---|---|---|---|---|---|---|
| Leu | Thr | Val | Gly | Met | Arg | Pro | Glu | Cys | Val | Val | Pro | Glu | Tyr | Gln | Cys | |
| | | | | 245 | | | | | 250 | | | | | 255 | | |

| gca | gtg | aaa | aga | aaa | gag | aaa | aag | gca | caa | aaa | gat | aaa | gat | aaa | cct | 1356 |
|---|---|---|---|---|---|---|---|---|---|---|---|---|---|---|---|---|
| Ala | Val | Lys | Arg | Lys | Glu | Lys | Lys | Ala | Gln | Lys | Asp | Lys | Asp | Lys | Pro | |
| | | | 260 | | | | | 265 | | | | | 270 | | | |

| aat | tct | act | acg | aat | ggt | tca | cca | gag | gtg | atg | atg | ttg | aaa | gac | ata | 1404 |
|---|---|---|---|---|---|---|---|---|---|---|---|---|---|---|---|---|
| Asn | Ser | Thr | Thr | Asn | Gly | Ser | Pro | Glu | Val | Met | Met | Leu | Lys | Asp | Ile | |

```
                    275               280               285
gat gcc aag gtg gaa cca gaa aga cct tta tca aat ggg ata aaa cct    1452
Asp Ala Lys Val Glu Pro Glu Arg Pro Leu Ser Asn Gly Ile Lys Pro
        290               295               300 gta agt cct gaa cag gaa gag ctt ata cat agg ctt gtg tac ttc cag    1500
Val Ser Pro Glu Gln Glu Glu Leu Ile His Arg Leu Val Tyr Phe Gln
305               310               315               320 aat gaa tat gag tct cct tcc gaa gaa gat tta aga cga gtt acg agt    1548
Asn Glu Tyr Glu Ser Pro Ser Glu Glu Asp Leu Arg Arg Val Thr Ser
                325               330               335 caa cct acg gaa gga gag gac caa agt gat gta agg ttt cga cac atc    1596
Gln Pro Thr Glu Gly Glu Asp Gln Ser Asp Val Arg Phe Arg His Ile
            340               345               350 act gag atc aca ata tta act gtt caa cta att gtt gaa ttt gcc aag    1644
Thr Glu Ile Thr Ile Leu Thr Val Gln Leu Ile Val Glu Phe Ala Lys
        355               360               365 cgg ttg cca gga ttt gac aaa ctg cta cgg gaa gat cag ata gca tta    1692
Arg Leu Pro Gly Phe Asp Lys Leu Leu Arg Glu Asp Gln Ile Ala Leu
370               375               380 ctg aag gca tgt tcc agt gaa gta atg atg ttc cgc atg gca cga cgc    1740
Leu Lys Ala Cys Ser Ser Glu Val Met Met Phe Arg Met Ala Arg Arg
385               390               395               400 tat gat gta aat tca gac tcc ata ctt ttt gcc aat aat cag cct tac    1788
Tyr Asp Val Asn Ser Asp Ser Ile Leu Phe Ala Asn Asn Gln Pro Tyr
                405               410               415 act aag gat tcc tac aac ctt gct ggt atg gga gaa acg ata gaa gac    1836
Thr Lys Asp Ser Tyr Asn Leu Ala Gly Met Gly Glu Thr Ile Glu Asp
            420               425               430 atg ttg cgg ttc tgc aga cag atg tat gca atg aag gtt gat aat gca    1884
Met Leu Arg Phe Cys Arg Gln Met Tyr Ala Met Lys Val Asp Asn Ala
        435               440               445 gaa tat gcc ctt ctg act gca ata gtc ata ttt tca gag cgc cca tct    1932
Glu Tyr Ala Leu Leu Thr Ala Ile Val Ile Phe Ser Glu Arg Pro Ser
    450               455               460 ctt gtt gaa ggg tgg aag gtg gag aag ata caa gaa atc tac ctg gaa    1980
Leu Val Glu Gly Trp Lys Val Glu Lys Ile Gln Glu Ile Tyr Leu Glu
465               470               475               480 gct ctc aaa gca tat gtg gac aac agg cgg cgt cct aag tct gga aca    2028
Ala Leu Lys Ala Tyr Val Asp Asn Arg Arg Arg Pro Lys Ser Gly Thr
                485               490               495 att ttt gca aag ttg ttg tca gtt ctt act gaa ctg cgt act cta gga    2076
Ile Phe Ala Lys Leu Leu Ser Val Leu Thr Glu Leu Arg Thr Leu Gly
            500               505               510 aac cag aac tca gaa atg tgc ttc tct ctc aaa ctg aag aac aag aag    2124
Asn Gln Asn Ser Glu Met Cys Phe Ser Leu Lys Leu Lys Asn Lys Lys
        515               520               525 ctg cca ccg ttc ctt gct gag atc tgg gat gtg atc cca taa            2166
Leu Pro Pro Phe Leu Ala Glu Ile Trp Asp Val Ile Pro
    530               535               540 acggcagtgt gttcagctgg tcctgaagta ctagtcctta caatactgaa attgactgtt    2226
tttcatatta atttgttttt aatgcatata tctaagtgga aggcagcata cagtttcata    2286
ctttcagtag atccccagag aatagagcat tatatatttt aagtctgtaa aatttaaatt    2346
aaaatgccaa tttgtttaac tattgaaaaa gttgatatta ttattcagtg aaact          2401

<210> SEQ ID NO 12
<211> LENGTH: 541
<212> TYPE: PRT
<213> ORGANISM: Locusta migratoria
```

-continued

```
<220> FEATURE:
<221> NAME/KEY: misc_feature
<222> LOCATION: (1)..(2401)
<223> OTHER INFORMATION: n = a, t, c, or g

<400> SEQUENCE: 12
```

| Met | Glu | Leu | Phe | Arg | Gly | Ala | Asp | Gly | Ala | Leu | Pro | Ser | Ala | Ser | Ala |
|---|---|---|---|---|---|---|---|---|---|---|---|---|---|---|---|
| 1 | | | | 5 | | | | | 10 | | | | | 15 | |

| Ser | Ala | Ser | Ala | Ser | Ala | Ser | Gly | Ala | Pro | Ala | Ala | Ser | Pro | Leu | Ala |
|---|---|---|---|---|---|---|---|---|---|---|---|---|---|---|---|
| | | 20 | | | | | 25 | | | | | 30 | | | |

| Val | Ser | Val | Pro | Leu | Ala | Leu | Pro | Leu | Pro | Gly | His | Ala | Ser | Pro | Ala |
|---|---|---|---|---|---|---|---|---|---|---|---|---|---|---|---|
| | 35 | | | | | 40 | | | | | 45 | | | | |

| Ser | Ala | Ala | Asp | Ala | Leu | Val | Val | Lys | Thr | Glu | Pro | Arg | Glu | Ala | Gly |
|---|---|---|---|---|---|---|---|---|---|---|---|---|---|---|---|
| 50 | | | | | 55 | | | | | 60 | | | | | |

| Ala | Leu | Phe | Ala | Ala | Ile | Ser | Ser | Pro | Gly | Gln | Gly | Pro | Gly | Pro | Ala |
|---|---|---|---|---|---|---|---|---|---|---|---|---|---|---|---|
| 65 | | | | | 70 | | | | | 75 | | | | | 80 |

| Lys | Arg | Ala | Arg | Leu | Asp | Ser | Asp | Trp | Leu | Ser | Ser | Pro | Gly | Ser | Asn |
|---|---|---|---|---|---|---|---|---|---|---|---|---|---|---|---|
| | | | | 85 | | | | | 90 | | | | | 95 | |

| Ala | Ala | Pro | Ser | Pro | Pro | His | His | Leu | Phe | Gly | Ala | Ala | Ala | Ser |
|---|---|---|---|---|---|---|---|---|---|---|---|---|---|---|
| | | | 100 | | | | | 105 | | | | | 110 | |

| Ala | Ser | Ala | Gly | Ala | Pro | Ala | Ala | Leu | Pro | Asn | Gly | Tyr | Ala | Ser | Pro |
|---|---|---|---|---|---|---|---|---|---|---|---|---|---|---|---|
| | | 115 | | | | | 120 | | | | | 125 | | | |

| Leu | Ser | Ser | Gly | Gly | Ser | Tyr | Asp | Pro | Tyr | Ser | Pro | Gly | Gly | Lys | Ile |
|---|---|---|---|---|---|---|---|---|---|---|---|---|---|---|---|
| | 130 | | | | | 135 | | | | | 140 | | | | |

| Gly | Arg | Glu | Asp | Leu | Ser | Pro | Leu | Ser | Ser | Leu | Asn | Gly | Tyr | Ser | Ala |
|---|---|---|---|---|---|---|---|---|---|---|---|---|---|---|---|
| 145 | | | | | 150 | | | | | 155 | | | | | 160 |

| Asp | Ser | Cys | Asp | Ala | Lys | Lys | Lys | Gly | Ala | Ala | Pro | Arg | Gln | Gln |
|---|---|---|---|---|---|---|---|---|---|---|---|---|---|---|
| | | | 165 | | | | | 170 | | | | | 175 | |

| Glu | Glu | Leu | Cys | Leu | Val | Cys | Gly | Asp | Arg | Ala | Ser | Gly | Tyr | His | Tyr |
|---|---|---|---|---|---|---|---|---|---|---|---|---|---|---|---|
| | | | 180 | | | | | 185 | | | | | 190 | | |

| Asn | Ala | Leu | Thr | Cys | Glu | Gly | Cys | Lys | Gly | Phe | Phe | Arg | Arg | Ser | Ile |
|---|---|---|---|---|---|---|---|---|---|---|---|---|---|---|---|
| | 195 | | | | | 200 | | | | | 205 | | | | |

| Thr | Lys | Asn | Ala | Val | Tyr | Gln | Cys | Lys | Tyr | Gly | Asn | Asn | Cys | Glu | Ile |
|---|---|---|---|---|---|---|---|---|---|---|---|---|---|---|---|
| | 210 | | | | | 215 | | | | | 220 | | | | |

| Asp | Met | Tyr | Met | Arg | Arg | Lys | Cys | Gln | Glu | Cys | Arg | Leu | Lys | Lys | Cys |
|---|---|---|---|---|---|---|---|---|---|---|---|---|---|---|---|
| 225 | | | | | 230 | | | | | 235 | | | | | 240 |

| Leu | Thr | Val | Gly | Met | Arg | Pro | Glu | Cys | Val | Val | Pro | Glu | Tyr | Gln | Cys |
|---|---|---|---|---|---|---|---|---|---|---|---|---|---|---|---|
| | | | 245 | | | | | 250 | | | | | 255 | | |

| Ala | Val | Lys | Arg | Lys | Glu | Lys | Lys | Ala | Gln | Lys | Asp | Lys | Asp | Lys | Pro |
|---|---|---|---|---|---|---|---|---|---|---|---|---|---|---|---|
| | | | 260 | | | | | 265 | | | | | 270 | | |

| Asn | Ser | Thr | Thr | Asn | Gly | Ser | Pro | Glu | Val | Met | Met | Leu | Lys | Asp | Ile |
|---|---|---|---|---|---|---|---|---|---|---|---|---|---|---|---|
| | 275 | | | | | 280 | | | | | 285 | | | | |

| Asp | Ala | Lys | Val | Glu | Pro | Glu | Arg | Pro | Leu | Ser | Asn | Gly | Ile | Lys | Pro |
|---|---|---|---|---|---|---|---|---|---|---|---|---|---|---|---|
| | 290 | | | | | 295 | | | | | 300 | | | | |

| Val | Ser | Pro | Glu | Gln | Glu | Glu | Leu | Ile | His | Arg | Leu | Val | Tyr | Phe | Gln |
|---|---|---|---|---|---|---|---|---|---|---|---|---|---|---|---|
| 305 | | | | | 310 | | | | | 315 | | | | | 320 |

| Asn | Glu | Tyr | Glu | Ser | Pro | Ser | Glu | Glu | Asp | Leu | Arg | Arg | Val | Thr | Ser |
|---|---|---|---|---|---|---|---|---|---|---|---|---|---|---|---|
| | | | 325 | | | | | 330 | | | | | 335 | | |

| Gln | Pro | Thr | Glu | Gly | Glu | Asp | Gln | Ser | Asp | Val | Arg | Phe | Arg | His | Ile |
|---|---|---|---|---|---|---|---|---|---|---|---|---|---|---|---|
| | | | 340 | | | | | 345 | | | | | 350 | | |

| Thr | Glu | Ile | Thr | Ile | Leu | Thr | Val | Gln | Leu | Ile | Val | Glu | Phe | Ala | Lys |
|---|---|---|---|---|---|---|---|---|---|---|---|---|---|---|---|
| | | 355 | | | | | 360 | | | | | 365 | | | |

| Arg | Leu | Pro | Gly | Phe | Asp | Lys | Leu | Leu | Arg | Glu | Asp | Gln | Ile | Ala | Leu |
|---|---|---|---|---|---|---|---|---|---|---|---|---|---|---|---|
| 370 | | | | | 375 | | | | | 380 | | | | | |

-continued

```
Leu Lys Ala Cys Ser Ser Glu Val Met Met Phe Arg Met Ala Arg Arg
385                 390                 395                 400

Tyr Asp Val Asn Ser Asp Ser Ile Leu Phe Ala Asn Asn Gln Pro Tyr
                405                 410                 415

Thr Lys Asp Ser Tyr Asn Leu Ala Gly Met Gly Glu Thr Ile Glu Asp
            420                 425                 430

Met Leu Arg Phe Cys Arg Gln Met Tyr Ala Met Lys Val Asp Asn Ala
        435                 440                 445

Glu Tyr Ala Leu Leu Thr Ala Ile Val Ile Phe Ser Glu Arg Pro Ser
    450                 455                 460

Leu Val Glu Gly Trp Lys Val Glu Lys Ile Gln Ile Tyr Leu Glu
465                 470                 475                 480

Ala Leu Lys Ala Tyr Val Asp Asn Arg Arg Arg Pro Lys Ser Gly Thr
                485                 490                 495

Ile Phe Ala Lys Leu Leu Ser Val Leu Thr Glu Leu Arg Thr Leu Gly
            500                 505                 510

Asn Gln Asn Ser Glu Met Cys Phe Ser Leu Lys Leu Lys Asn Lys Lys
        515                 520                 525

Leu Pro Pro Phe Leu Ala Glu Ile Trp Asp Val Ile Pro
    530                 535                 540
```

<210> SEQ ID NO 13
<211> LENGTH: 2349
<212> TYPE: DNA
<213> ORGANISM: Chironomus tentans
<220> FEATURE:
<221> NAME/KEY: CDS
<222> LOCATION: (209)..(1819)
<223> OTHER INFORMATION:
<300> PUBLICATION INFORMATION:
<301> AUTHORS: Imhof, et al.
<302> TITLE: Cloning of a Chironomus tentans cDNA encoding a protein
      (cEcRH) homologous to the Drosophila melanogaster ecdysteroid
      receptor (dEcR)
<303> JOURNAL: Insect Biochem. Mol. Biol.
<304> VOLUME: 23
<305> ISSUE: 1
<306> PAGES: 115-124
<307> DATE: 1993
<308> DATABASE ACCESSION NUMBER: Genbank/S60739
<309> DATABASE ENTRY DATE: 1993-08-25

<400> SEQUENCE: 13

```
gaattcgata aacatcattt ctgtttccaa atgtgtcttt ttttctttta ttaatttcaa      60
aaaggaagag aaaaattaat taaaatttgt ttgatattcc attttaattc atcattgttg     120
ttagatgtag ctttattatc aaaatctata agtctgcaat tgaactattt gttagtgatt     180
tgtccaaggc aattattgat gtgctaat atg aag aca gaa aac ttg att gtt       232
                              Met Lys Thr Glu Asn Leu Ile Val
                                1               5 act act gtt aag gtt gaa cca tta aac tat gct tca cag tct ttt gga      280
Thr Thr Val Lys Val Glu Pro Leu Asn Tyr Ala Ser Gln Ser Phe Gly
     10                  15                  20 gat aat aat ata tat gga gga gct aca aag aaa caa cga tta gaa agt      328
Asp Asn Asn Ile Tyr Gly Gly Ala Thr Lys Lys Gln Arg Leu Glu Ser
 25                  30                  35                  40 gac gaa tgg atg aat cac aat caa aca aat atg aat ctt gaa tct tcc      376
Asp Glu Trp Met Asn His Asn Gln Thr Asn Met Asn Leu Glu Ser Ser
                 45                  50                  55 aat atg aat cat aat aca ata agt ggc ttc tca tca ccg gac gtt aac      424
Asn Met Asn His Asn Thr Ile Ser Gly Phe Ser Ser Pro Asp Val Asn
             60                  65                  70
```

-continued

| | |
|---|---|
| tat gag gct tac agc ccc aat tca aaa ctt gat gat ggc aat atg agt<br>Tyr Glu Ala Tyr Ser Pro Asn Ser Lys Leu Asp Asp Gly Asn Met Ser<br>        75                      80                        85 | 472 |
| gtt cac atg ggt gat gga ctt gat ggc aag aaa tca tca tcg aaa aaa<br>Val His Met Gly Asp Gly Leu Asp Gly Lys Lys Ser Ser Ser Lys Lys<br>        90                      95                      100 | 520 |
| gga cct gtg cca cgt caa cag gaa gag ctg tgc ctc gtt tgc gga gat<br>Gly Pro Val Pro Arg Gln Gln Glu Glu Leu Cys Leu Val Cys Gly Asp<br>105                    110                    115                    120 | 568 |
| cgt gcc tcg gga tat cat tat aat gct tta aca tgt gaa ggg tgc aag<br>Arg Ala Ser Gly Tyr His Tyr Asn Ala Leu Thr Cys Glu Gly Cys Lys<br>                    125                    130                    135 | 616 |
| gga ttt ttc cgt cgt agt gtt aca aaa aat gct gtt tat tgt tgt aaa<br>Gly Phe Phe Arg Arg Ser Val Thr Lys Asn Ala Val Tyr Cys Cys Lys<br>            140                    145                    150 | 664 |
| ttt ggt cat gaa tgt gaa atg gac atg tat atg aga cga aag tgt cag<br>Phe Gly His Glu Cys Glu Met Asp Met Tyr Met Arg Arg Lys Cys Gln<br>              155                    160                    165 | 712 |
| gag tgc cgt ttg aaa aaa tgt ttg gct gtg gga atg cga cct gaa tgt<br>Glu Cys Arg Leu Lys Lys Cys Leu Ala Val Gly Met Arg Pro Glu Cys<br>        170                    175                    180 | 760 |
| gtc gtt cca gaa aat caa tgt gct att aag cgg aag gag aag aag gca<br>Val Val Pro Glu Asn Gln Cys Ala Ile Lys Arg Lys Glu Lys Lys Ala<br>185                    190                    195                    200 | 808 |
| caa aaa gag aag gat aag gtt cca ggc att gtc gga agt aat act tcg<br>Gln Lys Glu Lys Asp Lys Val Pro Gly Ile Val Gly Ser Asn Thr Ser<br>                    205                    210                    215 | 856 |
| tca tcg tct ctc ctc aat caa agc ttg aat aat gga tct tta aaa aat<br>Ser Ser Ser Leu Leu Asn Gln Ser Leu Asn Asn Gly Ser Leu Lys Asn<br>            220                    225                    230 | 904 |
| ctc gaa att tca tat cga gag gag ctc ctc gag cag ctt atg aaa tgt<br>Leu Glu Ile Ser Tyr Arg Glu Glu Leu Leu Glu Gln Leu Met Lys Cys<br>              235                    240                    245 | 952 |
| gat cca ccg cct cat cca atg caa caa ctt ttg cct gaa aag ctt tta<br>Asp Pro Pro Pro His Pro Met Gln Gln Leu Leu Pro Glu Lys Leu Leu<br>250                    255                    260 | 1000 |
| atg gag aat cgt gca aaa ggc aca cct caa ctc acg gcc aat caa gta<br>Met Glu Asn Arg Ala Lys Gly Thr Pro Gln Leu Thr Ala Asn Gln Val<br>265                    270                    275                    280 | 1048 |
| gcc gtt att tat aag ctt atc tgg tat caa gac ggt tat gaa cag ccg<br>Ala Val Ile Tyr Lys Leu Ile Trp Tyr Gln Asp Gly Tyr Glu Gln Pro<br>                    285                    290                    295 | 1096 |
| tcc gaa gaa gac tta aaa cgc ata aca acg gaa ctg gag gaa gaa gag<br>Ser Glu Glu Asp Leu Lys Arg Ile Thr Thr Glu Leu Glu Glu Glu Glu<br>            300                    305                    310 | 1144 |
| gat caa gag cac gag gca aat ttc cga tat ata aca gaa gtc aca ata<br>Asp Gln Glu His Glu Ala Asn Phe Arg Tyr Ile Thr Glu Val Thr Ile<br>              315                    320                    325 | 1192 |
| ttg aca gtg caa ctg att gtg gaa ttc gca aaa ggg ctt cca gca ttt<br>Leu Thr Val Gln Leu Ile Val Glu Phe Ala Lys Gly Leu Pro Ala Phe<br>330                    335                    340 | 1240 |
| att aaa ata cca caa gaa gat caa att act ctc ttg aag gct tgc tcc<br>Ile Lys Ile Pro Gln Glu Asp Gln Ile Thr Leu Leu Lys Ala Cys Ser<br>345                    350                    355                    360 | 1288 |
| agt gaa gtt atg atg ttg cgc atg gct cga cga tac gat cac gat tcc<br>Ser Glu Val Met Met Leu Arg Met Ala Arg Arg Tyr Asp His Asp Ser<br>                    365                    370                    375 | 1336 |
| gat tcg ata ttg ttt gca aat aat aca gcg tac act aag caa acg tat<br>Asp Ser Ile Leu Phe Ala Asn Asn Thr Ala Tyr Thr Lys Gln Thr Tyr | 1384 |

-continued

```
                380                385                390
caa tta gcg ggc atg gaa gag aca att gat gat tta ctg cac ttt tgt    1432
Gln Leu Ala Gly Met Glu Glu Thr Ile Asp Asp Leu Leu His Phe Cys
        395                400                405 cga caa atg tat gca tta tct att gat aat gtc gag tat gct ctt ctc    1480
Arg Gln Met Tyr Ala Leu Ser Ile Asp Asn Val Glu Tyr Ala Leu Leu
    410                415                420 aca gcc atc gtc atc ttc tca gat cga cct ggt cta gaa aag gct gaa    1528
Thr Ala Ile Val Ile Phe Ser Asp Arg Pro Gly Leu Glu Lys Ala Glu
425                430                435                440 atg gtg gac atc att caa agc tat tac aca gaa act ctt aag gtt tat    1576
Met Val Asp Ile Ile Gln Ser Tyr Tyr Thr Glu Thr Leu Lys Val Tyr
            445                450                455 atc gtc aat cgg cat ggt ggc gag tca aga tgc agc gtt caa ttt gca    1624
Ile Val Asn Arg His Gly Gly Glu Ser Arg Cys Ser Val Gln Phe Ala
        460                465                470 aaa cta ttg ggc att ctt act gaa tta cga aca atg ggc aat aaa aat    1672
Lys Leu Leu Gly Ile Leu Thr Glu Leu Arg Thr Met Gly Asn Lys Asn
    475                480                485 tct gaa atg tgc ttt tca tta aaa ctg aga aac cga aaa ctg cca cga    1720
Ser Glu Met Cys Phe Ser Leu Lys Leu Arg Asn Arg Lys Leu Pro Arg
490                495                500 ttc tta gaa gaa gtc tgg gat gtc ggc gat gtc aat aac caa acc acg    1768
Phe Leu Glu Glu Val Trp Asp Val Gly Asp Val Asn Asn Gln Thr Thr
505                510                515                520 gca aca aca aat aca gag aac atc gtt cgg gaa cga ata aat cga aac    1816
Ala Thr Thr Asn Thr Glu Asn Ile Val Arg Glu Arg Ile Asn Arg Asn
            525                530                535 taa agctatatga cttcgtattt tatatattta cctacctaaa atttcaacaa         1869
aaaaaattat gatgataagt gtaattacat ttcggatttt atgaaacata acaatatgga 1929 gataatatat atctagaatt acatttattt aggtataata caagaaaaga aatttaacga 1989 tgaacatgaa aagtcacata ttattcgaaa aaaaaaaaga aaaaaatata aagaattga  2049 aaaaaggaga agaaaagaat ataaaaaaat tggactggaa cgttgatttt tgaattaaag 2109 aaaaaaaaaa cgagagaaga aaggaaaag gggaaaaatg tcagaaagat ttaattaacc 2169 attatcgcat accattcgat ctcaattttt atttcatttc attctgctgt ttgaaatcat 2229 acacaaacga gagacccgaa aaaatataa aagaattgaa aaaaggagaa gaaaagaata  2289 taaaaaatt ggactggaac gttgattttt gtttcaagat attttaatcg cccggaattc  2349
```

<210> SEQ ID NO 14
<211> LENGTH: 536
<212> TYPE: PRT
<213> ORGANISM: Chironomus tentans

<400> SEQUENCE: 14

```
Met Lys Thr Glu Asn Leu Ile Val Thr Thr Val Lys Val Glu Pro Leu
1               5                   10                  15

Asn Tyr Ala Ser Gln Ser Phe Gly Asp Asn Asn Ile Tyr Gly Gly Ala
            20                  25                  30

Thr Lys Lys Gln Arg Leu Glu Ser Asp Glu Trp Met Asn His Asn Gln
        35                  40                  45

Thr Asn Met Asn Leu Glu Ser Asn Met Asn His Asn Thr Ile Ser
    50                  55                  60

Gly Phe Ser Ser Pro Asp Val Asn Tyr Glu Ala Tyr Ser Pro Asn Ser
65                  70                  75                  80
```

```
Lys Leu Asp Asp Gly Asn Met Ser Val His Met Gly Asp Gly Leu Asp
                85                  90                  95

Gly Lys Lys Ser Ser Lys Lys Gly Pro Val Pro Arg Gln Gln Glu
            100             105             110

Glu Leu Cys Leu Val Cys Gly Asp Arg Ala Ser Gly Tyr His Tyr Asn
            115             120             125

Ala Leu Thr Cys Glu Gly Cys Lys Gly Phe Phe Arg Arg Ser Val Thr
        130             135             140

Lys Asn Ala Val Tyr Cys Cys Lys Phe Gly His Glu Cys Glu Met Asp
145             150             155             160

Met Tyr Met Arg Arg Lys Cys Gln Glu Cys Arg Leu Lys Lys Cys Leu
            165             170             175

Ala Val Gly Met Arg Pro Glu Cys Val Val Pro Glu Asn Gln Cys Ala
            180             185             190

Ile Lys Arg Lys Glu Lys Lys Ala Gln Lys Glu Lys Asp Lys Val Pro
        195             200             205

Gly Ile Val Gly Ser Asn Thr Ser Ser Ser Ser Leu Leu Asn Gln Ser
        210             215             220

Leu Asn Asn Gly Ser Leu Lys Asn Leu Glu Ile Ser Tyr Arg Glu Glu
225             230             235             240

Leu Leu Glu Gln Leu Met Lys Cys Asp Pro Pro His Pro Met Gln
            245             250             255

Gln Leu Leu Pro Glu Lys Leu Leu Met Glu Asn Arg Ala Lys Gly Thr
            260             265             270

Pro Gln Leu Thr Ala Asn Gln Val Ala Val Ile Tyr Lys Leu Ile Trp
        275             280             285

Tyr Gln Asp Gly Tyr Glu Gln Pro Ser Glu Glu Asp Leu Lys Arg Ile
        290             295             300

Thr Thr Glu Leu Glu Glu Glu Asp Gln His Glu Ala Asn Phe
305             310             315             320

Arg Tyr Ile Thr Glu Val Thr Ile Leu Thr Val Gln Leu Ile Val Glu
            325             330             335

Phe Ala Lys Gly Leu Pro Ala Phe Ile Lys Ile Pro Gln Glu Asp Gln
            340             345             350

Ile Thr Leu Leu Lys Ala Cys Ser Ser Glu Val Met Met Leu Arg Met
        355             360             365

Ala Arg Arg Tyr Asp His Asp Ser Asp Ser Ile Leu Phe Ala Asn Asn
370             375             380

Thr Ala Tyr Thr Lys Gln Thr Tyr Gln Leu Ala Gly Met Glu Glu Thr
385             390             395             400

Ile Asp Asp Leu Leu His Phe Cys Arg Gln Met Tyr Ala Leu Ser Ile
            405             410             415

Asp Asn Val Glu Tyr Ala Leu Leu Thr Ala Ile Val Ile Phe Ser Asp
            420             425             430

Arg Pro Gly Leu Glu Lys Ala Glu Met Val Asp Ile Ile Gln Ser Tyr
        435             440             445

Tyr Thr Glu Thr Leu Lys Val Tyr Ile Val Asn Arg His Gly Gly Glu
        450             455             460

Ser Arg Cys Ser Val Gln Phe Ala Lys Leu Leu Gly Ile Leu Thr Glu
465             470             475             480

Leu Arg Thr Met Gly Asn Lys Asn Ser Glu Met Cys Phe Ser Leu Lys
            485             490             495

Leu Arg Asn Arg Lys Leu Pro Arg Phe Leu Glu Glu Val Trp Asp Val
```

```
                 500             505             510
Gly Asp Val Asn Asn Gln Thr Thr Ala Thr Thr Asn Thr Glu Asn Ile
        515                 520                 525

Val Arg Glu Arg Ile Asn Arg Asn
    530                 535

<210> SEQ ID NO 15
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: primer

<400> SEQUENCE: 15
gtgaagtgaa agcctacgtc                                              20

<210> SEQ ID NO 16
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 16
tgacgcgctc ttcgacatga gac                                          23

<210> SEQ ID NO 17
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 17
ggytgytcrt abccbtcctg gta                                          23

<210> SEQ ID NO 18
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer

<400> SEQUENCE: 18
ccbscsatha tgcartgtga hc                                           22

<210> SEQ ID NO 19
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer

<400> SEQUENCE: 19
ccacrtccca gatctcctcg a                                            21
```

```
<210> SEQ ID NO 20
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: primer

<400> SEQUENCE: 20
aagcttgccc ccccgaccg                                              19

<210> SEQ ID NO 21
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer

<400> SEQUENCE: 21
tctagaggat cctacccacc gtact                                       25

<210> SEQ ID NO 22
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 22
ggatcctaaa gcttcgtcgt cgacacttcg                                  30

<210> SEQ ID NO 23
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 23
ggatcctaaa gcttcccgcg ggattccacg                                  30

<210> SEQ ID NO 24
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer

<400> SEQUENCE: 24
ggatcctaaa gcttcacgtc ccagatctcc tc                               32

<210> SEQ ID NO 25
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer
```

-continued

```
<400> SEQUENCE: 25
ggatcctaaa gcttcacgtc ccagatctcc tccag                                35

<210> SEQ ID NO 26
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 26
ggatcctaaa gctttgggat cacatcccag                                      30

<210> SEQ ID NO 27
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 27
ggatcctaaa gctttggcgg gatggcatga                                      30

<210> SEQ ID NO 28
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer

<400> SEQUENCE: 28
ggatcctaaa gcttgacatc gccgacatcc cagac                                35

<210> SEQ ID NO 29
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: primer

<400> SEQUENCE: 29
ctgcaggatc cagacgccgc tggtcaaac                                       29

<210> SEQ ID NO 30
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 30
ggcaggatcc atgaagcggc gctggtc                                         27

<210> SEQ ID NO 31
<211> LENGTH: 27
<212> TYPE: DNA
<213> ORGANISM: Artificial Sequence
```

```
<220> FEATURE:
<221> NAME/KEY: misc_feature
<222> LOCATION: (1)..(27)
<223> OTHER INFORMATION: primer

<400> SEQUENCE: 31
cggaagatct cgtgcatggc cagcgtg                                27

<210> SEQ ID NO 32
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 32
ggatccatgg gycgagaaga attrtcaccr                             30

<210> SEQ ID NO 33
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: primer

<400> SEQUENCE: 33
ccacrtccca gatctcctcg a                                      21

<210> SEQ ID NO 34
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 34
ggatccatgg gycgagaaga attrtcaccr                             30

<210> SEQ ID NO 35
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 35
ggytgytcrt abccbtcctg gta                                    23

<210> SEQ ID NO 36
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 36
ggatccatgg gccgggagga cctctcgccg                             30
```

```
<210> SEQ ID NO 37
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 37
ggatcctaaa gctttgggat cacatcccag                                    30

<210> SEQ ID NO 38
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: primer

<400> SEQUENCE: 38
agcttgaggg tataatg                                                  17

<210> SEQ ID NO 39
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: primer

<400> SEQUENCE: 39
actcccatat tactcga                                                  17

<210> SEQ ID NO 40
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer

<400> SEQUENCE: 40
gatccgagac aagggttcaa tgcacttgtc caatga                             36

<210> SEQ ID NO 41
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer

<400> SEQUENCE: 41
gctctgttcc caagttacgt gaacaggtta ctctag                             36

<210> SEQ ID NO 42
<211> LENGTH: 147
<212> TYPE: DNA
<213> ORGANISM: synthetic construct
<220> FEATURE:
<221> NAME/KEY: misc_feature
<222> LOCATION: (1)..(147)
<223> OTHER INFORMATION: sequence in the inserted region of pCGS154
```

```
<400> SEQUENCE: 42
gatccgagac aagggttcaa tgcacttgtc caatgagatc cgagacaagg gttcaatgca    60
cttgtccaat gagatctcat tggacaagtg cattgaacct tgtctcggat ctcattggac  120
aagtgcattg aaccettgtc tcggatc                                      147

<210> SEQ ID NO 43
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 43
ggatccatga aacttgatga tggcaatatg                                     30

<210> SEQ ID NO 44
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 44
tggtaccaga taagcttata aataacg                                        27

<210> SEQ ID NO 45
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 45
tggtaccaag acggttatga acagccg                                        27

<210> SEQ ID NO 46
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer

<400> SEQUENCE: 46
ggatcctaaa gcttgacatc gccgacatcc cagac                               35

<210> SEQ ID NO 47
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 47
ggatccatgg gccgggagga cctctcgccg                                     30
```

<210> SEQ ID NO 48
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer

<400> SEQUENCE: 48
ggatccacac aagcctatgt ataag                                25

<210> SEQ ID NO 49
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 49
tgtggtacca gaatgaatat gagtctc                              27

<210> SEQ ID NO 50
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 50
ggatcctaaa gctttgggat cacatcccag                           30

<210> SEQ ID NO 51
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: primer bztata1

<400> SEQUENCE: 51
agcttcgcac gcgtggtcgc gcggaataaa gcggacacgt tgcgccccca g   51

<210> SEQ ID NO 52
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: primer bztata2

<400> SEQUENCE: 52
ttcgctgggg gcgcaacgtg tccgctttat tccgcgcgac cacgcgtgcg a   51

<210> SEQ ID NO 53
<211> LENGTH: 57
<212> TYPE: DNA
<213> ORGANISM: Artificial Sequence
<220> FEATURE:
<221> NAME/KEY: misc_feature
<222> LOCATION: (1)..(57)
<223> OTHER INFORMATION: primer bztata3

```
<400> SEQUENCE: 53
cgaagcccgc acgcatcgca ttcgcatcgc atcgcaggtc gcatccgacg ctagaag        57

<210> SEQ ID NO 54
<211> LENGTH: 57
<212> TYPE: DNA
<213> ORGANISM: Artificial Sequence
<220> FEATURE:
<221> NAME/KEY: misc_feature
<222> LOCATION: (1)..(57)
<223> OTHER INFORMATION: primer bztata4

<400> SEQUENCE: 54
aattcttcta gcgtcggatg cgacctgcga tgcgatgcga atgcgatgcg tgcgggc        57

<210> SEQ ID NO 55
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer bzintron1

<400> SEQUENCE: 55
ccgaattccg ggaggacgtt ggcgaccagg gt                                   32

<210> SEQ ID NO 56
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: primer bzintron2

<400> SEQUENCE: 56
ccgaattcgg tgggagatca gtagcccgtc ca                                   32

<210> SEQ ID NO 57
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer GAL4BDforward

<400> SEQUENCE: 57
aggatccgcc accatgaagc tactgtcttc                                      30

<210> SEQ ID NO 58
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: primer GAL4BDreverse

<400> SEQUENCE: 58
aacgcgtcga tacagtcaac tgtctttgac c                                    31

<210> SEQ ID NO 59
<211> LENGTH: 23
<212> TYPE: DNA
```

```
<213> ORGANISM: Artificial Sequence
<220> FEATURE:
<221> NAME/KEY: misc_feature
<222> LOCATION: (1)..(23)
<223> OTHER INFORMATION: primer MV forward

<400> SEQUENCE: 59
aacgcgtatg aggcccgagt gcg                                              23

<210> SEQ ID NO 60
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer MV reverse

<400> SEQUENCE: 60
aaatccggaa atacgactca ctatagggcg aat                                   33

<210> SEQ ID NO 61
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: top strand of d.s. oligo used to create a
      multiple cloning site

<400> SEQUENCE: 61
gatccccggg tcgacgaatt ctccggaagc ttctaga                               37

<210> SEQ ID NO 62
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: bottom strand of d.s. oligo used to create a
      multiple cloning site

<400> SEQUENCE: 62
gatctctaga agcttccgga gaattcgtcg acccggg                               37

<210> SEQ ID NO 63
<211> LENGTH: 1506
<212> TYPE: DNA
<213> ORGANISM: Synthetic construct
<220> FEATURE:
<221> NAME/KEY: CDS
<222> LOCATION: (1)..(1506)
<223> OTHER INFORMATION: Ecdysone Receptor chimera MDV

<400> SEQUENCE: 63 atg ggt cga gaa gaa tta tca ccg gcc tca agt ata aat gga tgt agt        48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag        96
Thr Asp Gly Glu Pro Arg Arg Gln Lys Lys Gly Pro Ala Pro Arg Gln
                20                  25                  30 cag gag gaa ctg tgc ctt gtt tgc ggc gac agg gct tcg gga tat cac       144
Gln Glu Glu Leu Cys Leu Val Cys Gly Asp Arg Ala Ser Gly Tyr His
            35                  40                  45 tat aac gcg ctt acg tgc gaa gga tgt aaa ggg ttc ttc agg cgg agt       192
```

| | | |
|---|---|---|
| Tyr Asn Ala Leu Thr Cys Glu Gly Cys Lys Gly Phe Phe Arg Arg Ser<br>50                        55                        60 | |
| gtg acc aag aat gcg gta tat att tgt aaa ttt gga cac gcc tgc gag<br>Val Thr Lys Asn Ala Val Tyr Ile Cys Lys Phe Gly His Ala Cys Glu<br>65                       70                     75                      80 | 240 |
| atg gac atg tac atg agg aga aaa tgc caa gag tgt cgg ttg aag aaa<br>Met Asp Met Tyr Met Arg Arg Lys Cys Gln Glu Cys Arg Leu Lys Lys<br>                        85                     90                     95 | 288 |
| tgc ctc gcg gtg ggc atg agg ccc gag tgc gtc gtc cca gag tcc acg<br>Cys Leu Ala Val Gly Met Arg Pro Glu Cys Val Val Pro Glu Ser Thr<br>                   100                  105                110 | 336 |
| tgc aag aac aaa aga aga gaa aag gaa gca cag aga gaa aaa gac aaa<br>Cys Lys Asn Lys Arg Arg Glu Lys Glu Ala Gln Arg Glu Lys Asp Lys<br>               115                   120                125 | 384 |
| ctg cca gtc agt acg acg aca gtg gac gat cat atg cct gcc ata atg<br>Leu Pro Val Ser Thr Thr Thr Val Asp Asp His Met Pro Ala Ile Met<br>130                       135                      140 | 432 |
| caa tgt gac cct ccg ccc cca gag gcg gca agg att cac gaa gtg gtc<br>Gln Cys Asp Pro Pro Pro Pro Glu Ala Ala Arg Ile His Glu Val Val<br>145                       150                     155                160 | 480 |
| ccg agg ttc cta acg gag aag cta atg gag cag aac aga ctg aag aat<br>Pro Arg Phe Leu Thr Glu Lys Leu Met Glu Gln Asn Arg Leu Lys Asn<br>                   165                  170                175 | 528 |
| gtg acg ccg ctg tcg gcg aac cag aag tcc ctg atc gcg agg ctc gtg<br>Val Thr Pro Leu Ser Ala Asn Gln Lys Ser Leu Ile Ala Arg Leu Val<br>                   180                  185                190 | 576 |
| tgg tac cag gat ggc tat gag cag cca tct gaa gag gat ctc agg cgt<br>Trp Tyr Gln Asp Gly Tyr Glu Gln Pro Ser Glu Glu Asp Leu Arg Arg<br>                   195                  200                205 | 624 |
| ata atg agt caa ccc gat gag aac gag agc caa acg gac gtc agc ttt<br>Ile Met Ser Gln Pro Asp Glu Asn Glu Ser Gln Thr Asp Val Ser Phe<br>210                       215                     220 | 672 |
| cgg cat ata acc gag ata acc ata ctc acg gtc cag ttg att gtt gag<br>Arg His Ile Thr Glu Ile Thr Ile Leu Thr Val Gln Leu Ile Val Glu<br>225                       230                     235                240 | 720 |
| ttt gct aaa ggt cta cca gcg ttt aca aag ata ccc cag gag gac cag<br>Phe Ala Lys Gly Leu Pro Ala Phe Thr Lys Ile Pro Gln Glu Asp Gln<br>                   245                  250                255 | 768 |
| atc acg tta cta aag gcc tgc tcg tcg gag gtg atg atg ctg cgt atg<br>Ile Thr Leu Leu Lys Ala Cys Ser Ser Glu Val Met Met Leu Arg Met<br>                   260                  265                270 | 816 |
| gca cga cgc tat gac cac agc tcg gac tca ata ttc ttc gcg aat aat<br>Ala Arg Arg Tyr Asp His Ser Ser Asp Ser Ile Phe Phe Ala Asn Asn<br>               275                   280                285 | 864 |
| aga tca tat acg cgg gat tct tac aaa atg gcc gga atg gct gat aac<br>Arg Ser Tyr Thr Arg Asp Ser Tyr Lys Met Ala Gly Met Ala Asp Asn<br>         290                  295                300 | 912 |
| att gaa gac ctg ctg cat ttc tgc cgc caa atg ttc tcg atg aag gtg<br>Ile Glu Asp Leu Leu His Phe Cys Arg Gln Met Phe Ser Met Lys Val<br>305                       310                     315                320 | 960 |
| gac aac gtc gaa tac gcg ctt ctc act gcc att gtg atc ttc tcg gac<br>Asp Asn Val Glu Tyr Ala Leu Leu Thr Ala Ile Val Ile Phe Ser Asp<br>                   325                  330                335 | 1008 |
| cgg ccg ggc ctg gag aag gcc caa cta gtc gaa gcg atc cag agc tac<br>Arg Pro Gly Leu Glu Lys Ala Gln Leu Val Glu Ala Ile Gln Ser Tyr<br>                   340                  345                350 | 1056 |
| tac atc gac acg cta cgc att tat ata ctc aac cgc cac tgc ggc gac<br>Tyr Ile Asp Thr Leu Arg Ile Tyr Ile Leu Asn Arg His Cys Gly Asp<br>               355                   360                365 | 1104 |

-continued

```
tca atg agc ctc gtc ttc tac gca aag ctg ctc tcg atc ctc acc gag    1152
Ser Met Ser Leu Val Phe Tyr Ala Lys Leu Leu Ser Ile Leu Thr Glu
    370                 375                 380 ctg cgt acg ctg ggc aac cag aac gcc gag atg tgt ttc tca cta aag    1200
Leu Arg Thr Leu Gly Asn Gln Asn Ala Glu Met Cys Phe Ser Leu Lys
385                 390                 395                 400 ctc aaa aac cgc aaa ctg ccc aag ttc ctc gag gag atc tgg gac gtt    1248
Leu Lys Asn Arg Lys Leu Pro Lys Phe Leu Glu Glu Ile Trp Asp Val
                405                 410                 415 cat gcc atc ccg cca aag ctt gcc ccc ccg acc gat gtc agc ctg ggg    1296
His Ala Ile Pro Pro Lys Leu Ala Pro Pro Thr Asp Val Ser Leu Gly
            420                 425                 430 gac gag ctc cac tta gac ggc gag gac gtg gcg atg gcg cat gcc gac    1344
Asp Glu Leu His Leu Asp Gly Glu Asp Val Ala Met Ala His Ala Asp
        435                 440                 445 gcg cta gac gat ttc gat ctg gac atg ttg ggg gac ggg gat tcc ccg    1392
Ala Leu Asp Asp Phe Asp Leu Asp Met Leu Gly Asp Gly Asp Ser Pro
450                 455                 460 ggt ccg gga ttt acc ccc cac gac tcc gcc ccc tac ggc gct ctg gat    1440
Gly Pro Gly Phe Thr Pro His Asp Ser Ala Pro Tyr Gly Ala Leu Asp
465                 470                 475                 480 atg gcc gac ttc gag ttt gag cag atg ttt acc gat gcc ctt gga att    1488
Met Ala Asp Phe Glu Phe Glu Gln Met Phe Thr Asp Ala Leu Gly Ile
                485                 490                 495 gac gag tac ggt ggg tag                                            1506
Asp Glu Tyr Gly Gly
            500
```

<210> SEQ ID NO 64
<211> LENGTH: 501
<212> TYPE: PRT
<213> ORGANISM: Synthetic construct

<400> SEQUENCE: 64

```
Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Ser Thr
            100                 105                 110

Cys Lys Asn Lys Arg Arg Glu Lys Glu Ala Gln Arg Glu Lys Asp Lys
        115                 120                 125

Leu Pro Val Ser Thr Thr Thr Val Asp Asp His Met Pro Ala Ile Met
    130                 135                 140

Gln Cys Asp Pro Pro Pro Glu Ala Ala Arg Ile His Glu Val Val
145                 150                 155                 160

Pro Arg Phe Leu Thr Glu Lys Leu Met Glu Gln Asn Arg Leu Lys Asn
                165                 170                 175

Val Thr Pro Leu Ser Ala Asn Gln Lys Ser Leu Ile Ala Arg Leu Val
            180                 185                 190
```

```
Trp Tyr Gln Asp Gly Tyr Glu Gln Pro Ser Glu Glu Asp Leu Arg Arg
            195                 200                 205

Ile Met Ser Gln Pro Asp Glu Asn Glu Ser Gln Thr Asp Val Ser Phe
    210                 215                 220

Arg His Ile Thr Glu Ile Thr Ile Leu Thr Val Gln Leu Ile Val Glu
225                 230                 235                 240

Phe Ala Lys Gly Leu Pro Ala Phe Thr Lys Ile Pro Gln Glu Asp Gln
                245                 250                 255

Ile Thr Leu Leu Lys Ala Cys Ser Ser Glu Val Met Met Leu Arg Met
            260                 265                 270

Ala Arg Arg Tyr Asp His Ser Ser Asp Ser Ile Phe Phe Ala Asn Asn
        275                 280                 285

Arg Ser Tyr Thr Arg Asp Ser Tyr Lys Met Ala Gly Met Ala Asp Asn
    290                 295                 300

Ile Glu Asp Leu Leu His Phe Cys Arg Gln Met Phe Ser Met Lys Val
305                 310                 315                 320

Asp Asn Val Glu Tyr Ala Leu Leu Thr Ala Ile Val Ile Phe Ser Asp
                325                 330                 335

Arg Pro Gly Leu Glu Lys Ala Gln Leu Val Glu Ala Ile Gln Ser Tyr
            340                 345                 350

Tyr Ile Asp Thr Leu Arg Ile Tyr Ile Leu Asn Arg His Cys Gly Asp
        355                 360                 365

Ser Met Ser Leu Val Phe Tyr Ala Lys Leu Leu Ser Ile Leu Thr Glu
    370                 375                 380

Leu Arg Thr Leu Gly Asn Gln Asn Ala Glu Met Cys Phe Ser Leu Lys
385                 390                 395                 400

Leu Lys Asn Arg Lys Leu Pro Lys Phe Leu Glu Glu Ile Trp Asp Val
                405                 410                 415

His Ala Ile Pro Pro Lys Leu Ala Pro Pro Thr Asp Val Ser Leu Gly
            420                 425                 430

Asp Glu Leu His Leu Asp Gly Glu Asp Val Ala Met Ala His Ala Asp
        435                 440                 445

Ala Leu Asp Asp Phe Asp Leu Asp Met Leu Gly Asp Gly Asp Ser Pro
    450                 455                 460

Gly Pro Gly Phe Thr Pro His Asp Ser Ala Pro Tyr Gly Ala Leu Asp
465                 470                 475                 480

Met Ala Asp Phe Glu Phe Glu Gln Met Phe Thr Asp Ala Leu Gly Ile
                485                 490                 495

Asp Glu Tyr Gly Gly
            500

<210> SEQ ID NO 65
<211> LENGTH: 1509
<212> TYPE: DNA
<213> ORGANISM: Synthetic construct
<220> FEATURE:
<221> NAME/KEY: CDS
<222> LOCATION: (1)..(1509)
<223> OTHER INFORMATION: Ecdysone Receptor chimera MBV

<400> SEQUENCE: 65 atg ggt cga gaa gaa tta tca ccg gcc tca agt ata aat gga tgt agt      48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag      96
Thr Asp Gly Glu Pro Arg Arg Gln Lys Lys Gly Pro Ala Pro Arg Gln
```

-continued

```
                     20                  25                  30
cag gag gaa ctg tgc ctt gtt tgc ggc gac agg gct tcg gga tat cac      144
Gln Glu Glu Leu Cys Leu Val Cys Gly Asp Arg Ala Ser Gly Tyr His
         35                  40                  45 tat aac gcg ctt acg tgc gaa gga tgt aaa ggg ttc ttc agg cgg agt      192
Tyr Asn Ala Leu Thr Cys Glu Gly Cys Lys Gly Phe Phe Arg Arg Ser
 50                  55                  60 gtg acc aag aat gcg gta tat att tgt aaa ttt gga cac gcc tgc gag      240
Val Thr Lys Asn Ala Val Tyr Ile Cys Lys Phe Gly His Ala Cys Glu
65                  70                  75                  80 atg gac atg tac atg agg aga aaa tgc caa gag tgt cgg ttg aag aaa      288
Met Asp Met Tyr Met Arg Arg Lys Cys Gln Glu Cys Arg Leu Lys Lys
                 85                  90                  95 tgc ctc gcg gtg ggc atg agg ccc gag tgc gtc gtc cca gag tcc acg      336
Cys Leu Ala Val Gly Met Arg Pro Glu Cys Val Val Pro Glu Ser Thr
             100                 105                 110 tgc aag aac aaa aga aga gaa aag gaa gca cag aga gaa aaa gac aaa      384
Cys Lys Asn Lys Arg Arg Glu Lys Glu Ala Gln Arg Glu Lys Asp Lys
         115                 120                 125 ctg cca gtc agt acg acg aca gtg gac gat cat atg cct gcc ata atg      432
Leu Pro Val Ser Thr Thr Thr Val Asp Asp His Met Pro Ala Ile Met
    130                 135                 140 caa tgt gac cct ccg ccc cca gag gcg gca agg att cac gaa gtg gtc      480
Gln Cys Asp Pro Pro Pro Pro Glu Ala Ala Arg Ile His Glu Val Val
145                 150                 155                 160 ccg agg ttc cta acg gag aag cta atg gag cag aac aga ctg aag aat      528
Pro Arg Phe Leu Thr Glu Lys Leu Met Glu Gln Asn Arg Leu Lys Asn
                 165                 170                 175 gtg acg ccg ctg tcg gcg aac cag aag tcc ctg atc gcg agg ctc gtg      576
Val Thr Pro Leu Ser Ala Asn Gln Lys Ser Leu Ile Ala Arg Leu Val
             180                 185                 190 tgg tac cag gaa ggc tat gaa caa cct tca gag gaa gac ctc aag agg      624
Trp Tyr Gln Glu Gly Tyr Glu Gln Pro Ser Glu Glu Asp Leu Lys Arg
         195                 200                 205 gtg acg cag acc tgg cag tcg gac gag gat gaa gag gag tca gat atg      672
Val Thr Gln Thr Trp Gln Ser Asp Glu Asp Glu Glu Glu Ser Asp Met
    210                 215                 220 ccg ttc cgc cag atc acc gag atg acg atc ctg aca gtt caa ctc atc      720
Pro Phe Arg Gln Ile Thr Glu Met Thr Ile Leu Thr Val Gln Leu Ile
225                 230                 235                 240 gta gaa ttc gca aaa ggc ctg cca ggc ttc gcc aag atc tcg cag tcg      768
Val Glu Phe Ala Lys Gly Leu Pro Gly Phe Ala Lys Ile Ser Gln Ser
                 245                 250                 255 gat caa atc acg tta cta aag gcg tgt tca agt gag gtg atg atg ctc      816
Asp Gln Ile Thr Leu Leu Lys Ala Cys Ser Ser Glu Val Met Met Leu
             260                 265                 270 cga gtg gcc cgg cgg tac gac gcg gcc acc gac agc gta ctg ttc gcc      864
Arg Val Ala Arg Arg Tyr Asp Ala Ala Thr Asp Ser Val Leu Phe Ala
         275                 280                 285 aac aac cag gcg tac tcc cgc gac aac tac cgc aag gca ggc atg tcc      912
Asn Asn Gln Ala Tyr Ser Arg Asp Asn Tyr Arg Lys Ala Gly Met Ser
    290                 295                 300 tac gtc atc gag gat ctc ttg cac ttc tgt cgg tgc atg tac tcc atg      960
Tyr Val Ile Glu Asp Leu Leu His Phe Cys Arg Cys Met Tyr Ser Met
305                 310                 315                 320 atg atg gat aac gtg cac tac gcg ctg ctt acg gcc att gtc att ttc     1008
Met Met Asp Asn Val His Tyr Ala Leu Leu Thr Ala Ile Val Ile Phe
                 325                 330                 335 tca gac cgg cct ggg ctc gag caa ccc tta ttg gtg gaa gaa atc cag     1056
```

-continued

```
Ser Asp Arg Pro Gly Leu Glu Gln Pro Leu Val Glu Glu Ile Gln
            340                 345                 350
cgg tat tac ctg aac acg ctg cgg gtg tac atc ttg aac caa aac agt      1104
Arg Tyr Tyr Leu Asn Thr Leu Arg Val Tyr Ile Leu Asn Gln Asn Ser
            355                 360                 365
gcg tcg ccg cgc tgc ccc gta gtc ttc gcc aag atc ctg ggg ata ttg      1152
Ala Ser Pro Arg Cys Pro Val Val Phe Ala Lys Ile Leu Gly Ile Leu
    370                 375                 380
acg gag ctg cgg acc ctc ggc atg cag aac tcc aac atg tgc atc tcg      1200
Thr Glu Leu Arg Thr Leu Gly Met Gln Asn Ser Asn Met Cys Ile Ser
385                 390                 395                 400
ttg aag ctg aag aat agg aag ctg ccg ccg ttc ctc gag gag atc tgg      1248
Leu Lys Leu Lys Asn Arg Lys Leu Pro Pro Phe Leu Glu Glu Ile Trp
                405                 410                 415
gac gtg gaa tcc cgc ggg aag ctt gcc ccc ccg acc gat gtc agc ctg      1296
Asp Val Glu Ser Arg Gly Lys Leu Ala Pro Pro Thr Asp Val Ser Leu
            420                 425                 430
ggg gac gag ctc cac tta gac ggc gag gac gtg gcg atg gcg cat gcc      1344
Gly Asp Glu Leu His Leu Asp Gly Glu Asp Val Ala Met Ala His Ala
        435                 440                 445
gac gcg cta gac gat ttc gat ctg gac atg ttg ggg gac ggg gat tcc      1392
Asp Ala Leu Asp Asp Phe Asp Leu Asp Met Leu Gly Asp Gly Asp Ser
    450                 455                 460
ccg ggt ccg gga ttt acc ccc cac gac tcc gcc ccc tac ggc gct ctg      1440
Pro Gly Pro Gly Phe Thr Pro His Asp Ser Ala Pro Tyr Gly Ala Leu
465                 470                 475                 480
gat atg gcc gac ttc gag ttt gag cag atg ttt acc gat gcc ctt gga      1488
Asp Met Ala Asp Phe Glu Phe Glu Gln Met Phe Thr Asp Ala Leu Gly
                485                 490                 495
att gac gag tac ggt ggg tag                                          1509
Ile Asp Glu Tyr Gly Gly
            500

<210> SEQ ID NO 66
<211> LENGTH: 502
<212> TYPE: PRT
<213> ORGANISM: Synthetic construct

<400> SEQUENCE: 66

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Ser Thr
            100                 105                 110

Cys Lys Asn Lys Arg Arg Glu Lys Glu Ala Gln Arg Glu Lys Asp Lys
        115                 120                 125

Leu Pro Val Ser Thr Thr Thr Val Asp Asp His Met Pro Ala Ile Met
    130                 135                 140

Gln Cys Asp Pro Pro Pro Glu Ala Ala Arg Ile His Glu Val Val
```

```
            145                 150                 155                 160
Pro Arg Phe Leu Thr Glu Lys Leu Met Glu Gln Asn Arg Leu Lys Asn
                165                 170                 175

Val Thr Pro Leu Ser Ala Asn Gln Lys Ser Leu Ile Ala Arg Leu Val
            180                 185                 190

Trp Tyr Gln Glu Gly Tyr Gln Pro Ser Glu Glu Asp Leu Lys Arg
            195                 200                 205

Val Thr Gln Thr Trp Gln Ser Asp Glu Asp Glu Glu Ser Asp Met
            210                 215                 220

Pro Phe Arg Gln Ile Thr Glu Met Thr Ile Leu Thr Val Gln Leu Ile
225                 230                 235                 240

Val Glu Phe Ala Lys Gly Leu Pro Gly Phe Ala Lys Ile Ser Gln Ser
                245                 250                 255

Asp Gln Ile Thr Leu Leu Lys Ala Cys Ser Ser Glu Val Met Met Leu
                260                 265                 270

Arg Val Ala Arg Arg Tyr Asp Ala Ala Thr Asp Ser Val Leu Phe Ala
                275                 280                 285

Asn Asn Gln Ala Tyr Ser Arg Asp Asn Tyr Arg Lys Ala Gly Met Ser
                290                 295                 300

Tyr Val Ile Glu Asp Leu Leu His Phe Cys Arg Cys Met Tyr Ser Met
305                 310                 315                 320

Met Met Asp Asn Val His Tyr Ala Leu Leu Thr Ala Ile Val Ile Phe
                325                 330                 335

Ser Asp Arg Pro Gly Leu Glu Gln Pro Leu Leu Val Glu Glu Ile Gln
                340                 345                 350

Arg Tyr Tyr Leu Asn Thr Leu Arg Val Tyr Ile Leu Asn Gln Asn Ser
                355                 360                 365

Ala Ser Pro Arg Cys Pro Val Val Phe Ala Lys Ile Leu Gly Ile Leu
                370                 375                 380

Thr Glu Leu Arg Thr Leu Gly Met Gln Asn Ser Asn Met Cys Ile Ser
385                 390                 395                 400

Leu Lys Leu Lys Asn Arg Lys Leu Pro Pro Phe Leu Glu Glu Ile Trp
                405                 410                 415

Asp Val Glu Ser Arg Gly Lys Leu Ala Pro Pro Thr Asp Val Ser Leu
                420                 425                 430

Gly Asp Glu Leu His Leu Asp Gly Glu Asp Val Ala Met Ala His Ala
                435                 440                 445

Asp Ala Leu Asp Asp Phe Asp Leu Asp Met Leu Gly Asp Gly Asp Ser
                450                 455                 460

Pro Gly Pro Gly Phe Thr Pro His Asp Ser Ala Pro Tyr Gly Ala Leu
465                 470                 475                 480

Asp Met Ala Asp Phe Glu Phe Glu Gln Met Phe Thr Asp Ala Leu Gly
                485                 490                 495

Ile Asp Glu Tyr Gly Gly
                500

<210> SEQ ID NO 67
<211> LENGTH: 1500
<212> TYPE: DNA
<213> ORGANISM: Synthetic construct
<220> FEATURE:
<221> NAME/KEY: CDS
<222> LOCATION: (1)..(1500)
<223> OTHER INFORMATION: Ecdysone Receptor chimera MEV

<400> SEQUENCE: 67
```

-continued

```
atg ggt cga gaa gaa tta tca ccg gcc tca agt ata aat gga tgt agt      48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag      96
Thr Asp Gly Glu Pro Arg Arg Gln Lys Lys Gly Pro Ala Pro Arg Gln
            20                  25                  30 cag gag gaa ctg tgc ctt gtt tgc ggc gac agg gct tcg gga tat cac     144
Gln Glu Glu Leu Cys Leu Val Cys Gly Asp Arg Ala Ser Gly Tyr His
        35                  40                  45 tat aac gcg ctt acg tgc gaa gga tgt aaa ggg ttc ttc agg cgg agt     192
Tyr Asn Ala Leu Thr Cys Glu Gly Cys Lys Gly Phe Phe Arg Arg Ser
50                  55                  60 gtg acc aag aat gcg gta tat att tgt aaa ttt gga cac gcc tgc gag     240
Val Thr Lys Asn Ala Val Tyr Ile Cys Lys Phe Gly His Ala Cys Glu
65                  70                  75                  80 atg gac atg tac atg agg aga aaa tgc caa gag tgt cgg ttg aag aaa     288
Met Asp Met Tyr Met Arg Arg Lys Cys Gln Glu Cys Arg Leu Lys Lys
                85                  90                  95 tgc ctc gcg gtg ggc atg agg ccc gag tgc gtc gtc cca gag tcc acg     336
Cys Leu Ala Val Gly Met Arg Pro Glu Cys Val Val Pro Glu Ser Thr
            100                 105                 110 tgc aag aac aaa aga aga gaa aag gaa gca cag aga gaa aaa gac aaa     384
Cys Lys Asn Lys Arg Arg Glu Lys Glu Ala Gln Arg Glu Lys Asp Lys
        115                 120                 125 ctg cca gtc agt acg acg aca gtg gac gat cat atg cct gcc ata atg     432
Leu Pro Val Ser Thr Thr Thr Val Asp Asp His Met Pro Ala Ile Met
    130                 135                 140 caa tgt gac cct ccg ccc cca gag gcg gca agg att cac gaa gtg gtc     480
Gln Cys Asp Pro Pro Pro Pro Glu Ala Ala Arg Ile His Glu Val Val
145                 150                 155                 160 ccg agg ttc cta acg gag aag cta atg gag cag aac aga ctg aag aat     528
Pro Arg Phe Leu Thr Glu Lys Leu Met Glu Gln Asn Arg Leu Lys Asn
                165                 170                 175 gtg acg ccg ctg tcg gcg aac cag aag tcc ctg atc gcg agg ctc gtg     576
Val Thr Pro Leu Ser Ala Asn Gln Lys Ser Leu Ile Ala Arg Leu Val
            180                 185                 190 tgg tac cag gac gga tac gag cag cct tcg gaa gag gat ctc aaa agg     624
Trp Tyr Gln Asp Gly Tyr Glu Gln Pro Ser Glu Glu Asp Leu Lys Arg
        195                 200                 205 gtg acg cag act tgg caa tca gca gat gaa gaa gac gaa gac tca gac     672
Val Thr Gln Thr Trp Gln Ser Ala Asp Glu Glu Asp Glu Asp Ser Asp
    210                 215                 220 atg cca ttc cgc cag atc aca gaa atg acc atc ctc aca gta cag cta     720
Met Pro Phe Arg Gln Ile Thr Glu Met Thr Ile Leu Thr Val Gln Leu
225                 230                 235                 240 ata gtc gag ttt gcc aaa ggc cta cct ggt ttt tca aag atc tca caa     768
Ile Val Glu Phe Ala Lys Gly Leu Pro Gly Phe Ser Lys Ile Ser Gln
                245                 250                 255 cct gac cag atc aca tta tta aag gca tgc tca agc gaa gtg atg atg     816
Pro Asp Gln Ile Thr Leu Leu Lys Ala Cys Ser Ser Glu Val Met Met
            260                 265                 270 ctg cga gta gcg agg cgg tac gac gcg gtg tcg gat agc gtt ctg ttc     864
Leu Arg Val Ala Arg Arg Tyr Asp Ala Val Ser Asp Ser Val Leu Phe
        275                 280                 285 gcc aac aac cag gcg tac act cgc gac aac tac cgc aag gcg ggc atg     912
Ala Asn Asn Gln Ala Tyr Thr Arg Asp Asn Tyr Arg Lys Ala Gly Met
    290                 295                 300 gcc tac gtc atc gaa gac ctg ctg cac ttc tgc cgc tgc atg tac tcg     960
Ala Tyr Val Ile Glu Asp Leu Leu His Phe Cys Arg Cys Met Tyr Ser
```

| | | | |
|---|---|---|---|
| atg tcg atg gac aac gtg cat tac gcg ctc ctc act gcc atc gtt ata | | | 1008 |
| Met Ser Met Asp Asn Val His Tyr Ala Leu Leu Thr Ala Ile Val Ile | | | |
| 325 | 330 | 335 | |
| ttc tcg gat cgg ccg ggc cta gag cag cca cag cta gta gaa gag atc | | | 1056 |
| Phe Ser Asp Arg Pro Gly Leu Glu Gln Pro Gln Leu Val Glu Glu Ile | | | |
| 340 | 345 | 350 | |
| cag cgg tat tac ctg aac acg ctg cgg gtg tac atc atg aac cag cac | | | 1104 |
| Gln Arg Tyr Tyr Leu Asn Thr Leu Arg Val Tyr Ile Met Asn Gln His | | | |
| 355 | 360 | 365 | |
| agc gcg tcg ccg cgt tgc gcc gtc atc tac gcg aag att ctg tcg gtg | | | 1152 |
| Ser Ala Ser Pro Arg Cys Ala Val Ile Tyr Ala Lys Ile Leu Ser Val | | | |
| 370 | 375 | 380 | |
| ctt acc gag ttg cgg acg ctg ggc atg cag aat tcg aac atg tgc atc | | | 1200 |
| Leu Thr Glu Leu Arg Thr Leu Gly Met Gln Asn Ser Asn Met Cys Ile | | | |
| 385 | 390 | 395 | 400 |
| tcg ctg aag ctc aag aac agg aag ctg ccg ccg ttc ctg gag gag atc | | | 1248 |
| Ser Leu Lys Leu Lys Asn Arg Lys Leu Pro Pro Phe Leu Glu Glu Ile | | | |
| | 405 | 410 | 415 |
| tgg gac gtg aag ctt gcc ccc ccg acc gat gtc agc ctg ggg gac gag | | | 1296 |
| Trp Asp Val Lys Leu Ala Pro Pro Thr Asp Val Ser Leu Gly Asp Glu | | | |
| 420 | 425 | 430 | |
| ctc cac tta gac ggc gag gac gtg gcg atg gcg cat gcc gac gcg cta | | | 1344 |
| Leu His Leu Asp Gly Glu Asp Val Ala Met Ala His Ala Asp Ala Leu | | | |
| 435 | 440 | 445 | |
| gac gat ttc gat ctg gac atg ttg ggg gac ggg gat tcc ccg ggt ccg | | | 1392 |
| Asp Asp Phe Asp Leu Asp Met Leu Gly Asp Gly Asp Ser Pro Gly Pro | | | |
| 450 | 455 | 460 | |
| gga ttt acc ccc cac gac tcc gcc ccc tac ggc gct ctg gat atg gcc | | | 1440 |
| Gly Phe Thr Pro His Asp Ser Ala Pro Tyr Gly Ala Leu Asp Met Ala | | | |
| 465 | 470 | 475 | 480 |
| gac ttc gag ttt gag cag atg ttt acc gat gcc ctt gga att gac gag | | | 1488 |
| Asp Phe Glu Phe Glu Gln Met Phe Thr Asp Ala Leu Gly Ile Asp Glu | | | |
| | 485 | 490 | 495 |
| tac ggt ggg tag | | | 1500 |
| Tyr Gly Gly | | | |

<210> SEQ ID NO 68
<211> LENGTH: 499
<212> TYPE: PRT
<213> ORGANISM: Synthetic construct

<400> SEQUENCE: 68

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Ser Thr
            100                 105                 110

Cys Lys Asn Lys Arg Arg Glu Lys Glu Ala Gln Arg Glu Lys Asp Lys

```
                115                 120                 125
Leu Pro Val Ser Thr Thr Val Asp Asp His Met Pro Ala Ile Met
130                 135                 140
Gln Cys Asp Pro Pro Pro Glu Ala Ala Arg Ile His Glu Val Val
145                 150                 155                 160
Pro Arg Phe Leu Thr Glu Lys Leu Met Glu Gln Asn Arg Leu Lys Asn
                165                 170                 175
Val Thr Pro Leu Ser Ala Asn Gln Lys Ser Leu Ile Ala Arg Leu Val
            180                 185                 190
Trp Tyr Gln Asp Gly Tyr Glu Gln Pro Ser Glu Asp Leu Lys Arg
        195                 200                 205
Val Thr Gln Thr Trp Gln Ser Ala Asp Glu Glu Asp Glu Ser Asp
210                 215                 220
Met Pro Phe Arg Gln Ile Thr Glu Met Thr Ile Leu Thr Val Gln Leu
225                 230                 235                 240
Ile Val Glu Phe Ala Lys Gly Leu Pro Gly Phe Ser Lys Ile Ser Gln
                245                 250                 255
Pro Asp Gln Ile Thr Leu Leu Lys Ala Cys Ser Ser Glu Val Met Met
                260                 265                 270
Leu Arg Val Ala Arg Arg Tyr Asp Ala Val Ser Asp Ser Val Leu Phe
            275                 280                 285
Ala Asn Asn Gln Ala Tyr Thr Arg Asp Asn Tyr Arg Lys Ala Gly Met
290                 295                 300
Ala Tyr Val Ile Glu Asp Leu Leu His Phe Cys Arg Cys Met Tyr Ser
305                 310                 315                 320
Met Ser Met Asp Asn Val His Tyr Ala Leu Leu Thr Ala Ile Val Ile
                325                 330                 335
Phe Ser Asp Arg Pro Gly Leu Glu Gln Pro Gln Leu Val Glu Glu Ile
                340                 345                 350
Gln Arg Tyr Tyr Leu Asn Thr Leu Arg Val Tyr Ile Met Asn Gln His
            355                 360                 365
Ser Ala Ser Pro Arg Cys Ala Val Ile Tyr Ala Lys Ile Leu Ser Val
370                 375                 380
Leu Thr Glu Leu Arg Thr Leu Gly Met Gln Asn Ser Asn Met Cys Ile
385                 390                 395                 400
Ser Leu Lys Leu Lys Asn Arg Lys Leu Pro Pro Phe Leu Glu Glu Ile
                405                 410                 415
Trp Asp Val Lys Leu Ala Pro Pro Thr Asp Val Ser Leu Gly Asp Glu
                420                 425                 430
Leu His Leu Asp Gly Glu Asp Val Ala Met Ala His Ala Asp Ala Leu
            435                 440                 445
Asp Asp Phe Asp Leu Asp Met Leu Gly Asp Gly Asp Ser Pro Gly Pro
450                 455                 460
Gly Phe Thr Pro His Asp Ser Ala Pro Tyr Gly Ala Leu Asp Met Ala
465                 470                 475                 480
Asp Phe Glu Phe Glu Gln Met Phe Thr Asp Ala Leu Gly Ile Asp Glu
                485                 490                 495
Tyr Gly Gly

<210> SEQ ID NO 69
<211> LENGTH: 1500
<212> TYPE: DNA
<213> ORGANISM: Synthetic construct
<220> FEATURE:
```

-continued

```
<221> NAME/KEY: CDS
<222> LOCATION: (1)..(1500)
<223> OTHER INFORMATION: Ecdysone Receptor chimera MFV

<400> SEQUENCE: 69 atg ggt cga gaa gaa tta tca ccg gcc tca agt ata aat gga tgt agt        48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag        96
Thr Asp Gly Glu Pro Arg Arg Gln Lys Lys Gly Pro Ala Pro Arg Gln
            20                  25                  30 cag gag gaa ctg tgc ctt gtt tgc ggc gac agg gct tcg gga tat cac       144
Gln Glu Glu Leu Cys Leu Val Cys Gly Asp Arg Ala Ser Gly Tyr His
        35                  40                  45 tat aac gcg ctt acg tgc gaa gga tgt aaa ggg ttc ttc agg cgg agt       192
Tyr Asn Ala Leu Thr Cys Glu Gly Cys Lys Gly Phe Phe Arg Arg Ser
    50                  55                  60 gtg acc aag aat gcg gta tat att tgt aaa ttt gga cac gcc tgc gag       240
Val Thr Lys Asn Ala Val Tyr Ile Cys Lys Phe Gly His Ala Cys Glu
65                  70                  75                  80 atg gac atg tac atg agg aga aaa tgc caa gag tgt cgg ttg aag aaa       288
Met Asp Met Tyr Met Arg Arg Lys Cys Gln Glu Cys Arg Leu Lys Lys
                85                  90                  95 tgc ctc gcg gtg ggc atg agg ccc gag tgc gtc gtc cca gag tcc acg       336
Cys Leu Ala Val Gly Met Arg Pro Glu Cys Val Val Pro Glu Ser Thr
            100                 105                 110 tgc aag aac aaa aga aga gaa aag gaa gca cag aga gaa aaa gac aaa       384
Cys Lys Asn Lys Arg Arg Glu Lys Glu Ala Gln Arg Glu Lys Asp Lys
        115                 120                 125 ctg cca gtc agt acg acg aca gtg gac gat cat atg cct gcc ata atg       432
Leu Pro Val Ser Thr Thr Thr Val Asp Asp His Met Pro Ala Ile Met
    130                 135                 140 caa tgt gac cct ccg ccc cca gag gcg gca agg att cac gaa gtg gtc       480
Gln Cys Asp Pro Pro Pro Pro Glu Ala Ala Arg Ile His Glu Val Val
145                 150                 155                 160 ccg agg ttc cta acg gag aag cta atg gag cag aac aga ctg aag aat       528
Pro Arg Phe Leu Thr Glu Lys Leu Met Glu Gln Asn Arg Leu Lys Asn
                165                 170                 175 gtg acg ccg ctg tcg gcg aac cag aag tcc ctg atc gcg agg ctc gtg       576
Val Thr Pro Leu Ser Ala Asn Gln Lys Ser Leu Ile Ala Arg Leu Val
            180                 185                 190 tgg tac cag gag ggg tac gag cag ccg tcg gag gaa gat ctc aag aga       624
Trp Tyr Gln Glu Gly Tyr Glu Gln Pro Ser Glu Glu Asp Leu Lys Arg
        195                 200                 205 gtt aca cag aca tgg cag tta gaa gaa gaa gaa gag gag gaa act gac       672
Val Thr Gln Thr Trp Gln Leu Glu Glu Glu Glu Glu Glu Glu Thr Asp
    210                 215                 220 atg ccc ttc cgt cag atc aca gag atg acg atc tta aca gtg cag ctt       720
Met Pro Phe Arg Gln Ile Thr Glu Met Thr Ile Leu Thr Val Gln Leu
225                 230                 235                 240 att gta gaa ttc gca aag gga cta ccg gga ttc tcc aag ata tct cag       768
Ile Val Glu Phe Ala Lys Gly Leu Pro Gly Phe Ser Lys Ile Ser Gln
                245                 250                 255 tcc gat caa att aca tta tta aag gcg tca tca agc gaa gtg atg atg       816
Ser Asp Gln Ile Thr Leu Leu Lys Ala Ser Ser Ser Glu Val Met Met
            260                 265                 270 ctg cga gtg gcg cga cgg tac gac gcg gcg acg gac agc gtg ctg ttc       864
Leu Arg Val Ala Arg Arg Tyr Asp Ala Ala Thr Asp Ser Val Leu Phe
        275                 280                 285 gcg aac aac cag gcg tac acg cgc gac aac tac cgc aag gcg ggc atg       912
Ala Asn Asn Gln Ala Tyr Thr Arg Asp Asn Tyr Arg Lys Ala Gly Met
```

```
Ala Asn Asn Gln Ala Tyr Thr Arg Asp Asn Tyr Arg Lys Ala Gly Met
    290                 295                 300 tcc tac gtc atc ggg gac ctg ctg cac ttc tgt cgg tgt atg tac tcc        960
Ser Tyr Val Ile Gly Asp Leu Leu His Phe Cys Arg Cys Met Tyr Ser
305                 310                 315                 320 atg agc atg gac aat gtg cac tac gcg ctg ctc acc gcc atc gtt ata       1008
Met Ser Met Asp Asn Val His Tyr Ala Leu Leu Thr Ala Ile Val Ile
                325                 330                 335 ttc tca gac cgg cca ggc ctc gag caa ccc ctt tta gtg gag gaa atc       1056
Phe Ser Asp Arg Pro Gly Leu Glu Gln Pro Leu Leu Val Glu Glu Ile
            340                 345                 350 cag aga tac tac ttg aag acg ctg cgg gtt tac att tta aat cag tac       1104
Gln Arg Tyr Tyr Leu Lys Thr Leu Arg Val Tyr Ile Leu Asn Gln Tyr
        355                 360                 365 agc gcg tcg cct cgc tgc gcc gtg ctg ttc ggc aag atc ctc ggc gtg       1152
Ser Ala Ser Pro Arg Cys Ala Val Leu Phe Gly Lys Ile Leu Gly Val
    370                 375                 380 ctg acg gaa ctg cgc acg ctc ggc acg cag aac tcc aac atg tgc atc       1200
Leu Thr Glu Leu Arg Thr Leu Gly Thr Gln Asn Ser Asn Met Cys Ile
385                 390                 395                 400 tcg ctg aag ctg aag aac agg aaa ctt ccg cca ttc ctc gag gag atc       1248
Ser Leu Lys Leu Lys Asn Arg Lys Leu Pro Pro Phe Leu Glu Glu Ile
                405                 410                 415 tgg gac gtg aag ctt gcc ccc ccg acc gat gtc agc ctg ggg gac gag       1296
Trp Asp Val Lys Leu Ala Pro Pro Thr Asp Val Ser Leu Gly Asp Glu
            420                 425                 430 ctc cac tta gac ggc gag gac gtg gcg atg gcg cat gcc gac gcg cta       1344
Leu His Leu Asp Gly Glu Asp Val Ala Met Ala His Ala Asp Ala Leu
        435                 440                 445 gac gat ttc gat ctg gac atg ttg ggg gac ggg gat tcc ccg ggt ccg       1392
Asp Asp Phe Asp Leu Asp Met Leu Gly Asp Gly Asp Ser Pro Gly Pro
    450                 455                 460 gga ttt acc ccc cac gac tcc gcc ccc tac ggc gct ctg gat atg gcc       1440
Gly Phe Thr Pro His Asp Ser Ala Pro Tyr Gly Ala Leu Asp Met Ala
465                 470                 475                 480 gac ttc gag ttt gag cag atg ttt acc gat gcc ctt gga att gac gag       1488
Asp Phe Glu Phe Glu Gln Met Phe Thr Asp Ala Leu Gly Ile Asp Glu
                485                 490                 495 tac ggt ggg tag                                                       1500
Tyr Gly Gly <210> SEQ ID NO 70
<211> LENGTH: 499
<212> TYPE: PRT
<213> ORGANISM: Synthetic construct

<400> SEQUENCE: 70

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
                20                  25                  30

Gln Glu Glu Leu Cys Leu Val Cys Gly Asp Arg Ala Ser Gly Tyr His
            35                  40                  45

Tyr Asn Ala Leu Thr Cys Glu Gly Cys Lys Gly Phe Phe Arg Arg Ser
        50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95
```

```
Cys Leu Ala Val Gly Met Arg Pro Glu Cys Val Val Pro Glu Ser Thr
            100                 105                 110
Cys Lys Asn Lys Arg Arg Glu Lys Glu Ala Gln Arg Glu Lys Asp Lys
            115                 120                 125
Leu Pro Val Ser Thr Thr Val Asp Asp His Met Pro Ala Ile Met
            130                 135                 140
Gln Cys Asp Pro Pro Pro Glu Ala Ala Arg Ile His Glu Val Val
145                 150                 155                 160
Pro Arg Phe Leu Thr Glu Lys Leu Met Glu Gln Asn Arg Leu Lys Asn
                    165                 170                 175
Val Thr Pro Leu Ser Ala Asn Gln Lys Ser Leu Ile Ala Arg Leu Val
                    180                 185                 190
Trp Tyr Gln Glu Gly Tyr Glu Gln Pro Ser Glu Glu Asp Leu Lys Arg
                    195                 200                 205
Val Thr Gln Thr Trp Gln Leu Glu Glu Glu Glu Glu Glu Thr Asp
                    210                 215                 220
Met Pro Phe Arg Gln Ile Thr Glu Met Thr Ile Leu Thr Val Gln Leu
225                 230                 235                 240
Ile Val Glu Phe Ala Lys Gly Leu Pro Gly Phe Ser Lys Ile Ser Gln
                    245                 250                 255
Ser Asp Gln Ile Thr Leu Leu Lys Ala Ser Ser Ser Glu Val Met Met
                    260                 265                 270
Leu Arg Val Ala Arg Arg Tyr Asp Ala Ala Thr Asp Ser Val Leu Phe
                    275                 280                 285
Ala Asn Asn Gln Ala Tyr Thr Arg Asp Asn Tyr Arg Lys Ala Gly Met
            290                 295                 300
Ser Tyr Val Ile Gly Asp Leu Leu His Phe Cys Arg Cys Met Tyr Ser
305                 310                 315                 320
Met Ser Met Asp Asn Val His Tyr Ala Leu Leu Thr Ala Ile Val Ile
                    325                 330                 335
Phe Ser Asp Arg Pro Gly Leu Glu Gln Pro Leu Leu Val Glu Glu Ile
                    340                 345                 350
Gln Arg Tyr Tyr Leu Lys Thr Leu Arg Val Tyr Ile Leu Asn Gln Tyr
                    355                 360                 365
Ser Ala Ser Pro Arg Cys Ala Val Leu Phe Gly Lys Ile Leu Gly Val
            370                 375                 380
Leu Thr Glu Leu Arg Thr Leu Gly Thr Gln Asn Ser Asn Met Cys Ile
385                 390                 395                 400
Ser Leu Lys Leu Lys Asn Arg Lys Leu Pro Pro Phe Leu Glu Glu Ile
                    405                 410                 415
Trp Asp Val Lys Leu Ala Pro Pro Thr Asp Val Ser Leu Gly Asp Glu
                    420                 425                 430
Leu His Leu Asp Gly Glu Asp Val Ala Met Ala His Ala Asp Ala Leu
                    435                 440                 445
Asp Asp Phe Asp Leu Asp Met Leu Gly Asp Gly Asp Ser Pro Gly Pro
            450                 455                 460
Gly Phe Thr Pro His Asp Ser Ala Pro Tyr Gly Ala Leu Asp Met Ala
465                 470                 475                 480
Asp Phe Glu Phe Glu Gln Met Phe Thr Asp Ala Leu Gly Ile Asp Glu
                    485                 490                 495
Tyr Gly Gly
```

-continued

```
<210> SEQ ID NO 71
<211> LENGTH: 1551
<212> TYPE: DNA
<213> ORGANISM: Synthetic construct
<220> FEATURE:
<221> NAME/KEY: CDS
<222> LOCATION: (1)..(1551)
<223> OTHER INFORMATION: Ecdysone Receptor chimera DMV

<400> SEQUENCE: 71 atg ggt cgc gat gat ctc tcg cct tcg agc agc ttg aac gga tac tcg        48
Met Gly Arg Asp Asp Leu Ser Pro Ser Ser Ser Leu Asn Gly Tyr Ser
1               5                   10                  15 gcg aac gaa agc tgc gat gcg aag aag agc aag aag gga cct gcg cca        96
Ala Asn Glu Ser Cys Asp Ala Lys Lys Ser Lys Lys Gly Pro Ala Pro
                20                  25                  30 cgg gtg caa gag gag ctg tgc ctg gtt tgc ggc gac agg gcc tcc ggc       144
Arg Val Gln Glu Glu Leu Cys Leu Val Cys Gly Asp Arg Ala Ser Gly
            35                  40                  45 tac cac tac aac gcc ctc acc tgt gag ggc tgc aag ggg ttc ttt cga       192
Tyr His Tyr Asn Ala Leu Thr Cys Glu Gly Cys Lys Gly Phe Phe Arg
        50                  55                  60 cgc agc gtt acg aag agc gcc gtc tac tgc tgc aag ttc ggg cgc gcc       240
Arg Ser Val Thr Lys Ser Ala Val Tyr Cys Cys Lys Phe Gly Arg Ala
65                  70                  75                  80 tgc gaa atg gac atg tac atg agg cga aag tgt cag gag tgc cgc ctg       288
Cys Glu Met Asp Met Tyr Met Arg Arg Lys Cys Gln Glu Cys Arg Leu
                85                  90                  95 aaa aag tgc ctg gcc gtg ggt atg cgg ccg gaa tgc gtc gtc ccg gag       336
Lys Lys Cys Leu Ala Val Gly Met Arg Pro Glu Cys Val Val Pro Glu
                100                 105                 110 aac caa tgt gcg atg aag cgg cgc gaa aag aag gcc cag aag gag aag       384
Asn Gln Cys Ala Met Lys Arg Arg Glu Lys Lys Ala Gln Lys Glu Lys
            115                 120                 125 gac aaa atg acc act tcg ccg agc tct cag cat ggc ggc aat ggc agc       432
Asp Lys Met Thr Thr Ser Pro Ser Ser Gln His Gly Gly Asn Gly Ser
        130                 135                 140 ttg gcc tct ggt ggc ggc caa gac ttt gtt aag aag gag att ctt gac       480
Leu Ala Ser Gly Gly Gly Gln Asp Phe Val Lys Lys Glu Ile Leu Asp
145                 150                 155                 160 ctt atg aca tgc gag ccg ccc cag cat gcc act att ccg cta cta cct       528
Leu Met Thr Cys Glu Pro Pro Gln His Ala Thr Ile Pro Leu Leu Pro
                165                 170                 175 gat gaa ata ttg gcc aag tgt caa gcg cgc aat ata cct tcc tta acg       576
Asp Glu Ile Leu Ala Lys Cys Gln Ala Arg Asn Ile Pro Ser Leu Thr
                180                 185                 190 tac aat cag ttg gcc gtt ata tac aag tta att tgg tac cag gag ggg       624
Tyr Asn Gln Leu Ala Val Ile Tyr Lys Leu Ile Trp Tyr Gln Glu Gly
            195                 200                 205 tac gag cag ccg tcg gag gaa gat ctc aag aga gtt aca cag aca tgg       672
Tyr Glu Gln Pro Ser Glu Glu Asp Leu Lys Arg Val Thr Gln Thr Trp
        210                 215                 220 cag tta gaa gaa gaa gaa gag gag gaa act gac atg ccc ttc cgt cag       720
Gln Leu Glu Glu Glu Glu Glu Glu Thr Asp Met Pro Phe Arg Gln
225                 230                 235                 240 atc aca gag atg acg atc tta aca gtg cag ctt att gta gaa ttc gca       768
Ile Thr Glu Met Thr Ile Leu Thr Val Gln Leu Ile Val Glu Phe Ala
                245                 250                 255 aag gga cta ccg gga ttc tcc aag ata tct cag tcc gat caa att aca       816
Lys Gly Leu Pro Gly Phe Ser Lys Ile Ser Gln Ser Asp Gln Ile Thr
                260                 265                 270
```

```
tta tta aag gcg tca tca agc gaa gtg atg atg ctg cga gtg gcg cga      864
Leu Leu Lys Ala Ser Ser Ser Glu Val Met Met Leu Arg Val Ala Arg
            275                 280                 285 cgg tac gac gcg gcg acg gac agc gtg ctg ttc gcg aac aac cag gcg      912
Arg Tyr Asp Ala Ala Thr Asp Ser Val Leu Phe Ala Asn Asn Gln Ala
        290                 295                 300 tac acg cgc gac aac tac cgc aag gcg ggc atg tcc tac gtc atc gag      960
Tyr Thr Arg Asp Asn Tyr Arg Lys Ala Gly Met Ser Tyr Val Ile Glu
305                 310                 315                 320 gac ctg ctg cac ttc tgt cgg tgt atg tac tcc atg agc atg gac aat     1008
Asp Leu Leu His Phe Cys Arg Cys Met Tyr Ser Met Ser Met Asp Asn
                325                 330                 335 gtg cac tac gcg ctg ctc acc gcc atc gtt ata ttc tca gac cgg cca     1056
Val His Tyr Ala Leu Leu Thr Ala Ile Val Ile Phe Ser Asp Arg Pro
            340                 345                 350 ggc ctc gag caa ccc ctt tta gtg gag gaa atc cag aga tac tac ttg     1104
Gly Leu Glu Gln Pro Leu Leu Val Glu Glu Ile Gln Arg Tyr Tyr Leu
        355                 360                 365 aag acg ctg cgg gtt tac att tta aat cag cac agc gcg tcg cct cgc     1152
Lys Thr Leu Arg Val Tyr Ile Leu Asn Gln His Ser Ala Ser Pro Arg
370                 375                 380 tgc gcc gtg ctg ttc ggc aag atc ctc ggc gtg ctg acg gaa ctg cgc     1200
Cys Ala Val Leu Phe Gly Lys Ile Leu Gly Val Leu Thr Glu Leu Arg
                385                 390                 395                 400 acg ctc ggc acg cag aac tcc aac atg tgc atc tcg ctg aag ctg aag     1248
Thr Leu Gly Thr Gln Asn Ser Asn Met Cys Ile Ser Leu Lys Leu Lys
            405                 410                 415 aac agg aaa ctt ccg cca ttc ctc gag gag atc tgg gac gtg gcc gaa     1296
Asn Arg Lys Leu Pro Pro Phe Leu Glu Glu Ile Trp Asp Val Ala Glu
        420                 425                 430 gtg tcg acg acg aag ctt gcc ccc ccg acc gat gtc agc ctg ggg gac     1344
Val Ser Thr Thr Lys Leu Ala Pro Pro Thr Asp Val Ser Leu Gly Asp
    435                 440                 445 gag ctc cac tta gac ggc gag gac gtg gcg atg gcg cat gcc gac gcg     1392
Glu Leu His Leu Asp Gly Glu Asp Val Ala Met Ala His Ala Asp Ala
450                 455                 460 cta gac gat ttc gat ctg gac atg ttg ggg gac ggg gat tcc ccg ggt     1440
Leu Asp Asp Phe Asp Leu Asp Met Leu Gly Asp Gly Asp Ser Pro Gly
465                 470                 475                 480 ccg gga ttt acc ccc cac gac tcc gcc ccc tac ggc gct ctg gat atg     1488
Pro Gly Phe Thr Pro His Asp Ser Ala Pro Tyr Gly Ala Leu Asp Met
            485                 490                 495 gcc gac ttc gag ttt gag cag atg ttt acc gat gcc ctt gga att gac     1536
Ala Asp Phe Glu Phe Glu Gln Met Phe Thr Asp Ala Leu Gly Ile Asp
        500                 505                 510 gag tac ggt ggg tag                                                  1551
Glu Tyr Gly Gly
        515
```

<210> SEQ ID NO 72
<211> LENGTH: 516
<212> TYPE: PRT
<213> ORGANISM: Synthetic construct

<400> SEQUENCE: 72

```
Met Gly Arg Asp Asp Leu Ser Pro Ser Ser Ser Leu Asn Gly Tyr Ser
1               5                   10                  15

Ala Asn Glu Ser Cys Asp Ala Lys Lys Ser Lys Lys Gly Pro Ala Pro
            20                  25                  30

Arg Val Gln Glu Glu Leu Cys Leu Val Cys Gly Asp Arg Ala Ser Gly
```

-continued

```
                35                  40                  45
Tyr His Tyr Asn Ala Leu Thr Cys Glu Gly Cys Lys Gly Phe Phe Arg
 50                  55                  60

Arg Ser Val Thr Lys Ser Ala Val Tyr Cys Cys Lys Phe Gly Arg Ala
 65                  70                  75                  80

Cys Glu Met Asp Met Tyr Met Arg Arg Lys Cys Gln Glu Cys Arg Leu
                 85                  90                  95

Lys Lys Cys Leu Ala Val Gly Met Arg Pro Glu Cys Val Val Pro Glu
                100                 105                 110

Asn Gln Cys Ala Met Lys Arg Arg Glu Lys Lys Ala Gln Lys Glu Lys
                115                 120                 125

Asp Lys Met Thr Thr Ser Pro Ser Ser Gln His Gly Gly Asn Gly Ser
130                 135                 140

Leu Ala Ser Gly Gly Gly Gln Asp Phe Val Lys Lys Glu Ile Leu Asp
145                 150                 155                 160

Leu Met Thr Cys Glu Pro Pro Gln His Ala Thr Ile Pro Leu Leu Pro
                165                 170                 175

Asp Glu Ile Leu Ala Lys Cys Gln Ala Arg Asn Ile Pro Ser Leu Thr
                180                 185                 190

Tyr Asn Gln Leu Ala Val Ile Tyr Lys Leu Ile Trp Tyr Gln Glu Gly
                195                 200                 205

Tyr Glu Gln Pro Ser Glu Glu Asp Leu Lys Arg Val Thr Gln Thr Trp
210                 215                 220

Gln Leu Glu Glu Glu Glu Glu Glu Thr Asp Met Pro Phe Arg Gln
225                 230                 235                 240

Ile Thr Glu Met Thr Ile Leu Thr Val Gln Leu Ile Val Glu Phe Ala
                245                 250                 255

Lys Gly Leu Pro Gly Phe Ser Lys Ile Ser Gln Ser Asp Gln Ile Thr
                260                 265                 270

Leu Leu Lys Ala Ser Ser Ser Glu Val Met Met Leu Arg Val Ala Arg
                275                 280                 285

Arg Tyr Asp Ala Ala Thr Asp Ser Val Leu Phe Ala Asn Asn Gln Ala
290                 295                 300

Tyr Thr Arg Asp Asn Tyr Arg Lys Ala Gly Met Ser Tyr Val Ile Glu
305                 310                 315                 320

Asp Leu Leu His Phe Cys Arg Cys Met Tyr Ser Met Ser Met Asp Asn
                325                 330                 335

Val His Tyr Ala Leu Leu Thr Ala Ile Val Ile Phe Ser Asp Arg Pro
                340                 345                 350

Gly Leu Glu Gln Pro Leu Leu Val Glu Glu Ile Gln Arg Tyr Tyr Leu
                355                 360                 365

Lys Thr Leu Arg Val Tyr Ile Leu Asn Gln His Ser Ala Ser Pro Arg
370                 375                 380

Cys Ala Val Leu Phe Gly Lys Ile Leu Gly Val Leu Thr Glu Leu Arg
385                 390                 395                 400

Thr Leu Gly Thr Gln Asn Ser Asn Met Cys Ile Ser Leu Lys Leu Lys
                405                 410                 415

Asn Arg Lys Leu Pro Pro Phe Leu Glu Glu Ile Trp Asp Val Ala Glu
                420                 425                 430

Val Ser Thr Thr Lys Leu Ala Pro Pro Thr Asp Val Ser Leu Gly Asp
                435                 440                 445

Glu Leu His Leu Asp Gly Glu Asp Val Ala Met Ala His Ala Asp Ala
                450                 455                 460
```

-continued

```
Leu Asp Asp Phe Asp Leu Asp Met Leu Gly Asp Gly Asp Ser Pro Gly
465                 470                 475                 480

Pro Gly Phe Thr Pro His Asp Ser Ala Pro Tyr Gly Ala Leu Asp Met
                485                 490                 495

Ala Asp Phe Glu Phe Glu Gln Met Phe Thr Asp Ala Leu Gly Ile Asp
            500                 505                 510

Glu Tyr Gly Gly
        515

<210> SEQ ID NO 73
<211> LENGTH: 1542
<212> TYPE: DNA
<213> ORGANISM: Synthetic construct
<220> FEATURE:
<221> NAME/KEY: CDS
<222> LOCATION: (1)..(1542)
<223> OTHER INFORMATION: Ecdysone Receptor chimera DBV

<400> SEQUENCE: 73 atg ggt cgc gat gat ctc tcg cct tcg agc agc ttg aac gga tac tcg    48
Met Gly Arg Asp Asp Leu Ser Pro Ser Ser Ser Leu Asn Gly Tyr Ser
1               5                   10                  15 gcg aac gaa agc tgc gat gcg aag aag agc aag aag gga cct gcg cca    96
Ala Asn Glu Ser Cys Asp Ala Lys Lys Ser Lys Lys Gly Pro Ala Pro
            20                  25                  30 cgg gtg caa gag gag ctg tgc ctg gtt tgc ggc gac agg gcc tcc ggc    144
Arg Val Gln Glu Glu Leu Cys Leu Val Cys Gly Asp Arg Ala Ser Gly
        35                  40                  45 tac cac tac aac gcc ctc acc tgt gag ggc tgc aag ggg ttc ttt cga    192
Tyr His Tyr Asn Ala Leu Thr Cys Glu Gly Cys Lys Gly Phe Phe Arg
    50                  55                  60 cgc agc gtt acg aag agc gcc gtc tac tgc tgc aag ttc ggg cgc gcc    240
Arg Ser Val Thr Lys Ser Ala Val Tyr Cys Cys Lys Phe Gly Arg Ala
65                  70                  75                  80 tgc gaa atg gac atg tac atg agg cga aag tgt cag gag tgc cgc ctg    288
Cys Glu Met Asp Met Tyr Met Arg Arg Lys Cys Gln Glu Cys Arg Leu
                85                  90                  95 aaa aag tgc ctg gcc gtg ggt atg cgg ccg gaa tgc gtc gtc ccg gag    336
Lys Lys Cys Leu Ala Val Gly Met Arg Pro Glu Cys Val Val Pro Glu
            100                 105                 110 aac caa tgt gcg atg aag cgg cgc gaa aag aag gcc cag aag gag aag    384
Asn Gln Cys Ala Met Lys Arg Arg Glu Lys Lys Ala Gln Lys Glu Lys
        115                 120                 125 gac aaa atg acc act tcg ccg agc tct cag cat ggc ggc aat ggc agc    432
Asp Lys Met Thr Thr Ser Pro Ser Ser Gln His Gly Gly Asn Gly Ser
    130                 135                 140 ttg gcc tct ggt ggc ggc caa gac ttt gtt aag aag gag att ctt gac    480
Leu Ala Ser Gly Gly Gly Gln Asp Phe Val Lys Lys Glu Ile Leu Asp
145                 150                 155                 160 ctt atg aca tgc gag ccg ccc cag cat gcc act att ccg cta cta cct    528
Leu Met Thr Cys Glu Pro Pro Gln His Ala Thr Ile Pro Leu Leu Pro
                165                 170                 175 gat gaa ata ttg gcc aag tgt caa gcg cgc aat ata cct tcc tta acg    576
Asp Glu Ile Leu Ala Lys Cys Gln Ala Arg Asn Ile Pro Ser Leu Thr
            180                 185                 190 tac aat cag ttg gcc gtt ata tac aag tta att tgg tac cag gaa ggc    624
Tyr Asn Gln Leu Ala Val Ile Tyr Lys Leu Ile Trp Tyr Gln Glu Gly
        195                 200                 205 tat gaa caa cct tca gag gaa gac ctc aag agg gtg acg cag acc tgg    672
Tyr Glu Gln Pro Ser Glu Glu Asp Leu Lys Arg Val Thr Gln Thr Trp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 210 |     |     |     |     | 215 |     |     |     |     | 220 |     |     |     |      |
| cag | tcg | gac | gag | gat | gaa | gag | gag | tca | gat | atg | ccg | ttc | cgc | cag | atc | 720  |
| Gln | Ser | Asp | Glu | Asp | Glu | Glu | Glu | Ser | Asp | Met | Pro | Phe | Arg | Gln | Ile |      |
| 225 |     |     |     |     | 230 |     |     |     |     | 235 |     |     |     |     | 240 |      |
| acc | gag | atg | acg | atc | ctg | aca | gtt | caa | ctc | atc | gta | gaa | ttc | gca | aaa | 768  |
| Thr | Glu | Met | Thr | Ile | Leu | Thr | Val | Gln | Leu | Ile | Val | Glu | Phe | Ala | Lys |      |
|     |     |     |     | 245 |     |     |     |     | 250 |     |     |     |     | 255 |     |      |
| ggc | ctg | cca | ggc | ttc | gcc | aag | atc | tcg | cag | tcg | gat | caa | atc | acg | tta | 816  |
| Gly | Leu | Pro | Gly | Phe | Ala | Lys | Ile | Ser | Gln | Ser | Asp | Gln | Ile | Thr | Leu |      |
|     |     |     | 260 |     |     |     |     | 265 |     |     |     |     | 270 |     |     |      |
| cta | aag | gcg | tgt | tca | agt | gag | gtg | atg | atg | ctc | cga | gtg | gcc | cgg | cgg | 864  |
| Leu | Lys | Ala | Cys | Ser | Ser | Glu | Val | Met | Met | Leu | Arg | Val | Ala | Arg | Arg |      |
|     |     | 275 |     |     |     |     | 280 |     |     |     |     | 285 |     |     |     |      |
| tac | gac | gcg | gcc | acc | gac | agc | gta | ctg | ttc | gcc | aac | aac | cag | gcg | tac | 912  |
| Tyr | Asp | Ala | Ala | Thr | Asp | Ser | Val | Leu | Phe | Ala | Asn | Asn | Gln | Ala | Tyr |      |
|     | 290 |     |     |     |     | 295 |     |     |     |     | 300 |     |     |     |     |      |
| tcc | cgc | gac | aac | tac | cgc | aag | gca | ggc | atg | tcc | tac | gtc | atc | gag | gat | 960  |
| Ser | Arg | Asp | Asn | Tyr | Arg | Lys | Ala | Gly | Met | Ser | Tyr | Val | Ile | Glu | Asp |      |
| 305 |     |     |     |     | 310 |     |     |     |     | 315 |     |     |     |     | 320 |      |
| ctc | ttg | cac | ttc | tgt | cgg | tgc | atg | tac | tcc | atg | atg | atg | gat | aac | gtg | 1008 |
| Leu | Leu | His | Phe | Cys | Arg | Cys | Met | Tyr | Ser | Met | Met | Met | Asp | Asn | Val |      |
|     |     |     |     | 325 |     |     |     |     | 330 |     |     |     |     | 335 |     |      |
| cac | tac | gcg | ctg | ctt | acg | gcc | att | gtc | att | ttc | tca | gac | cgg | cct | ggg | 1056 |
| His | Tyr | Ala | Leu | Leu | Thr | Ala | Ile | Val | Ile | Phe | Ser | Asp | Arg | Pro | Gly |      |
|     |     |     | 340 |     |     |     |     | 345 |     |     |     |     | 350 |     |     |      |
| ctc | gag | caa | ccc | tta | ttg | gtg | gaa | gaa | atc | cag | cgg | tat | tac | ctg | aac | 1104 |
| Leu | Glu | Gln | Pro | Leu | Leu | Val | Glu | Glu | Ile | Gln | Arg | Tyr | Tyr | Leu | Asn |      |
|     |     | 355 |     |     |     |     | 360 |     |     |     |     | 365 |     |     |     |      |
| acg | ctg | cgg | gtg | tac | atc | ttg | aac | caa | aac | agt | gcg | tcg | ccg | cgc | tgc | 1152 |
| Thr | Leu | Arg | Val | Tyr | Ile | Leu | Asn | Gln | Asn | Ser | Ala | Ser | Pro | Arg | Cys |      |
|     | 370 |     |     |     |     | 375 |     |     |     |     | 380 |     |     |     |     |      |
| ccc | gta | gtc | ttc | gcc | aag | atc | ctg | ggg | ata | ttg | acg | gag | ctg | cgg | acc | 1200 |
| Pro | Val | Val | Phe | Ala | Lys | Ile | Leu | Gly | Ile | Leu | Thr | Glu | Leu | Arg | Thr |      |
| 385 |     |     |     |     | 390 |     |     |     |     | 395 |     |     |     |     | 400 |      |
| ctc | ggc | atg | cag | aac | tcc | aac | atg | tgc | atc | tcg | ttg | aag | ctg | aag | aat | 1248 |
| Leu | Gly | Met | Gln | Asn | Ser | Asn | Met | Cys | Ile | Ser | Leu | Lys | Leu | Lys | Asn |      |
|     |     |     |     | 405 |     |     |     |     | 410 |     |     |     |     | 415 |     |      |
| agg | aag | ctg | ccg | ccg | ttc | ctc | gag | gag | atc | tgg | gac | gtg | gaa | tcc | cgc | 1296 |
| Arg | Lys | Leu | Pro | Pro | Phe | Leu | Glu | Glu | Ile | Trp | Asp | Val | Glu | Ser | Arg |      |
|     |     |     | 420 |     |     |     |     | 425 |     |     |     |     | 430 |     |     |      |
| ggg | aag | ctt | gcc | ccc | ccg | acc | gat | gtc | agc | ctg | ggg | gac | gag | ctc | cac | 1344 |
| Gly | Lys | Leu | Ala | Pro | Pro | Thr | Asp | Val | Ser | Leu | Gly | Asp | Glu | Leu | His |      |
|     |     | 435 |     |     |     |     | 440 |     |     |     |     | 445 |     |     |     |      |
| tta | gac | ggc | gag | gac | gtg | gcg | atg | gcg | cat | gcc | gac | gcg | cta | gac | gat | 1392 |
| Leu | Asp | Gly | Glu | Asp | Val | Ala | Met | Ala | His | Ala | Asp | Ala | Leu | Asp | Asp |      |
|     | 450 |     |     |     |     | 455 |     |     |     |     | 460 |     |     |     |     |      |
| ttc | gat | ctg | gac | atg | ttg | ggg | gac | ggg | gat | tcc | ccg | ggt | ccg | gga | ttt | 1440 |
| Phe | Asp | Leu | Asp | Met | Leu | Gly | Asp | Gly | Asp | Ser | Pro | Gly | Pro | Gly | Phe |      |
| 465 |     |     |     |     | 470 |     |     |     |     | 475 |     |     |     |     | 480 |      |
| acc | ccc | cac | gac | tcc | gcc | ccc | tac | ggc | gct | ctg | gat | atg | gcc | gac | ttc | 1488 |
| Thr | Pro | His | Asp | Ser | Ala | Pro | Tyr | Gly | Ala | Leu | Asp | Met | Ala | Asp | Phe |      |
|     |     |     |     | 485 |     |     |     |     | 490 |     |     |     |     | 495 |     |      |
| gag | ttt | gag | cag | atg | ttt | acc | gat | gcc | ctt | gga | att | gac | gag | tac | ggt | 1536 |
| Glu | Phe | Glu | Gln | Met | Phe | Thr | Asp | Ala | Leu | Gly | Ile | Asp | Glu | Tyr | Gly |      |
|     |     |     | 500 |     |     |     |     | 505 |     |     |     |     | 510 |     |     |      |
| ggg | tag |     |     |     |     |     |     |     |     |     |     |     |     |     |     | 1542 |
| Gly |     |     |     |     |     |     |     |     |     |     |     |     |     |     |     |      |

<210> SEQ ID NO 74

-continued

<211> LENGTH: 513
<212> TYPE: PRT
<213> ORGANISM: Synthetic construct

<400> SEQUENCE: 74

```
Met Gly Arg Asp Asp Leu Ser Pro Ser Ser Leu Asn Gly Tyr Ser
 1               5                  10                  15

Ala Asn Glu Ser Cys Asp Ala Lys Lys Ser Lys Lys Gly Pro Ala Pro
            20                  25                  30

Arg Val Gln Glu Glu Leu Cys Leu Val Cys Gly Asp Arg Ala Ser Gly
        35                  40                  45

Tyr His Tyr Asn Ala Leu Thr Cys Glu Gly Cys Lys Gly Phe Phe Arg
    50                  55                  60

Arg Ser Val Thr Lys Ser Ala Val Tyr Cys Cys Lys Phe Gly Arg Ala
65                  70                  75                  80

Cys Glu Met Asp Met Tyr Met Arg Arg Lys Cys Gln Glu Cys Arg Leu
                85                  90                  95

Lys Lys Cys Leu Ala Val Gly Met Arg Pro Glu Cys Val Val Pro Glu
            100                 105                 110

Asn Gln Cys Ala Met Lys Arg Glu Lys Lys Ala Gln Lys Glu Lys
            115                 120                 125

Asp Lys Met Thr Thr Ser Pro Ser Ser Gln His Gly Gly Asn Gly Ser
    130                 135                 140

Leu Ala Ser Gly Gly Gly Gln Asp Phe Val Lys Lys Glu Ile Leu Asp
145                 150                 155                 160

Leu Met Thr Cys Glu Pro Pro Gln His Ala Thr Ile Pro Leu Leu Pro
                165                 170                 175

Asp Glu Ile Leu Ala Lys Cys Gln Ala Arg Asn Ile Pro Ser Leu Thr
            180                 185                 190

Tyr Asn Gln Leu Ala Val Ile Tyr Lys Leu Ile Trp Tyr Gln Glu Gly
        195                 200                 205

Tyr Glu Gln Pro Ser Glu Glu Asp Leu Lys Arg Val Thr Gln Thr Trp
    210                 215                 220

Gln Ser Asp Glu Asp Glu Glu Ser Asp Met Pro Phe Arg Gln Ile
225                 230                 235                 240

Thr Glu Met Thr Ile Leu Thr Val Gln Leu Ile Val Glu Phe Ala Lys
                245                 250                 255

Gly Leu Pro Gly Phe Ala Lys Ile Ser Gln Ser Asp Gln Ile Thr Leu
            260                 265                 270

Leu Lys Ala Cys Ser Ser Glu Val Met Met Leu Arg Val Ala Arg Arg
        275                 280                 285

Tyr Asp Ala Ala Thr Asp Ser Val Leu Phe Ala Asn Asn Gln Ala Tyr
    290                 295                 300

Ser Arg Asp Asn Tyr Arg Lys Ala Gly Met Ser Tyr Val Ile Glu Asp
305                 310                 315                 320

Leu Leu His Phe Cys Arg Cys Met Tyr Ser Met Met Asp Asn Val
                325                 330                 335

His Tyr Ala Leu Leu Thr Ala Ile Val Ile Phe Ser Asp Arg Pro Gly
            340                 345                 350

Leu Glu Gln Pro Leu Leu Val Glu Glu Ile Gln Arg Tyr Tyr Leu Asn
        355                 360                 365

Thr Leu Arg Val Tyr Ile Leu Asn Gln Asn Ser Ala Ser Pro Arg Cys
    370                 375                 380

Pro Val Val Phe Ala Lys Ile Leu Gly Ile Leu Thr Glu Leu Arg Thr
```

-continued

```
                385                 390                 395                 400
Leu Gly Met Gln Asn Ser Asn Met Cys Ile Ser Leu Lys Leu Lys Asn
                    405                 410                 415

Arg Lys Leu Pro Pro Phe Leu Glu Glu Ile Trp Asp Val Glu Ser Arg
                420                 425                 430

Gly Lys Leu Ala Pro Pro Thr Asp Val Ser Leu Gly Asp Glu Leu His
            435                 440                 445

Leu Asp Gly Glu Asp Val Ala Met Ala His Ala Asp Ala Leu Asp Asp
        450                 455                 460

Phe Asp Leu Asp Met Leu Gly Asp Gly Asp Ser Pro Gly Pro Gly Phe
465                 470                 475                 480

Thr Pro His Asp Ser Ala Pro Tyr Gly Ala Leu Asp Met Ala Asp Phe
                485                 490                 495

Glu Phe Glu Gln Met Phe Thr Asp Ala Leu Gly Ile Asp Glu Tyr Gly
                500                 505                 510

Gly
```

<210> SEQ ID NO 75
<211> LENGTH: 1515
<212> TYPE: DNA
<213> ORGANISM: Synthetic construct
<220> FEATURE:
<221> NAME/KEY: CDS
<222> LOCATION: (1)..(1515)
<223> OTHER INFORMATION: Ecdysone Receptor chimera EEV

<400> SEQUENCE: 75

```
atg ggc cga gaa gaa ttg tca cca gct tcg agc gta aac ggt tgc agt        48
Met Gly Arg Glu Glu Leu Ser Pro Ala Ser Ser Val Asn Gly Cys Ser
1               5                   10                  15 aca gat ggc gag gca aga cga cag aaa aag ggc ccc gcg cct cgc cag        96
Thr Asp Gly Glu Ala Arg Arg Gln Lys Lys Gly Pro Ala Pro Arg Gln
                20                  25                  30 cag gag gaa tta tgt ctc gtc tgc ggc gac aga gcc tcc gga tac cat       144
Gln Glu Glu Leu Cys Leu Val Cys Gly Asp Arg Ala Ser Gly Tyr His
            35                  40                  45 tac aac gcg ctt acg tgt gaa gga tgc aaa ggt ttc ttc agg cgg agt       192
Tyr Asn Ala Leu Thr Cys Glu Gly Cys Lys Gly Phe Phe Arg Arg Ser
        50                  55                  60 gtg acc aaa aat gcg gtg tac att tgc aag ttt ggg cat gcg tgc gaa       240
Val Thr Lys Asn Ala Val Tyr Ile Cys Lys Phe Gly His Ala Cys Glu
65                  70                  75                  80 atg gac atg tat atg cgg cgg aaa tgt caa gaa tgc cgg ttg aag aag       288
Met Asp Met Tyr Met Arg Arg Lys Cys Gln Glu Cys Arg Leu Lys Lys
                85                  90                  95 tgt tta gcg gtg ggc atg agg ccc gag tgc gtg gtg cca gaa acg cag       336
Cys Leu Ala Val Gly Met Arg Pro Glu Cys Val Val Pro Glu Thr Gln
                100                 105                 110 tgt gcg caa aaa agg aaa gag aag aaa gca cag aga gaa aaa gac aaa       384
Cys Ala Gln Lys Arg Lys Glu Lys Lys Ala Gln Arg Glu Lys Asp Lys
            115                 120                 125 cta cca gtg agc aca acg aca gta gac gat cat atg ccc cca atc atg       432
Leu Pro Val Ser Thr Thr Thr Val Asp Asp His Met Pro Pro Ile Met
        130                 135                 140 cag tgt gat cca cca ccc ccg gag gca gcg agg att ctg gaa tgt ttg       480
Gln Cys Asp Pro Pro Pro Pro Glu Ala Ala Arg Ile Leu Glu Cys Leu
145                 150                 155                 160 cag cat gaa gtg gtc ccg cgg ttc ctc tcg gag aag ctg atg gag cag       528
Gln His Glu Val Val Pro Arg Phe Leu Ser Glu Lys Leu Met Glu Gln
```

-continued

|  | 165 | | | | 170 | | | | 175 | | | | |
|---|---|---|---|---|---|---|---|---|---|---|---|---|---|
| aat | cgg | ctg | aag | aac | ata | ccc | ccc | ctc | acc | gcc | aac | cag | cag ttc ctg | 576 |
| Asn | Arg | Leu | Lys | Asn | Ile | Pro | Pro | Leu | Thr | Ala | Asn | Gln | Gln Phe Leu | |
| | | | 180 | | | | | 185 | | | | | 190 | |

| atc gcg agg ctg gtg tgg tac cag gac gga tac gag cag cct tcg gaa | 624 |
| Ile Ala Arg Leu Val Trp Tyr Gln Asp Gly Tyr Glu Gln Pro Ser Glu | |
| 195 200 205 | |

| gag gat ctc aaa agg gtg acg cag act tgg caa tca gca gat gaa gaa | 672 |
| Glu Asp Leu Lys Arg Val Thr Gln Thr Trp Gln Ser Ala Asp Glu Glu | |
| 210 215 220 | |

| gac gaa gac tca gac atg cca ttc cgc cag atc aca gaa atg acc atc | 720 |
| Asp Glu Asp Ser Asp Met Pro Phe Arg Gln Ile Thr Glu Met Thr Ile | |
| 225 230 235 240 | |

| ctc aca gta cag cta ata gtc gag ttt gcc aaa ggc cta cct ggt ttt | 768 |
| Leu Thr Val Gln Leu Ile Val Glu Phe Ala Lys Gly Leu Pro Gly Phe | |
| 245 250 255 | |

| tca aag atc tca caa cct gac cag atc aca tta tta aag gca tgc tca | 816 |
| Ser Lys Ile Ser Gln Pro Asp Gln Ile Thr Leu Leu Lys Ala Cys Ser | |
| 260 265 270 | |

| agc gaa gtg atg atg ctg cga gta gcg agg cgg tac gac gcg gtg tcg | 864 |
| Ser Glu Val Met Met Leu Arg Val Ala Arg Arg Tyr Asp Ala Val Ser | |
| 275 280 285 | |

| gat agc gtt ctg ttc gcc aac aac cag gcg tac act cgc gac aac tac | 912 |
| Asp Ser Val Leu Phe Ala Asn Asn Gln Ala Tyr Thr Arg Asp Asn Tyr | |
| 290 295 300 | |

| cgc aag gcg ggc atg gcc tac gtc atc gaa gac ctg ctg cac ttc tgc | 960 |
| Arg Lys Ala Gly Met Ala Tyr Val Ile Glu Asp Leu Leu His Phe Cys | |
| 305 310 315 320 | |

| cgc tgc atg tac tcg atg tcg atg gac aac gtg cat tac gcg ctc ctc | 1008 |
| Arg Cys Met Tyr Ser Met Ser Met Asp Asn Val His Tyr Ala Leu Leu | |
| 325 330 335 | |

| act gcc atc gtt ata ttc tcg gat cgg ccg ggc cta gag cag cca cag | 1056 |
| Thr Ala Ile Val Ile Phe Ser Asp Arg Pro Gly Leu Glu Gln Pro Gln | |
| 340 345 350 | |

| cta gta gaa gag atc cag cgg tat tac ctg aac acg ctg cgg gtg tac | 1104 |
| Leu Val Glu Glu Ile Gln Arg Tyr Tyr Leu Asn Thr Leu Arg Val Tyr | |
| 355 360 365 | |

| atc atg aac cag cac agc gcg tcg ccg cgt tgc gcc gtc atc tac gcg | 1152 |
| Ile Met Asn Gln His Ser Ala Ser Pro Arg Cys Ala Val Ile Tyr Ala | |
| 370 375 380 | |

| aag att ctg tcg gtg ctt acc gag ttg cgg acg ctg ggc atg cag aat | 1200 |
| Lys Ile Leu Ser Val Leu Thr Glu Leu Arg Thr Leu Gly Met Gln Asn | |
| 385 390 395 400 | |

| tcg aac atg tgc atc tcg ctg aag ctc aag aac agg aag ctg ccg ccg | 1248 |
| Ser Asn Met Cys Ile Ser Leu Lys Leu Lys Asn Arg Lys Leu Pro Pro | |
| 405 410 415 | |

| ttc ctg gag gag atc tgg gac gtg aag ctt gcc ccc ccg acc gat gtc | 1296 |
| Phe Leu Glu Glu Ile Trp Asp Val Lys Leu Ala Pro Pro Thr Asp Val | |
| 420 425 430 | |

| agc ctg ggg gac gag ctc cac tta gac ggc gag gac gtg gcg atg gcg | 1344 |
| Ser Leu Gly Asp Glu Leu His Leu Asp Gly Glu Asp Val Ala Met Ala | |
| 435 440 445 | |

| cat gcc gac gcg cta gac gat ttc gat ctg gac atg ttg ggg gac ggg | 1392 |
| His Ala Asp Ala Leu Asp Asp Phe Asp Leu Asp Met Leu Gly Asp Gly | |
| 450 455 460 | |

| gat tcc ccg ggt ccg gga ttt acc ccc cac gac tcc gcc ccc tac ggc | 1440 |
| Asp Ser Pro Gly Pro Gly Phe Thr Pro His Asp Ser Ala Pro Tyr Gly | |
| 465 470 475 480 | |

| gct ctg gat atg gcc gac ttc gag ttt gag cag atg ttt acc gat gcc | 1488 |

```
Ala Leu Asp Met Ala Asp Phe Glu Phe Glu Gln Met Phe Thr Asp Ala
            485                 490                 495 ctt gga att gac gag tac ggt ggg tag                              1515
Leu Gly Ile Asp Glu Tyr Gly Gly
                500
```

<210> SEQ ID NO 76
<211> LENGTH: 504
<212> TYPE: PRT
<213> ORGANISM: Synthetic construct

<400> SEQUENCE: 76

```
Met Gly Arg Glu Glu Leu Ser Pro Ala Ser Ser Val Asn Gly Cys Ser
1               5                   10                  15

Thr Asp Gly Glu Ala Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Thr Gln
            100                 105                 110

Cys Ala Gln Lys Arg Lys Glu Lys Lys Ala Gln Arg Glu Lys Asp Lys
        115                 120                 125

Leu Pro Val Ser Thr Thr Thr Val Asp Asp His Met Pro Pro Ile Met
    130                 135                 140

Gln Cys Asp Pro Pro Pro Glu Ala Ala Arg Ile Leu Glu Cys Leu
145                 150                 155                 160

Gln His Glu Val Val Pro Arg Phe Leu Ser Glu Lys Leu Met Glu Gln
                165                 170                 175

Asn Arg Leu Lys Asn Ile Pro Pro Leu Thr Ala Asn Gln Gln Phe Leu
            180                 185                 190

Ile Ala Arg Leu Val Trp Tyr Gln Asp Gly Tyr Glu Gln Pro Ser Glu
        195                 200                 205

Glu Asp Leu Lys Arg Val Thr Gln Thr Trp Gln Ser Ala Asp Glu Glu
    210                 215                 220

Asp Glu Asp Ser Asp Met Pro Phe Arg Gln Ile Thr Glu Met Thr Ile
225                 230                 235                 240

Leu Thr Val Gln Leu Ile Val Glu Phe Ala Lys Gly Leu Pro Gly Phe
                245                 250                 255

Ser Lys Ile Ser Gln Pro Asp Gln Ile Thr Leu Leu Lys Ala Cys Ser
            260                 265                 270

Ser Glu Val Met Met Leu Arg Val Ala Arg Arg Tyr Asp Ala Val Ser
        275                 280                 285

Asp Ser Val Leu Phe Ala Asn Asn Gln Ala Tyr Thr Arg Asp Asn Tyr
    290                 295                 300

Arg Lys Ala Gly Met Ala Tyr Val Ile Glu Asp Leu Leu His Phe Cys
305                 310                 315                 320

Arg Cys Met Tyr Ser Met Ser Met Asp Asn Val His Tyr Ala Leu Leu
                325                 330                 335

Thr Ala Ile Val Ile Phe Ser Asp Arg Pro Gly Leu Glu Gln Pro Gln
```

-continued

```
                340                 345                 350
Leu Val Glu Glu Ile Gln Arg Tyr Tyr Leu Asn Thr Leu Arg Val Tyr
                355                 360                 365

Ile Met Asn Gln His Ser Ala Ser Pro Arg Cys Ala Val Ile Tyr Ala
    370                 375                 380

Lys Ile Leu Ser Val Leu Thr Glu Leu Arg Thr Leu Gly Met Gln Asn
385                 390                 395                 400

Ser Asn Met Cys Ile Ser Leu Lys Leu Lys Asn Arg Lys Leu Pro Pro
                405                 410                 415

Phe Leu Glu Glu Ile Trp Asp Val Lys Leu Ala Pro Pro Thr Asp Val
            420                 425                 430

Ser Leu Gly Asp Glu Leu His Leu Asp Gly Glu Asp Val Ala Met Ala
        435                 440                 445

His Ala Asp Ala Leu Asp Asp Phe Asp Leu Asp Met Leu Gly Asp Gly
    450                 455                 460

Asp Ser Pro Gly Pro Gly Phe Thr Pro His Asp Ser Ala Pro Tyr Gly
465                 470                 475                 480

Ala Leu Asp Met Ala Asp Phe Glu Phe Glu Gln Met Phe Thr Asp Ala
                485                 490                 495

Leu Gly Ile Asp Glu Tyr Gly Gly
            500

<210> SEQ ID NO 77
<211> LENGTH: 1524
<212> TYPE: DNA
<213> ORGANISM: Synthetic construct
<220> FEATURE:
<221> NAME/KEY: CDS
<222> LOCATION: (1)..(1524)
<223> OTHER INFORMATION: Ecdysone Receptor chimera EBV

<400> SEQUENCE: 77 atg ggc cga gaa gaa ttg tca cca gct tcg agc gta aac ggt tgc agt        48
Met Gly Arg Glu Glu Leu Ser Pro Ala Ser Ser Val Asn Gly Cys Ser
1               5                   10                  15 aca gat ggc gag gca aga cga cag aaa aag ggc ccc gcg cct cgc cag        96
Thr Asp Gly Glu Ala Arg Arg Gln Lys Lys Gly Pro Ala Pro Arg Gln
            20                  25                  30 cag gag gaa tta tgt ctc gtc tgc ggc gac aga gcc tcc gga tac cat       144
Gln Glu Glu Leu Cys Leu Val Cys Gly Asp Arg Ala Ser Gly Tyr His
        35                  40                  45 tac aac gcg ctt acg tgt gaa gga tgc aaa ggt ttc ttc agg cgg agt       192
Tyr Asn Ala Leu Thr Cys Glu Gly Cys Lys Gly Phe Phe Arg Arg Ser
    50                  55                  60 gtg acc aaa aat gcg gtg tac att tgc aag ttt ggg cat gcg tgc gaa       240
Val Thr Lys Asn Ala Val Tyr Ile Cys Lys Phe Gly His Ala Cys Glu
65                  70                  75                  80 atg gac atg tat atg cgg cgg aaa tgt caa gaa tgc cgg ttg aag aag       288
Met Asp Met Tyr Met Arg Arg Lys Cys Gln Glu Cys Arg Leu Lys Lys
                85                  90                  95 tgt tta gcg gtg ggc atg agg ccc gag tgc gtg gtg cca gaa acg cag       336
Cys Leu Ala Val Gly Met Arg Pro Glu Cys Val Val Pro Glu Thr Gln
            100                 105                 110 tgt gcg caa aaa agg aaa gag aag aaa gca cag aga gaa aaa gac aaa       384
Cys Ala Gln Lys Arg Lys Glu Lys Lys Ala Gln Arg Glu Lys Asp Lys
        115                 120                 125 cta cca gtg agc aca acg aca gta gac gat cat atg ccc cca atc atg       432
Leu Pro Val Ser Thr Thr Thr Val Asp Asp His Met Pro Pro Ile Met
    130                 135                 140
```

-continued

```
cag tgt gat cca cca ccc ccg gag gca gcg agg att ctg gaa tgt ttg        480
Gln Cys Asp Pro Pro Pro Pro Glu Ala Ala Arg Ile Leu Glu Cys Leu
145                 150                 155                 160 cag cat gaa gtg gtc ccg cgg ttc ctc tcg gag aag ctg atg gag cag        528
Gln His Glu Val Val Pro Arg Phe Leu Ser Glu Lys Leu Met Glu Gln
                165                 170                 175 aat cgg ctg aag aac ata ccc ccc ctc acc gcc aac cag cag ttc ctg        576
Asn Arg Leu Lys Asn Ile Pro Pro Leu Thr Ala Asn Gln Gln Phe Leu
            180                 185                 190 atc gcg agg ctg gtg tgg tac cag gaa ggc tat gaa caa cct tca gag        624
Ile Ala Arg Leu Val Trp Tyr Gln Glu Gly Tyr Glu Gln Pro Ser Glu
        195                 200                 205 gaa gac ctc aag agg gtg acg cag acc tgg cag tcg gac gag gat gaa        672
Glu Asp Leu Lys Arg Val Thr Gln Thr Trp Gln Ser Asp Glu Asp Glu
    210                 215                 220 gag gag tca gat atg ccg ttc cgc cag atc acc gag atg acg atc ctg        720
Glu Glu Ser Asp Met Pro Phe Arg Gln Ile Thr Glu Met Thr Ile Leu
225                 230                 235                 240 aca gtt caa ctc atc gta gaa ttc gca aaa ggc ctg cca ggc ttc gcc        768
Thr Val Gln Leu Ile Val Glu Phe Ala Lys Gly Leu Pro Gly Phe Ala
                245                 250                 255 aag atc tcg cag tcg gat caa atc acg tta cta aag gcg tgt tca agt        816
Lys Ile Ser Gln Ser Asp Gln Ile Thr Leu Leu Lys Ala Cys Ser Ser
            260                 265                 270 gag gtg atg atg ctc cga gtg gcc cgg cgg tac gac gcg gcc acc gac        864
Glu Val Met Met Leu Arg Val Ala Arg Arg Tyr Asp Ala Ala Thr Asp
        275                 280                 285 agc gta ctg ttc gcc aac aac cag gcg tac tcc cgc gac aac tac cgc        912
Ser Val Leu Phe Ala Asn Asn Gln Ala Tyr Ser Arg Asp Asn Tyr Arg
    290                 295                 300 aag gca ggc atg tcc tac gtc atc gag gat ctc ttg cac ttc tgt cgg        960
Lys Ala Gly Met Ser Tyr Val Ile Glu Asp Leu Leu His Phe Cys Arg
305                 310                 315                 320 tgc atg tac tcc atg atg atg gat aac gtg cac tac gcg ctg ctt acg       1008
Cys Met Tyr Ser Met Met Met Asp Asn Val His Tyr Ala Leu Leu Thr
                325                 330                 335 gcc att gtc att ttc tca gac cgg cct ggg ctc gag caa ccc tta ttg       1056
Ala Ile Val Ile Phe Ser Asp Arg Pro Gly Leu Glu Gln Pro Leu Leu
            340                 345                 350 gtg gaa gaa atc cag cgg tat tac ctg aac acg ctg cgg gtg tac atc       1104
Val Glu Glu Ile Gln Arg Tyr Tyr Leu Asn Thr Leu Arg Val Tyr Ile
        355                 360                 365 ttg aac caa aac agt gcg tcg ccg cgc tgc ccc gta gtc ttc gcc aag       1152
Leu Asn Gln Asn Ser Ala Ser Pro Arg Cys Pro Val Val Phe Ala Lys
    370                 375                 380 atc ctg ggg ata ttg acg gag ctg cgg acc ctc ggc atg cag aac tcc       1200
Ile Leu Gly Ile Leu Thr Glu Leu Arg Thr Leu Gly Met Gln Asn Ser
385                 390                 395                 400 aac atg tgc atc tcg ttg aag ctg aag aat agg aag ctg ccg ccg ttc       1248
Asn Met Cys Ile Ser Leu Lys Leu Lys Asn Arg Lys Leu Pro Pro Phe
                405                 410                 415 ctc gag gag atc tgg gac gtg gaa tcc cgc ggg aag ctt gcc ccc ccg       1296
Leu Glu Glu Ile Trp Asp Val Glu Ser Arg Gly Lys Leu Ala Pro Pro
            420                 425                 430 acc gat gtc agc ctg ggg gac gag ctc cac tta gac ggc gag gac gtg       1344
Thr Asp Val Ser Leu Gly Asp Glu Leu His Leu Asp Gly Glu Asp Val
        435                 440                 445 gcg atg gcg cat gcc gac gcg cta gac gat ttc gat ctg gac atg ttg       1392
Ala Met Ala His Ala Asp Ala Leu Asp Asp Phe Asp Leu Asp Met Leu
```

```
                       450                 455                 460
ggg gac ggg gat tcc ccg ggt ccg gga ttt acc ccc cac gac tcc gcc      1440
Gly Asp Gly Asp Ser Pro Gly Pro Gly Phe Thr Pro His Asp Ser Ala
465                 470                 475                 480 ccc tac ggc gct ctg gat atg gcc gac ttc gag ttt gag cag atg ttt      1488
Pro Tyr Gly Ala Leu Asp Met Ala Asp Phe Glu Phe Glu Gln Met Phe
                485                 490                 495 acc gat gcc ctt gga att gac gag tac ggt ggg tag                      1524
Thr Asp Ala Leu Gly Ile Asp Glu Tyr Gly Gly
                500                 505
```

<210> SEQ ID NO 78
<211> LENGTH: 507
<212> TYPE: PRT
<213> ORGANISM: Synthetic construct

<400> SEQUENCE: 78

```
Met Gly Arg Glu Glu Leu Ser Pro Ala Ser Ser Val Asn Gly Cys Ser
1               5                   10                  15

Thr Asp Gly Glu Ala Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Thr Gln
            100                 105                 110

Cys Ala Gln Lys Arg Lys Glu Lys Lys Ala Gln Arg Glu Lys Asp Lys
        115                 120                 125

Leu Pro Val Ser Thr Thr Thr Val Asp Asp His Met Pro Pro Ile Met
    130                 135                 140

Gln Cys Asp Pro Pro Pro Glu Ala Ala Arg Ile Leu Glu Cys Leu
145                 150                 155                 160

Gln His Glu Val Val Pro Arg Phe Leu Ser Glu Lys Leu Met Glu Gln
                165                 170                 175

Asn Arg Leu Lys Asn Ile Pro Pro Leu Thr Ala Asn Gln Gln Phe Leu
            180                 185                 190

Ile Ala Arg Leu Val Trp Tyr Gln Glu Gly Tyr Glu Gln Pro Ser Glu
        195                 200                 205

Glu Asp Leu Lys Arg Val Thr Gln Thr Trp Gln Ser Asp Glu Asp Glu
    210                 215                 220

Glu Glu Ser Asp Met Pro Phe Arg Gln Ile Thr Glu Met Thr Ile Leu
225                 230                 235                 240

Thr Val Gln Leu Ile Val Glu Phe Ala Lys Gly Leu Pro Gly Phe Ala
                245                 250                 255

Lys Ile Ser Gln Ser Asp Gln Ile Thr Leu Leu Lys Ala Cys Ser Ser
            260                 265                 270

Glu Val Met Met Leu Arg Val Ala Arg Arg Tyr Asp Ala Ala Thr Asp
        275                 280                 285

Ser Val Leu Phe Ala Asn Asn Gln Ala Tyr Ser Arg Asp Asn Tyr Arg
    290                 295                 300
```

```
              Lys Ala Gly Met Ser Tyr Val Ile Glu Asp Leu Leu His Phe Cys Arg
              305                 310                 315                 320

Cys Met Tyr Ser Met Met Asp Asn Val His Tyr Ala Leu Leu Thr
                              325                 330                 335

Ala Ile Val Ile Phe Ser Asp Arg Pro Gly Leu Glu Gln Pro Leu Leu
                          340                 345                 350

Val Glu Glu Ile Gln Arg Tyr Tyr Leu Asn Thr Leu Arg Val Tyr Ile
                          355                 360                 365

Leu Asn Gln Asn Ser Ala Ser Pro Arg Cys Pro Val Val Phe Ala Lys
                      370                 375                 380

Ile Leu Gly Ile Leu Thr Glu Leu Arg Thr Leu Gly Met Gln Asn Ser
              385                 390                 395                 400

Asn Met Cys Ile Ser Leu Lys Leu Lys Asn Arg Lys Leu Pro Pro Phe
                              405                 410                 415

Leu Glu Glu Ile Trp Asp Val Glu Ser Arg Gly Lys Leu Ala Pro Pro
                          420                 425                 430

Thr Asp Val Ser Leu Gly Asp Glu Leu His Leu Asp Gly Glu Asp Val
                          435                 440                 445

Ala Met Ala His Ala Asp Ala Leu Asp Asp Phe Asp Leu Asp Met Leu
                      450                 455                 460

Gly Asp Gly Asp Ser Pro Gly Pro Gly Phe Thr Pro His Asp Ser Ala
              465                 470                 475                 480

Pro Tyr Gly Ala Leu Asp Met Ala Asp Phe Glu Phe Glu Gln Met Phe
                              485                 490                 495

Thr Asp Ala Leu Gly Ile Asp Glu Tyr Gly Gly
                          500                 505

<210> SEQ ID NO 79
<211> LENGTH: 1533
<212> TYPE: DNA
<213> ORGANISM: Synthetic construct
<220> FEATURE:
<221> NAME/KEY: CDS
<222> LOCATION: (1)..(1533)
<223> OTHER INFORMATION: Ecdysone Receptor chimera EMV

<400> SEQUENCE: 79 atg ggc cga gaa gaa ttg tca cca gct tcg agc gta aac ggt tgc agt        48
Met Gly Arg Glu Glu Leu Ser Pro Ala Ser Ser Val Asn Gly Cys Ser
1               5                   10                  15 aca gat ggc gag gca aga cga cag aaa aag ggc ccc gcg cct cgc cag        96
Thr Asp Gly Glu Ala Arg Arg Gln Lys Lys Gly Pro Ala Pro Arg Gln
            20                  25                  30 cag gag gaa tta tgt ctc gtc tgc ggc gac aga gcc tcc gga tac cat       144
Gln Glu Glu Leu Cys Leu Val Cys Gly Asp Arg Ala Ser Gly Tyr His
        35                  40                  45 tac aac gcg ctt acg tgt gaa gga tgc aaa ggt ttc ttc agg cgg agt       192
Tyr Asn Ala Leu Thr Cys Glu Gly Cys Lys Gly Phe Phe Arg Arg Ser
    50                  55                  60 gtg acc aaa aat gcg gtg tac att tgc aag ttt ggg cat gcg tgc gaa       240
Val Thr Lys Asn Ala Val Tyr Ile Cys Lys Phe Gly His Ala Cys Glu
65                  70                  75                  80 atg gac atg tat atg cgg cgg aaa tgt caa gaa tgc cgg ttg aag aag       288
Met Asp Met Tyr Met Arg Arg Lys Cys Gln Glu Cys Arg Leu Lys Lys
                85                  90                  95 tgt tta gcg gtg ggc atg agg ccc gag tgc gtg gtg cca gaa acg cag       336
Cys Leu Ala Val Gly Met Arg Pro Glu Cys Val Val Pro Glu Thr Gln
            100                 105                 110
```

```
tgt gcg caa aaa agg aaa gag aag aaa gca cag aga gaa aaa gac aaa      384
Cys Ala Gln Lys Arg Lys Glu Lys Lys Ala Gln Arg Glu Lys Asp Lys
        115                 120                 125 cta cca gtg agc aca acg aca gta gac gat cat atg ccc cca atc atg      432
Leu Pro Val Ser Thr Thr Thr Val Asp Asp His Met Pro Pro Ile Met
130                 135                 140 cag tgt gat cca cca ccc ccg gag gca gcg agg att ctg gaa tgt ttg      480
Gln Cys Asp Pro Pro Pro Pro Glu Ala Ala Arg Ile Leu Glu Cys Leu
145                 150                 155                 160 cag cat gaa gtg gtc ccg cgg ttc ctc tcg gag aag ctg atg gag cag      528
Gln His Glu Val Val Pro Arg Phe Leu Ser Glu Lys Leu Met Glu Gln
                165                 170                 175 aat cgg ctg aag aac ata ccc ccc ctc acc gcc aac cag cag ttc ctg      576
Asn Arg Leu Lys Asn Ile Pro Pro Leu Thr Ala Asn Gln Gln Phe Leu
            180                 185                 190 atc gcg agg ctg gtg tgg tac cag gag ggg tac gag cag ccg tcg gag      624
Ile Ala Arg Leu Val Trp Tyr Gln Glu Gly Tyr Glu Gln Pro Ser Glu
        195                 200                 205 gaa gat ctc aag aga gtt aca cag aca tgg cag tta gaa gaa gaa gaa      672
Glu Asp Leu Lys Arg Val Thr Gln Thr Trp Gln Leu Glu Glu Glu Glu
210                 215                 220 gag gag gaa act gac atg ccc ttc cgt cag atc aca gag atg acg atc      720
Glu Glu Glu Thr Asp Met Pro Phe Arg Gln Ile Thr Glu Met Thr Ile
225                 230                 235                 240 tta aca gtg cag ctt att gta gaa ttc gca aag gga cta ccg gga ttc      768
Leu Thr Val Gln Leu Ile Val Glu Phe Ala Lys Gly Leu Pro Gly Phe
                245                 250                 255 tcc aag ata tct cag tcc gat caa att aca tta tta aag gcg tca tca      816
Ser Lys Ile Ser Gln Ser Asp Gln Ile Thr Leu Leu Lys Ala Ser Ser
            260                 265                 270 agc gaa gtg atg atg ctg cga gtg gcg cga cgg tac gac gcg gcg acg      864
Ser Glu Val Met Met Leu Arg Val Ala Arg Arg Tyr Asp Ala Ala Thr
        275                 280                 285 gac agc gtg ctg ttc gcg aac aac cag gcg tac acg cgc gac aac tac      912
Asp Ser Val Leu Phe Ala Asn Asn Gln Ala Tyr Thr Arg Asp Asn Tyr
290                 295                 300 cgc aag gcg ggc atg tcc tac gtc atc gag gac ctg ctg cac ttc tgt      960
Arg Lys Ala Gly Met Ser Tyr Val Ile Glu Asp Leu Leu His Phe Cys
305                 310                 315                 320 cgg tgt atg tac tcc atg agc atg gac aat gtg cac tac gcg ctg ctc     1008
Arg Cys Met Tyr Ser Met Ser Met Asp Asn Val His Tyr Ala Leu Leu
                325                 330                 335 acc gcc atc gtt ata ttc tca gac cgg cca ggc ctc gag caa ccc ctt     1056
Thr Ala Ile Val Ile Phe Ser Asp Arg Pro Gly Leu Glu Gln Pro Leu
            340                 345                 350 tta gtg gag gaa atc cag aga tac tac ttg aag acg ctg cgg gtt tac     1104
Leu Val Glu Glu Ile Gln Arg Tyr Tyr Leu Lys Thr Leu Arg Val Tyr
        355                 360                 365 att tta aat cag cac agc gcg tcg cct cgc tgc gcc gtg ctg ttc ggc     1152
Ile Leu Asn Gln His Ser Ala Ser Pro Arg Cys Ala Val Leu Phe Gly
370                 375                 380 aag atc ctc ggc gtg ctg acg gaa ctg cgc acg ctc ggc acg cag aac     1200
Lys Ile Leu Gly Val Leu Thr Glu Leu Arg Thr Leu Gly Thr Gln Asn
385                 390                 395                 400 tcc aac atg tgc atc tcg ctg aag ctg aag aac agg aaa ctt ccg cca     1248
Ser Asn Met Cys Ile Ser Leu Lys Leu Lys Asn Arg Lys Leu Pro Pro
                405                 410                 415 ttc ctc gag gag atc tgg gac gtg gcc gaa gtg tcg acg acg aag ctt     1296
Phe Leu Glu Glu Ile Trp Asp Val Ala Glu Val Ser Thr Thr Lys Leu
            420                 425                 430
```

-continued

```
gcc ccc ccg acc gat gtc agc ctg ggg gac gag ctc cac tta gac ggc      1344
Ala Pro Pro Thr Asp Val Ser Leu Gly Asp Glu Leu His Leu Asp Gly
        435                 440                 445 gag gac gtg gcg atg gcg cat gcc gac gcg cta gac gat ttc gat ctg      1392
Glu Asp Val Ala Met Ala His Ala Asp Ala Leu Asp Asp Phe Asp Leu
    450                 455                 460 gac atg ttg ggg gac ggg gat tcc ccg ggt ccg gga ttt acc ccc cac      1440
Asp Met Leu Gly Asp Gly Asp Ser Pro Gly Pro Gly Phe Thr Pro His
465                 470                 475                 480 gac tcc gcc ccc tac ggc gct ctg gat atg gcc gac ttc gag ttt gag      1488
Asp Ser Ala Pro Tyr Gly Ala Leu Asp Met Ala Asp Phe Glu Phe Glu
                485                 490                 495 cag atg ttt acc gat gcc ctt gga att gac gag tac ggt ggg tag          1533
Gln Met Phe Thr Asp Ala Leu Gly Ile Asp Glu Tyr Gly Gly
            500                 505                 510

<210> SEQ ID NO 80
<211> LENGTH: 510
<212> TYPE: PRT
<213> ORGANISM: Synthetic construct

<400> SEQUENCE: 80

Met Gly Arg Glu Glu Leu Ser Pro Ala Ser Ser Val Asn Gly Cys Ser
1               5                   10                  15

Thr Asp Gly Glu Ala Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Thr Gln
            100                 105                 110

Cys Ala Gln Lys Arg Lys Glu Lys Lys Ala Gln Arg Glu Lys Asp Lys
        115                 120                 125

Leu Pro Val Ser Thr Thr Thr Val Asp Asp His Met Pro Pro Ile Met
    130                 135                 140

Gln Cys Asp Pro Pro Pro Glu Ala Ala Arg Ile Leu Glu Cys Leu
145                 150                 155                 160

Gln His Glu Val Val Pro Arg Phe Leu Ser Glu Lys Leu Met Glu Gln
                165                 170                 175

Asn Arg Leu Lys Asn Ile Pro Pro Leu Thr Ala Asn Gln Gln Phe Leu
            180                 185                 190

Ile Ala Arg Leu Val Trp Tyr Gln Glu Gly Tyr Glu Gln Pro Ser Glu
        195                 200                 205

Glu Asp Leu Lys Arg Val Thr Gln Thr Trp Gln Leu Glu Glu Glu Glu
    210                 215                 220

Glu Glu Glu Thr Asp Met Pro Phe Arg Gln Ile Thr Glu Met Thr Ile
225                 230                 235                 240

Leu Thr Val Gln Leu Ile Val Glu Phe Ala Lys Gly Leu Pro Gly Phe
                245                 250                 255

Ser Lys Ile Ser Gln Ser Asp Gln Ile Thr Leu Leu Lys Ala Ser Ser
            260                 265                 270
```

```
Ser Glu Val Met Met Leu Arg Val Ala Arg Arg Tyr Asp Ala Ala Thr
        275                 280                 285

Asp Ser Val Leu Phe Ala Asn Asn Gln Ala Tyr Thr Arg Asp Asn Tyr
        290                 295                 300

Arg Lys Ala Gly Met Ser Tyr Val Ile Glu Asp Leu Leu His Phe Cys
305                 310                 315                 320

Arg Cys Met Tyr Ser Met Ser Met Asp Asn Val His Tyr Ala Leu Leu
                325                 330                 335

Thr Ala Ile Val Ile Phe Ser Asp Arg Pro Gly Leu Glu Gln Pro Leu
            340                 345                 350

Leu Val Glu Glu Ile Gln Arg Tyr Tyr Leu Lys Thr Leu Arg Val Tyr
        355                 360                 365

Ile Leu Asn Gln His Ser Ala Ser Pro Arg Cys Ala Val Leu Phe Gly
        370                 375                 380

Lys Ile Leu Gly Val Leu Thr Glu Leu Arg Thr Leu Gly Thr Gln Asn
385                 390                 395                 400

Ser Asn Met Cys Ile Ser Leu Lys Leu Lys Asn Arg Lys Leu Pro Pro
                405                 410                 415

Phe Leu Glu Glu Ile Trp Asp Val Ala Glu Val Ser Thr Thr Lys Leu
            420                 425                 430

Ala Pro Pro Thr Asp Val Ser Leu Gly Asp Glu Leu His Leu Asp Gly
            435                 440                 445

Glu Asp Val Ala Met Ala His Ala Asp Ala Leu Asp Asp Phe Asp Leu
450                 455                 460

Asp Met Leu Gly Asp Gly Asp Ser Pro Gly Pro Gly Phe Thr Pro His
465                 470                 475                 480

Asp Ser Ala Pro Tyr Gly Ala Leu Asp Met Ala Asp Phe Glu Phe Glu
                485                 490                 495

Gln Met Phe Thr Asp Ala Leu Gly Ile Asp Glu Tyr Gly Gly
                500                 505                 510

<210> SEQ ID NO 81
<211> LENGTH: 1437
<212> TYPE: DNA
<213> ORGANISM: Synthetic construct
<220> FEATURE:
<221> NAME/KEY: CDS
<222> LOCATION: (1)..(1437)
<223> OTHER INFORMATION: Ecdysone Receptor chimera LLV

<400> SEQUENCE: 81 atg ggc cgg gag gac ctc tcg ccg cta agc agt ctg aac ggt tac agc     48
Met Gly Arg Glu Asp Leu Ser Pro Leu Ser Ser Leu Asn Gly Tyr Ser
1               5                   10                  15 gcg gac agc tgt gac gcc aaa aag aag aag ggc gct gca ccg cgc cag     96
Ala Asp Ser Cys Asp Ala Lys Lys Lys Lys Gly Ala Ala Pro Arg Gln
            20                  25                  30 cag gag gag ctg tgc ctc gtc tgt gga gac cgc gcc tcc gga tac cac    144
Gln Glu Glu Leu Cys Leu Val Cys Gly Asp Arg Ala Ser Gly Tyr His
        35                  40                  45 tac aat gct ctc acc tgc gag ggc tgc aaa ggt ttc ttc agg agg agc    192
Tyr Asn Ala Leu Thr Cys Glu Gly Cys Lys Gly Phe Phe Arg Arg Ser
    50                  55                  60 ata aca aaa aat gcc gtg tac cag tgc aaa tat ggc aat aat tgt gaa    240
Ile Thr Lys Asn Ala Val Tyr Gln Cys Lys Tyr Gly Asn Asn Cys Glu
65                  70                  75                  80 att gat atg tat atg agg aga aag tgc cag gag tgc cga ctg aag aag    288
```

-continued

```
Ile Asp Met Tyr Met Arg Arg Lys Cys Gln Glu Cys Arg Leu Lys Lys
                85                  90                  95 tgc ctc aca gtg ggc atg agg cca gag tgt gta gta cct gaa tac caa       336
Cys Leu Thr Val Gly Met Arg Pro Glu Cys Val Val Pro Glu Tyr Gln
            100                 105                 110 tgt gca gtg aaa aga aaa gag aaa aag gca caa aaa gat aaa gat aaa       384
Cys Ala Val Lys Arg Lys Glu Lys Lys Ala Gln Lys Asp Lys Asp Lys
            115                 120                 125 cct aat tct act acg aat ggt tca cca gag gtg atg atg ttg aaa gac       432
Pro Asn Ser Thr Thr Asn Gly Ser Pro Glu Val Met Met Leu Lys Asp
        130                 135                 140 ata gat gcc aag gtg gaa cca gaa aga cct tta tca aat ggg ata aaa       480
Ile Asp Ala Lys Val Glu Pro Glu Arg Pro Leu Ser Asn Gly Ile Lys
145                 150                 155                 160 cct gta agt cct gaa cag gaa gag ctt ata cat agg ctt gtg tac ttc       528
Pro Val Ser Pro Glu Gln Glu Glu Leu Ile His Arg Leu Val Tyr Phe
                165                 170                 175 cag aat gaa tat gag tct cct tcc gaa gaa gat tta aga cga gtt acg       576
Gln Asn Glu Tyr Glu Ser Pro Ser Glu Glu Asp Leu Arg Arg Val Thr
            180                 185                 190 agt caa cct acg gaa gga gag gac caa agt gat gta agg ttt cga cac       624
Ser Gln Pro Thr Glu Gly Glu Asp Gln Ser Asp Val Arg Phe Arg His
            195                 200                 205 atc act gag atc aca ata tta act gtt caa cta att gtt gaa ttt gcc       672
Ile Thr Glu Ile Thr Ile Leu Thr Val Gln Leu Ile Val Glu Phe Ala
        210                 215                 220 aag cgg ttg cca gga ttt gac aaa ctg cta cgg gaa gat cag ata gca       720
Lys Arg Leu Pro Gly Phe Asp Lys Leu Leu Arg Glu Asp Gln Ile Ala
225                 230                 235                 240 tta ctg aag gca tgt tcc agt gaa gta atg atg ttc cgc atg gca cga       768
Leu Leu Lys Ala Cys Ser Ser Glu Val Met Met Phe Arg Met Ala Arg
                245                 250                 255 cgc tat gat gta aat tca gac tcc ata ctt ttt gcc aat aat cag cct       816
Arg Tyr Asp Val Asn Ser Asp Ser Ile Leu Phe Ala Asn Asn Gln Pro
            260                 265                 270 tac act aag gat tcc tac aac ctt gct ggt atg gga gaa acg ata gaa       864
Tyr Thr Lys Asp Ser Tyr Asn Leu Ala Gly Met Gly Glu Thr Ile Glu
            275                 280                 285 gac atg ttg cgg ttc tgc aga cag atg tat gca atg aag gtt gat aat       912
Asp Met Leu Arg Phe Cys Arg Gln Met Tyr Ala Met Lys Val Asp Asn
        290                 295                 300 gca gaa tat gcc ctt ctg act gca ata gtc ata ttt tca gag cgc cca       960
Ala Glu Tyr Ala Leu Leu Thr Ala Ile Val Ile Phe Ser Glu Arg Pro
305                 310                 315                 320 tct ctt gtt gaa ggg tgg aag gtg gag aag ata caa gaa atc tac ctg      1008
Ser Leu Val Glu Gly Trp Lys Val Glu Lys Ile Gln Glu Ile Tyr Leu
                325                 330                 335 gaa gct ctc aaa gca tat gtg gac aac agg cgg cgt cct aag tct gga      1056
Glu Ala Leu Lys Ala Tyr Val Asp Asn Arg Arg Arg Pro Lys Ser Gly
            340                 345                 350 aca att ttt gca aag ttg ttg tca gtt ctt act gaa ctg cgt act cta      1104
Thr Ile Phe Ala Lys Leu Leu Ser Val Leu Thr Glu Leu Arg Thr Leu
            355                 360                 365 gga aac cag aac tca gaa atg tgc ttc tct ctc aaa ctg aag aac aag      1152
Gly Asn Gln Asn Ser Glu Met Cys Phe Ser Leu Lys Leu Lys Asn Lys
        370                 375                 380 aag ctg cca ccg ttc ctt gct gag atc tgg gat gtg atc cca aag ctt      1200
Lys Leu Pro Pro Phe Leu Ala Glu Ile Trp Asp Val Ile Pro Lys Leu
385                 390                 395                 400
```

```
gcc ccc ccg acc gat gtc agc ctg ggg gac gag ctc cac tta gac ggc        1248
Ala Pro Pro Thr Asp Val Ser Leu Gly Asp Glu Leu His Leu Asp Gly
            405                 410                 415 gag gac gtg gcg atg gcg cat gcc gac gcg cta gac gat ttc gat ctg        1296
Glu Asp Val Ala Met Ala His Ala Asp Ala Leu Asp Asp Phe Asp Leu
        420                 425                 430 gac atg ttg ggg gac ggg gat tcc ccg ggt ccg gga ttt acc ccc cac        1344
Asp Met Leu Gly Asp Gly Asp Ser Pro Gly Pro Gly Phe Thr Pro His
    435                 440                 445 gac tcc gcc ccc tac ggc gct ctg gat atg gcc gac ttc gag ttt gag        1392
Asp Ser Ala Pro Tyr Gly Ala Leu Asp Met Ala Asp Phe Glu Phe Glu
450                 455                 460 cag atg ttt acc gat gcc ctt gga att gac gag tac ggt ggg tag            1437
Gln Met Phe Thr Asp Ala Leu Gly Ile Asp Glu Tyr Gly Gly
465                 470                 475
```

<210> SEQ ID NO 82
<211> LENGTH: 478
<212> TYPE: PRT
<213> ORGANISM: Synthetic construct

<400> SEQUENCE: 82

```
Met Gly Arg Glu Asp Leu Ser Pro Leu Ser Leu Asn Gly Tyr Ser
1               5                   10                  15

Ala Asp Ser Cys Asp Ala Lys Lys Lys Gly Ala Ala Pro Arg Gln
            20                  25                  30

Gln Glu Glu Leu Cys Leu Val Cys Gly Asp Arg Ala Ser Gly Tyr His
            35                  40                  45

Tyr Asn Ala Leu Thr Cys Glu Gly Cys Lys Gly Phe Phe Arg Arg Ser
    50                  55                  60

Ile Thr Lys Asn Ala Val Tyr Gln Cys Lys Tyr Gly Asn Asn Cys Glu
65                  70                  75                  80

Ile Asp Met Tyr Met Arg Arg Lys Cys Gln Glu Cys Arg Leu Lys Lys
                85                  90                  95

Cys Leu Thr Val Gly Met Arg Pro Glu Cys Val Val Pro Glu Tyr Gln
            100                 105                 110

Cys Ala Val Lys Arg Lys Glu Lys Lys Ala Gln Lys Asp Lys Asp Lys
        115                 120                 125

Pro Asn Ser Thr Thr Asn Gly Ser Pro Glu Val Met Met Leu Lys Asp
    130                 135                 140

Ile Asp Ala Lys Val Glu Pro Glu Arg Pro Leu Ser Asn Gly Ile Lys
145                 150                 155                 160

Pro Val Ser Pro Glu Gln Glu Glu Leu Ile His Arg Leu Val Tyr Phe
                165                 170                 175

Gln Asn Glu Tyr Glu Ser Pro Ser Glu Glu Asp Leu Arg Arg Val Thr
            180                 185                 190

Ser Gln Pro Thr Glu Gly Glu Asp Gln Ser Asp Val Arg Phe Arg His
        195                 200                 205

Ile Thr Glu Ile Thr Ile Leu Thr Val Gln Leu Ile Val Glu Phe Ala
    210                 215                 220

Lys Arg Leu Pro Gly Phe Asp Lys Leu Leu Arg Glu Asp Gln Ile Ala
225                 230                 235                 240

Leu Leu Lys Ala Cys Ser Ser Glu Val Met Met Phe Arg Met Ala Arg
                245                 250                 255

Arg Tyr Asp Val Asn Ser Asp Ser Ile Leu Phe Ala Asn Asn Gln Pro
            260                 265                 270
```

-continued

```
Tyr Thr Lys Asp Ser Tyr Asn Leu Ala Gly Met Gly Glu Thr Ile Glu
        275                 280                 285

Asp Met Leu Arg Phe Cys Arg Gln Met Tyr Ala Met Lys Val Asp Asn
        290                 295                 300

Ala Glu Tyr Ala Leu Leu Thr Ala Ile Val Ile Phe Ser Glu Arg Pro
305                 310                 315                 320

Ser Leu Val Glu Gly Trp Lys Val Glu Lys Ile Gln Glu Ile Tyr Leu
                325                 330                 335

Glu Ala Leu Lys Ala Tyr Val Asp Asn Arg Arg Arg Pro Lys Ser Gly
            340                 345                 350

Thr Ile Phe Ala Lys Leu Leu Ser Val Leu Thr Glu Leu Arg Thr Leu
        355                 360                 365

Gly Asn Gln Asn Ser Glu Met Cys Phe Ser Leu Lys Leu Lys Asn Lys
    370                 375                 380

Lys Leu Pro Pro Phe Leu Ala Glu Ile Trp Asp Val Ile Pro Lys Leu
385                 390                 395                 400

Ala Pro Pro Thr Asp Val Ser Leu Gly Asp Glu Leu His Leu Asp Gly
                405                 410                 415

Glu Asp Val Ala Met Ala His Ala Asp Ala Leu Asp Asp Phe Asp Leu
            420                 425                 430

Asp Met Leu Gly Asp Gly Asp Ser Pro Gly Pro Gly Phe Thr Pro His
        435                 440                 445

Asp Ser Ala Pro Tyr Gly Ala Leu Asp Met Ala Asp Phe Glu Phe Glu
    450                 455                 460

Gln Met Phe Thr Asp Ala Leu Gly Ile Asp Glu Tyr Gly Gly
465                 470                 475
```

<210> SEQ ID NO 83
<211> LENGTH: 1464
<212> TYPE: DNA
<213> ORGANISM: Synthetic construct
<220> FEATURE:
<221> NAME/KEY: CDS
<222> LOCATION: (1)..(1464)
<223> OTHER INFORMATION: Ecdysone Receptor chimera LMV

<400> SEQUENCE: 83

```
atg ggc cgg gag gac ctc tcg ccg cta agc agt ctg aac ggt tac agc      48
Met Gly Arg Glu Asp Leu Ser Pro Leu Ser Ser Leu Asn Gly Tyr Ser
1               5                   10                  15 gcg gac agc tgt gac gcc aaa aag aag aag ggc gct gca ccg cgc cag      96
Ala Asp Ser Cys Asp Ala Lys Lys Lys Lys Gly Ala Ala Pro Arg Gln
                20                  25                  30 cag gag gag ctg tgc ctc gtc tgt gga gac cgc gcc tcc gga tac cac     144
Gln Glu Glu Leu Cys Leu Val Cys Gly Asp Arg Ala Ser Gly Tyr His
            35                  40                  45 tac aat gct ctc acc tgc gag ggc tgc aaa ggt ttc ttc agg agg agc     192
Tyr Asn Ala Leu Thr Cys Glu Gly Cys Lys Gly Phe Phe Arg Arg Ser
        50                  55                  60 ata aca aaa aat gcc gtg tac cag tgc aaa tat ggc aat aat tgt gaa     240
Ile Thr Lys Asn Ala Val Tyr Gln Cys Lys Tyr Gly Asn Asn Cys Glu
65                  70                  75                  80 att gat atg tat atg agg aga aag tgc cag gag tgc cga ctg aag aag     288
Ile Asp Met Tyr Met Arg Arg Lys Cys Gln Glu Cys Arg Leu Lys Lys
                85                  90                  95 tgc ctc aca gtg ggc atg agg cca gag tgt gta gta cct gaa tac caa     336
Cys Leu Thr Val Gly Met Arg Pro Glu Cys Val Val Pro Glu Tyr Gln
                100                 105                 110
```

-continued

| | |
|---|---|
| tgt gca gtg aaa aga aaa gag aaa aag gca caa aaa gat aaa gat aaa<br>Cys Ala Val Lys Arg Lys Glu Lys Lys Ala Gln Lys Asp Lys Asp Lys<br>            115                      120                      125 | 384 |
| cct aat tct act acg aat ggt tca cca gag gtg atg atg ttg aaa gac<br>Pro Asn Ser Thr Thr Asn Gly Ser Pro Glu Val Met Met Leu Lys Asp<br>130                      135                      140 | 432 |
| ata gat gcc aag gtg gaa cca gaa aga cct tta tca aat ggg ata aaa<br>Ile Asp Ala Lys Val Glu Pro Glu Arg Pro Leu Ser Asn Gly Ile Lys<br>145                      150                      155                      160 | 480 |
| cct gta agt cct gaa cag gaa gag ctt ata cat agg ctt gtg tgg tac<br>Pro Val Ser Pro Glu Gln Glu Glu Leu Ile His Arg Leu Val Trp Tyr<br>                      165                      170                      175 | 528 |
| cag gag ggg tac gag cag ccg tcg gag gaa gat ctc aag aga gtt aca<br>Gln Glu Gly Tyr Glu Gln Pro Ser Glu Glu Asp Leu Lys Arg Val Thr<br>                      180                      185                      190 | 576 |
| cag aca tgg cag tta gaa gaa gaa gag gag gaa act gac atg ccc<br>Gln Thr Trp Gln Leu Glu Glu Glu Glu Glu Glu Thr Asp Met Pro<br>                      195                      200                      205 | 624 |
| ttc cgt cag atc aca gag atg acg atc tta aca gtg cag ctt att gta<br>Phe Arg Gln Ile Thr Glu Met Thr Ile Leu Thr Val Gln Leu Ile Val<br>            210                      215                      220 | 672 |
| gaa ttc gca aag gga cta ccg gga ttc tcc aag ata tct cag tcc gat<br>Glu Phe Ala Lys Gly Leu Pro Gly Phe Ser Lys Ile Ser Gln Ser Asp<br>225                      230                      235                      240 | 720 |
| caa att aca tta tta aag gcg tca tca agc gaa gtg atg atg ctg cga<br>Gln Ile Thr Leu Leu Lys Ala Ser Ser Ser Glu Val Met Met Leu Arg<br>                      245                      250                      255 | 768 |
| gtg gcg cga cgg tac gac gcg gcg acg gac agc gtg ctg ttc gcg aac<br>Val Ala Arg Arg Tyr Asp Ala Ala Thr Asp Ser Val Leu Phe Ala Asn<br>            260                      265                      270 | 816 |
| aac cag gcg tac acg cgc gac aac tac cgc aag gcg ggc atg tcc tac<br>Asn Gln Ala Tyr Thr Arg Asp Asn Tyr Arg Lys Ala Gly Met Ser Tyr<br>                      275                      280                      285 | 864 |
| gtc atc gag gac ctg ctg cac ttc tgt cgg tgt atg tac tcc atg agc<br>Val Ile Glu Asp Leu Leu His Phe Cys Arg Cys Met Tyr Ser Met Ser<br>            290                      295                      300 | 912 |
| atg gac aat gtg cac tac gcg ctg ctc acc gcc atc gtt ata ttc tca<br>Met Asp Asn Val His Tyr Ala Leu Leu Thr Ala Ile Val Ile Phe Ser<br>305                      310                      315                      320 | 960 |
| gac cgg cca ggc ctc gag caa ccc ctt tta gtg gag gaa atc cag aga<br>Asp Arg Pro Gly Leu Glu Gln Pro Leu Leu Val Glu Glu Ile Gln Arg<br>                      325                      330                      335 | 1008 |
| tac tac ttg aag acg ctg cgg gtt tac att tta aat cag cac agc gcg<br>Tyr Tyr Leu Lys Thr Leu Arg Val Tyr Ile Leu Asn Gln His Ser Ala<br>                      340                      345                      350 | 1056 |
| tcg cct cgc tgc gcc gtg ctg ttc ggc aag atc ctc ggc gtg ctg acg<br>Ser Pro Arg Cys Ala Val Leu Phe Gly Lys Ile Leu Gly Val Leu Thr<br>            355                      360                      365 | 1104 |
| gaa ctg cgc acg ctc ggc acg cag aac tcc aac atg tgc atc tcg ctg<br>Glu Leu Arg Thr Leu Gly Thr Gln Asn Ser Asn Met Cys Ile Ser Leu<br>370                      375                      380 | 1152 |
| aag ctg aag aac agg aaa ctt ccg cca ttc ctc gag gag atc tgg gac<br>Lys Leu Lys Asn Arg Lys Leu Pro Pro Phe Leu Glu Glu Ile Trp Asp<br>385                      390                      395                      400 | 1200 |
| gtg gcc gaa gtg tcg acg acg aag ctt gcc ccc cgg acc gat gtc agc<br>Val Ala Glu Val Ser Thr Thr Lys Leu Ala Pro Pro Thr Asp Val Ser<br>                      405                      410                      415 | 1248 |
| ctg ggg gac gag ctc cac tta gac ggc gag gac gtg gcg atg gcg cat<br>Leu Gly Asp Glu Leu His Leu Asp Gly Glu Asp Val Ala Met Ala His<br>            420                      425                      430 | 1296 |

```
gcc gac gcg cta gac gat ttc gat ctg gac atg ttg ggg gac ggg gat      1344
Ala Asp Ala Leu Asp Asp Phe Asp Leu Asp Met Leu Gly Asp Gly Asp
            435                 440                 445 tcc ccg ggt ccg gga ttt acc ccc cac gac tcc gcc ccc tac ggc gct      1392
Ser Pro Gly Pro Gly Phe Thr Pro His Asp Ser Ala Pro Tyr Gly Ala
450                 455                 460 ctg gat atg gcc gac ttc gag ttt gag cag atg ttt acc gat gcc ctt      1440
Leu Asp Met Ala Asp Phe Glu Phe Glu Gln Met Phe Thr Asp Ala Leu
465                 470                 475                 480 gga att gac gag tac ggt ggg tag                                      1464
Gly Ile Asp Glu Tyr Gly Gly
                485

<210> SEQ ID NO 84
<211> LENGTH: 487
<212> TYPE: PRT
<213> ORGANISM: Synthetic construct

<400> SEQUENCE: 84
```

Met Gly Arg Glu Asp Leu Ser Pro Leu Ser Ser Leu Asn Gly Tyr Ser
1               5                   10                  15

Ala Asp Ser Cys Asp Ala Lys Lys Lys Gly Ala Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
50                  55                  60

Ile Thr Lys Asn Ala Val Tyr Gln Cys Lys Tyr Gly Asn Asn Cys Glu
65                  70                  75                  80

Ile Asp Met Tyr Met Arg Arg Lys Cys Gln Glu Cys Arg Leu Lys Lys
                85                  90                  95

Cys Leu Thr Val Gly Met Arg Pro Glu Cys Val Val Pro Glu Tyr Gln
            100                 105                 110

Cys Ala Val Lys Arg Lys Glu Lys Lys Ala Gln Lys Asp Lys Asp Lys
        115                 120                 125

Pro Asn Ser Thr Thr Asn Gly Ser Pro Glu Val Met Met Leu Lys Asp
130                 135                 140

Ile Asp Ala Lys Val Glu Pro Glu Arg Pro Leu Ser Asn Gly Ile Lys
145                 150                 155                 160

Pro Val Ser Pro Glu Gln Glu Glu Leu Ile His Arg Leu Val Trp Tyr
                165                 170                 175

Gln Glu Gly Tyr Glu Gln Pro Ser Glu Glu Asp Leu Lys Arg Val Thr
            180                 185                 190

Gln Thr Trp Gln Leu Glu Glu Glu Glu Glu Glu Thr Asp Met Pro
        195                 200                 205

Phe Arg Gln Ile Thr Glu Met Thr Ile Leu Thr Val Gln Leu Ile Val
        210                 215                 220

Glu Phe Ala Lys Gly Leu Pro Gly Phe Ser Lys Ile Ser Gln Ser Asp
225                 230                 235                 240

Gln Ile Thr Leu Leu Lys Ala Ser Ser Glu Val Met Met Leu Arg
            245                 250                 255

Val Ala Arg Arg Tyr Asp Ala Ala Thr Asp Ser Val Leu Phe Ala Asn
            260                 265                 270

Asn Gln Ala Tyr Thr Arg Asp Asn Tyr Arg Lys Ala Gly Met Ser Tyr
        275                 280                 285

```
Val Ile Glu Asp Leu Leu His Phe Cys Arg Cys Met Tyr Ser Met Ser
    290                 295                 300

Met Asp Asn Val His Tyr Ala Leu Leu Thr Ala Ile Val Ile Phe Ser
305                 310                 315                 320

Asp Arg Pro Gly Leu Glu Gln Pro Leu Leu Val Glu Glu Ile Gln Arg
                325                 330                 335

Tyr Tyr Leu Lys Thr Leu Arg Val Tyr Ile Leu Asn Gln His Ser Ala
                340                 345                 350

Ser Pro Arg Cys Ala Val Leu Phe Gly Lys Ile Leu Gly Val Leu Thr
                355                 360                 365

Glu Leu Arg Thr Leu Gly Thr Gln Asn Ser Asn Met Cys Ile Ser Leu
    370                 375                 380

Lys Leu Lys Asn Arg Lys Leu Pro Pro Phe Leu Glu Glu Ile Trp Asp
385                 390                 395                 400

Val Ala Glu Val Ser Thr Thr Lys Leu Ala Pro Pro Thr Asp Val Ser
                405                 410                 415

Leu Gly Asp Glu Leu His Leu Asp Gly Glu Asp Val Ala Met Ala His
                420                 425                 430

Ala Asp Ala Leu Asp Asp Phe Asp Leu Asp Met Leu Gly Asp Gly Asp
                435                 440                 445

Ser Pro Gly Pro Gly Phe Thr Pro His Asp Ser Ala Pro Tyr Gly Ala
450                 455                 460

Leu Asp Met Ala Asp Phe Glu Phe Glu Gln Met Phe Thr Asp Ala Leu
465                 470                 475                 480

Gly Ile Asp Glu Tyr Gly Gly
                485

<210> SEQ ID NO 85
<211> LENGTH: 1491
<212> TYPE: DNA
<213> ORGANISM: Synthetic construct
<220> FEATURE:
<221> NAME/KEY: CDS
<222> LOCATION: (1)..(1491)
<223> OTHER INFORMATION: Ecdysone Receptor chimera MLV

<400> SEQUENCE: 85 atg ggt cga gaa gaa tta tca ccg gcc tca agt ata aat gga tgt agt      48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag      96
Thr Asp Gly Glu Pro Arg Arg Gln Lys Lys Gly Pro Ala Pro Arg Gln
            20                  25                  30 cag gag gaa ctg tgc ctt gtt tgc ggc gac agg gct tcg gga tat cac     144
Gln Glu Glu Leu Cys Leu Val Cys Gly Asp Arg Ala Ser Gly Tyr His
        35                  40                  45 tat aac gcg ctt acg tgc gaa gga tgt aaa ggg ttc ttc agg cgg agt     192
Tyr Asn Ala Leu Thr Cys Glu Gly Cys Lys Gly Phe Phe Arg Arg Ser
    50                  55                  60 gtg acc aag aat gcg gta tat att tgt aaa ttt gga cac gcc tgc gag     240
Val Thr Lys Asn Ala Val Tyr Ile Cys Lys Phe Gly His Ala Cys Glu
65                  70                  75                  80 atg gac atg tac atg agg aga aaa tgc caa gag tgt cgg ttg aag aaa     288
Met Asp Met Tyr Met Arg Arg Lys Cys Gln Glu Cys Arg Leu Lys Lys
                85                  90                  95 tgc ctc gcg gtg ggc atg agg ccc gag tgc gtc gtc cca gag tcc acg     336
Cys Leu Ala Val Gly Met Arg Pro Glu Cys Val Val Pro Glu Ser Thr
            100                 105                 110
```

```
tgc aag aac aaa aga aga gaa aag gaa gca cag aga gaa aaa gac aaa       384
Cys Lys Asn Lys Arg Arg Glu Lys Glu Ala Gln Arg Glu Lys Asp Lys
        115                 120                 125 ctg cca gtc agt acg acg aca gtg gac gat cat atg cct gcc ata atg       432
Leu Pro Val Ser Thr Thr Thr Val Asp Asp His Met Pro Ala Ile Met
130                 135                 140 caa tgt gac cct ccg ccc cca gag gcg gca agg att cac gaa gtg gtc       480
Gln Cys Asp Pro Pro Pro Pro Glu Ala Ala Arg Ile His Glu Val Val
145                 150                 155                 160 ccg agg ttc cta acg gag aag cta atg gag cag aac aga ctg aag aat       528
Pro Arg Phe Leu Thr Glu Lys Leu Met Glu Gln Asn Arg Leu Lys Asn
                165                 170                 175 gtg acg ccg ctg tcg gcg aac cag aag tcc ctg atc gcg agg ctc gtg       576
Val Thr Pro Leu Ser Ala Asn Gln Lys Ser Leu Ile Ala Arg Leu Val
            180                 185                 190 tgg tac cag aat gaa tat gag tct cct tcc gaa gaa gat tta aga cga       624
Trp Tyr Gln Asn Glu Tyr Glu Ser Pro Ser Glu Glu Asp Leu Arg Arg
        195                 200                 205 gtt acg agt caa cct acg gaa gga gag gac caa agt gat gta agg ttt       672
Val Thr Ser Gln Pro Thr Glu Gly Glu Asp Gln Ser Asp Val Arg Phe
210                 215                 220 cga cac atc act gag atc aca ata tta act gtt caa cta att gtt gaa       720
Arg His Ile Thr Glu Ile Thr Ile Leu Thr Val Gln Leu Ile Val Glu
225                 230                 235                 240 ttt gcc aag cgg ttg cca gga ttt gac aaa ctg cta cgg gaa gat cag       768
Phe Ala Lys Arg Leu Pro Gly Phe Asp Lys Leu Leu Arg Glu Asp Gln
                245                 250                 255 ata gca tta ctg aag gca tgt tcc agt gaa gta atg atg ttc cgc atg       816
Ile Ala Leu Leu Lys Ala Cys Ser Ser Glu Val Met Met Phe Arg Met
            260                 265                 270 gca cga cgc tat gat gta aat tca gac tcc ata ctt ttt gcc aat aat       864
Ala Arg Arg Tyr Asp Val Asn Ser Asp Ser Ile Leu Phe Ala Asn Asn
        275                 280                 285 cag cct tac act aag gat tcc tac aac ctt gct ggt atg gga gaa acg       912
Gln Pro Tyr Thr Lys Asp Ser Tyr Asn Leu Ala Gly Met Gly Glu Thr
290                 295                 300 ata gaa gac atg ttg cgg ttc tgc aga cag atg tat gca atg aag gtt       960
Ile Glu Asp Met Leu Arg Phe Cys Arg Gln Met Tyr Ala Met Lys Val
305                 310                 315                 320 gat aat gca gaa tat gcc ctt ctg act gca ata gtc ata ttt tca gag      1008
Asp Asn Ala Glu Tyr Ala Leu Leu Thr Ala Ile Val Ile Phe Ser Glu
                325                 330                 335 cgc cca tct ctt gtt gaa ggg tgg aag gtg gag aag ata caa gaa atc      1056
Arg Pro Ser Leu Val Glu Gly Trp Lys Val Glu Lys Ile Gln Glu Ile
            340                 345                 350 tac ctg gaa gct ctc aaa gca tat gtg gac aac agg cgg cgt cct aag      1104
Tyr Leu Glu Ala Leu Lys Ala Tyr Val Asp Asn Arg Arg Arg Pro Lys
        355                 360                 365 tct gga aca att ttt gca aag ttg ttg tca gtt ctt act gaa ctg cgt      1152
Ser Gly Thr Ile Phe Ala Lys Leu Leu Ser Val Leu Thr Glu Leu Arg
370                 375                 380 act cta gga aac cag aac tca gaa atg tgc ttc tct ctc aaa ctg aag      1200
Thr Leu Gly Asn Gln Asn Ser Glu Met Cys Phe Ser Leu Lys Leu Lys
385                 390                 395                 400 aac aag aag ctg cca ccg ttc ctt gct gag atc tgg gat gtg atc cca      1248
Asn Lys Lys Leu Pro Pro Phe Leu Ala Glu Ile Trp Asp Val Ile Pro
                405                 410                 415 aag ctt gcc ccc ccg acc gat gtc agc ctg ggg gac gag ctc cac tta      1296
Lys Leu Ala Pro Pro Thr Asp Val Ser Leu Gly Asp Glu Leu His Leu
            420                 425                 430
```

| | | | | | | | | | | | | | | | |
|---|---|---|---|---|---|---|---|---|---|---|---|---|---|---|---|
| gac | ggc | gag | gac | gtg | gcg | atg | gcg | cat | gcc | gac | gcg | cta | gac | gat | ttc | 1344 |
| Asp | Gly | Glu | Asp | Val | Ala | Met | Ala | His | Ala | Asp | Ala | Leu | Asp | Asp | Phe |
| | | | 435 | | | | 440 | | | | 445 | | | | |
| gat | ctg | gac | atg | ttg | ggg | gac | ggg | gat | tcc | ccg | ggt | ccg | gga | ttt | acc | 1392 |
| Asp | Leu | Asp | Met | Leu | Gly | Asp | Gly | Asp | Ser | Pro | Gly | Pro | Gly | Phe | Thr |
| | 450 | | | | | 455 | | | | | 460 | | | | |
| ccc | cac | gac | tcc | gcc | ccc | tac | ggc | gct | ctg | gat | atg | gcc | gac | ttc | gag | 1440 |
| Pro | His | Asp | Ser | Ala | Pro | Tyr | Gly | Ala | Leu | Asp | Met | Ala | Asp | Phe | Glu |
| 465 | | | | 470 | | | | | 475 | | | | | 480 | |
| ttt | gag | cag | atg | ttt | acc | gat | gcc | ctt | gga | att | gac | gag | tac | ggt | ggg | 1488 |
| Phe | Glu | Gln | Met | Phe | Thr | Asp | Ala | Leu | Gly | Ile | Asp | Glu | Tyr | Gly | Gly |
| | | | 485 | | | | | 490 | | | | | 495 | | |
| tag | | | | | | | | | | | | | | | | 1491 |

<210> SEQ ID NO 86
<211> LENGTH: 496
<212> TYPE: PRT
<213> ORGANISM: Synthetic construct

<400> SEQUENCE: 86

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Ser Thr
            100                 105                 110

Cys Lys Asn Lys Arg Arg Glu Lys Glu Ala Gln Arg Glu Lys Asp Lys
        115                 120                 125

Leu Pro Val Ser Thr Thr Thr Val Asp Asp His Met Pro Ala Ile Met
    130                 135                 140

Gln Cys Asp Pro Pro Pro Glu Ala Ala Arg Ile His Glu Val Val
145                 150                 155                 160

Pro Arg Phe Leu Thr Glu Lys Leu Met Glu Gln Asn Arg Leu Lys Asn
                165                 170                 175

Val Thr Pro Leu Ser Ala Asn Gln Lys Ser Leu Ile Ala Arg Leu Val
            180                 185                 190

Trp Tyr Gln Asn Glu Tyr Glu Ser Pro Ser Glu Glu Asp Leu Arg Arg
        195                 200                 205

Val Thr Ser Gln Pro Thr Glu Gly Glu Asp Gln Ser Asp Val Arg Phe
    210                 215                 220

Arg His Ile Thr Glu Ile Thr Ile Leu Thr Val Gln Leu Ile Val Glu
225                 230                 235                 240

Phe Ala Lys Arg Leu Pro Gly Phe Asp Lys Leu Leu Arg Glu Asp Gln
                245                 250                 255

Ile Ala Leu Leu Lys Ala Cys Ser Ser Glu Val Met Met Phe Arg Met
            260                 265                 270

Ala Arg Arg Tyr Asp Val Asn Ser Asp Ser Ile Leu Phe Ala Asn Asn

```
              275                 280                 285
Gln Pro Tyr Thr Lys Asp Ser Tyr Asn Leu Ala Gly Met Gly Glu Thr
        290                 295                 300

Ile Glu Asp Met Leu Arg Phe Cys Arg Gln Met Tyr Ala Met Lys Val
305                 310                 315                 320

Asp Asn Ala Glu Tyr Ala Leu Leu Thr Ala Ile Val Ile Phe Ser Glu
                325                 330                 335

Arg Pro Ser Leu Val Glu Gly Trp Lys Val Glu Lys Ile Gln Glu Ile
            340                 345                 350

Tyr Leu Glu Ala Leu Lys Ala Tyr Val Asp Asn Arg Arg Arg Pro Lys
        355                 360                 365

Ser Gly Thr Ile Phe Ala Lys Leu Leu Ser Val Leu Thr Glu Leu Arg
    370                 375                 380

Thr Leu Gly Asn Gln Asn Ser Glu Met Cys Phe Ser Leu Lys Leu Lys
385                 390                 395                 400

Asn Lys Lys Leu Pro Pro Phe Leu Ala Glu Ile Trp Asp Val Ile Pro
                405                 410                 415

Lys Leu Ala Pro Pro Thr Asp Val Ser Leu Gly Asp Glu Leu His Leu
            420                 425                 430

Asp Gly Glu Asp Val Ala Met Ala His Ala Asp Ala Leu Asp Asp Phe
        435                 440                 445

Asp Leu Asp Met Leu Gly Asp Gly Asp Ser Pro Gly Pro Gly Phe Thr
    450                 455                 460

Pro His Asp Ser Ala Pro Tyr Gly Ala Leu Asp Met Ala Asp Phe Glu
465                 470                 475                 480

Phe Glu Gln Met Phe Thr Asp Ala Leu Gly Ile Asp Glu Tyr Gly Gly
                485                 490                 495

<210> SEQ ID NO 87
<211> LENGTH: 1551
<212> TYPE: DNA
<213> ORGANISM: Synthetic construct
<220> FEATURE:
<221> NAME/KEY: CDS
<222> LOCATION: (1)..(1551)
<223> OTHER INFORMATION: Ecdysone Receptor chimera CCV

<400> SEQUENCE: 87 atg aaa ctt gat gat ggc aat atg agt gtt cac atg ggt gat gga ctt      48
Met Lys Leu Asp Asp Gly Asn Met Ser Val His Met Gly Asp Gly Leu
1               5                  10                  15 gat ggc aag aaa tca tca tcg aaa aaa gga cct gtg cca cgt caa cag      96
Asp Gly Lys Lys Ser Ser Ser Lys Lys Gly Pro Val Pro Arg Gln Gln
            20                  25                  30 gaa gag ctg tgc ctc gtt tgc gga gat cgt gcc tcg gga tat cat tat     144
Glu Glu Leu Cys Leu Val Cys Gly Asp Arg Ala Ser Gly Tyr His Tyr
        35                  40                  45 aat gct tta aca tgt gaa ggg tgc aag gga ttt ttc cgt cgt agt gtt     192
Asn Ala Leu Thr Cys Glu Gly Cys Lys Gly Phe Phe Arg Arg Ser Val
    50                  55                  60 aca aaa aat gct gtt tat tgt tgt aaa ttt ggt cat gaa tgt gaa atg     240
Thr Lys Asn Ala Val Tyr Cys Cys Lys Phe Gly His Glu Cys Glu Met
65                  70                  75                  80 gac atg tat atg aaa cga aag tgt cag gag tgc cgt ttg aaa aaa tgt     288
Asp Met Tyr Met Lys Arg Lys Cys Gln Glu Cys Arg Leu Lys Lys Cys
                85                  90                  95 ttg gct gtg gga atg cga cct gaa tgt gtc gtt cca gaa aat caa tgt     336
Leu Ala Val Gly Met Arg Pro Glu Cys Val Val Pro Glu Asn Gln Cys
```

-continued

```
            100                 105                 110
gct att aag cgg aag gag aag aag gca caa aaa gag aag gat aag gtt    384
Ala Ile Lys Arg Lys Glu Lys Lys Ala Gln Lys Glu Lys Asp Lys Val
            115                 120                 125 cca ggc att gtc gga agt aat act tcg tca tcg tct ctc ctc aat caa    432
Pro Gly Ile Val Gly Ser Asn Thr Ser Ser Ser Ser Leu Leu Asn Gln
130                 135                 140 agc ttg aat aat gga tct tta aaa aat ctc gaa att tca tat cga gag    480
Ser Leu Asn Asn Gly Ser Leu Lys Asn Leu Glu Ile Ser Tyr Arg Glu
145                 150                 155                 160 gag ctc ctc gag cag ctt atg aaa tgt gat cca ccg cct cat cca atg    528
Glu Leu Leu Glu Gln Leu Met Lys Cys Asp Pro Pro Pro His Pro Met
                165                 170                 175 caa caa ctt ttg cct gaa aag ctt tta atg gag aat cgt gca aaa ggc    576
Gln Gln Leu Leu Pro Glu Lys Leu Leu Met Glu Asn Arg Ala Lys Gly
            180                 185                 190 aca cct caa ctc acg gcc aat caa gta gcc gtt att tat aag ctt atc    624
Thr Pro Gln Leu Thr Ala Asn Gln Val Ala Val Ile Tyr Lys Leu Ile
        195                 200                 205 tgg tac caa gac ggt tat gaa cag ccg tcc gaa gaa gac tta aag cgc    672
Trp Tyr Gln Asp Gly Tyr Glu Gln Pro Ser Glu Glu Asp Leu Lys Arg
    210                 215                 220 ata aca acg gaa ctg gag gaa gaa gag gat caa gag cac gag gca aat    720
Ile Thr Thr Glu Leu Glu Glu Glu Glu Asp Gln Glu His Glu Ala Asn
225                 230                 235                 240 ttc cga tat ata aca gaa gtc aca ata ttg aca gtg caa ctg gtt gtg    768
Phe Arg Tyr Ile Thr Glu Val Thr Ile Leu Thr Val Gln Leu Val Val
                245                 250                 255 gaa ttc gca aaa ggg ctt cca gca ttt att aaa ata cca caa gaa gat    816
Glu Phe Ala Lys Gly Leu Pro Ala Phe Ile Lys Ile Pro Gln Glu Asp
            260                 265                 270 caa att act ctc ttg aag gct tgc tcc agt gaa gtt atg atg ttg cgc    864
Gln Ile Thr Leu Leu Lys Ala Cys Ser Ser Glu Val Met Met Leu Arg
        275                 280                 285 atg gct cga cga tac gat cac gat tcc gat tcg ata ttg ttt gca aat    912
Met Ala Arg Arg Tyr Asp His Asp Ser Asp Ser Ile Leu Phe Ala Asn
    290                 295                 300 aat aca gcg tac act aag caa acg tat caa tta gcg ggc atg gaa gag    960
Asn Thr Ala Tyr Thr Lys Gln Thr Tyr Gln Leu Ala Gly Met Glu Glu
305                 310                 315                 320 aca att gat gat tta ctg cac ttt tgt cga caa atg tat gca tta tct    1008
Thr Ile Asp Asp Leu Leu His Phe Cys Arg Gln Met Tyr Ala Leu Ser
                325                 330                 335 att gat aat gtc gag tat gct ctt ctc aca gcc atc gtc atc ttc tca    1056
Ile Asp Asn Val Glu Tyr Ala Leu Leu Thr Ala Ile Val Ile Phe Ser
            340                 345                 350 gat cga cct ggt cta gaa aag gct gaa atg gtg gac atc att caa agc    1104
Asp Arg Pro Gly Leu Glu Lys Ala Glu Met Val Asp Ile Ile Gln Ser
        355                 360                 365 tat tac aca gaa act ctt aag gtt tat atc gcc aat cgg cat ggt ggc    1152
Tyr Tyr Thr Glu Thr Leu Lys Val Tyr Ile Ala Asn Arg His Gly Gly
    370                 375                 380 gag tca aga tgc agc gtt caa ttt gca aaa cta ttg ggc att ctt act    1200
Glu Ser Arg Cys Ser Val Gln Phe Ala Lys Leu Leu Gly Ile Leu Thr
385                 390                 395                 400 gaa tta cga aca atg ggc aat aaa aat tct gaa atg tgc ttt tca tta    1248
Glu Leu Arg Thr Met Gly Asn Lys Asn Ser Glu Met Cys Phe Ser Leu
                405                 410                 415 aaa ctg aga aac cga aaa ctg cca cga ttc tta gaa gaa gtc tgg gat    1296
```

-continued

```
Lys Leu Arg Asn Arg Lys Leu Pro Arg Phe Leu Glu Glu Val Trp Asp
            420                 425                 430
gtc ggc gat gtc aag ctt gcc ccc ccg acc gat gtc agc ctg ggg gac      1344
Val Gly Asp Val Lys Leu Ala Pro Pro Thr Asp Val Ser Leu Gly Asp
            435                 440                 445 gag ctc cac tta gac ggc gag gac gtg gcg atg gcg cat gcc gac gcg      1392
Glu Leu His Leu Asp Gly Glu Asp Val Ala Met Ala His Ala Asp Ala
            450                 455                 460 cta gac gat ttc gat ctg gac atg ttg ggg gac ggg gat tcc ccg ggt      1440
Leu Asp Asp Phe Asp Leu Asp Met Leu Gly Asp Gly Asp Ser Pro Gly
465                 470                 475                 480 ccg gga ttt acc ccc cac gac tcc gcc ccc tac ggc gct ctg gat atg      1488
Pro Gly Phe Thr Pro His Asp Ser Ala Pro Tyr Gly Ala Leu Asp Met
                    485                 490                 495 gcc gac ttc gag ttt gag cag atg ttt acc gat gcc ctt gga att gac      1536
Ala Asp Phe Glu Phe Glu Gln Met Phe Thr Asp Ala Leu Gly Ile Asp
            500                 505                 510 gag tac ggt ggg tag                                                   1551
Glu Tyr Gly Gly
        515
```

<210> SEQ ID NO 88
<211> LENGTH: 516
<212> TYPE: PRT
<213> ORGANISM: Synthetic construct

<400> SEQUENCE: 88

```
Met Lys Leu Asp Asp Gly Asn Met Ser Val His Met Gly Asp Gly Leu
1               5                   10                  15

Asp Gly Lys Lys Ser Ser Lys Lys Gly Pro Val Pro Arg Gln Gln
            20                  25                  30

Glu Glu Leu Cys Leu Val Cys Gly Asp Arg Ala Ser Gly Tyr His Tyr
            35                  40                  45

Asn Ala Leu Thr Cys Glu Gly Cys Lys Gly Phe Phe Arg Arg Ser Val
        50                  55                  60

Thr Lys Asn Ala Val Tyr Cys Cys Lys Phe Gly His Glu Cys Glu Met
65                  70                  75                  80

Asp Met Tyr Met Lys Arg Lys Cys Gln Glu Cys Arg Leu Lys Lys Cys
                85                  90                  95

Leu Ala Val Gly Met Arg Pro Glu Cys Val Val Pro Glu Asn Gln Cys
            100                 105                 110

Ala Ile Lys Arg Lys Glu Lys Lys Ala Gln Lys Glu Lys Asp Lys Val
            115                 120                 125

Pro Gly Ile Val Gly Ser Asn Thr Ser Ser Ser Leu Leu Asn Gln
        130                 135                 140

Ser Leu Asn Asn Gly Ser Leu Lys Asn Leu Glu Ile Ser Tyr Arg Glu
145                 150                 155                 160

Glu Leu Leu Glu Gln Leu Met Lys Cys Asp Pro Pro His Pro Met
                    165                 170                 175

Gln Gln Leu Leu Pro Glu Lys Leu Leu Met Glu Asn Arg Ala Lys Gly
            180                 185                 190

Thr Pro Gln Leu Thr Ala Asn Gln Val Ala Val Ile Tyr Lys Leu Ile
            195                 200                 205

Trp Tyr Gln Asp Gly Tyr Glu Gln Pro Ser Glu Glu Asp Leu Lys Arg
        210                 215                 220

Ile Thr Thr Glu Leu Glu Glu Glu Asp Gln Glu His Glu Ala Asn
225                 230                 235                 240
```

```
Phe Arg Tyr Ile Thr Glu Val Thr Ile Leu Thr Val Gln Leu Val Val
                245                 250                 255
Glu Phe Ala Lys Gly Leu Pro Ala Phe Ile Lys Ile Pro Gln Glu Asp
            260                 265                 270
Gln Ile Thr Leu Leu Lys Ala Cys Ser Ser Glu Val Met Met Leu Arg
        275                 280                 285
Met Ala Arg Arg Tyr Asp His Asp Ser Asp Ser Ile Leu Phe Ala Asn
    290                 295                 300
Asn Thr Ala Tyr Thr Lys Gln Thr Tyr Gln Leu Ala Gly Met Glu Glu
305                 310                 315                 320
Thr Ile Asp Asp Leu Leu His Phe Cys Arg Gln Met Tyr Ala Leu Ser
                325                 330                 335
Ile Asp Asn Val Glu Tyr Ala Leu Leu Thr Ala Ile Val Ile Phe Ser
            340                 345                 350
Asp Arg Pro Gly Leu Glu Lys Ala Glu Met Val Asp Ile Ile Gln Ser
        355                 360                 365
Tyr Tyr Thr Glu Thr Leu Lys Val Tyr Ile Ala Asn Arg His Gly Gly
    370                 375                 380
Glu Ser Arg Cys Ser Val Gln Phe Ala Lys Leu Leu Gly Ile Leu Thr
385                 390                 395                 400
Glu Leu Arg Thr Met Gly Asn Lys Asn Ser Glu Met Cys Phe Ser Leu
                405                 410                 415
Lys Leu Arg Asn Arg Lys Leu Pro Arg Phe Leu Glu Glu Val Trp Asp
            420                 425                 430
Val Gly Asp Val Lys Leu Ala Pro Pro Thr Asp Val Ser Leu Gly Asp
        435                 440                 445
Glu Leu His Leu Asp Gly Glu Asp Val Ala Met Ala His Ala Asp Ala
    450                 455                 460
Leu Asp Asp Phe Asp Leu Asp Met Leu Gly Asp Gly Asp Ser Pro Gly
465                 470                 475                 480
Pro Gly Phe Thr Pro His Asp Ser Ala Pro Tyr Gly Ala Leu Asp Met
                485                 490                 495
Ala Asp Phe Glu Phe Glu Gln Met Phe Thr Asp Ala Leu Gly Ile Asp
            500                 505                 510
Glu Tyr Gly Gly
        515

<210> SEQ ID NO 89
<211> LENGTH: 1566
<212> TYPE: DNA
<213> ORGANISM: Synthetic construct
<220> FEATURE:
<221> NAME/KEY: CDS
<222> LOCATION: (1)..(1566)
<223> OTHER INFORMATION: Ecdysone Receptor chimera CMV

<400> SEQUENCE: 89 atg aaa ctt gat gat ggc aat atg agt gtt cac atg ggt gat gga ctt      48
Met Lys Leu Asp Asp Gly Asn Met Ser Val His Met Gly Asp Gly Leu
1               5                   10                  15 gat ggc aag aaa tca tca tcg aaa aaa gga cct gtg cca cgt caa cag      96
Asp Gly Lys Lys Ser Ser Ser Lys Lys Gly Pro Val Pro Arg Gln Gln
            20                  25                  30 gaa gag ctg tgc ctc gtt tgc gga gat cgt gcc tcg gga tat cat tat     144
Glu Glu Leu Cys Leu Val Cys Gly Asp Arg Ala Ser Gly Tyr His Tyr
        35                  40                  45
```

-continued

```
aat gct tta aca tgt gaa ggg tgc aag gga ttt ttc cgt cgt agt gtt      192
Asn Ala Leu Thr Cys Glu Gly Cys Lys Gly Phe Phe Arg Arg Ser Val
     50                  55                  60 aca aaa aat gct gtt tat tgt tgt aaa ttt ggt cat gaa tgt gaa atg      240
Thr Lys Asn Ala Val Tyr Cys Cys Lys Phe Gly His Glu Cys Glu Met
 65                  70                  75                  80 gac atg tat atg aaa cga aag tgt cag gag tgc cgt ttg aaa aaa tgt      288
Asp Met Tyr Met Lys Arg Lys Cys Gln Glu Cys Arg Leu Lys Lys Cys
                 85                  90                  95 ttg gct gtg gga atg cga cct gaa tgt gtc gtt cca gaa aat caa tgt      336
Leu Ala Val Gly Met Arg Pro Glu Cys Val Val Pro Glu Asn Gln Cys
            100                 105                 110 gct att aag cgg aag gag aag aag gca caa aaa gag aag gat aag gtt      384
Ala Ile Lys Arg Lys Glu Lys Lys Ala Gln Lys Glu Lys Asp Lys Val
        115                 120                 125 cca ggc att gtc gga agt aat act tcg tca tcg tct ctc ctc aat caa      432
Pro Gly Ile Val Gly Ser Asn Thr Ser Ser Ser Ser Leu Leu Asn Gln
130                 135                 140 agc ttg aat aat gga tct tta aaa aat ctc gaa att tca tat cga gag      480
Ser Leu Asn Asn Gly Ser Leu Lys Asn Leu Glu Ile Ser Tyr Arg Glu
145                 150                 155                 160 gag ctc ctc gag cag ctt atg aaa tgt gat cca ccg cct cat cca atg      528
Glu Leu Leu Glu Gln Leu Met Lys Cys Asp Pro Pro Pro His Pro Met
                165                 170                 175 caa caa ctt ttg cct gaa aag ctt tta atg gag aat cgt gca aaa ggc      576
Gln Gln Leu Leu Pro Glu Lys Leu Leu Met Glu Asn Arg Ala Lys Gly
            180                 185                 190 aca cct caa ctc acg gcc aat caa gta gcc gtt att tat aag ctt atc      624
Thr Pro Gln Leu Thr Ala Asn Gln Val Ala Val Ile Tyr Lys Leu Ile
        195                 200                 205 tgg tac cag gag ggg tac gag cag ccg tcg gag gaa gat ctc aag aga      672
Trp Tyr Gln Glu Gly Tyr Glu Gln Pro Ser Glu Glu Asp Leu Lys Arg
210                 215                 220 gtt aca cag aca tgg cag tta gaa gaa gaa gaa gag gag gaa act gac      720
Val Thr Gln Thr Trp Gln Leu Glu Glu Glu Glu Glu Glu Glu Thr Asp
225                 230                 235                 240 atg ccc ttc cgt cag atc aca gag atg acg atc tta aca gtg cag ctt      768
Met Pro Phe Arg Gln Ile Thr Glu Met Thr Ile Leu Thr Val Gln Leu
                245                 250                 255 att gta gaa ttc gca aag gga cta ccg gga ttc tcc aag ata tct cag      816
Ile Val Glu Phe Ala Lys Gly Leu Pro Gly Phe Ser Lys Ile Ser Gln
            260                 265                 270 tcc gat caa att aca tta tta aag gcg tca tca agc gaa gtg atg atg      864
Ser Asp Gln Ile Thr Leu Leu Lys Ala Ser Ser Ser Glu Val Met Met
        275                 280                 285 ctg cga gtg gcg cga cgg tac gac gcg gcg acg gac agc gtg ctg ttc      912
Leu Arg Val Ala Arg Arg Tyr Asp Ala Ala Thr Asp Ser Val Leu Phe
290                 295                 300 gcg aac aac cag gcg tac acg cgc gac aac tac cgc aag gcg ggc atg      960
Ala Asn Asn Gln Ala Tyr Thr Arg Asp Asn Tyr Arg Lys Ala Gly Met
305                 310                 315                 320 tcc tac gtc atc gag gac ctg ctg cac ttc tgt cgg tgt atg tac tcc     1008
Ser Tyr Val Ile Glu Asp Leu Leu His Phe Cys Arg Cys Met Tyr Ser
                325                 330                 335 atg agc atg gac aat gtg cac tac gcg ctg ctc acc gcc atc gtt ata     1056
Met Ser Met Asp Asn Val His Tyr Ala Leu Leu Thr Ala Ile Val Ile
            340                 345                 350 ttc tca gac cgg cca ggc ctc gag caa ccc ctt tta gtg gag gaa atc     1104
Phe Ser Asp Arg Pro Gly Leu Glu Gln Pro Leu Leu Val Glu Glu Ile
        355                 360                 365
```

-continued

```
cag aga tac tac ttg aag acg ctg cgg gtt tac att tta aat cag cac    1152
Gln Arg Tyr Tyr Leu Lys Thr Leu Arg Val Tyr Ile Leu Asn Gln His
    370                 375                 380 agc gcg tcg cct cgc tgc gcc gtg ctg ttc ggc aag atc ctc ggc gtg    1200
Ser Ala Ser Pro Arg Cys Ala Val Leu Phe Gly Lys Ile Leu Gly Val
385                 390                 395                 400 ctg acg gaa ctg cgc acg ctc ggc acg cag aac tcc aac atg tgc atc    1248
Leu Thr Glu Leu Arg Thr Leu Gly Thr Gln Asn Ser Asn Met Cys Ile
                405                 410                 415 tcg ctg aag ctg aag aac agg aaa ctt ccg cca ttc ctc gag gag atc    1296
Ser Leu Lys Leu Lys Asn Arg Lys Leu Pro Pro Phe Leu Glu Glu Ile
            420                 425                 430 tgg gac gtg gcc gaa gtg tcg acg acg aag ctt gcc ccc ccg acc gat    1344
Trp Asp Val Ala Glu Val Ser Thr Thr Lys Leu Ala Pro Pro Thr Asp
        435                 440                 445 gtc agc ctg ggg gac gag ctc cac tta gac ggc gag gac gtg gcg atg    1392
Val Ser Leu Gly Asp Glu Leu His Leu Asp Gly Glu Asp Val Ala Met
    450                 455                 460 gcg cat gcc gac gcg cta gac gat ttc gat ctg gac atg ttg ggg gac    1440
Ala His Ala Asp Ala Leu Asp Asp Phe Asp Leu Asp Met Leu Gly Asp
465                 470                 475                 480 ggg gat tcc ccg ggt ccg gga ttt acc ccc cac gac tcc gcc ccc tac    1488
Gly Asp Ser Pro Gly Pro Gly Phe Thr Pro His Asp Ser Ala Pro Tyr
                485                 490                 495 ggc gct ctg gat atg gcc gac ttc gag ttt gag cag atg ttt acc gat    1536
Gly Ala Leu Asp Met Ala Asp Phe Glu Phe Glu Gln Met Phe Thr Asp
            500                 505                 510 gcc ctt gga att gac gag tac ggt ggg tag                            1566
Ala Leu Gly Ile Asp Glu Tyr Gly Gly
        515                 520

<210> SEQ ID NO 90
<211> LENGTH: 521
<212> TYPE: PRT
<213> ORGANISM: Synthetic construct

<400> SEQUENCE: 90

Met Lys Leu Asp Asp Gly Asn Met Ser Val His Met Gly Asp Gly Leu
1               5                   10                  15

Asp Gly Lys Lys Ser Ser Lys Lys Gly Pro Val Pro Arg Gln Gln
            20                  25                  30

Glu Glu Leu Cys Leu Val Cys Gly Asp Arg Ala Ser Gly Tyr His Tyr
            35                  40                  45

Asn Ala Leu Thr Cys Glu Gly Cys Lys Gly Phe Phe Arg Arg Ser Val
    50                  55                  60

Thr Lys Asn Ala Val Tyr Cys Cys Lys Phe Gly His Glu Cys Glu Met
65                  70                  75                  80

Asp Met Tyr Met Lys Arg Lys Cys Gln Glu Cys Arg Leu Lys Lys Cys
                85                  90                  95

Leu Ala Val Gly Met Arg Pro Glu Cys Val Val Pro Glu Asn Gln Cys
            100                 105                 110

Ala Ile Lys Arg Lys Glu Lys Ala Gln Lys Glu Lys Asp Lys Val
            115                 120                 125

Pro Gly Ile Val Gly Ser Asn Thr Ser Ser Ser Leu Leu Asn Gln
        130                 135                 140

Ser Leu Asn Asn Gly Ser Leu Lys Asn Leu Glu Ile Ser Tyr Arg Glu
145                 150                 155                 160
```

-continued

```
Glu Leu Leu Glu Gln Leu Met Lys Cys Asp Pro Pro His Pro Met
                165                 170                 175
Gln Gln Leu Leu Pro Glu Lys Leu Leu Met Glu Asn Arg Ala Lys Gly
            180                 185                 190
Thr Pro Gln Leu Thr Ala Asn Gln Val Ala Val Ile Tyr Lys Leu Ile
        195                 200                 205
Trp Tyr Gln Glu Gly Tyr Glu Gln Pro Ser Glu Glu Asp Leu Lys Arg
    210                 215                 220
Val Thr Gln Thr Trp Gln Leu Glu Glu Glu Glu Glu Glu Thr Asp
225                 230                 235                 240
Met Pro Phe Arg Gln Ile Thr Glu Met Thr Ile Leu Thr Val Gln Leu
                245                 250                 255
Ile Val Glu Phe Ala Lys Gly Leu Pro Gly Phe Ser Lys Ile Ser Gln
            260                 265                 270
Ser Asp Gln Ile Thr Leu Leu Lys Ala Ser Ser Ser Glu Val Met Met
        275                 280                 285
Leu Arg Val Ala Arg Arg Tyr Asp Ala Ala Thr Asp Ser Val Leu Phe
    290                 295                 300
Ala Asn Asn Gln Ala Tyr Thr Arg Asp Asn Tyr Arg Lys Ala Gly Met
305                 310                 315                 320
Ser Tyr Val Ile Glu Asp Leu Leu His Phe Cys Arg Cys Met Tyr Ser
                325                 330                 335
Met Ser Met Asp Asn Val His Tyr Ala Leu Leu Thr Ala Ile Val Ile
            340                 345                 350
Phe Ser Asp Arg Pro Gly Leu Glu Gln Pro Leu Leu Val Glu Glu Ile
        355                 360                 365
Gln Arg Tyr Tyr Leu Lys Thr Leu Arg Val Tyr Ile Leu Asn Gln His
    370                 375                 380
Ser Ala Ser Pro Arg Cys Ala Val Leu Phe Gly Lys Ile Leu Gly Val
385                 390                 395                 400
Leu Thr Glu Leu Arg Thr Leu Gly Thr Gln Asn Ser Asn Met Cys Ile
                405                 410                 415
Ser Leu Lys Leu Lys Asn Arg Lys Leu Pro Pro Phe Leu Glu Glu Ile
            420                 425                 430
Trp Asp Val Ala Glu Val Ser Thr Thr Lys Leu Ala Pro Pro Thr Asp
        435                 440                 445
Val Ser Leu Gly Asp Glu Leu His Leu Asp Gly Glu Asp Val Ala Met
    450                 455                 460
Ala His Ala Asp Ala Leu Asp Asp Phe Asp Leu Asp Met Leu Gly Asp
465                 470                 475                 480
Gly Asp Ser Pro Gly Pro Gly Phe Thr Pro His Asp Ser Ala Pro Tyr
                485                 490                 495
Gly Ala Leu Asp Met Ala Asp Phe Glu Phe Glu Gln Met Phe Thr Asp
            500                 505                 510
Ala Leu Gly Ile Asp Glu Tyr Gly Gly
        515                 520
```

<210> SEQ ID NO 91
<211> LENGTH: 1503
<212> TYPE: DNA
<213> ORGANISM: Synthetic construct
<220> FEATURE:
<221> NAME/KEY: CDS
<222> LOCATION: (1)..(1503)
<223> OTHER INFORMATION: Ecdysone Receptor chimera MCV

<400> SEQUENCE: 91

| | | |
|---|---|---|
| atg ggt cga gaa gaa tta tca ccg gcc tca agt ata aat gga tgt agt<br>Met Gly Arg Glu Glu Leu Ser Pro Ala Ser Ser Ile Asn Gly Cys Ser<br>1               5                   10                  15 | 48 |
| act gat ggg gaa cca aga cga cag aag aaa ggg cca gcg ccg cgc cag<br>Thr Asp Gly Glu Pro Arg Arg Gln Lys Lys Gly Pro Ala Pro Arg Gln<br>            20                  25                  30 | 96 |
| cag gag gaa ctg tgc ctt gtt tgc ggc gac agg gct tcg gga tat cac<br>Gln Glu Glu Leu Cys Leu Val Cys Gly Asp Arg Ala Ser Gly Tyr His<br>        35                  40                  45 | 144 |
| tat aac gcg ctt acg tgc gaa gga tgt aaa ggg ttc ttc agg cgg agt<br>Tyr Asn Ala Leu Thr Cys Glu Gly Cys Lys Gly Phe Phe Arg Arg Ser<br>    50                  55                  60 | 192 |
| gtg acc aag aat gcg gta tat att tgt aaa ttt gga cac gcc tgc gag<br>Val Thr Lys Asn Ala Val Tyr Ile Cys Lys Phe Gly His Ala Cys Glu<br>65                  70                  75                  80 | 240 |
| atg gac atg tac atg agg aga aaa tgc caa gag tgt cgg ttg aag aaa<br>Met Asp Met Tyr Met Arg Arg Lys Cys Gln Glu Cys Arg Leu Lys Lys<br>                85                  90                  95 | 288 |
| tgc ctc gcg gtg ggc atg agg ccc gag tgc gtc gtc cca gag tcc acg<br>Cys Leu Ala Val Gly Met Arg Pro Glu Cys Val Val Pro Glu Ser Thr<br>            100                 105                 110 | 336 |
| tgc aag aac aaa aga aga gaa aag gaa gca cag aga gaa aaa gac aaa<br>Cys Lys Asn Lys Arg Arg Glu Lys Glu Ala Gln Arg Glu Lys Asp Lys<br>        115                 120                 125 | 384 |
| ctg cca gtc agt acg acg aca gtg gac gat cat atg cct gcc ata atg<br>Leu Pro Val Ser Thr Thr Thr Val Asp Asp His Met Pro Ala Ile Met<br>    130                 135                 140 | 432 |
| caa tgt gac cct ccg ccc cca gag gcg gca agg att cac gaa gtg gtc<br>Gln Cys Asp Pro Pro Pro Pro Glu Ala Ala Arg Ile His Glu Val Val<br>145                 150                 155                 160 | 480 |
| ccg agg ttc cta acg gag aag cta atg gag cag aac aga ctg aag aat<br>Pro Arg Phe Leu Thr Glu Lys Leu Met Glu Gln Asn Arg Leu Lys Asn<br>                165                 170                 175 | 528 |
| gtg acg ccg ctg tcg gcg aac cag aag tcc ctg atc gcg agg ctc gtg<br>Val Thr Pro Leu Ser Ala Asn Gln Lys Ser Leu Ile Ala Arg Leu Val<br>            180                 185                 190 | 576 |
| tgg tac caa gac ggt tat gaa cag ccg tcc gaa gaa gac tta aag cgc<br>Trp Tyr Gln Asp Gly Tyr Glu Gln Pro Ser Glu Glu Asp Leu Lys Arg<br>        195                 200                 205 | 624 |
| ata aca acg gaa ctg gag gaa gaa gag gat caa gag cac gag gca aat<br>Ile Thr Thr Glu Leu Glu Glu Glu Asp Gln Glu His Glu Ala Asn<br>    210                 215                 220 | 672 |
| ttc cga tat ata aca gaa gtc aca ata ttg aca gtg caa ctg gtt gtg<br>Phe Arg Tyr Ile Thr Glu Val Thr Ile Leu Thr Val Gln Leu Val Val<br>225                 230                 235                 240 | 720 |
| gaa ttc gca aaa ggg ctt cca gca ttt att aaa ata cca caa gaa gat<br>Glu Phe Ala Lys Gly Leu Pro Ala Phe Ile Lys Ile Pro Gln Glu Asp<br>                245                 250                 255 | 768 |
| caa att act ctc ttg aag gct tgc tcc agt gaa gtt atg atg ttg cgc<br>Gln Ile Thr Leu Leu Lys Ala Cys Ser Ser Glu Val Met Met Leu Arg<br>            260                 265                 270 | 816 |
| atg gct cga cga tac gat cac gat tcc gat tcg ata ttg ttt gca aat<br>Met Ala Arg Arg Tyr Asp His Asp Ser Asp Ser Ile Leu Phe Ala Asn<br>        275                 280                 285 | 864 |
| aat aca gcg tac act aag caa acg tat caa tta gcg ggc atg gaa gag<br>Asn Thr Ala Tyr Thr Lys Gln Thr Tyr Gln Leu Ala Gly Met Glu Glu<br>    290                 295                 300 | 912 |
| aca att gat gat tta ctg cac ttt tgt cga caa atg tat gca tta tct<br> | 960 |

```
Thr Ile Asp Asp Leu Leu His Phe Cys Arg Gln Met Tyr Ala Leu Ser
305                 310                 315                 320 att gat aat gtc gag tat gct ctt ctc aca gcc atc gtc atc ttc tca      1008
Ile Asp Asn Val Glu Tyr Ala Leu Leu Thr Ala Ile Val Ile Phe Ser
                325                 330                 335 gat cga cct ggt cta gaa aag gct gaa atg gtg gac atc att caa agc      1056
Asp Arg Pro Gly Leu Glu Lys Ala Glu Met Val Asp Ile Ile Gln Ser
        340                 345                 350 tat tac aca gaa act ctt aag gtt tat atc gcc aat cgg cat ggt ggc      1104
Tyr Tyr Thr Glu Thr Leu Lys Val Tyr Ile Ala Asn Arg His Gly Gly
    355                 360                 365 gag tca aga tgc agc gtt caa ttt gca aaa cta ttg ggc att ctt act      1152
Glu Ser Arg Cys Ser Val Gln Phe Ala Lys Leu Leu Gly Ile Leu Thr
370                 375                 380 gaa tta cga aca atg ggc aat aaa aat tct gaa atg tgc ttt tca tta      1200
Glu Leu Arg Thr Met Gly Asn Lys Asn Ser Glu Met Cys Phe Ser Leu
385                 390                 395                 400 aaa ctg aga aac cga aaa ctg cca cga ttc tta gaa gaa gtc tgg gat      1248
Lys Leu Arg Asn Arg Lys Leu Pro Arg Phe Leu Glu Glu Val Trp Asp
            405                 410                 415 gtc ggc gat gtc aag ctt gcc ccc ccg acc gat gtc agc ctg ggg gac      1296
Val Gly Asp Val Lys Leu Ala Pro Pro Thr Asp Val Ser Leu Gly Asp
        420                 425                 430 gag ctc cac tta gac ggc gag gac gtg gcg atg gcg cat gcc gac gcg      1344
Glu Leu His Leu Asp Gly Glu Asp Val Ala Met Ala His Ala Asp Ala
    435                 440                 445 cta gac gat ttc gat ctg gac atg ttg ggg gac ggg gat tcc ccg ggt      1392
Leu Asp Asp Phe Asp Leu Asp Met Leu Gly Asp Gly Asp Ser Pro Gly
450                 455                 460 ccg gga ttt acc ccc cac gac tcc gcc ccc tac ggc gct ctg gat atg      1440
Pro Gly Phe Thr Pro His Asp Ser Ala Pro Tyr Gly Ala Leu Asp Met
465                 470                 475                 480 gcc gac ttc gag ttt gag cag atg ttt acc gat gcc ctt gga att gac      1488
Ala Asp Phe Glu Phe Glu Gln Met Phe Thr Asp Ala Leu Gly Ile Asp
            485                 490                 495 gag tac ggt ggg tag                                                   1503
Glu Tyr Gly Gly
            500

<210> SEQ ID NO 92
<211> LENGTH: 500
<212> TYPE: PRT
<213> ORGANISM: Synthetic construct

<400> SEQUENCE: 92

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
65                  70                  75                  80

Met Asp Met Tyr Met Arg Arg Lys Cys Gln Glu Cys Arg Leu Lys Lys
                85                  90                  95

Cys Leu Ala Val Gly Met Arg Pro Glu Cys Val Val Pro Glu Ser Thr
            100                 105                 110
```

-continued

```
Cys Lys Asn Lys Arg Arg Glu Lys Glu Ala Gln Arg Glu Lys Asp Lys
        115                 120                 125

Leu Pro Val Ser Thr Thr Val Asp Asp His Met Pro Ala Ile Met
    130                 135                 140

Gln Cys Asp Pro Pro Pro Glu Ala Ala Arg Ile His Glu Val Val
145                 150                 155                 160

Pro Arg Phe Leu Thr Glu Lys Leu Met Glu Gln Asn Arg Leu Lys Asn
                165                 170                 175

Val Thr Pro Leu Ser Ala Asn Gln Lys Ser Leu Ile Ala Arg Leu Val
            180                 185                 190

Trp Tyr Gln Asp Gly Tyr Glu Gln Pro Ser Glu Glu Asp Leu Lys Arg
        195                 200                 205

Ile Thr Thr Glu Leu Glu Glu Glu Asp Gln Glu His Glu Ala Asn
    210                 215                 220

Phe Arg Tyr Ile Thr Glu Val Thr Ile Leu Thr Val Gln Leu Val Val
225                 230                 235                 240

Glu Phe Ala Lys Gly Leu Pro Ala Phe Ile Lys Ile Pro Gln Glu Asp
                245                 250                 255

Gln Ile Thr Leu Leu Lys Ala Cys Ser Ser Glu Val Met Met Leu Arg
            260                 265                 270

Met Ala Arg Arg Tyr Asp His Asp Ser Asp Ser Ile Leu Phe Ala Asn
        275                 280                 285

Asn Thr Ala Tyr Thr Lys Gln Thr Tyr Gln Leu Ala Gly Met Glu Glu
    290                 295                 300

Thr Ile Asp Asp Leu Leu His Phe Cys Arg Gln Met Tyr Ala Leu Ser
305                 310                 315                 320

Ile Asp Asn Val Glu Tyr Ala Leu Leu Thr Ala Ile Val Ile Phe Ser
                325                 330                 335

Asp Arg Pro Gly Leu Glu Lys Ala Glu Met Val Asp Ile Ile Gln Ser
            340                 345                 350

Tyr Tyr Thr Glu Thr Leu Lys Val Tyr Ile Ala Asn Arg His Gly Gly
        355                 360                 365

Glu Ser Arg Cys Ser Val Gln Phe Ala Lys Leu Leu Gly Ile Leu Thr
    370                 375                 380

Glu Leu Arg Thr Met Gly Asn Lys Asn Ser Glu Met Cys Phe Ser Leu
385                 390                 395                 400

Lys Leu Arg Asn Arg Lys Leu Pro Arg Phe Leu Glu Glu Val Trp Asp
                405                 410                 415

Val Gly Asp Val Lys Leu Ala Pro Pro Thr Asp Val Ser Leu Gly Asp
            420                 425                 430

Glu Leu His Leu Asp Gly Glu Asp Val Ala Met Ala His Ala Asp Ala
        435                 440                 445

Leu Asp Asp Phe Asp Leu Asp Met Leu Asp Gly Asp Ser Pro Gly
    450                 455                 460

Pro Gly Phe Thr Pro His Asp Ser Ala Pro Tyr Gly Ala Leu Asp Met
465                 470                 475                 480

Ala Asp Phe Glu Phe Glu Gln Met Phe Thr Asp Ala Leu Gly Ile Asp
                485                 490                 495

Glu Tyr Gly Gly
            500
```

<210> SEQ ID NO 93
<211> LENGTH: 1518

-continued

```
<212> TYPE: DNA
<213> ORGANISM: Synthetic construct
<220> FEATURE:
<221> NAME/KEY: CDS
<222> LOCATION: (1)..(1518)
<223> OTHER INFORMATION: Ecdysone Receptor chimera MMV

<400> SEQUENCE: 93 atg ggt cga gaa gaa tta tca ccg gcc tca agt ata aat gga tgt agt       48
Met Gly Arg Glu Glu Leu Ser Pro Ala Ser Ser Ile Asn Gly Cys Ser
1               5                   10                  15 act gat ggg gaa cca aga cga cag aag aaa ggg cca gcg ccg cgc cag       96
Thr Asp Gly Glu Pro Arg Arg Gln Lys Lys Gly Pro Ala Pro Arg Gln
            20                  25                  30 cag gag gaa ctg tgc ctt gtt tgc ggc gac agg gct tcg gga tat cac      144
Gln Glu Glu Leu Cys Leu Val Cys Gly Asp Arg Ala Ser Gly Tyr His
        35                  40                  45 tat aac gcg ctt acg tgc gaa gga tgt aaa ggg ttc ttc agg cgg agt      192
Tyr Asn Ala Leu Thr Cys Glu Gly Cys Lys Gly Phe Phe Arg Arg Ser
    50                  55                  60 gtg acc aag aat gcg gta tat att tgt aaa ttt gga cac gcc tgc gag      240
Val Thr Lys Asn Ala Val Tyr Ile Cys Lys Phe Gly His Ala Cys Glu
65                  70                  75                  80 atg gac atg tac atg agg aga aaa tgc caa gag tgt cgg ttg aag aaa      288
Met Asp Met Tyr Met Arg Arg Lys Cys Gln Glu Cys Arg Leu Lys Lys
                85                  90                  95 tgc ctc gcg gtg ggc atg agg ccc gag tgc gtc gtc cca gag tcc acg      336
Cys Leu Ala Val Gly Met Arg Pro Glu Cys Val Val Pro Glu Ser Thr
            100                 105                 110 tgc aag aac aaa aga aga gaa aag gaa gca cag aga gaa aaa gac aaa      384
Cys Lys Asn Lys Arg Arg Glu Lys Glu Ala Gln Arg Glu Lys Asp Lys
        115                 120                 125 ctg cca gtc agt acg acg aca gtg gac gat cat atg cct gcc ata atg      432
Leu Pro Val Ser Thr Thr Thr Val Asp Asp His Met Pro Ala Ile Met
    130                 135                 140 caa tgt gac cct ccg ccc cca gag gcg gca agg att cac gaa gtg gtc      480
Gln Cys Asp Pro Pro Pro Pro Glu Ala Ala Arg Ile His Glu Val Val
145                 150                 155                 160 ccg agg ttc cta acg gag aag cta atg gag cag aac aga ctg aag aat      528
Pro Arg Phe Leu Thr Glu Lys Leu Met Glu Gln Asn Arg Leu Lys Asn
                165                 170                 175 gtg acg ccg ctg tcg gcg aac cag aag tcc ctg atc gcg agg ctc gtg      576
Val Thr Pro Leu Ser Ala Asn Gln Lys Ser Leu Ile Ala Arg Leu Val
            180                 185                 190 tgg tac cag gag ggg tac gag cag ccg tcg gag gaa gat ctc aag aga      624
Trp Tyr Gln Glu Gly Tyr Glu Gln Pro Ser Glu Glu Asp Leu Lys Arg
        195                 200                 205 gtt aca cag aca tgg cag tta gaa gaa gaa gaa gag gag gaa act gac      672
Val Thr Gln Thr Trp Gln Leu Glu Glu Glu Glu Glu Glu Glu Thr Asp
    210                 215                 220 atg ccc ttc cgt cag atc aca gag atg acg atc tta aca gtg cag ctt      720
Met Pro Phe Arg Gln Ile Thr Glu Met Thr Ile Leu Thr Val Gln Leu
225                 230                 235                 240 att gta gaa ttc gca aag gga cta ccg gga ttc tcc aag ata tct cag      768
Ile Val Glu Phe Ala Lys Gly Leu Pro Gly Phe Ser Lys Ile Ser Gln
                245                 250                 255 tcc gat caa att aca tta tta aag gcg tca tca agc gaa gtg atg atg      816
Ser Asp Gln Ile Thr Leu Leu Lys Ala Ser Ser Ser Glu Val Met Met
            260                 265                 270 ctg cga gtg gcg cga cgg tac gac gcg gcg acg gac agc gtg ctg ttc      864
Leu Arg Val Ala Arg Arg Tyr Asp Ala Ala Thr Asp Ser Val Leu Phe
```

```
                275                 280                 285
gcg aac aac cag gcg tac acg cgc gac aac tac cgc aag gcg ggc atg    912
Ala Asn Asn Gln Ala Tyr Thr Arg Asp Asn Tyr Arg Lys Ala Gly Met
    290                 295                 300 tcc tac gtc atc gag gac ctg ctg cac ttc tgt cgg tgt atg tac tcc    960
Ser Tyr Val Ile Glu Asp Leu Leu His Phe Cys Arg Cys Met Tyr Ser
305                 310                 315                 320 atg agc atg gac aat gtg cac tac gcg ctg ctc acc gcc atc gtt ata   1008
Met Ser Met Asp Asn Val His Tyr Ala Leu Leu Thr Ala Ile Val Ile
                325                 330                 335 ttc tca gac cgg cca ggc ctc gag caa ccc ctt tta gtg gag gaa atc   1056
Phe Ser Asp Arg Pro Gly Leu Glu Gln Pro Leu Leu Val Glu Glu Ile
            340                 345                 350 cag aga tac tac ttg aag acg ctg cgg gtt tac att tta aat cag cac   1104
Gln Arg Tyr Tyr Leu Lys Thr Leu Arg Val Tyr Ile Leu Asn Gln His
        355                 360                 365 agc gcg tcg cct cgc tgc gcc gtg ctg ttc ggc aag atc ctc ggc gtg   1152
Ser Ala Ser Pro Arg Cys Ala Val Leu Phe Gly Lys Ile Leu Gly Val
    370                 375                 380 ctg acg gaa ctg cgc acg ctc ggc acg cag aac tcc aac atg tgc atc   1200
Leu Thr Glu Leu Arg Thr Leu Gly Thr Gln Asn Ser Asn Met Cys Ile
385                 390                 395                 400 tcg ctg aag ctg aag aac agg aaa ctt ccg cca ttc ctc gag gag atc   1248
Ser Leu Lys Leu Lys Asn Arg Lys Leu Pro Pro Phe Leu Glu Glu Ile
                405                 410                 415 tgg gac gtg gcc gaa gtg tcg acg acg aag ctt gcc ccc ccg acc gat   1296
Trp Asp Val Ala Glu Val Ser Thr Thr Lys Leu Ala Pro Pro Thr Asp
            420                 425                 430 gtc agc ctg ggg gac gag ctc cac tta gac ggc gag gac gtg gcg atg   1344
Val Ser Leu Gly Asp Glu Leu His Leu Asp Gly Glu Asp Val Ala Met
        435                 440                 445 gcg cat gcc gac gcg cta gac gat ttc gat ctg gac atg ttg ggg gac   1392
Ala His Ala Asp Ala Leu Asp Asp Phe Asp Leu Asp Met Leu Gly Asp
    450                 455                 460 ggg gat tcc ccg ggt ccg gga ttt acc ccc cac gac tcc gcc ccc tac   1440
Gly Asp Ser Pro Gly Pro Gly Phe Thr Pro His Asp Ser Ala Pro Tyr
465                 470                 475                 480 ggc gct ctg gat atg gcc gac ttc gag ttt gag cag atg ttt acc gat   1488
Gly Ala Leu Asp Met Ala Asp Phe Glu Phe Glu Gln Met Phe Thr Asp
                485                 490                 495 gcc ctt gga att gac gag tac ggt ggg tag                            1518
Ala Leu Gly Ile Asp Glu Tyr Gly Gly
            500                 505

<210> SEQ ID NO 94
<211> LENGTH: 505
<212> TYPE: PRT
<213> ORGANISM: Synthetic construct

<400> SEQUENCE: 94

Met Gly Arg Glu Glu Leu Ser Pro Ala Ser Ser Ile Asn Gly Cys Ser
1               5                   10                  15

Thr Asp Gly Glu Pro Arg Arg Gln Lys Lys Gly Pro Ala Pro Arg Gln
            20                  25                  30

Gln Glu Glu Leu Cys Leu Val Cys Gly Asp Arg Ala Ser Gly Tyr His
        35                  40                  45

Tyr Asn Ala Leu Thr Cys Glu Gly Cys Lys Gly Phe Phe Arg Arg Ser
    50                  55                  60

Val Thr Lys Asn Ala Val Tyr Ile Cys Lys Phe Gly His Ala Cys Glu
```

-continued

```
            65                  70                  75                  80
Met Asp Met Tyr Met Arg Arg Lys Cys Gln Glu Cys Arg Leu Lys Lys
                    85                  90                  95
Cys Leu Ala Val Gly Met Arg Pro Glu Cys Val Val Pro Glu Ser Thr
                100                 105                 110
Cys Lys Asn Lys Arg Arg Glu Lys Glu Ala Gln Arg Glu Lys Asp Lys
                115                 120                 125
Leu Pro Val Ser Thr Thr Val Asp Asp His Met Pro Ala Ile Met
                130                 135                 140
Gln Cys Asp Pro Pro Pro Glu Ala Arg Ile His Glu Val Val
145                 150                 155                 160
Pro Arg Phe Leu Thr Glu Lys Leu Met Glu Gln Asn Arg Leu Lys Asn
                165                 170                 175
Val Thr Pro Leu Ser Ala Asn Gln Lys Ser Leu Ile Ala Arg Leu Val
                180                 185                 190
Trp Tyr Gln Glu Gly Tyr Glu Gln Pro Ser Glu Glu Asp Leu Lys Arg
                195                 200                 205
Val Thr Gln Thr Trp Gln Leu Glu Glu Glu Glu Glu Glu Thr Asp
                210                 215                 220
Met Pro Phe Arg Gln Ile Thr Glu Met Thr Ile Leu Thr Val Gln Leu
225                 230                 235                 240
Ile Val Glu Phe Ala Lys Gly Leu Pro Gly Phe Ser Lys Ile Ser Gln
                245                 250                 255
Ser Asp Gln Ile Thr Leu Leu Lys Ala Ser Ser Ser Glu Val Met Met
                260                 265                 270
Leu Arg Val Ala Arg Arg Tyr Asp Ala Ala Thr Asp Ser Val Leu Phe
                275                 280                 285
Ala Asn Asn Gln Ala Tyr Thr Arg Asp Asn Tyr Arg Lys Ala Gly Met
                290                 295                 300
Ser Tyr Val Ile Glu Asp Leu Leu His Phe Cys Arg Cys Met Tyr Ser
305                 310                 315                 320
Met Ser Met Asp Asn Val His Tyr Ala Leu Leu Thr Ala Ile Val Ile
                325                 330                 335
Phe Ser Asp Arg Pro Gly Leu Glu Gln Pro Leu Leu Val Glu Glu Ile
                340                 345                 350
Gln Arg Tyr Tyr Leu Lys Thr Leu Arg Val Tyr Ile Leu Asn Gln His
                355                 360                 365
Ser Ala Ser Pro Arg Cys Ala Val Leu Phe Gly Lys Ile Leu Gly Val
                370                 375                 380
Leu Thr Glu Leu Arg Thr Leu Gly Thr Gln Asn Ser Asn Met Cys Ile
385                 390                 395                 400
Ser Leu Lys Leu Lys Asn Arg Lys Leu Pro Pro Phe Leu Glu Glu Ile
                405                 410                 415
Trp Asp Val Ala Glu Val Ser Thr Thr Lys Leu Ala Pro Thr Asp
                420                 425                 430
Val Ser Leu Gly Asp Glu Leu His Leu Asp Gly Glu Asp Val Ala Met
                435                 440                 445
Ala His Ala Asp Ala Leu Asp Asp Phe Asp Leu Asp Met Leu Gly Asp
                450                 455                 460
Gly Asp Ser Pro Gly Pro Gly Phe Thr Pro His Asp Ser Ala Pro Tyr
465                 470                 475                 480
Gly Ala Leu Asp Met Ala Asp Phe Glu Phe Glu Gln Met Phe Thr Asp
                485                 490                 495
```

```
Ala Leu Gly Ile Asp Glu Tyr Gly Gly
        500                 505

<210> SEQ ID NO 95
<211> LENGTH: 1539
<212> TYPE: DNA
<213> ORGANISM: Synthetic construct
<220> FEATURE:
<221> NAME/KEY: CDS
<222> LOCATION: (1)..(1539)
<223> OTHER INFORMATION: Ecdysone Receptor chimera DDV

<400> SEQUENCE: 95 atg ggt cgc gat gat ctc tcg cct tcg agc agc ttg aac gga tac tcg       48
Met Gly Arg Asp Asp Leu Ser Pro Ser Ser Ser Leu Asn Gly Tyr Ser
1               5                  10                  15 gcg aac gaa agc tgc gat gcg aag aag agc aag aag gga cct gcg cca       96
Ala Asn Glu Ser Cys Asp Ala Lys Lys Ser Lys Lys Gly Pro Ala Pro
                20                  25                  30 cgg gtg caa gag gag ctg tgc ctg gtt tgc ggc gac agg gcc tcc ggc      144
Arg Val Gln Glu Glu Leu Cys Leu Val Cys Gly Asp Arg Ala Ser Gly
            35                  40                  45 tac cac tac aac gcc ctc acc tgt gag ggc tgc aag ggg ttc ttt cga      192
Tyr His Tyr Asn Ala Leu Thr Cys Glu Gly Cys Lys Gly Phe Phe Arg
        50                  55                  60 cgc agc gtt acg aag agc gcc gtc tac tgc tgc aag ttc ggg cgc gcc      240
Arg Ser Val Thr Lys Ser Ala Val Tyr Cys Cys Lys Phe Gly Arg Ala
65                  70                  75                  80 tgc gaa atg gac atg tac atg agg cga aag tgt cag gag tgc cgc ctg      288
Cys Glu Met Asp Met Tyr Met Arg Arg Lys Cys Gln Glu Cys Arg Leu
                85                  90                  95 aaa aag tgc ctg gcc gtg ggt atg cgg ccg gaa tgc gtc gtc ccg gag      336
Lys Lys Cys Leu Ala Val Gly Met Arg Pro Glu Cys Val Val Pro Glu
            100                 105                 110 aac caa tgt gcg atg aag cgg cgc gaa aag aag gcc cag aag gag aag      384
Asn Gln Cys Ala Met Lys Arg Arg Glu Lys Lys Ala Gln Lys Glu Lys
        115                 120                 125 gac aaa atg acc act tcg ccg agc tct cag cat ggc ggc aat ggc agc      432
Asp Lys Met Thr Thr Ser Pro Ser Ser Gln His Gly Gly Asn Gly Ser
    130                 135                 140 ttg gcc tct ggt ggc ggc caa gac ttt gtt aag aag gag att ctt gac      480
Leu Ala Ser Gly Gly Gly Gln Asp Phe Val Lys Lys Glu Ile Leu Asp
145                 150                 155                 160 ctt atg aca tgc gag ccg ccc cag cat gcc act att ccg cta cta cct      528
Leu Met Thr Cys Glu Pro Pro Gln His Ala Thr Ile Pro Leu Leu Pro
                165                 170                 175 gat gaa ata ttg gcc aag tgt caa gcg cgc aat ata cct tcc tta acg      576
Asp Glu Ile Leu Ala Lys Cys Gln Ala Arg Asn Ile Pro Ser Leu Thr
            180                 185                 190 tac aat cag ttg gcc gtt ata tac aag tta att tgg tac cag gat ggc      624
Tyr Asn Gln Leu Ala Val Ile Tyr Lys Leu Ile Trp Tyr Gln Asp Gly
        195                 200                 205 tat gag cag cca tct gaa gag gat ctc agg cgt ata atg agt caa ccc      672
Tyr Glu Gln Pro Ser Glu Glu Asp Leu Arg Arg Ile Met Ser Gln Pro
    210                 215                 220 gat gag aac gag agc caa acg gac gtc agc ttt cgg cat ata acc gag      720
Asp Glu Asn Glu Ser Gln Thr Asp Val Ser Phe Arg His Ile Thr Glu
225                 230                 235                 240 ata acc ata ctc acg gtc cag ttg att gtt gag ttt gct aaa ggt cta      768
Ile Thr Ile Leu Thr Val Gln Leu Ile Val Glu Phe Ala Lys Gly Leu
                245                 250                 255
```

```
cca gcg ttt aca aag ata ccc cag gag gac cag atc acg tta cta aag     816
Pro Ala Phe Thr Lys Ile Pro Gln Glu Asp Gln Ile Thr Leu Leu Lys
            260                 265                 270 gcc tgc tcg tcg gag gtg atg atg ctg cgt atg gca cga cgc tat gac     864
Ala Cys Ser Ser Glu Val Met Met Leu Arg Met Ala Arg Arg Tyr Asp
        275                 280                 285 cac agc tcg gac tca ata ttc ttc gcg aat aat aga tca tat acg cgg     912
His Ser Ser Asp Ser Ile Phe Phe Ala Asn Asn Arg Ser Tyr Thr Arg
290                 295                 300 gat tct tac aaa atg gcc gga atg gct gat aac att gaa gac ctg ctg     960
Asp Ser Tyr Lys Met Ala Gly Met Ala Asp Asn Ile Glu Asp Leu Leu
305                 310                 315                 320 cat ttc tgc cgc caa atg ttc tcg atg aag gtg gac aac gtc gaa tac    1008
His Phe Cys Arg Gln Met Phe Ser Met Lys Val Asp Asn Val Glu Tyr
                325                 330                 335 gcg ctt ctc act gcc att gtg atc ttc tcg gac cgg ccg ggc ctg gag    1056
Ala Leu Leu Thr Ala Ile Val Ile Phe Ser Asp Arg Pro Gly Leu Glu
            340                 345                 350 aag gcc caa cta gtc gaa gcg atc cag agc tac tac atc gac acg cta    1104
Lys Ala Gln Leu Val Glu Ala Ile Gln Ser Tyr Tyr Ile Asp Thr Leu
        355                 360                 365 cgc att tat ata ctc aac cgc cac tgc ggc gac tca atg agc ctc gtc    1152
Arg Ile Tyr Ile Leu Asn Arg His Cys Gly Asp Ser Met Ser Leu Val
370                 375                 380 ttc tac gca aag ctg ctc tcg atc ctc acc gag ctg cgt acg ctg ggc    1200
Phe Tyr Ala Lys Leu Leu Ser Ile Leu Thr Glu Leu Arg Thr Leu Gly
385                 390                 395                 400 aac cag aac gcc gag atg tgt ttc tca cta aag ctc aaa aac cgc aaa    1248
Asn Gln Asn Ala Glu Met Cys Phe Ser Leu Lys Leu Lys Asn Arg Lys
                405                 410                 415 ctg ccc aag ttc ctc gag gag atc tgg gac gtt cat gcc atc ccg cca    1296
Leu Pro Lys Phe Leu Glu Glu Ile Trp Asp Val His Ala Ile Pro Pro
            420                 425                 430 aag ctt gcc ccc ccg acc gat gtc agc ctg ggg gac gag ctc cac tta    1344
Lys Leu Ala Pro Pro Thr Asp Val Ser Leu Gly Asp Glu Leu His Leu
        435                 440                 445 gac ggc gag gac gtg gcg atg gcg cat gcc gac gcg cta gac gat ttc    1392
Asp Gly Glu Asp Val Ala Met Ala His Ala Asp Ala Leu Asp Asp Phe
450                 455                 460 gat ctg gac atg ttg ggg gac ggg gat tcc ccg ggt ccg gga ttt acc    1440
Asp Leu Asp Met Leu Gly Asp Gly Asp Ser Pro Gly Pro Gly Phe Thr
465                 470                 475                 480 ccc cac gac tcc gcc ccc tac ggc gct ctg gat atg gcc gac ttc gag    1488
Pro His Asp Ser Ala Pro Tyr Gly Ala Leu Asp Met Ala Asp Phe Glu
                485                 490                 495 ttt gag cag atg ttt acc gat gcc ctt gga att gac gag tac ggt ggg    1536
Phe Glu Gln Met Phe Thr Asp Ala Leu Gly Ile Asp Glu Tyr Gly Gly
            500                 505                 510 tag                                                                1539

<210> SEQ ID NO 96
<211> LENGTH: 512
<212> TYPE: PRT
<213> ORGANISM: Synthetic construct

<400> SEQUENCE: 96

Met Gly Arg Asp Asp Leu Ser Pro Ser Ser Leu Asn Gly Tyr Ser
1               5                   10                  15

Ala Asn Glu Ser Cys Asp Ala Lys Lys Ser Lys Lys Gly Pro Ala Pro
```

-continued

```
                  20                  25                  30
Arg Val Gln Glu Glu Leu Cys Leu Val Cys Gly Asp Arg Ala Ser Gly
             35                  40                  45
Tyr His Tyr Asn Ala Leu Thr Cys Glu Gly Cys Lys Gly Phe Phe Arg
         50                  55                  60
Arg Ser Val Thr Lys Ser Ala Val Tyr Cys Cys Lys Phe Gly Arg Ala
65                  70                  75                  80
Cys Glu Met Asp Met Tyr Met Arg Arg Lys Cys Gln Glu Cys Arg Leu
                 85                  90                  95
Lys Lys Cys Leu Ala Val Gly Met Arg Pro Glu Cys Val Val Pro Glu
            100                 105                 110
Asn Gln Cys Ala Met Lys Arg Arg Glu Lys Lys Ala Gln Lys Glu Lys
            115                 120                 125
Asp Lys Met Thr Thr Ser Pro Ser Ser Gln His Gly Gly Asn Gly Ser
       130                 135                 140
Leu Ala Ser Gly Gly Gln Asp Phe Val Lys Lys Glu Ile Leu Asp
145                 150                 155                 160
Leu Met Thr Cys Glu Pro Pro Gln His Ala Thr Ile Pro Leu Leu Pro
                165                 170                 175
Asp Glu Ile Leu Ala Lys Cys Gln Ala Arg Asn Ile Pro Ser Leu Thr
            180                 185                 190
Tyr Asn Gln Leu Ala Val Ile Tyr Lys Leu Ile Trp Tyr Gln Asp Gly
        195                 200                 205
Tyr Glu Gln Pro Ser Glu Glu Asp Leu Arg Arg Ile Met Ser Gln Pro
    210                 215                 220
Asp Glu Asn Glu Ser Gln Thr Asp Val Ser Phe Arg His Ile Thr Glu
225                 230                 235                 240
Ile Thr Ile Leu Thr Val Gln Leu Ile Val Glu Phe Ala Lys Gly Leu
                245                 250                 255
Pro Ala Phe Thr Lys Ile Pro Gln Glu Asp Gln Ile Thr Leu Leu Lys
            260                 265                 270
Ala Cys Ser Ser Glu Val Met Met Leu Arg Met Ala Arg Arg Tyr Asp
        275                 280                 285
His Ser Ser Asp Ser Ile Phe Phe Ala Asn Asn Arg Ser Tyr Thr Arg
    290                 295                 300
Asp Ser Tyr Lys Met Ala Gly Met Ala Asp Asn Ile Glu Asp Leu Leu
305                 310                 315                 320
His Phe Cys Arg Gln Met Phe Ser Met Lys Val Asp Asn Val Glu Tyr
                325                 330                 335
Ala Leu Leu Thr Ala Ile Val Ile Phe Ser Asp Arg Pro Gly Leu Glu
            340                 345                 350
Lys Ala Gln Leu Val Glu Ala Ile Gln Ser Tyr Tyr Ile Asp Thr Leu
        355                 360                 365
Arg Ile Tyr Ile Leu Asn Arg His Cys Gly Asp Ser Met Ser Leu Val
    370                 375                 380
Phe Tyr Ala Lys Leu Leu Ser Ile Leu Thr Glu Leu Arg Thr Leu Gly
385                 390                 395                 400
Asn Gln Asn Ala Glu Met Cys Phe Ser Leu Lys Leu Lys Asn Arg Lys
                405                 410                 415
Leu Pro Lys Phe Leu Glu Glu Ile Trp Asp Val His Ala Ile Pro Pro
            420                 425                 430
Lys Leu Ala Pro Pro Thr Asp Val Ser Leu Gly Asp Glu Leu His Leu
        435                 440                 445
```

```
Asp Gly Glu Asp Val Ala Met Ala His Ala Asp Ala Leu Asp Asp Phe
    450                 455                 460

Asp Leu Asp Met Leu Gly Asp Gly Asp Ser Pro Gly Pro Gly Phe Thr
465                 470                 475                 480

Pro His Asp Ser Ala Pro Tyr Gly Ala Leu Asp Met Ala Asp Phe Glu
            485                 490                 495

Phe Glu Gln Met Phe Thr Asp Ala Leu Gly Ile Asp Glu Tyr Gly Gly
            500                 505                 510

<210> SEQ ID NO 97
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 97
ggcaagcttc ccaaggccgt gcgg                                          24

<210> SEQ ID NO 98
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 98
ggctctagac tacgcaagct gcccggc                                       27

<210> SEQ ID NO 99
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 99
ggcacgcgtc ccaaggccgt gcgg                                          24

<210> SEQ ID NO 100
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 100
gccacgcgtc gcaagctgcc cggc                                          24

<210> SEQ ID NO 101
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer
```

<400> SEQUENCE: 101
ccgggatccg ccaccatgcc caaggccgtg cgg        33

<210> SEQ ID NO 102
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 102
ccgggatccc gcaagctgcc cggc        24

<210> SEQ ID NO 103
<211> LENGTH: 2477
<212> TYPE: DNA
<213> ORGANISM: synthetic construct
<220> FEATURE:
<221> NAME/KEY: misc_feature
<222> LOCATION: (1)..(2477)
<223> OTHER INFORMATION: reporter fragment cloned into pCGS601

<400> SEQUENCE: 103

```
tcatgtttga cagcttatca tcggatctag taacatagat gacaccgcgc gcgataattt     60
atcctagttt gcgcgctata ttttgttttc tatcgcgtat taaatgtata attgcgggac    120
tctaatcata aaaacccatc tcataaataa cgtcatgcat tacatgttaa ttattacatg    180
cttaacgtaa ttcaacagaa attatatgat aatcatcgca agaccggcaa caggattcaa    240
tcttaagaaa cttttattgcc aaatgtttga acgatcggcc gctctagaat tacacggcga    300
tctttccgcc cttcttggcc tttatgagga tctctctgat ttttcttgcg tcgagttttc    360
cggtaagacc tttcggtact tcgtccacaa acacaactcc tccgcgcaac ttttttcgcgg    420
ttgttacttg actggcgacg taatccacga tctcttttttc cgtcatcgtc tttccgtgct    480
ccaaaacaac aacggcggcg ggaagttcac cggcgtcatc gtcggaagaa cctgcgacac    540
ctgcgtcgaa gatgttgggg tgttggagca agatggattc caattcagcg ggagccacct    600
gatagccttt gtacttaatc agagacttca ggcggtcaac gatgaagaag tgttcgtctt    660
cgtcccagta agctatgtct ccagaatgta gccatccatc cttgtcaatc aaggcgttgg    720
tcgcttccgg attgtttaca taaccggaca taatcatagg acctctcaca cacagttcgc    780
ctctttgatt aacgcccagc gttttcccgg tatccagatc cacaaccttc gcttcaaaaa    840
atggaacaac tttaccgacc gcgcccggtt tatcatcccc ctcgggtgta atcagaatag    900
ctgatgtagt ctcagtgagc ccatatcctt gcctgatacc tggcagatgg aacctcttgg    960
caaccgcttc cccgacttcc ttagagaggg gagcgccacc agaagcaatt tcgtgtaaat   1020
tagataaatc gtatttgtca atcagagtgc ttttggcgaa gaaggagaat agggttggca   1080
ccagcagcgc actttgaatc ttgtaatcct gaaggctcct cagaaacagc tcttcttcaa   1140
atctatacat taagacgact cgaaatccac atatcaaata tccgagtgta gtaaacattc   1200
caaaccgtg atggaatgga acaacactta aaatcgcagt atccggaatg atttgattgc   1260
caaaatagg atctctggca tgcgagaatc tcacgcaggc agttctatga ggcagagcga   1320
caccttagg cagaccagta gatccagagg agttcatgat cagtgcaatt gtcttgtccc   1380
tatcgaagga ctctggcaca aaatcgtatt cattaaaacc gggaggtaga tgagatgtga   1440
cgaacgtgta catcgactga aatccctggt aatccgtttt agaatccatg ataataattt   1500
```

-continued

```
tttggatgat tgggagcttt ttttgcacgt tcaaaatttt ttgcaacccc tttttggaaa    1560
cgaacaccac ggtaggctgc gaaatgccca tactgttgag caattcacgt tcattataaa    1620
tgtcgttcgc gggcgcaact gcaactccga taaataacgc gcccaacacc ggcataaaga    1680
attgaagaga gttttcactg catacgacga ttctgtgatt tgtattcagc ccatatcgtt    1740
tcatagcttc tgccaaccga acggacattt cgaagtactc agcgtaagtg atgtccacct    1800
cgatatgtgc atctgtaaaa gcaattgttc caggaaccag ggcgtatctc ttcatagcct    1860
tatgcagttg ctctccagcg gttccatctt ccagcggata gaatggcgcc gggcctttct    1920
ttatgttttt ggcgtcttcc atggtggctt taccaacagt accggaatgc caagctgggc    1980
tgcaggaatt cggtgggaga tcagtagccc gtccccctg tttgctgctg cgaacgatgg     2040
aaatgcaaca gccattcgat catcaaaccc gcgcgcaatg aagggacaag aagggagag     2100 aagtagtagt agtagaatcc aacgcaccct ggtcgccaac gtcctcccgg aattcttcta    2160
gcgtcggatg cgacctgcga tgcgatgcga atgcgatgcg tgcgggcttc gctgggggcg    2220
caacgtgtcc gctttattcc gcgcgaccac gcgtgcgaag cttatcgata ccgtcgacct    2280
cgagatcccc cggagtactg tcctccgagc ggagtactgt cctccgagcg gagtactgtc    2340
ctccgagcgg agtactgtcc tccgagcgga gtactgtcct ccgagcggag tactgtcctc    2400
cgagcggagt actgtcctcc gagcggagta ctgtcctccg agcggagtac tgtcctccgg    2460
cggagtactg tcctccg                                                   2477
```

<210> SEQ ID NO 104
<211> LENGTH: 3972
<212> TYPE: DNA
<213> ORGANISM: synthetic construct
<220> FEATURE:
<221> NAME/KEY: misc_feature
<222> LOCATION: (1)..(3972)
<223> OTHER INFORMATION: GAL4-Manduca EcR-VP16 fragment in pCGS202
<221> NAME/KEY: CDS
<222> LOCATION: (2007)..(3668)
<223> OTHER INFORMATION: GAL4-Manduca EcR-VP16 chimera

<400> SEQUENCE: 104

```
cctgcagtgc agcgtgaccc ggtcgtgccc ctctctagag ataatgagca ttgcatgtct     60
aagttataaa aaattaccac atatttttt tgtcacactt gtttgaagtg cagtttatct    120
atctttatac atatatttaa actttactct acgaataata taatctatag tactacaata    180
atatcagtgt tttagagaat catataaatg aacagttaga catggtctaa aggacaattg    240
agtattttga caacaggact ctacagtttt atctttttag tgtgcatgtg ttctcctttt    300
tttttgcaaa tagcttcacc tatataatac ttcatccatt ttattagtac atccatttag    360
ggtttagggt taatggtttt tatagactaa tttttttagt acatctattt tattctattt    420
tagcctctaa attaagaaaa ctaaaactct attttagttt ttttatttaa taatttagat    480
ataaaataga ataaaataaa gtgactaaaa attaaacaaa tacccttta gaaattaaaa    540 aaactaagga aacattttc ttgtttcgag tagataatgc cagcctgtta aacgccgtcg    600
acgagtctaa cggacaccaa ccagcgaacc agcagcgtcg cgtcgggcca agcgaagcag    660
acggcacggc atctctgtcg ctgcctctgg acccctctcg agagttccgc tccaccgttg    720
gacttgctcc gctgtcggca tccagaaatt gcgtggcgga gcggcagacg tgagccggca    780
cggcaggcgg cctcctcctc ctctcacggc accggcagct acgggggatt cctttcccac    840
cgctccttcg cttcccttc ctcgcccgcc gtaataaata gacaccccct ccacccctc     900
```

```
                                                              -continued tttccccaac ctcgtgttgt tcggagcgca cacacacaca accagatctc ccccaaatcc      960
acccgtcggc acctccgctt caaggtacgc cgctcgtcct ccccccccc ccctctctac      1020 cttctctaga tcggcgttcc ggtccatggt tagggcccgg tagttctact tctgttcatg      1080
tttgtgttag atccgtgttt gtgttagatc cgtgctgcta gcgttcgtac acggatgcga      1140
cctgtacgtc agacacgttc tgattgctaa cttgccagtg tttctctttg gggaatcctg      1200
ggatggctct agccgttccg cagacgggat cgatttcatg atttttttg tttcgttgca      1260 tagggtttgg tttgcccttt tcctttattt caatatatgc cgtgcacttg tttgtcgggt      1320
catcttttca tgctttttttt tgtcttggtt gtgatgatgt ggtctggttg ggcggtcgtt      1380
ctagatcgga gtagaattct gtttcaaact acctggtgga tttattaatt ttggatctgt      1440
atgtgtgtgc catacatatt catagttacg aattgaagat gatggatgga aatatcgatc      1500
taggataggt atacatgttg atgcgggttt tactgatgca tatacagaga tgcttttgt      1560 tcgcttggtt gtgatgatgt ggtgtggttg ggcggtcgtt cattcgttct agatcggagt      1620
agaatactgt ttcaaactac ctggtgtatt tattaatttt ggaactgtat gtgtgtgtca      1680
tacatcttca tagttacgag tttaagatgg atggaaatat cgatctagga taggtataca      1740
tgttgatgtg ggttttactg atgcatatac atgatggcat atgcagcatc tattcatatg      1800
ctctaacctt gagtacctat ctattataat aaacaagtat gttttataat tattttgatc      1860
ttgatatact tggatgatgg catatgcagc agctatatgt ggattttttt agccctgcct      1920
tcatacgcta tttatttgct tggtactgtt tcttttgtcg atgctcaccc tgttgtttgg      1980
tgttacttct gcagggatcc gccacc atg aag cta ctg tct tct atc gaa caa      2033
                                  Met Lys Leu Leu Ser Ser Ile Glu Gln
                                   1               5 gca tgc gat att tgc cga ctt aaa aag ctc aag tgt tcc aaa gaa aaa      2081
Ala Cys Asp Ile Cys Arg Leu Lys Lys Leu Lys Cys Ser Lys Glu Lys
 10              15                  20                  25 ccg aag tgc gcc aag tgt ctg aag aac aac tgg gag tgt cgc tac tct      2129
Pro Lys Cys Ala Lys Cys Leu Lys Asn Asn Trp Glu Cys Arg Tyr Ser
                 30                  35                  40 ccc aaa acc aaa agg tct ccg ctg act agg gca cat ctg aca gaa gtg      2177
Pro Lys Thr Lys Arg Ser Pro Leu Thr Arg Ala His Leu Thr Glu Val
             45                  50                  55 gaa tca agg cta gaa aga ctg gaa cag cta ttt cta ctg att ttt cct      2225
Glu Ser Arg Leu Glu Arg Leu Glu Gln Leu Phe Leu Leu Ile Phe Pro
         60                  65                  70 cga gaa gac ctt gac atg att ttg aaa atg gat tct tta cag gat ata      2273
Arg Glu Asp Leu Asp Met Ile Leu Lys Met Asp Ser Leu Gln Asp Ile
     75                  80                  85 aaa gca ttg tta aca gga tta ttt gta caa gat aat gtg aat aaa gat      2321
Lys Ala Leu Leu Thr Gly Leu Phe Val Gln Asp Asn Val Asn Lys Asp
 90                  95                 100                 105 gcc gtc aca gat aga ttg gct tca gtg gag act gat atg cct cta aca      2369
Ala Val Thr Asp Arg Leu Ala Ser Val Glu Thr Asp Met Pro Leu Thr
                110                 115                 120 ttg aga cag cat aga ata agt gcg aca tca tca tcg gaa gag agt agt      2417
Leu Arg Gln His Arg Ile Ser Ala Thr Ser Ser Ser Glu Glu Ser Ser
            125                 130                 135 aac aaa ggt caa aga cag ttg act gta tcg acg cgt atg agg ccc gag      2465
Asn Lys Gly Gln Arg Gln Leu Thr Val Ser Thr Arg Met Arg Pro Glu
        140                 145                 150 tgc gtc gtc cca gag tcc acg tgc aag aac aaa aga aga gaa aag gaa      2513
Cys Val Val Pro Glu Ser Thr Cys Lys Asn Lys Arg Arg Glu Lys Glu
```

```
            155                 160                 165
gca cag aga gaa aaa gac aaa ctg cca gtc agt acg acg aca gtg gac        2561
Ala Gln Arg Glu Lys Asp Lys Leu Pro Val Ser Thr Thr Thr Val Asp
170             175                 180                 185 gat cat atg cct gcc ata atg caa tgt gac cct ccg ccc cca gag gcg        2609
Asp His Met Pro Ala Ile Met Gln Cys Asp Pro Pro Pro Pro Glu Ala
                190                 195                 200 gca agg att cac gaa gtg gtc ccg agg ttc cta acg gag aag cta atg        2657
Ala Arg Ile His Glu Val Val Pro Arg Phe Leu Thr Glu Lys Leu Met
            205                 210                 215 gag cag aac aga ctg aag aat gtg acg ccg ctg tcg gcg aac cag aag        2705
Glu Gln Asn Arg Leu Lys Asn Val Thr Pro Leu Ser Ala Asn Gln Lys
        220                 225                 230 tcc ctg atc gcg agg ctc gtg tgg tac cag gag ggg tac gag cag ccg        2753
Ser Leu Ile Ala Arg Leu Val Trp Tyr Gln Glu Gly Tyr Glu Gln Pro
    235                 240                 245 tcg gag gaa gat ctc aag aga gtt aca cag aca tgg cag tta gaa gaa        2801
Ser Glu Glu Asp Leu Lys Arg Val Thr Gln Thr Trp Gln Leu Glu Glu
250                 255                 260                 265 gaa gaa gag gag gaa act gac atg ccc ttc cgt cag atc aca gag atg        2849
Glu Glu Glu Glu Glu Thr Asp Met Pro Phe Arg Gln Ile Thr Glu Met
                270                 275                 280 acg atc tta aca gtg cag ctt att gta gaa ttc gca aag gga cta ccg        2897
Thr Ile Leu Thr Val Gln Leu Ile Val Glu Phe Ala Lys Gly Leu Pro
            285                 290                 295 gga ttc tcc aag ata tct cag tcc gat caa att aca tta tta aag gcg        2945
Gly Phe Ser Lys Ile Ser Gln Ser Asp Gln Ile Thr Leu Leu Lys Ala
        300                 305                 310 tca tca agc gaa gtg atg atg ctg cga gtg gcg cga cgg tac gac gcg        2993
Ser Ser Ser Glu Val Met Met Leu Arg Val Ala Arg Arg Tyr Asp Ala
    315                 320                 325 gcg acg gac agc gtg ctg ttc gcg aac aac cag gcg tac acg cgc gac        3041
Ala Thr Asp Ser Val Leu Phe Ala Asn Asn Gln Ala Tyr Thr Arg Asp
330                 335                 340                 345 aac tac cgc aag gcg ggc atg tcc tac gtc atc gag gac ctg ctg cac        3089
Asn Tyr Arg Lys Ala Gly Met Ser Tyr Val Ile Glu Asp Leu Leu His
                350                 355                 360 ttc tgt cgg tgt atg tac tcc atg agc atg gac aat gtg cac tac gcg        3137
Phe Cys Arg Cys Met Tyr Ser Met Ser Met Asp Asn Val His Tyr Ala
            365                 370                 375 ctg ctc acc gcc atc gtt ata ttc tca gac cgg cca ggc ctc gag caa        3185
Leu Leu Thr Ala Ile Val Ile Phe Ser Asp Arg Pro Gly Leu Glu Gln
        380                 385                 390 ccc ctt tta gtg gag gaa atc cag aga tac tac ttg aag acg ctg cgg        3233
Pro Leu Leu Val Glu Glu Ile Gln Arg Tyr Tyr Leu Lys Thr Leu Arg
    395                 400                 405 gtt tac att tta aat cag cac agc gcg tcg cct cgc tgc gcc gtg ctg        3281
Val Tyr Ile Leu Asn Gln His Ser Ala Ser Pro Arg Cys Ala Val Leu
410                 415                 420                 425 ttc ggc aag atc ctc ggc gtg ctg acg gaa ctg cgc acg ctc ggc acg        3329
Phe Gly Lys Ile Leu Gly Val Leu Thr Glu Leu Arg Thr Leu Gly Thr
                430                 435                 440 cag aac tcc aac atg tgc atc tcg ctg aag ctg aag aac agg aaa ctt        3377
Gln Asn Ser Asn Met Cys Ile Ser Leu Lys Leu Lys Asn Arg Lys Leu
            445                 450                 455 ccg cca ttc ctc gag gag atc tgg gac gtg gcc gaa gtg tcg acg acg        3425
Pro Pro Phe Leu Glu Glu Ile Trp Asp Val Ala Glu Val Ser Thr Thr
        460                 465                 470 aag ctt gcc ccc ccg acc gat gtc agc ctg ggg gac gag ctc cac tta        3473
```

```

Lys Leu Ala Pro Pro Thr Asp Val Ser Leu Gly Asp Glu Leu His Leu
    475                 480                 485 gac ggc gag gac gtg gcg atg gcg cat gcc gac gcg cta gac gat ttc       3521
Asp Gly Glu Asp Val Ala Met Ala His Ala Asp Ala Leu Asp Asp Phe
490                 495                 500                 505 gat ctg gac atg ttg ggg gac ggg gat tcc ccg ggt ccg gga ttt acc       3569
Asp Leu Asp Met Leu Gly Asp Gly Asp Ser Pro Gly Pro Gly Phe Thr
                510                 515                 520 ccc cac gac tcc gcc ccc tac ggc gct ctg gat atg gcc gac ttc gag       3617
Pro His Asp Ser Ala Pro Tyr Gly Ala Leu Asp Met Ala Asp Phe Glu
            525                 530                 535 ttt gag cag atg ttt acc gat gcc ctt gga att gac gag tac ggt ggg       3665
Phe Glu Gln Met Phe Thr Asp Ala Leu Gly Ile Asp Glu Tyr Gly Gly
        540                 545                 550 tag gatcctctag agcggccgcc accctagatc cccgaatttc cccgatcgtt            3718
caaacatttg gcaataaagt ttcttaagat tgaatcctgt tgccggtctt gcgatgatta     3778
tcatataatt tctgttgaat tacgttaagc atgtaataat taacatgtaa tgcatgacgt     3838
tatttatgag atgggttttt atgattagag tcccgcaatt atacatttaa tacgcgatag     3898
aaaacaaaat atagcgcgca aactaggata aattatcgcg cgcggtgtca tctatgttac     3958
tagatcggga attg                                                       3972

<210> SEQ ID NO 105
<211> LENGTH: 553
<212> TYPE: PRT
<213> ORGANISM: synthetic construct
<220> FEATURE:
<221> NAME/KEY: misc_feature
<222> LOCATION: (1)..(3972)
<223> OTHER INFORMATION: GAL4-Manduca EcR-VP16 fragment in pCGS202

<400> SEQUENCE: 105

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Thr Arg Met Arg Pro Glu Cys Val Val Pro Glu Ser Thr
145                 150                 155                 160

Cys Lys Asn Lys Arg Arg Glu Lys Glu Ala Gln Arg Glu Lys Asp Lys
                165                 170                 175

Leu Pro Val Ser Thr Thr Thr Val Asp Asp His Met Pro Ala Ile Met
            180                 185                 190
```

```
Gln Cys Asp Pro Pro Pro Glu Ala Ala Arg Ile His Glu Val Val
        195                 200                 205
Pro Arg Phe Leu Thr Glu Lys Leu Met Glu Gln Asn Arg Leu Lys Asn
210                 215                 220
Val Thr Pro Leu Ser Ala Asn Gln Lys Ser Leu Ile Ala Arg Leu Val
225                 230                 235                 240
Trp Tyr Gln Glu Gly Tyr Glu Gln Pro Ser Glu Glu Asp Leu Lys Arg
                245                 250                 255
Val Thr Gln Thr Trp Gln Leu Glu Glu Glu Glu Glu Glu Glu Thr Asp
                260                 265                 270
Met Pro Phe Arg Gln Ile Thr Glu Met Thr Ile Leu Thr Val Gln Leu
            275                 280                 285
Ile Val Glu Phe Ala Lys Gly Leu Pro Gly Phe Ser Lys Ile Ser Gln
290                 295                 300
Ser Asp Gln Ile Thr Leu Leu Lys Ala Ser Ser Ser Glu Val Met Met
305                 310                 315                 320
Leu Arg Val Ala Arg Arg Tyr Asp Ala Ala Thr Asp Ser Val Leu Phe
                325                 330                 335
Ala Asn Asn Gln Ala Tyr Thr Arg Asp Asn Tyr Arg Lys Ala Gly Met
                340                 345                 350
Ser Tyr Val Ile Glu Asp Leu Leu His Phe Cys Arg Cys Met Tyr Ser
                355                 360                 365
Met Ser Met Asp Asn Val His Tyr Ala Leu Leu Thr Ala Ile Val Ile
            370                 375                 380
Phe Ser Asp Arg Pro Gly Leu Glu Gln Pro Leu Leu Val Glu Glu Ile
385                 390                 395                 400
Gln Arg Tyr Tyr Leu Lys Thr Leu Arg Val Tyr Ile Leu Asn Gln His
                405                 410                 415
Ser Ala Ser Pro Arg Cys Ala Val Leu Phe Gly Lys Ile Leu Gly Val
                420                 425                 430
Leu Thr Glu Leu Arg Thr Leu Gly Thr Gln Asn Ser Asn Met Cys Ile
            435                 440                 445
Ser Leu Lys Leu Lys Asn Arg Lys Leu Pro Pro Phe Leu Glu Glu Ile
            450                 455                 460
Trp Asp Val Ala Glu Val Ser Thr Thr Lys Leu Ala Pro Pro Thr Asp
465                 470                 475                 480
Val Ser Leu Gly Asp Glu Leu His Leu Asp Gly Glu Asp Val Ala Met
                485                 490                 495
Ala His Ala Asp Ala Leu Asp Phe Asp Leu Asp Met Leu Gly Asp
                500                 505                 510
Gly Asp Ser Pro Gly Pro Gly Phe Thr Pro His Asp Ser Ala Pro Tyr
            515                 520                 525
Gly Ala Leu Asp Met Ala Asp Phe Glu Phe Gln Met Phe Thr Asp
            530                 535                 540
Ala Leu Gly Ile Asp Glu Tyr Gly Gly
545                 550
```

<210> SEQ ID NO 106
<211> LENGTH: 549
<212> TYPE: DNA
<213> ORGANISM: Zea mays

<400> SEQUENCE: 106
agtgcaaagg tccgccttgt ttctcctctg tctcttgatc tgactaatct tggtttatga     60

| | |
|---|---:|
| ttcgttgagt aattttgggg aaagcttcgt ccacagttttt ttttcgatga acagtgccgc | 120 |
| agtggcgctg atcttgtatg ctatcctgca atcgtggtga acttatttct tttatatcct | 180 |
| tcactcccat gaaaaggcta gtaatctttc tcgatgtaac atcgtccagc actgctatta | 240 |
| ccgtgtggtc catccgacag tctggctgaa cacatcatac gatattgagc aaagatctat | 300 |
| cttccctgtt cttaatgaa agacgtcatt ttcatcagta tgatctaaga atgttgcaac | 360 |
| ttgcaaggag gcgtttcttt ctttgaattt aactaactcg ttgagtggcc ctgtttctcg | 420 |
| gacgtaaggc ctttgctgct ccacacatgt ccattcgaat tttaccgtgt ttagcaaggg | 480 |
| cgaaaagttt gcatcttgat gatttagctt gactatgcga ttgctttcct ggacccgtgc | 540 |
| agctgcggt | 549 |

<210> SEQ ID NO 107
<211> LENGTH: 1088
<212> TYPE: DNA
<213> ORGANISM: Zea mays

<400> SEQUENCE: 107

| | |
|---|---:|
| gtcgaccaat tcgagctcgg tacccgacca ttggggtatg cttgctgcct tgctctcctg | 60 |
| ttcatctccg tgctaaacct ctgtcctctg ggtgggtttt tgctgggatt ttgagctaat | 120 |
| ctgctggtcc cggtagaaaa gatcatgtcc cctgacgagc tcaagcgctc gccttagccg | 180 |
| cgtccttgcc ccccgccatt ttttgcggtt tcggtgtgtt cccgtgactc gccgggtgcg | 240 |
| tcatcgcctg aatcttgtct gggctctgct gacatgttct tggctagttg ggtttataga | 300 |
| ttcctctgat ctaaaccgtg cctgtgctgc gcacagaact ctcccctgtc cttttcctggg | 360 |
| gttttggtta cgtggtggta gtaagcttgg atttgcacat ggataaagtt gttctaagct | 420 |
| ccgtgggttg cttgagatct tgctgktatt gcgtgccgtg ctcactttttt ttgcaatccg | 480 |
| aggaatgaat ttgtcgttta ctcgttttgg tggattatta gcgcgaaaaa aaaactcttt | 540 |
| ttttttttttg ktcttttact acgaaaagca tcttcttgga ttttgctatc ttcttttact | 600 |
| acgaaaaact cttgagtcta ggaatttgaa tttgkgatgt ccattcttgc agtgcgctgt | 660 |
| gctttattgg gaagccaaat cctattattt tctgcctcta gggtctgaat ggaatcagta | 720 |
| ctcttgagac agaaaatcaa tccaatcaag ttgatttctt tctttaaaaa tattatcaca | 780 |
| gaactaagtg cttgtgcgga atcagtactg gcttttgttt ggtggaggat caatacttgc | 840 |
| ttttgtttgg gggtggcaac tgttttgcta aagattcca tgtgttcctg ttgagatgaa | 900 |
| tcatatatag tatagctgca tactacaaat ctgtttttca aatttaggtt gctttggcat | 960 |
| gatctatttt tttgtcagac agactttcta agtggtagct cttgattcct tgttcttgta | 1020 |
| caactggtgc tgctgaatct tgaccgtata gctcgaattg cagtattctg aaccatcgac | 1080 |
| cggtcgac | 1088 |

<210> SEQ ID NO 108
<211> LENGTH: 963
<212> TYPE: DNA
<213> ORGANISM: Zea mays

<400> SEQUENCE: 108

| | |
|---|---:|
| ctgcagggcg ttccggtcca tggttagggc ccggtagttc tacttctgtt catgtttgtg | 60 |
| ttagatccgt gtttgtgtta gatccgtgct gctagcgttc gtacacggat gcgacctgta | 120 |
| cgtcagacac gttctgattg ctaacttgcc agtgttctc tttggggaat cctgggatgg | 180 |
| ctctagccgt tccgcagacg ggatcgattt catgattttt tttgtttcgt tgcataggggt | 240 |

```
ttggtttgcc cttttccttt atttcaatat atgccgtgca cttgtttgtc gggtcatctt      300
ttcatgcttt tttttgtctt ggttgtgatg atgtggtctg gttgggcggt cgttctagat      360
cggagtagaa ttctgtttca aactacctgg tggatttatt aatttggat ctgtatgtgt       420 gtgccataca tattcatagt tacgaattga agatgatgga tggaaatatc gatctaggat      480
aggtatacat gttgatgcgg gttttactga tgcatataca gagatgcttt ttgttcgctt     540
ggttgtgatg atgtggtgtg gttgggcggt cgttcattcg ttctagatcg gagtagaata     600
ctgtttcaaa ctacctggtg tatttattaa ttttggaact gtatgtgtgt gtcatacatc     660
ttcatagtta cgagtttaag atggatggaa atatcgatct aggataggta tacatgttga     720
tgtgggtttt actgatgcat atacatgatg gcatatgcag catctattca tatgctctaa     780
ccttgagtac ctatctatta taataaacaa gtatgtttta taattatttt gatcttgata     840
tacttggatg atggcatatg cagcagctat atgtggattt ttttagcccct gccttcatac    900 gctatttatt tgcttggtac tgtttctttt gtcgatgctc accctgttgt ttggtgttac     960
ttc                                                                   963

<210> SEQ ID NO 109
<211> LENGTH: 470
<212> TYPE: DNA
<213> ORGANISM: Oryza sp.

<400> SEQUENCE: 109
ccggtaacca ccccgcccct ctcctctttc tttctccgtt ttttttttcc gtctcggtct      60
cgatctttgg ccttggtagt ttgggtgggc gagaggcggc ttcgtgcgcg cccagatcgg     120
tgcgcgggag gggcgggatc tcgcggctgg ggctctcgcc ggcgtggatc ctcgcgggga    180
atggggctct cggatgtaga tctgatccgc cgttgttggg ggagatgatg gggcgtttaa    240
aatttcgcca tgctaaacaa gatcaggaag aggggaaaag ggcactatgg tttatatttt    300
tatatatttc tgctgctgct cgtcaggctt agatgtgcta gatctttctt tcttcttttt    360
gtgggtagaa tttgaatccc tcagcattgt tcatcggtag ttttctttt catgatttgt     420 gacaaatgca gcctcgtgcg gagctttttt gtaggtagaa gctgcaggga                470

<210> SEQ ID NO 110
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer

<400> SEQUENCE: 110
ggcctgcagg gcgttccggt ccatggttag ggc                                   33

<210> SEQ ID NO 111
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer

<400> SEQUENCE: 111
tccctgcaga agtaacacca aacaaca                                          27
```

```
<210> SEQ ID NO 112
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 112
ggcgaattcc cggtaaccac cccgcccctc                                       30

<210> SEQ ID NO 113
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer

<400> SEQUENCE: 113
cgcgaattct ccctgcagct tctacctaca aaa                                    33

<210> SEQ ID NO 114
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: primer

<400> SEQUENCE: 114
gctcgacgcg tatgaggccc gagtgcgtcg tcccagag                               38

<210> SEQ ID NO 115
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer

<400> SEQUENCE: 115
gctcgacgcg tatgaggccc gagtgcgtgg tgccag                                 36

<210> SEQ ID NO 116
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer

<400> SEQUENCE: 116
tgccagctgc tagaggatcc tacccaccgt actcg                                  35

<210> SEQ ID NO 117
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: primer
```

-continued

<400> SEQUENCE: 117
tgcgatatcg gatcctaccc accgtactcg tcaattcc                        38

<210> SEQ ID NO 118
<211> LENGTH: 1776
<212> TYPE: DNA
<213> ORGANISM: Synthetic Construct
<220> FEATURE:
<221> NAME/KEY: CDS
<222> LOCATION: (1)..(1776)
<223> OTHER INFORMATION: Ecdysone receptor chimera G(M)BV

<400> SEQUENCE: 118

| | | | | | | | | | | | | | | | | |
|---|---|---|---|---|---|---|---|---|---|---|---|---|---|---|---|---|
| atg | cag | cag | cta | tat | gtg | gat | ttt | ttt | agc | cct | gcc | ttc | ata | cgc | tat | 48 |
| Met | Gln | Gln | Leu | Tyr | Val | Asp | Phe | Phe | Ser | Pro | Ala | Phe | Ile | Arg | Tyr | |
| 1 | | | | 5 | | | | | 10 | | | | | 15 | | |
| tta | ttt | gct | tgg | tac | tgt | ttc | ttt | tgt | cga | tgc | tca | ccc | tgt | tgt | ttg | 96 |
| Leu | Phe | Ala | Trp | Tyr | Cys | Phe | Phe | Cys | Arg | Cys | Ser | Pro | Cys | Cys | Leu | |
| | | | 20 | | | | | 25 | | | | | 30 | | | |
| gtg | tta | ctt | ctg | cag | gga | tcc | gcc | acc | atg | aag | cta | ctg | tct | tct | atc | 144 |
| Val | Leu | Leu | Leu | Gln | Gly | Ser | Ala | Thr | Met | Lys | Leu | Leu | Ser | Ser | Ile | |
| | | 35 | | | | | 40 | | | | | 45 | | | | |
| gaa | caa | gca | tgc | gat | att | tgc | cga | ctt | aaa | aag | ctc | aag | tgc | tcc | aaa | 192 |
| Glu | Gln | Ala | Cys | Asp | Ile | Cys | Arg | Leu | Lys | Lys | Leu | Lys | Cys | Ser | Lys | |
| | 50 | | | | | 55 | | | | | 60 | | | | | |
| gaa | aaa | ccg | aag | tgc | gcc | aag | tgt | ctg | aag | aac | aac | tgg | gag | tgt | cgc | 240 |
| Glu | Lys | Pro | Lys | Cys | Ala | Lys | Cys | Leu | Lys | Asn | Asn | Trp | Glu | Cys | Arg | |
| 65 | | | | | 70 | | | | | 75 | | | | | 80 | |
| tac | tct | ccc | aaa | acc | aaa | agg | tct | ccg | ctg | act | agg | gca | cat | ctg | aca | 288 |
| Tyr | Ser | Pro | Lys | Thr | Lys | Arg | Ser | Pro | Leu | Thr | Arg | Ala | His | Leu | Thr | |
| | | | | 85 | | | | | 90 | | | | | 95 | | |
| gaa | gtg | gaa | tca | agg | cta | gaa | aga | ctg | gaa | cag | cta | ttt | cta | ctg | att | 336 |
| Glu | Val | Glu | Ser | Arg | Leu | Glu | Arg | Leu | Glu | Gln | Leu | Phe | Leu | Leu | Ile | |
| | | | 100 | | | | | 105 | | | | | 110 | | | |
| ttt | cct | cga | gaa | gac | ctt | gac | atg | att | ttg | aaa | atg | gat | tct | tta | cag | 384 |
| Phe | Pro | Arg | Glu | Asp | Leu | Asp | Met | Ile | Leu | Lys | Met | Asp | Ser | Leu | Gln | |
| | | 115 | | | | | 120 | | | | | 125 | | | | |
| gat | ata | aaa | gca | ttg | tta | aca | gga | tta | ttt | gta | caa | gat | aat | gtg | aat | 432 |
| Asp | Ile | Lys | Ala | Leu | Leu | Thr | Gly | Leu | Phe | Val | Gln | Asp | Asn | Val | Asn | |
| | 130 | | | | | 135 | | | | | 140 | | | | | |
| aaa | gat | gcc | gtc | aca | gat | aga | ttg | gct | tca | gtg | gag | act | gat | atg | cct | 480 |
| Lys | Asp | Ala | Val | Thr | Asp | Arg | Leu | Ala | Ser | Val | Glu | Thr | Asp | Met | Pro | |
| 145 | | | | | 150 | | | | | 155 | | | | | 160 | |
| cta | aca | ttg | aga | cag | cat | aga | ata | agt | gcg | aca | tca | tca | tcg | gaa | gag | 528 |
| Leu | Thr | Leu | Arg | Gln | His | Arg | Ile | Ser | Ala | Thr | Ser | Ser | Ser | Glu | Glu | |
| | | | | 165 | | | | | 170 | | | | | 175 | | |
| agt | agt | aac | aaa | ggt | caa | aga | cag | ttg | act | gta | tcg | acg | cgt | atg | agg | 576 |
| Ser | Ser | Asn | Lys | Gly | Gln | Arg | Gln | Leu | Thr | Val | Ser | Thr | Arg | Met | Arg | |
| | | | 180 | | | | | 185 | | | | | 190 | | | |
| ccc | gag | tgc | gtc | gtc | cca | gag | tcc | acg | tgc | aag | aac | aaa | aga | aga | gaa | 624 |
| Pro | Glu | Cys | Val | Val | Pro | Glu | Ser | Thr | Cys | Lys | Asn | Lys | Arg | Arg | Glu | |
| | | 195 | | | | | 200 | | | | | 205 | | | | |
| aag | gaa | gca | cag | aga | gaa | aaa | gac | aaa | ctg | cca | gtc | agt | acg | acg | aca | 672 |
| Lys | Glu | Ala | Gln | Arg | Glu | Lys | Asp | Lys | Leu | Pro | Val | Ser | Thr | Thr | Thr | |
| | 210 | | | | | 215 | | | | | 220 | | | | | |
| gtg | gac | gat | cat | atg | cct | gcc | ata | atg | caa | tgt | gac | cct | ccg | ccc | cca | 720 |
| Val | Asp | Asp | His | Met | Pro | Ala | Ile | Met | Gln | Cys | Asp | Pro | Pro | Pro | Pro | |
| 225 | | | | | 230 | | | | | 235 | | | | | 240 | |
| gag | gcg | gca | agg | att | cac | gaa | gtg | gtc | ccg | agg | ttc | cta | acg | gag | aag | 768 |
| Glu | Ala | Ala | Arg | Ile | His | Glu | Val | Val | Pro | Arg | Phe | Leu | Thr | Glu | Lys | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 245 |     |     |     |     | 250 |     |     |     |     | 255 |     |     |     |      |
| cta | atg | gag | cag | aac | aga | ctg | aag | aat | gtg | acg | ccg | ctg | tcg | gcg | aac | 816  |
| Leu | Met | Glu | Gln | Asn | Arg | Leu | Lys | Asn | Val | Thr | Pro | Leu | Ser | Ala | Asn |      |
|     |     | 260 |     |     |     |     | 265 |     |     |     |     | 270 |     |     |     |      |
| cag | aag | tcc | ctg | atc | gcg | agg | ctc | gtg | tgg | tac | cag | gaa | ggc | tat | gaa | 864  |
| Gln | Lys | Ser | Leu | Ile | Ala | Arg | Leu | Val | Trp | Tyr | Gln | Glu | Gly | Tyr | Glu |      |
|     |     | 275 |     |     |     |     | 280 |     |     |     |     | 285 |     |     |     |      |
| caa | cct | tca | gag | gaa | gac | ctc | aag | agg | gtg | acg | cag | acc | tgg | cag | tcg | 912  |
| Gln | Pro | Ser | Glu | Glu | Asp | Leu | Lys | Arg | Val | Thr | Gln | Thr | Trp | Gln | Ser |      |
|     |     | 290 |     |     |     |     | 295 |     |     |     |     | 300 |     |     |     |      |
| gac | gag | gat | gaa | gag | gag | tca | gat | atg | ccg | ttc | cgc | cag | atc | acc | gag | 960  |
| Asp | Glu | Asp | Glu | Glu | Glu | Ser | Asp | Met | Pro | Phe | Arg | Gln | Ile | Thr | Glu |      |
| 305 |     |     |     |     |     | 310 |     |     |     |     | 315 |     |     |     | 320 |      |
| atg | acg | atc | ctg | aca | gtt | caa | ctc | atc | gta | gaa | ttc | gca | aaa | ggc | ctg | 1008 |
| Met | Thr | Ile | Leu | Thr | Val | Gln | Leu | Ile | Val | Glu | Phe | Ala | Lys | Gly | Leu |      |
|     |     |     |     | 325 |     |     |     |     | 330 |     |     |     |     | 335 |     |      |
| cca | ggc | ttc | gcc | aag | atc | tcg | cag | tcg | gat | caa | atc | acg | tta | cta | aag | 1056 |
| Pro | Gly | Phe | Ala | Lys | Ile | Ser | Gln | Ser | Asp | Gln | Ile | Thr | Leu | Leu | Lys |      |
|     |     |     |     | 340 |     |     |     |     | 345 |     |     |     |     | 350 |     |      |
| gcg | tgt | tca | agt | gag | gtg | atg | atg | ctc | cga | gtg | gcc | cgg | cgg | tac | gac | 1104 |
| Ala | Cys | Ser | Ser | Glu | Val | Met | Met | Leu | Arg | Val | Ala | Arg | Arg | Tyr | Asp |      |
|     |     |     |     | 355 |     |     |     |     | 360 |     |     |     |     | 365 |     |      |
| gcg | gcc | acc | gac | agc | gta | ctg | ttc | gcc | aac | aac | cag | gcg | tac | tcc | cgc | 1152 |
| Ala | Ala | Thr | Asp | Ser | Val | Leu | Phe | Ala | Asn | Asn | Gln | Ala | Tyr | Ser | Arg |      |
|     |     | 370 |     |     |     |     | 375 |     |     |     |     | 380 |     |     |     |      |
| gac | aac | tac | cgc | aag | gca | ggc | atg | tcc | tac | gtc | atc | gag | gat | ctc | ttg | 1200 |
| Asp | Asn | Tyr | Arg | Lys | Ala | Gly | Met | Ser | Tyr | Val | Ile | Glu | Asp | Leu | Leu |      |
| 385 |     |     |     |     | 390 |     |     |     |     | 395 |     |     |     |     | 400 |      |
| cac | ttc | tgt | cgg | tgc | atg | tac | tcc | atg | atg | atg | gat | aac | gtg | cac | tac | 1248 |
| His | Phe | Cys | Arg | Cys | Met | Tyr | Ser | Met | Met | Met | Asp | Asn | Val | His | Tyr |      |
|     |     |     |     | 405 |     |     |     |     | 410 |     |     |     |     | 415 |     |      |
| gcg | ctg | ctt | acg | gcc | att | gtc | att | ttc | tca | gac | cgg | cct | ggg | ctc | gag | 1296 |
| Ala | Leu | Leu | Thr | Ala | Ile | Val | Ile | Phe | Ser | Asp | Arg | Pro | Gly | Leu | Glu |      |
|     |     |     |     | 420 |     |     |     |     | 425 |     |     |     |     | 430 |     |      |
| caa | ccc | tta | ttg | gtg | gaa | gaa | atc | cag | cgg | tat | tac | ctg | aac | acg | ctg | 1344 |
| Gln | Pro | Leu | Leu | Val | Glu | Glu | Ile | Gln | Arg | Tyr | Tyr | Leu | Asn | Thr | Leu |      |
|     |     |     |     | 435 |     |     |     |     | 440 |     |     |     |     | 445 |     |      |
| cgg | gtg | tac | atc | ttg | aac | caa | aac | agt | gcg | tcg | ccg | cgc | tgc | ccc | gta | 1392 |
| Arg | Val | Tyr | Ile | Leu | Asn | Gln | Asn | Ser | Ala | Ser | Pro | Arg | Cys | Pro | Val |      |
| 450 |     |     |     |     | 455 |     |     |     |     | 460 |     |     |     |     |     |      |
| gtc | ttc | gcc | aag | atc | ctg | ggg | ata | ttg | acg | gag | ctg | cgg | acc | ctc | ggc | 1440 |
| Val | Phe | Ala | Lys | Ile | Leu | Gly | Ile | Leu | Thr | Glu | Leu | Arg | Thr | Leu | Gly |      |
| 465 |     |     |     |     | 470 |     |     |     |     | 475 |     |     |     |     | 480 |      |
| atg | cag | aac | tcc | aac | atg | tgc | atc | tcg | ttg | aag | ctg | aag | aat | agg | aag | 1488 |
| Met | Gln | Asn | Ser | Asn | Met | Cys | Ile | Ser | Leu | Lys | Leu | Lys | Asn | Arg | Lys |      |
|     |     |     |     | 485 |     |     |     |     | 490 |     |     |     |     | 495 |     |      |
| ctg | ccg | ccg | ttc | ctc | gag | gag | atc | tgg | gac | gtg | gaa | tcc | cgc | ggg | aag | 1536 |
| Leu | Pro | Pro | Phe | Leu | Glu | Glu | Ile | Trp | Asp | Val | Glu | Ser | Arg | Gly | Lys |      |
|     |     |     |     | 500 |     |     |     |     | 505 |     |     |     |     | 510 |     |      |
| ctt | gcc | ccc | ccg | acc | gat | gtc | agc | ctg | ggg | gac | gag | ctc | cac | tta | gac | 1584 |
| Leu | Ala | Pro | Pro | Thr | Asp | Val | Ser | Leu | Gly | Asp | Glu | Leu | His | Leu | Asp |      |
|     |     |     |     | 515 |     |     |     |     | 520 |     |     |     |     | 525 |     |      |
| ggc | gag | gac | gtg | gcg | atg | gcg | cat | gcc | gac | gcg | cta | gac | gat | ttc | gat | 1632 |
| Gly | Glu | Asp | Val | Ala | Met | Ala | His | Ala | Asp | Ala | Leu | Asp | Asp | Phe | Asp |      |
|     |     | 530 |     |     |     |     | 535 |     |     |     |     | 540 |     |     |     |      |
| ctg | gac | atg | ttg | ggg | gac | ggg | gat | tcc | ccg | ggt | ccg | gga | ttt | acc | ccc | 1680 |
| Leu | Asp | Met | Leu | Gly | Asp | Gly | Asp | Ser | Pro | Gly | Pro | Gly | Phe | Thr | Pro |      |
| 545 |     |     |     |     | 550 |     |     |     |     | 555 |     |     |     |     | 560 |      |
| cac | gac | tcc | gcc | ccc | tac | ggc | gct | ctg | gat | atg | gcc | gac | ttc | gag | ttt | 1728 |

```
                          His Asp Ser Ala Pro Tyr Gly Ala Leu Asp Met Ala Asp Phe Glu Phe
                                          565                 570                 575 gag cag atg ttt acc gat gcc ctt gga att gac gag tac ggt ggg tag                              1776
Glu Gln Met Phe Thr Asp Ala Leu Gly Ile Asp Glu Tyr Gly Gly
                580                 585                 590
```

<210> SEQ ID NO 119
<211> LENGTH: 591
<212> TYPE: PRT
<213> ORGANISM: Synthetic Construct

<400> SEQUENCE: 119

```
Met Gln Gln Leu Tyr Val Asp Phe Phe Ser Pro Ala Phe Ile Arg Tyr
1               5                   10                  15

Leu Phe Ala Trp Tyr Cys Phe Cys Arg Cys Ser Pro Cys Cys Leu
                20                  25                  30

Val Leu Leu Leu Gln Gly Ser Ala Thr Met Lys Leu Leu Ser Ser Ile
                35                  40                  45

Glu Gln Ala Cys Asp Ile Cys Arg Leu Lys Lys Leu Lys Cys Ser Lys
        50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
                100                 105                 110

Phe Pro Arg Glu Asp Leu Asp Met Ile Leu Lys Met Asp Ser Leu Gln
            115                 120                 125

Asp Ile Lys Ala Leu Leu Thr Gly Leu Phe Val Gln Asp Asn Val Asn
        130                 135                 140

Lys Asp Ala Val Thr Asp Arg Leu Ala Ser Val Glu Thr Asp Met Pro
145                 150                 155                 160

Leu Thr Leu Arg Gln His Arg Ile Ser Ala Thr Ser Ser Ser Glu Glu
                165                 170                 175

Ser Ser Asn Lys Gly Gln Arg Gln Leu Thr Val Ser Thr Arg Met Arg
            180                 185                 190

Pro Glu Cys Val Val Pro Glu Ser Thr Cys Lys Asn Lys Arg Arg Glu
        195                 200                 205

Lys Glu Ala Gln Arg Glu Lys Asp Lys Leu Pro Val Ser Thr Thr Thr
210                 215                 220

Val Asp Asp His Met Pro Ala Ile Met Gln Cys Asp Pro Pro Pro
225                 230                 235                 240

Glu Ala Ala Arg Ile His Glu Val Val Pro Arg Phe Leu Thr Glu Lys
                245                 250                 255

Leu Met Glu Gln Asn Arg Leu Lys Asn Val Thr Pro Leu Ser Ala Asn
            260                 265                 270

Gln Lys Ser Leu Ile Ala Arg Leu Val Trp Tyr Gln Glu Gly Tyr Glu
        275                 280                 285

Gln Pro Ser Glu Glu Asp Leu Lys Arg Val Thr Gln Thr Trp Gln Ser
    290                 295                 300

Asp Glu Asp Glu Glu Ser Asp Met Pro Phe Arg Gln Ile Thr Glu
305                 310                 315                 320

Met Thr Ile Leu Thr Val Gln Leu Ile Val Glu Phe Ala Lys Gly Leu
                325                 330                 335

Pro Gly Phe Ala Lys Ile Ser Gln Ser Asp Gln Ile Thr Leu Leu Lys
```

-continued

```
                340                 345                 350
Ala Cys Ser Ser Glu Val Met Met Leu Arg Val Ala Arg Arg Tyr Asp
            355                 360                 365

Ala Ala Thr Asp Ser Val Leu Phe Ala Asn Asn Gln Ala Tyr Ser Arg
        370                 375                 380

Asp Asn Tyr Arg Lys Ala Gly Met Ser Tyr Val Ile Glu Asp Leu Leu
385                 390                 395                 400

His Phe Cys Arg Cys Met Tyr Ser Met Met Met Asp Asn Val His Tyr
                405                 410                 415

Ala Leu Leu Thr Ala Ile Val Ile Phe Ser Asp Arg Pro Gly Leu Glu
            420                 425                 430

Gln Pro Leu Leu Val Glu Glu Ile Gln Arg Tyr Tyr Leu Asn Thr Leu
        435                 440                 445

Arg Val Tyr Ile Leu Asn Gln Asn Ser Ala Ser Pro Arg Cys Pro Val
    450                 455                 460

Val Phe Ala Lys Ile Leu Gly Ile Leu Thr Glu Leu Arg Thr Leu Gly
465                 470                 475                 480

Met Gln Asn Ser Asn Met Cys Ile Ser Leu Lys Leu Lys Asn Arg Lys
                485                 490                 495

Leu Pro Pro Phe Leu Glu Glu Ile Trp Asp Val Glu Ser Arg Gly Lys
            500                 505                 510

Leu Ala Pro Pro Thr Asp Val Ser Leu Gly Asp Glu Leu His Leu Asp
        515                 520                 525

Gly Glu Asp Val Ala Met Ala His Ala Asp Ala Leu Asp Asp Phe Asp
    530                 535                 540

Leu Asp Met Leu Gly Asp Gly Asp Ser Pro Gly Pro Gly Phe Thr Pro
545                 550                 555                 560

His Asp Ser Ala Pro Tyr Gly Ala Leu Asp Met Ala Asp Phe Glu Phe
                565                 570                 575

Glu Gln Met Phe Thr Asp Ala Leu Gly Ile Asp Glu Tyr Gly Gly
            580                 585                 590

<210> SEQ ID NO 120
<211> LENGTH: 1767
<212> TYPE: DNA
<213> ORGANISM: Synthetic Construct
<220> FEATURE:
<221> NAME/KEY: CDS
<222> LOCATION: (1)..(1767)
<223> OTHER INFORMATION: Ecdysone receptor chimera G(M)EV

<400> SEQUENCE: 120 atg cag cag cta tat gtg gat ttt ttt agc cct gcc ttc ata cgc tat      48
Met Gln Gln Leu Tyr Val Asp Phe Phe Ser Pro Ala Phe Ile Arg Tyr
1               5                   10                  15 tta ttt gct tgg tac tgt ttc ttt tgt cga tgc tca ccc tgt tgt ttg      96
Leu Phe Ala Trp Tyr Cys Phe Phe Cys Arg Cys Ser Pro Cys Cys Leu
                20                  25                  30 gtg tta ctt ctg cag gga tcc gcc acc atg aag cta ctg tct tct atc     144
Val Leu Leu Leu Gln Gly Ser Ala Thr Met Lys Leu Leu Ser Ser Ile
            35                  40                  45 gaa caa gca tgc gat att tgc cga ctt aaa aag ctc aag tgc tcc aaa     192
Glu Gln Ala Cys Asp Ile Cys Arg Leu Lys Lys Leu Lys Cys Ser Lys
        50                  55                  60 gaa aaa ccg aag tgc gcc aag tgt ctg aag aac aac tgg gag tgt cgc     240
Glu Lys Pro Lys Cys Ala Lys Cys Leu Lys Asn Asn Trp Glu Cys Arg
65                  70                  75                  80
```

-continued

| | | |
|---|---|---|
| tac tct ccc aaa acc aaa agg tct ccg ctg act agg gca cat ctg aca<br>Tyr Ser Pro Lys Thr Lys Arg Ser Pro Leu Thr Arg Ala His Leu Thr<br>                      85                      90              95 | 288 |
| gaa gtg gaa tca agg cta gaa aga ctg gaa cag cta ttt cta ctg att<br>Glu Val Glu Ser Arg Leu Glu Arg Leu Glu Gln Leu Phe Leu Leu Ile<br>           100                  105               110 | 336 |
| ttt cct cga gaa gac ctt gac atg att ttg aaa atg gat tct tta cag<br>Phe Pro Arg Glu Asp Leu Asp Met Ile Leu Lys Met Asp Ser Leu Gln<br>         115                  120               125 | 384 |
| gat ata aaa gca ttg tta aca gga tta ttt gta caa gat aat gtg aat<br>Asp Ile Lys Ala Leu Leu Thr Gly Leu Phe Val Gln Asp Asn Val Asn<br>130                   135               140 | 432 |
| aaa gat gcc gtc aca gat aga ttg gct tca gtg gag act gat atg cct<br>Lys Asp Ala Val Thr Asp Arg Leu Ala Ser Val Glu Thr Asp Met Pro<br>145                   150               155              160 | 480 |
| cta aca ttg aga cag cat aga ata agt gcg aca tca tca tcg gaa gag<br>Leu Thr Leu Arg Gln His Arg Ile Ser Ala Thr Ser Ser Ser Glu Glu<br>               165               170             175 | 528 |
| agt agt aac aaa ggt caa aga cag ttg act gta tcg acg cgt atg agg<br>Ser Ser Asn Lys Gly Gln Arg Gln Leu Thr Val Ser Thr Arg Met Arg<br>        180                 185               190 | 576 |
| ccc gag tgc gtc gtc cca gag tcc acg tgc aag aac aaa aga aga gaa<br>Pro Glu Cys Val Val Pro Glu Ser Thr Cys Lys Asn Lys Arg Arg Glu<br>           195                  200               205 | 624 |
| aag gaa gca cag aga gaa aaa gac aaa ctg cca gtc agt acg acg aca<br>Lys Glu Ala Gln Arg Glu Lys Asp Lys Leu Pro Val Ser Thr Thr Thr<br>210                   215               220 | 672 |
| gtg gac gat cat atg cct gcc ata atg caa tgt gac cct ccg ccc cca<br>Val Asp Asp His Met Pro Ala Ile Met Gln Cys Asp Pro Pro Pro Pro<br>225                   230               235              240 | 720 |
| gag gcg gca agg att cac gaa gtg gtc ccg agg ttc cta acg gag aag<br>Glu Ala Ala Arg Ile His Glu Val Val Pro Arg Phe Leu Thr Glu Lys<br>               245               250             255 | 768 |
| cta atg gag cag aac aga ctg aag aat gtg acg ccg ctg tcg gcg aac<br>Leu Met Glu Gln Asn Arg Leu Lys Asn Val Thr Pro Leu Ser Ala Asn<br>             260               265               270 | 816 |
| cag aag tcc ctg atc gcg agg ctc gtg tgg tac cag gac gga tac gag<br>Gln Lys Ser Leu Ile Ala Arg Leu Val Trp Tyr Gln Asp Gly Tyr Glu<br>       275                 280               285 | 864 |
| cag cct tcg gaa gag gat ctc aaa agg gtg acg cag act tgg caa tca<br>Gln Pro Ser Glu Glu Asp Leu Lys Arg Val Thr Gln Thr Trp Gln Ser<br>           290                  295               300 | 912 |
| gca gat gaa gaa gac gaa gac tca gac atg cca ttc cgc cag atc aca<br>Ala Asp Glu Glu Asp Glu Asp Ser Asp Met Pro Phe Arg Gln Ile Thr<br>305                   310               315              320 | 960 |
| gaa atg acc atc ctc aca gta cag cta ata gtc gag ttt gcc aaa ggc<br>Glu Met Thr Ile Leu Thr Val Gln Leu Ile Val Glu Phe Ala Lys Gly<br>               325               330             335 | 1008 |
| cta cct ggt ttt tca aag atc tca caa cct gac cag atc aca tta tta<br>Leu Pro Gly Phe Ser Lys Ile Ser Gln Pro Asp Gln Ile Thr Leu Leu<br>                 340               345             350 | 1056 |
| aag gca tgc tca agc gaa gtg atg atg ctg cga gta gcg agg cgg tac<br>Lys Ala Cys Ser Ser Glu Val Met Met Leu Arg Val Ala Arg Arg Tyr<br>             355               360               365 | 1104 |
| gac gcg gtg tcg gat agc gtt ctg ttc gcc aac aac cag gcg tac act<br>Asp Ala Val Ser Asp Ser Val Leu Phe Ala Asn Asn Gln Ala Tyr Thr<br>           370                  375               380 | 1152 |
| cgc gac aac tac cgc aag gcg ggc atg gcc tac gtc atc gaa gac ctg<br>Arg Asp Asn Tyr Arg Lys Ala Gly Met Ala Tyr Val Ile Glu Asp Leu<br>385                   390               395              400 | 1200 |

```
ctg cac ttc tgc cgc tgc atg tac tcg atg tcg atg gac aac gtg cat      1248
Leu His Phe Cys Arg Cys Met Tyr Ser Met Ser Met Asp Asn Val His
            405                 410                 415 tac gcg ctc ctc act gcc atc gtt ata ttc tcg gat cgg ccg ggc cta      1296
Tyr Ala Leu Leu Thr Ala Ile Val Ile Phe Ser Asp Arg Pro Gly Leu
        420                 425                 430 gag cag cca cag cta gta gaa gag atc cag cgg tat tac ctg aac acg      1344
Glu Gln Pro Gln Leu Val Glu Glu Ile Gln Arg Tyr Tyr Leu Asn Thr
    435                 440                 445 ctg cgg gtg tac atc atg aac cag cac agc gcg tcg ccg cgt tgc gcc      1392
Leu Arg Val Tyr Ile Met Asn Gln His Ser Ala Ser Pro Arg Cys Ala
450                 455                 460 gtc atc tac gcg aag att ctg tcg gtg ctt acc gag ttg cgg acg ctg      1440
Val Ile Tyr Ala Lys Ile Leu Ser Val Leu Thr Glu Leu Arg Thr Leu
465                 470                 475                 480 ggc atg cag aat tcg aac atg tgc atc tcg ctg aag ctc aag aac agg      1488
Gly Met Gln Asn Ser Asn Met Cys Ile Ser Leu Lys Leu Lys Asn Arg
                485                 490                 495 aag ctg ccg ccg ttc ctg gag gag atc tgg gac gtg aag ctt gcc ccc      1536
Lys Leu Pro Pro Phe Leu Glu Glu Ile Trp Asp Val Lys Leu Ala Pro
            500                 505                 510 ccg acc gat gtc agc ctg ggg gac gag ctc cac tta gac ggc gag gac      1584
Pro Thr Asp Val Ser Leu Gly Asp Glu Leu His Leu Asp Gly Glu Asp
        515                 520                 525 gtg gcg atg gcg cat gcc gac gcg cta gac gat ttc gat ctg gac atg      1632
Val Ala Met Ala His Ala Asp Ala Leu Asp Asp Phe Asp Leu Asp Met
    530                 535                 540 ttg ggg gac ggg gat tcc ccg ggt ccg gga ttt acc ccc cac gac tcc      1680
Leu Gly Asp Gly Asp Ser Pro Gly Pro Gly Phe Thr Pro His Asp Ser
545                 550                 555                 560 gcc ccc tac ggc gct ctg gat atg gcc gac ttc gag ttt gag cag atg      1728
Ala Pro Tyr Gly Ala Leu Asp Met Ala Asp Phe Glu Phe Glu Gln Met
                565                 570                 575 ttt acc gat gcc ctt gga att gac gag tac ggt ggg tag                  1767
Phe Thr Asp Ala Leu Gly Ile Asp Glu Tyr Gly Gly
            580                 585

<210> SEQ ID NO 121
<211> LENGTH: 588
<212> TYPE: PRT
<213> ORGANISM: Synthetic Construct

<400> SEQUENCE: 121

Met Gln Gln Leu Tyr Val Asp Phe Phe Ser Pro Ala Phe Ile Arg Tyr
1               5                   10                  15

Leu Phe Ala Trp Tyr Cys Phe Cys Arg Cys Ser Pro Cys Cys Leu
            20                  25                  30

Val Leu Leu Leu Gln Gly Ser Ala Thr Met Lys Leu Leu Ser Ser Ile
        35                  40                  45

Glu Gln Ala Cys Asp Ile Cys Arg Leu Lys Lys Leu Lys Cys Ser Lys
    50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
            100                 105                 110

Phe Pro Arg Glu Asp Leu Asp Met Ile Leu Lys Met Asp Ser Leu Gln
```

-continued

```
            115                 120                 125
Asp Ile Lys Ala Leu Leu Thr Gly Leu Phe Val Gln Asp Asn Val Asn
        130                 135                 140
Lys Asp Ala Val Thr Asp Arg Leu Ala Ser Val Glu Thr Asp Met Pro
145                 150                 155                 160
Leu Thr Leu Arg Gln His Arg Ile Ser Ala Thr Ser Ser Ser Glu Glu
                165                 170                 175
Ser Ser Asn Lys Gly Gln Arg Gln Leu Thr Val Ser Thr Arg Met Arg
            180                 185                 190
Pro Glu Cys Val Val Pro Glu Ser Thr Cys Lys Asn Lys Arg Arg Glu
        195                 200                 205
Lys Glu Ala Gln Arg Glu Lys Asp Lys Leu Pro Val Ser Thr Thr Thr
210                 215                 220
Val Asp Asp His Met Pro Ala Ile Met Gln Cys Asp Pro Pro Pro Pro
225                 230                 235                 240
Glu Ala Ala Arg Ile His Glu Val Val Pro Arg Phe Leu Thr Glu Lys
                245                 250                 255
Leu Met Glu Gln Asn Arg Leu Lys Asn Val Thr Pro Leu Ser Ala Asn
            260                 265                 270
Gln Lys Ser Leu Ile Ala Arg Leu Val Trp Tyr Gln Asp Gly Tyr Glu
        275                 280                 285
Gln Pro Ser Glu Glu Asp Leu Lys Arg Val Thr Gln Thr Trp Gln Ser
    290                 295                 300
Ala Asp Glu Glu Asp Glu Asp Ser Asp Met Pro Phe Arg Gln Ile Thr
305                 310                 315                 320
Glu Met Thr Ile Leu Thr Val Gln Leu Ile Val Glu Phe Ala Lys Gly
                325                 330                 335
Leu Pro Gly Phe Ser Lys Ile Ser Gln Pro Asp Gln Ile Thr Leu Leu
            340                 345                 350
Lys Ala Cys Ser Ser Glu Val Met Met Leu Arg Val Ala Arg Arg Tyr
        355                 360                 365
Asp Ala Val Ser Asp Ser Val Leu Phe Ala Asn Asn Gln Ala Tyr Thr
    370                 375                 380
Arg Asp Asn Tyr Arg Lys Ala Gly Met Ala Tyr Val Ile Glu Asp Leu
385                 390                 395                 400
Leu His Phe Cys Arg Cys Met Tyr Ser Met Ser Met Asp Asn Val His
                405                 410                 415
Tyr Ala Leu Leu Thr Ala Ile Val Ile Phe Ser Asp Arg Pro Gly Leu
            420                 425                 430
Glu Gln Pro Gln Leu Val Glu Glu Ile Gln Arg Tyr Tyr Leu Asn Thr
        435                 440                 445
Leu Arg Val Tyr Ile Met Asn Gln His Ser Ala Ser Pro Arg Cys Ala
    450                 455                 460
Val Ile Tyr Ala Lys Ile Leu Ser Val Leu Thr Glu Leu Arg Thr Leu
465                 470                 475                 480
Gly Met Gln Asn Ser Asn Met Cys Ile Ser Leu Lys Leu Lys Asn Arg
                485                 490                 495
Lys Leu Pro Pro Phe Leu Glu Glu Ile Trp Asp Val Lys Leu Ala Pro
            500                 505                 510
Pro Thr Asp Val Ser Leu Gly Asp Glu Leu His Leu Asp Gly Glu Asp
        515                 520                 525
Val Ala Met Ala His Ala Asp Ala Leu Asp Asp Phe Asp Leu Asp Met
    530                 535                 540
```

```
Leu Gly Asp Gly Asp Ser Pro Gly Pro Gly Phe Thr Pro His Asp Ser
545                 550                 555                 560

Ala Pro Tyr Gly Ala Leu Asp Met Ala Asp Phe Glu Phe Glu Gln Met
                565                 570                 575

Phe Thr Asp Ala Leu Gly Ile Asp Glu Tyr Gly Gly
            580                 585

<210> SEQ ID NO 122
<211> LENGTH: 1767
<212> TYPE: DNA
<213> ORGANISM: Synthetic Construct
<220> FEATURE:
<221> NAME/KEY: CDS
<222> LOCATION: (1)..(1767)
<223> OTHER INFORMATION: Ecdysone receptor chimera G(M)FV

<400> SEQUENCE: 122
```

| | | | | | | | | | | | | | | | | |
|---|---|---|---|---|---|---|---|---|---|---|---|---|---|---|---|---|
| atg | cag | cag | cta | tat | gtg | gat | ttt | ttt | agc | cct | gcc | ttc | ata | cgc | tat | 48 |
| Met | Gln | Gln | Leu | Tyr | Val | Asp | Phe | Phe | Ser | Pro | Ala | Phe | Ile | Arg | Tyr | |
| 1 | | | | 5 | | | | | 10 | | | | | 15 | | |
| tta | ttt | gct | tgg | tac | tgt | ttc | ttt | tgt | cga | tgc | tca | ccc | tgt | tgt | ttg | 96 |
| Leu | Phe | Ala | Trp | Tyr | Cys | Phe | Phe | Cys | Arg | Cys | Ser | Pro | Cys | Cys | Leu | |
| | | | 20 | | | | | 25 | | | | | 30 | | | |
| gtg | tta | ctt | ctg | cag | gga | tcc | gcc | acc | atg | aag | cta | ctg | tct | tct | atc | 144 |
| Val | Leu | Leu | Leu | Gln | Gly | Ser | Ala | Thr | Met | Lys | Leu | Leu | Ser | Ser | Ile | |
| | | | 35 | | | | | 40 | | | | | 45 | | | |
| gaa | caa | gca | tgc | gat | att | tgc | cga | ctt | aaa | aag | ctc | aag | tgc | tcc | aaa | 192 |
| Glu | Gln | Ala | Cys | Asp | Ile | Cys | Arg | Leu | Lys | Lys | Leu | Lys | Cys | Ser | Lys | |
| 50 | | | | | 55 | | | | | 60 | | | | | | |
| gaa | aaa | ccg | aag | tgc | gcc | aag | tgt | ctg | aag | aac | aac | tgg | gag | tgt | cgc | 240 |
| Glu | Lys | Pro | Lys | Cys | Ala | Lys | Cys | Leu | Lys | Asn | Asn | Trp | Glu | Cys | Arg | |
| 65 | | | | | 70 | | | | | 75 | | | | | 80 | |
| tac | tct | ccc | aaa | acc | aaa | agg | tct | ccg | ctg | act | agg | gca | cat | ctg | aca | 288 |
| Tyr | Ser | Pro | Lys | Thr | Lys | Arg | Ser | Pro | Leu | Thr | Arg | Ala | His | Leu | Thr | |
| | | | | 85 | | | | | 90 | | | | | 95 | | |
| gaa | gtg | gaa | tca | agg | cta | gaa | aga | ctg | gaa | cag | cta | ttt | cta | ctg | att | 336 |
| Glu | Val | Glu | Ser | Arg | Leu | Glu | Arg | Leu | Glu | Gln | Leu | Phe | Leu | Leu | Ile | |
| | | | | 100 | | | | | 105 | | | | | 110 | | |
| ttt | cct | cga | gaa | gac | ctt | gac | atg | att | ttg | aaa | atg | gat | tct | tta | cag | 384 |
| Phe | Pro | Arg | Glu | Asp | Leu | Asp | Met | Ile | Leu | Lys | Met | Asp | Ser | Leu | Gln | |
| | | | 115 | | | | | 120 | | | | | 125 | | | |
| gat | ata | aaa | gca | ttg | tta | aca | gga | tta | ttt | gta | caa | gat | aat | gtg | aat | 432 |
| Asp | Ile | Lys | Ala | Leu | Leu | Thr | Gly | Leu | Phe | Val | Gln | Asp | Asn | Val | Asn | |
| 130 | | | | | 135 | | | | | 140 | | | | | | |
| aaa | gat | gcc | gtc | aca | gat | aga | ttg | gct | tca | gtg | gag | act | gat | atg | cct | 480 |
| Lys | Asp | Ala | Val | Thr | Asp | Arg | Leu | Ala | Ser | Val | Glu | Thr | Asp | Met | Pro | |
| 145 | | | | | 150 | | | | | 155 | | | | | 160 | |
| cta | aca | ttg | aga | cag | cat | aga | ata | agt | gcg | aca | tca | tca | tcg | gaa | gag | 528 |
| Leu | Thr | Leu | Arg | Gln | His | Arg | Ile | Ser | Ala | Thr | Ser | Ser | Ser | Glu | Glu | |
| | | | | 165 | | | | | 170 | | | | | 175 | | |
| agt | agt | aac | aaa | ggt | caa | aga | cag | ttg | act | gta | tcg | acg | cgt | atg | agg | 576 |
| Ser | Ser | Asn | Lys | Gly | Gln | Arg | Gln | Leu | Thr | Val | Ser | Thr | Arg | Met | Arg | |
| | | | 180 | | | | | 185 | | | | | 190 | | | |
| ccc | gag | tgc | gtc | gtc | cca | gag | tcc | acg | tgc | aag | aac | aaa | aga | aga | gaa | 624 |
| Pro | Glu | Cys | Val | Val | Pro | Glu | Ser | Thr | Cys | Lys | Asn | Lys | Arg | Arg | Glu | |
| | | | 195 | | | | | 200 | | | | | 205 | | | |
| aag | gaa | gca | cag | aga | gaa | aaa | gac | aaa | ctg | cca | gtc | agt | acg | acg | aca | 672 |
| Lys | Glu | Ala | Gln | Arg | Glu | Lys | Asp | Lys | Leu | Pro | Val | Ser | Thr | Thr | Thr | |
| | | 210 | | | | | 215 | | | | | 220 | | | | |
| gtg | gac | gat | cat | atg | cct | gcc | ata | atg | caa | tgt | gac | cct | ccg | ccc | cca | 720 |

| | | |
|---|---|---|
| Val Asp Asp His Met Pro Ala Ile Met Gln Cys Asp Pro Pro Pro<br>225 230 235 240 | | |
| gag gcg gca agg att cac gaa gtg gtc ccg agg ttc cta acg gag aag<br>Glu Ala Ala Arg Ile His Glu Val Val Pro Arg Phe Leu Thr Glu Lys<br>245 250 255 | | 768 |
| cta atg gag cag aac aga ctg aag aat gtg acg ccg ctg tcg gcg aac<br>Leu Met Glu Gln Asn Arg Leu Lys Asn Val Thr Pro Leu Ser Ala Asn<br>260 265 270 | | 816 |
| cag aag tcc ctg atc gcg agg ctc gtg tgg tac cag gag ggg tac gag<br>Gln Lys Ser Leu Ile Ala Arg Leu Val Trp Tyr Gln Glu Gly Tyr Glu<br>275 280 285 | | 864 |
| cag ccg tcg gag gaa gat ctc aag aga gtt aca cag aca tgg cag tta<br>Gln Pro Ser Glu Glu Asp Leu Lys Arg Val Thr Gln Thr Trp Gln Leu<br>290 295 300 | | 912 |
| gaa gaa gaa gaa gag gag gaa act gac atg ccc ttc cgt cag atc aca<br>Glu Glu Glu Glu Glu Glu Thr Asp Met Pro Phe Arg Gln Ile Thr<br>305 310 315 320 | | 960 |
| gag atg acg atc tta aca gtg cag ctt att gta gaa ttc gca aag gga<br>Glu Met Thr Ile Leu Thr Val Gln Leu Ile Val Glu Phe Ala Lys Gly<br>325 330 335 | | 1008 |
| cta ccg gga ttc tcc aag ata tct cag tcc gat caa att aca tta tta<br>Leu Pro Gly Phe Ser Lys Ile Ser Gln Ser Asp Gln Ile Thr Leu Leu<br>340 345 350 | | 1056 |
| aag gcg tca tca agc gaa gtg atg atg ctg cga gtg gcg cga cgg tac<br>Lys Ala Ser Ser Ser Glu Val Met Met Leu Arg Val Ala Arg Arg Tyr<br>355 360 365 | | 1104 |
| gac gcg gcg acg gac agc gtg ctg ttc gcg aac aac cag gcg tac acg<br>Asp Ala Ala Thr Asp Ser Val Leu Phe Ala Asn Asn Gln Ala Tyr Thr<br>370 375 380 | | 1152 |
| cgc gac aac tac cgc aag gcg ggc atg tcc tac gtc atc ggg gac ctg<br>Arg Asp Asn Tyr Arg Lys Ala Gly Met Ser Tyr Val Ile Gly Asp Leu<br>385 390 395 400 | | 1200 |
| ctg cac ttc tgt cgg tgt atg tac tcc atg agc atg gac aat gtg cac<br>Leu His Phe Cys Arg Cys Met Tyr Ser Met Ser Met Asp Asn Val His<br>405 410 415 | | 1248 |
| tac gcg ctg ctc acc gcc atc gtt ata ttc tca gac cgg cca ggc ctc<br>Tyr Ala Leu Leu Thr Ala Ile Val Ile Phe Ser Asp Arg Pro Gly Leu<br>420 425 430 | | 1296 |
| gag caa ccc ctt tta gtg gag gaa atc cag aga tac tac ttg aag acg<br>Glu Gln Pro Leu Leu Val Glu Glu Ile Gln Arg Tyr Tyr Leu Lys Thr<br>435 440 445 | | 1344 |
| ctg cgg gtt tac att tta aat cag tac agc gcg tcg cct cgc tgc gcc<br>Leu Arg Val Tyr Ile Leu Asn Gln Tyr Ser Ala Ser Pro Arg Cys Ala<br>450 455 460 | | 1392 |
| gtg ctg ttc ggc aag atc ctc ggc gtg ctg acg gaa ctg cgc acg ctc<br>Val Leu Phe Gly Lys Ile Leu Gly Val Leu Thr Glu Leu Arg Thr Leu<br>465 470 475 480 | | 1440 |
| ggc acg cag aac tcc aac atg tgc atc tcg ctg aag ctg aag aac agg<br>Gly Thr Gln Asn Ser Asn Met Cys Ile Ser Leu Lys Leu Lys Asn Arg<br>485 490 495 | | 1488 |
| aaa ctt ccg cca ttc ctc gag gag atc tgg gac gtg aag ctt gcc ccc<br>Lys Leu Pro Pro Phe Leu Glu Glu Ile Trp Asp Val Lys Leu Ala Pro<br>500 505 510 | | 1536 |
| ccg acc gat gtc agc ctg ggg gac gag ctc cac tta gac ggc gag gac<br>Pro Thr Asp Val Ser Leu Gly Asp Glu Leu His Leu Asp Gly Glu Asp<br>515 520 525 | | 1584 |
| gtg gcg atg gcg cat gcc gac gcg cta gac gat ttc gat ctg gac atg<br>Val Ala Met Ala His Ala Asp Ala Leu Asp Asp Phe Asp Leu Asp Met<br>530 535 540 | | 1632 |

-continued

```
ttg ggg gac ggg gat tcc ccg ggt ccg gga ttt acc ccc cac gac tcc        1680
Leu Gly Asp Gly Asp Ser Pro Gly Pro Gly Phe Thr Pro His Asp Ser
545                 550                 555                 560 gcc ccc tac ggc gct ctg gat atg gcc gac ttc gag ttt gag cag atg        1728
Ala Pro Tyr Gly Ala Leu Asp Met Ala Asp Phe Glu Phe Glu Gln Met
                565                 570                 575 ttt acc gat gcc ctt gga att gac gag tac ggt ggg tag                    1767
Phe Thr Asp Ala Leu Gly Ile Asp Glu Tyr Gly Gly
            580                 585
```

<210> SEQ ID NO 123
<211> LENGTH: 588
<212> TYPE: PRT
<213> ORGANISM: Synthetic Construct

<400> SEQUENCE: 123

```
Met Gln Gln Leu Tyr Val Asp Phe Phe Ser Pro Ala Phe Ile Arg Tyr
1               5                   10                  15

Leu Phe Ala Trp Tyr Cys Phe Phe Cys Arg Cys Ser Pro Cys Cys Leu
            20                  25                  30

Val Leu Leu Leu Gln Gly Ser Ala Thr Met Lys Leu Leu Ser Ser Ile
        35                  40                  45

Glu Gln Ala Cys Asp Ile Cys Arg Leu Lys Lys Leu Lys Cys Ser Lys
    50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
            100                 105                 110

Phe Pro Arg Glu Asp Leu Asp Met Ile Leu Lys Met Asp Ser Leu Gln
        115                 120                 125

Asp Ile Lys Ala Leu Leu Thr Gly Leu Phe Val Gln Asp Asn Val Asn
    130                 135                 140

Lys Asp Ala Val Thr Asp Arg Leu Ala Ser Val Glu Thr Asp Met Pro
145                 150                 155                 160

Leu Thr Leu Arg Gln His Arg Ile Ser Ala Thr Ser Ser Ser Glu Glu
                165                 170                 175

Ser Ser Asn Lys Gly Gln Arg Gln Leu Thr Val Ser Thr Arg Met Arg
            180                 185                 190

Pro Glu Cys Val Val Pro Glu Ser Thr Cys Lys Asn Lys Arg Arg Glu
        195                 200                 205

Lys Glu Ala Gln Arg Glu Lys Asp Lys Leu Pro Val Ser Thr Thr Thr
    210                 215                 220

Val Asp Asp His Met Pro Ala Ile Met Gln Cys Asp Pro Pro Pro
225                 230                 235                 240

Glu Ala Ala Arg Ile His Glu Val Val Pro Arg Phe Leu Thr Glu Lys
                245                 250                 255

Leu Met Glu Gln Asn Arg Leu Lys Asn Val Thr Pro Leu Ser Ala Asn
            260                 265                 270

Gln Lys Ser Leu Ile Ala Arg Leu Val Trp Tyr Gln Glu Gly Tyr Glu
        275                 280                 285

Gln Pro Ser Glu Glu Asp Leu Lys Arg Val Thr Gln Thr Trp Gln Leu
    290                 295                 300

Glu Glu Glu Glu Glu Glu Thr Asp Met Pro Phe Arg Gln Ile Thr
305                 310                 315                 320
```

```
Glu Met Thr Ile Leu Thr Val Gln Leu Ile Val Glu Phe Ala Lys Gly
                325                 330                 335

Leu Pro Gly Phe Ser Lys Ile Ser Gln Ser Asp Gln Ile Thr Leu Leu
            340                 345                 350

Lys Ala Ser Ser Glu Val Met Met Leu Arg Val Ala Arg Arg Tyr
        355                 360                 365

Asp Ala Ala Thr Asp Ser Val Leu Phe Ala Asn Asn Gln Ala Tyr Thr
        370                 375                 380

Arg Asp Asn Tyr Arg Lys Ala Gly Met Ser Tyr Val Ile Gly Asp Leu
385                 390                 395                 400

Leu His Phe Cys Arg Cys Met Tyr Ser Met Ser Met Asp Asn Val His
            405                 410                 415

Tyr Ala Leu Leu Thr Ala Ile Val Ile Phe Ser Asp Arg Pro Gly Leu
                420                 425                 430

Glu Gln Pro Leu Leu Val Glu Glu Ile Gln Arg Tyr Tyr Leu Lys Thr
            435                 440                 445

Leu Arg Val Tyr Ile Leu Asn Gln Tyr Ser Ala Ser Pro Arg Cys Ala
        450                 455                 460

Val Leu Phe Gly Lys Ile Leu Gly Val Leu Thr Glu Leu Arg Thr Leu
465                 470                 475                 480

Gly Thr Gln Asn Ser Asn Met Cys Ile Ser Leu Lys Leu Lys Asn Arg
                485                 490                 495

Lys Leu Pro Pro Phe Leu Glu Glu Ile Trp Asp Val Lys Leu Ala Pro
            500                 505                 510

Pro Thr Asp Val Ser Leu Gly Asp Glu Leu His Leu Asp Gly Glu Asp
        515                 520                 525

Val Ala Met Ala His Ala Asp Ala Leu Asp Asp Phe Asp Leu Asp Met
530                 535                 540

Leu Gly Asp Gly Asp Ser Pro Gly Pro Gly Phe Thr Pro His Asp Ser
545                 550                 555                 560

Ala Pro Tyr Gly Ala Leu Asp Met Ala Asp Phe Glu Phe Glu Gln Met
                565                 570                 575

Phe Thr Asp Ala Leu Gly Ile Asp Glu Tyr Gly Gly
                580                 585

<210> SEQ ID NO 124
<211> LENGTH: 1782
<212> TYPE: DNA
<213> ORGANISM: Synthetic Construct
<220> FEATURE:
<221> NAME/KEY: CDS
<222> LOCATION: (1)..(1782)
<223> OTHER INFORMATION: Ecdysone receptor chimera G(E)EV

<400> SEQUENCE: 124 atg cag cag cta tat gtg gat ttt ttt agc cct gcc ttc ata cgc tat      48
Met Gln Gln Leu Tyr Val Asp Phe Phe Ser Pro Ala Phe Ile Arg Tyr
1               5                   10                  15 tta ttt gct tgg tac tgt ttc ttt tgt cga tgc tca ccc tgt tgt ttg      96
Leu Phe Ala Trp Tyr Cys Phe Phe Cys Arg Cys Ser Pro Cys Cys Leu
            20                  25                  30 gtg tta ctt ctg cag gga tcc gcc acc atg aag cta ctg tct tct atc     144
Val Leu Leu Leu Gln Gly Ser Ala Thr Met Lys Leu Leu Ser Ser Ile
        35                  40                  45 gaa caa gca tgc gat att tgc cga ctt aaa aag ctc aag tgc tcc aaa     192
Glu Gln Ala Cys Asp Ile Cys Arg Leu Lys Lys Leu Lys Cys Ser Lys
    50                  55                  60
```

|  |  |
|---|---:|
| gaa aaa ccg aag tgc gcc aag tgt ctg aag aac aac tgg gag tgt cgc<br>Glu Lys Pro Lys Cys Ala Lys Cys Leu Lys Asn Asn Trp Glu Cys Arg<br>65                            70                     75                       80 | 240 |
| tac tct ccc aaa acc aaa agg tct ccg ctg act agg gca cat ctg aca<br>Tyr Ser Pro Lys Thr Lys Arg Ser Pro Leu Thr Arg Ala His Leu Thr<br>                     85                     90                       95 | 288 |
| gaa gtg gaa tca agg cta gaa aga ctg gaa cag cta ttt cta ctg att<br>Glu Val Glu Ser Arg Leu Glu Arg Leu Glu Gln Leu Phe Leu Leu Ile<br>                100                    105                   110 | 336 |
| ttt cct cga gaa gac ctt gac atg att ttg aaa atg gat tct tta cag<br>Phe Pro Arg Glu Asp Leu Asp Met Ile Leu Lys Met Asp Ser Leu Gln<br>          115                    120                   125 | 384 |
| gat ata aaa gca ttg tta aca gga tta ttt gta caa gat aat gtg aat<br>Asp Ile Lys Ala Leu Leu Thr Gly Leu Phe Val Gln Asp Asn Val Asn<br>130                         135                    140 | 432 |
| aaa gat gcc gtc aca gat aga ttg gct tca gtg gag act gat atg cct<br>Lys Asp Ala Val Thr Asp Arg Leu Ala Ser Val Glu Thr Asp Met Pro<br>145                      150                   155                   160 | 480 |
| cta aca ttg aga cag cat aga ata agt gcg aca tca tca tcg gaa gag<br>Leu Thr Leu Arg Gln His Arg Ile Ser Ala Thr Ser Ser Ser Glu Glu<br>                165                    170                   175 | 528 |
| agt agt aac aaa ggt caa aga cag ttg act gta tcg acg cgt atg agg<br>Ser Ser Asn Lys Gly Gln Arg Gln Leu Thr Val Ser Thr Arg Met Arg<br>                    180                    185                   190 | 576 |
| ccc gag tgc gtg gtg cca gaa acg cag tgt gcg caa aaa agg aaa gag<br>Pro Glu Cys Val Val Pro Glu Thr Gln Cys Ala Gln Lys Arg Lys Glu<br>          195                    200                   205 | 624 |
| aag aaa gca cag aga gaa aaa gac aaa cta cca gtg agc aca acg aca<br>Lys Lys Ala Gln Arg Glu Lys Asp Lys Leu Pro Val Ser Thr Thr Thr<br>210                         215                    220 | 672 |
| gta gac gat cat atg ccc cca atc atg cag tgt gat cca cca ccc ccg<br>Val Asp Asp His Met Pro Pro Ile Met Gln Cys Asp Pro Pro Pro Pro<br>225                      230                   235                   240 | 720 |
| gag gca gcg agg att ctg gaa tgt ttg cag cat gaa gtg gtc ccg cgg<br>Glu Ala Ala Arg Ile Leu Glu Cys Leu Gln His Glu Val Val Pro Arg<br>                245                    250                   255 | 768 |
| ttc ctc tcg gag aag ctg atg gag cag aat cgg ctg aag aac ata ccc<br>Phe Leu Ser Glu Lys Leu Met Glu Gln Asn Arg Leu Lys Asn Ile Pro<br>                    260                    265                   270 | 816 |
| ccc ctc acc gcc aac cag cag ttc ctg atc gcg agg ctg gtg tgg tac<br>Pro Leu Thr Ala Asn Gln Gln Phe Leu Ile Ala Arg Leu Val Trp Tyr<br>          275                    280                   285 | 864 |
| cag gac gga tac gag cag cct tcg gaa gag gat ctc aaa agg gtg acg<br>Gln Asp Gly Tyr Glu Gln Pro Ser Glu Glu Asp Leu Lys Arg Val Thr<br>290                         295                    300 | 912 |
| cag act tgg caa tca gca gat gaa gaa gac gaa gac tca gac atg cca<br>Gln Thr Trp Gln Ser Ala Asp Glu Glu Asp Glu Asp Ser Asp Met Pro<br>305                      310                   315                   320 | 960 |
| ttc cgc cag atc aca gaa atg acc atc ctc aca gta cag cta ata gtc<br>Phe Arg Gln Ile Thr Glu Met Thr Ile Leu Thr Val Gln Leu Ile Val<br>                325                    330                   335 | 1008 |
| gag ttt gcc aaa ggc cta cct ggt ttt tca aag atc tca caa cct gac<br>Glu Phe Ala Lys Gly Leu Pro Gly Phe Ser Lys Ile Ser Gln Pro Asp<br>                    340                    345                   350 | 1056 |
| cag atc aca tta tta aag gca tgc tca agc gaa gtg atg atg ctg cga<br>Gln Ile Thr Leu Leu Lys Ala Cys Ser Ser Glu Val Met Met Leu Arg<br>          355                    360                   365 | 1104 |
| gta gcg agg cgg tac gac gcg gtg tcg gat agc gtt ctg ttc gcc aac<br>Val Ala Arg Arg Tyr Asp Ala Val Ser Asp Ser Val Leu Phe Ala Asn | 1152 |

-continued

```
                    370                 375                 380
aac cag gcg tac act cgc gac aac tac cgc aag gcg ggc atg gcc tac    1200
Asn Gln Ala Tyr Thr Arg Asp Asn Tyr Arg Lys Ala Gly Met Ala Tyr
385                 390                 395                 400 gtc atc gaa gac ctg ctg cac ttc tgc cgc tgc atg tac tcg atg tcg    1248
Val Ile Glu Asp Leu Leu His Phe Cys Arg Cys Met Tyr Ser Met Ser
                405                 410                 415 atg gac aac gtg cat tac gcg ctc ctc act gcc atc gtt ata ttc tcg    1296
Met Asp Asn Val His Tyr Ala Leu Leu Thr Ala Ile Val Ile Phe Ser
            420                 425                 430 gat cgg ccg ggc cta gag cag cca cag cta gta gaa gag atc cag cgg    1344
Asp Arg Pro Gly Leu Glu Gln Pro Gln Leu Val Glu Glu Ile Gln Arg
        435                 440                 445 tat tac ctg aac acg ctg cgg gtg tac atc atg aac cag cac agc gcg    1392
Tyr Tyr Leu Asn Thr Leu Arg Val Tyr Ile Met Asn Gln His Ser Ala
    450                 455                 460 tcg ccg cgt tgc gcc gtc atc tac gcg aag att ctg tcg gtg ctt acc    1440
Ser Pro Arg Cys Ala Val Ile Tyr Ala Lys Ile Leu Ser Val Leu Thr
465                 470                 475                 480 gag ttg cgg acg ctg ggc atg cag aat tcg aac atg tgc atc tcg ctg    1488
Glu Leu Arg Thr Leu Gly Met Gln Asn Ser Asn Met Cys Ile Ser Leu
                485                 490                 495 aag ctc aag aac agg aag ctg ccg ccg ttc ctg gag gag atc tgg gac    1536
Lys Leu Lys Asn Arg Lys Leu Pro Pro Phe Leu Glu Glu Ile Trp Asp
            500                 505                 510 gtg aag ctt gcc ccc ccg acc gat gtc agc ctg ggg gac gag ctc cac    1584
Val Lys Leu Ala Pro Pro Thr Asp Val Ser Leu Gly Asp Glu Leu His
        515                 520                 525 tta gac ggc gag gac gtg gcg atg gcg cat gcc gac gcg cta gac gat    1632
Leu Asp Gly Glu Asp Val Ala Met Ala His Ala Asp Ala Leu Asp Asp
    530                 535                 540 ttc gat ctg gac atg ttg ggg gac ggg gat tcc ccg ggt ccg gga ttt    1680
Phe Asp Leu Asp Met Leu Gly Asp Gly Asp Ser Pro Gly Pro Gly Phe
545                 550                 555                 560 acc ccc cac gac tcc gcc ccc tac ggc gct ctg gat atg gcc gac ttc    1728
Thr Pro His Asp Ser Ala Pro Tyr Gly Ala Leu Asp Met Ala Asp Phe
                565                 570                 575 gag ttt gag cag atg ttt acc gat gcc ctt gga att gac gag tac ggt    1776
Glu Phe Glu Gln Met Phe Thr Asp Ala Leu Gly Ile Asp Glu Tyr Gly
            580                 585                 590 ggg tag                                                            1782
Gly

<210> SEQ ID NO 125
<211> LENGTH: 593
<212> TYPE: PRT
<213> ORGANISM: Synthetic Construct

<400> SEQUENCE: 125

Met Gln Gln Leu Tyr Val Asp Phe Phe Ser Pro Ala Phe Ile Arg Tyr
1               5                   10                  15

Leu Phe Ala Trp Tyr Cys Phe Pro Cys Arg Cys Ser Pro Cys Cys Leu
                20                  25                  30

Val Leu Leu Leu Gln Gly Ser Ala Thr Met Lys Leu Leu Ser Ser Ile
            35                  40                  45

Glu Gln Ala Cys Asp Ile Cys Arg Leu Lys Lys Leu Lys Cys Ser Lys
        50                  55                  60

Glu Lys Pro Lys Cys Ala Lys Cys Leu Lys Asn Asn Trp Glu Cys Arg
65                  70                  75                  80
```

-continued

```
Tyr Ser Pro Lys Thr Lys Arg Ser Pro Leu Thr Arg Ala His Leu Thr
             85                  90                  95
Glu Val Glu Ser Arg Leu Glu Arg Leu Glu Gln Leu Phe Leu Leu Ile
            100                 105                 110
Phe Pro Arg Glu Asp Leu Asp Met Ile Leu Lys Met Asp Ser Leu Gln
            115                 120                 125
Asp Ile Lys Ala Leu Leu Thr Gly Leu Phe Val Gln Asp Asn Val Asn
        130                 135                 140
Lys Asp Ala Val Thr Asp Arg Leu Ala Ser Val Glu Thr Asp Met Pro
145                 150                 155                 160
Leu Thr Leu Arg Gln His Arg Ile Ser Ala Thr Ser Ser Ser Glu Glu
                165                 170                 175
Ser Ser Asn Lys Gly Gln Arg Gln Leu Thr Val Ser Thr Arg Met Arg
            180                 185                 190
Pro Glu Cys Val Val Pro Glu Thr Gln Cys Ala Gln Lys Arg Lys Glu
            195                 200                 205
Lys Lys Ala Gln Arg Glu Lys Asp Lys Leu Pro Val Ser Thr Thr Thr
        210                 215                 220
Val Asp Asp His Met Pro Pro Ile Met Gln Cys Asp Pro Pro Pro Pro
225                 230                 235                 240
Glu Ala Ala Arg Ile Leu Glu Cys Leu Gln His Glu Val Val Pro Arg
                245                 250                 255
Phe Leu Ser Glu Lys Leu Met Glu Gln Asn Arg Leu Lys Asn Ile Pro
            260                 265                 270
Pro Leu Thr Ala Asn Gln Gln Phe Leu Ile Ala Arg Leu Val Trp Tyr
            275                 280                 285
Gln Asp Gly Tyr Glu Gln Pro Ser Glu Glu Asp Leu Lys Arg Val Thr
        290                 295                 300
Gln Thr Trp Gln Ser Ala Asp Glu Glu Asp Ser Asp Met Pro
305                 310                 315                 320
Phe Arg Gln Ile Thr Glu Met Thr Ile Leu Thr Val Gln Leu Ile Val
                325                 330                 335
Glu Phe Ala Lys Gly Leu Pro Gly Phe Ser Lys Ile Ser Gln Pro Asp
            340                 345                 350
Gln Ile Thr Leu Leu Lys Ala Cys Ser Ser Glu Val Met Met Leu Arg
        355                 360                 365
Val Ala Arg Arg Tyr Asp Ala Val Ser Asp Ser Val Leu Phe Ala Asn
370                 375                 380
Asn Gln Ala Tyr Thr Arg Asp Asn Tyr Arg Lys Ala Gly Met Ala Tyr
385                 390                 395                 400
Val Ile Glu Asp Leu Leu His Phe Cys Arg Cys Met Tyr Ser Met Ser
                405                 410                 415
Met Asp Asn Val His Tyr Ala Leu Leu Thr Ala Ile Val Ile Phe Ser
            420                 425                 430
Asp Arg Pro Gly Leu Glu Gln Pro Gln Leu Val Glu Glu Ile Gln Arg
        435                 440                 445
Tyr Tyr Leu Asn Thr Leu Arg Val Tyr Ile Met Asn Gln His Ser Ala
        450                 455                 460
Ser Pro Arg Cys Ala Val Ile Tyr Ala Lys Ile Leu Ser Val Leu Thr
465                 470                 475                 480
Glu Leu Arg Thr Leu Gly Met Gln Asn Ser Asn Met Cys Ile Ser Leu
                485                 490                 495
```

```
                Lys Leu Lys Asn Arg Lys Leu Pro Pro Phe Leu Glu Glu Ile Trp Asp
                                500                 505                 510

Val Lys Leu Ala Pro Pro Thr Asp Val Ser Leu Gly Asp Glu Leu His
                            515                 520                 525

Leu Asp Gly Glu Asp Val Ala Met Ala His Ala Asp Ala Leu Asp Asp
                        530                 535                 540

Phe Asp Leu Asp Met Leu Gly Asp Gly Asp Ser Pro Gly Pro Gly Phe
                545                 550                 555                 560

Thr Pro His Asp Ser Ala Pro Tyr Gly Ala Leu Asp Met Ala Asp Phe
                                565                 570                 575

Glu Phe Glu Gln Met Phe Thr Asp Ala Leu Gly Ile Asp Glu Tyr Gly
                            580                 585                 590

Gly

<210> SEQ ID NO 126
<211> LENGTH: 1800
<212> TYPE: DNA
<213> ORGANISM: Synthetic Construct
<220> FEATURE:
<221> NAME/KEY: CDS
<222> LOCATION: (1)..(1800)
<223> OTHER INFORMATION: Ecdysone receptor chimera G(E)MV

<400> SEQUENCE: 126 atg cag cag cta tat gtg gat ttt ttt agc cct gcc ttc ata cgc tat         48
Met Gln Gln Leu Tyr Val Asp Phe Phe Ser Pro Ala Phe Ile Arg Tyr
 1               5                  10                  15 tta ttt gct tgg tac tgt ttc ttt tgt cga tgc tca ccc tgt tgt ttg         96
Leu Phe Ala Trp Tyr Cys Phe Phe Cys Arg Cys Ser Pro Cys Cys Leu
             20                  25                  30 gtg tta ctt ctg cag gga tcc gcc acc atg aag cta ctg tct tct atc        144
Val Leu Leu Leu Gln Gly Ser Ala Thr Met Lys Leu Leu Ser Ser Ile
         35                  40                  45 gaa caa gca tgc gat att tgc cga ctt aaa aag ctc aag tgc tcc aaa        192
Glu Gln Ala Cys Asp Ile Cys Arg Leu Lys Lys Leu Lys Cys Ser Lys
     50                  55                  60 gaa aaa ccg aag tgc gcc aag tgt ctg aag aac aac tgg gag tgt cgc        240
Glu Lys Pro Lys Cys Ala Lys Cys Leu Lys Asn Asn Trp Glu Cys Arg
 65                  70                  75                  80 tac tct ccc aaa acc aaa agg tct ccg ctg act agg gca cat ctg aca        288
Tyr Ser Pro Lys Thr Lys Arg Ser Pro Leu Thr Arg Ala His Leu Thr
                 85                  90                  95 gaa gtg gaa tca agg cta gaa aga ctg gaa cag cta ttt cta ctg att        336
Glu Val Glu Ser Arg Leu Glu Arg Leu Glu Gln Leu Phe Leu Leu Ile
            100                 105                 110 ttt cct cga gaa gac ctt gac atg att ttg aaa atg gat tct tta cag        384
Phe Pro Arg Glu Asp Leu Asp Met Ile Leu Lys Met Asp Ser Leu Gln
        115                 120                 125 gat ata aaa gca ttg tta aca gga tta ttt gta caa gat aat gtg aat        432
Asp Ile Lys Ala Leu Leu Thr Gly Leu Phe Val Gln Asp Asn Val Asn
    130                 135                 140 aaa gat gcc gtc aca gat aga ttg gct tca gtg gag act gat atg cct        480
Lys Asp Ala Val Thr Asp Arg Leu Ala Ser Val Glu Thr Asp Met Pro
145                 150                 155                 160 cta aca ttg aga cag cat aga ata agt gcg aca tca tcg gaa gag             528
Leu Thr Leu Arg Gln His Arg Ile Ser Ala Thr Ser Ser Glu Glu
                165                 170                 175 agt agt aac aaa ggt caa aga cag ttg act gta tcg acg cgt atg agg        576
Ser Ser Asn Lys Gly Gln Arg Gln Leu Thr Val Ser Thr Arg Met Arg
            180                 185                 190
```

```
ccc gag tgc gtg gtg cca gaa acg cag tgt gcg caa aaa agg aaa gag    624
Pro Glu Cys Val Val Pro Glu Thr Gln Cys Ala Gln Lys Arg Lys Glu
        195                 200                 205 aag aaa gca cag aga gaa aaa gac aaa cta cca gtg agc aca acg aca    672
Lys Lys Ala Gln Arg Glu Lys Asp Lys Leu Pro Val Ser Thr Thr Thr
    210                 215                 220 gta gac gat cat atg ccc cca atc atg cag tgt gat cca cca ccc ccg    720
Val Asp Asp His Met Pro Pro Ile Met Gln Cys Asp Pro Pro Pro Pro
225                 230                 235                 240 gag gca gcg agg att ctg gaa tgt ttg cag cat gaa gtg gtc ccg cgg    768
Glu Ala Ala Arg Ile Leu Glu Cys Leu Gln His Glu Val Val Pro Arg
                245                 250                 255 ttc ctc tcg gag aag ctg atg gag cag aat cgg ctg aag aac ata ccc    816
Phe Leu Ser Glu Lys Leu Met Glu Gln Asn Arg Leu Lys Asn Ile Pro
            260                 265                 270 ccc ctc acc gcc aac cag cag ttc ctg atc gcg agg ctg gtg tgg tac    864
Pro Leu Thr Ala Asn Gln Gln Phe Leu Ile Ala Arg Leu Val Trp Tyr
        275                 280                 285 cag gag ggg tac gag cag ccg tcg gag gaa gat ctc aag aga gtt aca    912
Gln Glu Gly Tyr Glu Gln Pro Ser Glu Glu Asp Leu Lys Arg Val Thr
    290                 295                 300 cag aca tgg cag tta gaa gaa gaa gaa gag gag gaa act gac atg ccc    960
Gln Thr Trp Gln Leu Glu Glu Glu Glu Glu Glu Thr Asp Met Pro
305                 310                 315                 320 ttc cgt cag atc aca gag atg acg atc tta aca gtg cag ctt att gta   1008
Phe Arg Gln Ile Thr Glu Met Thr Ile Leu Thr Val Gln Leu Ile Val
                325                 330                 335 gaa ttc gca aag gga cta ccg gga ttc tcc aag ata tct cag tcc gat   1056
Glu Phe Ala Lys Gly Leu Pro Gly Phe Ser Lys Ile Ser Gln Ser Asp
            340                 345                 350 caa att aca tta tta aag gcg tca tca agc gaa gtg atg atg ctg cga   1104
Gln Ile Thr Leu Leu Lys Ala Ser Ser Ser Glu Val Met Met Leu Arg
        355                 360                 365 gtg gcg cga cgg tac gac gcg gcg acg gac agc gtg ctg ttc gcg aac   1152
Val Ala Arg Arg Tyr Asp Ala Ala Thr Asp Ser Val Leu Phe Ala Asn
    370                 375                 380 aac cag gcg tac acg cgc gac aac tac cgc aag gcg ggc atg tcc tac   1200
Asn Gln Ala Tyr Thr Arg Asp Asn Tyr Arg Lys Ala Gly Met Ser Tyr
385                 390                 395                 400 gtc atc gag gac ctg ctg cac ttc tgt cgg tgt atg tac tcc atg agc   1248
Val Ile Glu Asp Leu Leu His Phe Cys Arg Cys Met Tyr Ser Met Ser
                405                 410                 415 atg gac aat gtg cac tac gcg ctg ctc acc gcc atc gtt ata ttc tca   1296
Met Asp Asn Val His Tyr Ala Leu Leu Thr Ala Ile Val Ile Phe Ser
            420                 425                 430 gac cgg cca ggc ctc gag caa ccc ctt tta gtg gag gaa atc cag aga   1344
Asp Arg Pro Gly Leu Glu Gln Pro Leu Leu Val Glu Glu Ile Gln Arg
        435                 440                 445 tac tac ttg aag acg ctg cgg gtt tac att tta aat cag cac agc gcg   1392
Tyr Tyr Leu Lys Thr Leu Arg Val Tyr Ile Leu Asn Gln His Ser Ala
    450                 455                 460 tcg cct cgc tgc gcc gtg ctg ttc ggc aag atc ctc ggc gtg ctg acg   1440
Ser Pro Arg Cys Ala Val Leu Phe Gly Lys Ile Leu Gly Val Leu Thr
465                 470                 475                 480 gaa ctg cgc acg ctc ggc acg cag aac tcc aac atg tgc atc tcg ctg   1488
Glu Leu Arg Thr Leu Gly Thr Gln Asn Ser Asn Met Cys Ile Ser Leu
                485                 490                 495 aag ctg aag aac agg aaa ctt ccg cca ttc ctc gag gag atc tgg gac   1536
Lys Leu Lys Asn Arg Lys Leu Pro Pro Phe Leu Glu Glu Ile Trp Asp
```

```
                500                 505                 510
gtg gcc gaa gtg tcg acg acg aag ctt gcc ccc ccg acc gat gtc agc    1584
Val Ala Glu Val Ser Thr Thr Lys Leu Ala Pro Pro Thr Asp Val Ser
        515                 520                 525 ctg ggg gac gag ctc cac tta gac ggc gag gac gtg gcg atg gcg cat    1632
Leu Gly Asp Glu Leu His Leu Asp Gly Glu Asp Val Ala Met Ala His
530                 535                 540 gcc gac gcg cta gac gat ttc gat ctg gac atg ttg ggg gac ggg gat    1680
Ala Asp Ala Leu Asp Asp Phe Asp Leu Asp Met Leu Gly Asp Gly Asp
545                 550                 555                 560 tcc ccg ggt ccg gga ttt acc ccc cac gac tcc gcc ccc tac ggc gct    1728
Ser Pro Gly Pro Gly Phe Thr Pro His Asp Ser Ala Pro Tyr Gly Ala
                565                 570                 575 ctg gat atg gcc gac ttc gag ttt gag cag atg ttt acc gat gcc ctt    1776
Leu Asp Met Ala Asp Phe Glu Phe Glu Gln Met Phe Thr Asp Ala Leu
            580                 585                 590 gga att gac gag tac ggt ggg tag                                    1800
Gly Ile Asp Glu Tyr Gly Gly
        595

<210> SEQ ID NO 127
<211> LENGTH: 599
<212> TYPE: PRT
<213> ORGANISM: Synthetic Construct

<400> SEQUENCE: 127

Met Gln Gln Leu Tyr Val Asp Phe Phe Ser Pro Ala Phe Ile Arg Tyr
1               5                   10                  15

Leu Phe Ala Trp Tyr Cys Phe Phe Cys Arg Cys Ser Pro Cys Cys Leu
            20                  25                  30

Val Leu Leu Leu Gln Gly Ser Ala Thr Met Lys Leu Leu Ser Ser Ile
        35                  40                  45

Glu Gln Ala Cys Asp Ile Cys Arg Leu Lys Lys Leu Lys Cys Ser Lys
    50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
            100                 105                 110

Phe Pro Arg Glu Asp Leu Asp Met Ile Leu Lys Met Asp Ser Leu Gln
        115                 120                 125

Asp Ile Lys Ala Leu Leu Thr Gly Leu Phe Val Gln Asp Asn Val Asn
    130                 135                 140

Lys Asp Ala Val Thr Asp Arg Leu Ala Ser Val Glu Thr Asp Met Pro
145                 150                 155                 160

Leu Thr Leu Arg Gln His Arg Ile Ser Ala Thr Ser Ser Ser Glu Glu
                165                 170                 175

Ser Ser Asn Lys Gly Gln Arg Gln Leu Thr Val Ser Thr Arg Met Arg
            180                 185                 190

Pro Glu Cys Val Val Pro Glu Thr Gln Cys Ala Gln Lys Arg Lys Glu
        195                 200                 205

Lys Lys Ala Gln Arg Glu Lys Asp Lys Leu Pro Val Ser Thr Thr Thr
    210                 215                 220

Val Asp Asp His Met Pro Pro Ile Met Gln Cys Asp Pro Pro Pro
225                 230                 235                 240
```

-continued

```
Glu Ala Ala Arg Ile Leu Glu Cys Leu Gln His Glu Val Val Pro Arg
                245                 250                 255
Phe Leu Ser Glu Lys Leu Met Glu Gln Asn Arg Leu Lys Asn Ile Pro
            260                 265                 270
Pro Leu Thr Ala Asn Gln Gln Phe Leu Ile Ala Arg Leu Val Trp Tyr
        275                 280                 285
Gln Glu Gly Tyr Glu Gln Pro Ser Glu Glu Asp Leu Lys Arg Val Thr
    290                 295                 300
Gln Thr Trp Gln Leu Glu Glu Glu Glu Glu Thr Asp Met Pro
305                 310                 315                 320
Phe Arg Gln Ile Thr Glu Met Thr Ile Leu Thr Val Gln Leu Ile Val
                325                 330                 335
Glu Phe Ala Lys Gly Leu Pro Gly Phe Ser Lys Ile Ser Gln Ser Asp
            340                 345                 350
Gln Ile Thr Leu Leu Lys Ala Ser Ser Ser Glu Val Met Met Leu Arg
        355                 360                 365
Val Ala Arg Arg Tyr Asp Ala Ala Thr Asp Ser Val Leu Phe Ala Asn
    370                 375                 380
Asn Gln Ala Tyr Thr Arg Asp Asn Tyr Arg Lys Ala Gly Met Ser Tyr
385                 390                 395                 400
Val Ile Glu Asp Leu Leu His Phe Cys Arg Cys Met Tyr Ser Met Ser
                405                 410                 415
Met Asp Asn Val His Tyr Ala Leu Leu Thr Ala Ile Val Ile Phe Ser
            420                 425                 430
Asp Arg Pro Gly Leu Glu Gln Pro Leu Leu Val Glu Glu Ile Gln Arg
        435                 440                 445
Tyr Tyr Leu Lys Thr Leu Arg Val Tyr Ile Leu Asn Gln His Ser Ala
    450                 455                 460
Ser Pro Arg Cys Ala Val Leu Phe Gly Lys Ile Leu Gly Val Leu Thr
465                 470                 475                 480
Glu Leu Arg Thr Leu Gly Thr Gln Asn Ser Asn Met Cys Ile Ser Leu
                485                 490                 495
Lys Leu Lys Asn Arg Lys Leu Pro Pro Phe Leu Glu Glu Ile Trp Asp
            500                 505                 510
Val Ala Glu Val Ser Thr Thr Lys Leu Ala Pro Pro Thr Asp Val Ser
        515                 520                 525
Leu Gly Asp Glu Leu His Leu Asp Gly Glu Asp Val Ala Met Ala His
    530                 535                 540
Ala Asp Ala Leu Asp Asp Phe Asp Leu Asp Met Leu Gly Asp Gly Asp
545                 550                 555                 560
Ser Pro Gly Pro Gly Phe Thr Pro His Asp Ser Ala Pro Tyr Gly Ala
                565                 570                 575
Leu Asp Met Ala Asp Phe Glu Phe Glu Gln Met Phe Thr Asp Ala Leu
            580                 585                 590
Gly Ile Asp Glu Tyr Gly Gly
        595
```

<210> SEQ ID NO 128
<211> LENGTH: 1428
<212> TYPE: DNA
<213> ORGANISM: Synthetic Construct
<220> FEATURE:
<221> NAME/KEY: CDS
<222> LOCATION: (1)..(1428)
<223> OTHER INFORMATION: G(M)M (GAL4 DNA Binding Domain fused to the Manduca EcR Hinge and Ligand Binding Domain)

-continued

```
<400> SEQUENCE: 128 atg aag cta ctg tct tct atc gaa caa gca tgc gat att tgc cga ctt      48
Met Lys Leu Leu Ser Ser Ile Glu Gln Ala Cys Asp Ile Cys Arg Leu
1               5                   10                  15 aaa aag ctc aag tgc tcc aaa gaa aaa ccg aag tgc gcc aag tgt ctg      96
Lys Lys Leu Lys Cys Ser Lys Glu Lys Pro Lys Cys Ala Lys Cys Leu
            20                  25                  30 aag aac aac tgg gag tgt cgc tac tct ccc aaa acc aaa agg tct ccg     144
Lys Asn Asn Trp Glu Cys Arg Tyr Ser Pro Lys Thr Lys Arg Ser Pro
        35                  40                  45 ctg act agg gca cat ctg aca gaa gtg gaa tca agg cta gaa aga ctg     192
Leu Thr Arg Ala His Leu Thr Glu Val Glu Ser Arg Leu Glu Arg Leu
    50                  55                  60 gaa cag cta ttt cta ctg att ttt cct cga gaa gac ctt gac atg att     240
Glu Gln Leu Phe Leu Leu Ile Phe Pro Arg Glu Asp Leu Asp Met Ile
65                  70                  75                  80 ttg aaa atg gat tct tta cag gat ata aaa gca ttg tta aca gga tta     288
Leu Lys Met Asp Ser Leu Gln Asp Ile Lys Ala Leu Leu Thr Gly Leu
                85                  90                  95 ttt gta caa gat aat gtg aat aaa gat gcc gtc aca gat aga ttg gct     336
Phe Val Gln Asp Asn Val Asn Lys Asp Ala Val Thr Asp Arg Leu Ala
            100                 105                 110 tca gtg gag act gat atg cct cta aca ttg aga cag cat aga ata agt     384
Ser Val Glu Thr Asp Met Pro Leu Thr Leu Arg Gln His Arg Ile Ser
        115                 120                 125 gcg aca tca tca tcg gaa gag agt agt aac aaa ggt caa aga cag ttg     432
Ala Thr Ser Ser Ser Glu Glu Ser Ser Asn Lys Gly Gln Arg Gln Leu
    130                 135                 140 act gta tcg acg cgt atg agg ccc gag tgc gtc gtc cca gag tcc acg     480
Thr Val Ser Thr Arg Met Arg Pro Glu Cys Val Val Pro Glu Ser Thr
145                 150                 155                 160 tgc aag aac aaa aga aga gaa aag gaa gca cag aga gaa aaa gac aaa     528
Cys Lys Asn Lys Arg Arg Glu Lys Glu Ala Gln Arg Glu Lys Asp Lys
                165                 170                 175 ctg cca gtc agt acg acg aca gtg gac gat cat atg cct gcc ata atg     576
Leu Pro Val Ser Thr Thr Thr Val Asp Asp His Met Pro Ala Ile Met
            180                 185                 190 caa tgt gac cct ccg ccc cca gag gcg gca agg att cac gaa gtg gtc     624
Gln Cys Asp Pro Pro Pro Pro Glu Ala Ala Arg Ile His Glu Val Val
        195                 200                 205 ccg agg ttc cta acg gag aag cta atg gag cag aac aga ctg aag aat     672
Pro Arg Phe Leu Thr Glu Lys Leu Met Glu Gln Asn Arg Leu Lys Asn
    210                 215                 220 gtg acg ccg ctg tcg gcg aac cag aag tcc ctg atc gcg agg ctc gtg     720
Val Thr Pro Leu Ser Ala Asn Gln Lys Ser Leu Ile Ala Arg Leu Val
225                 230                 235                 240 tgg tac cag gag ggg tac gag cag ccg tcg gag gaa gat ctc aag aga     768
Trp Tyr Gln Glu Gly Tyr Glu Gln Pro Ser Glu Glu Asp Leu Lys Arg
                245                 250                 255 gtt aca cag aca tgg cag tta gaa gaa gaa gaa gag gag gaa act gac     816
Val Thr Gln Thr Trp Gln Leu Glu Glu Glu Glu Glu Glu Glu Thr Asp
            260                 265                 270 atg ccc ttc cgt cag atc aca gag atg acg atc tta aca gtg cag ctt     864
Met Pro Phe Arg Gln Ile Thr Glu Met Thr Ile Leu Thr Val Gln Leu
        275                 280                 285 att gta gaa ttc gca aag gga cta ccg gga ttc tcc aag ata tct cag     912
Ile Val Glu Phe Ala Lys Gly Leu Pro Gly Phe Ser Lys Ile Ser Gln
    290                 295                 300
```

|  |  |
|---|---|
| tcc gat caa att aca tta tta aag gcg tca tca agc gaa gtg atg atg<br>Ser Asp Gln Ile Thr Leu Leu Lys Ala Ser Ser Ser Glu Val Met Met<br>305      310      315      320 | 960 |
| ctg cga gtg gcg cga cgg tac gac gcg gcg acg gac agc gtg ctg ttc<br>Leu Arg Val Ala Arg Arg Tyr Asp Ala Ala Thr Asp Ser Val Leu Phe<br>      325      330      335 | 1008 |
| gcg aac aac cag gcg tac acg cgc gac aac tac cgc aag gcg ggc atg<br>Ala Asn Asn Gln Ala Tyr Thr Arg Asp Asn Tyr Arg Lys Ala Gly Met<br>    340      345      350 | 1056 |
| tcc tac gtc atc gag gac ctg ctg cac ttc tgt cgg tgt atg tac tcc<br>Ser Tyr Val Ile Glu Asp Leu Leu His Phe Cys Arg Cys Met Tyr Ser<br>    355      360      365 | 1104 |
| atg agc atg gac aat gtg cac tac gcg ctg ctc acc gcc atc gtt ata<br>Met Ser Met Asp Asn Val His Tyr Ala Leu Leu Thr Ala Ile Val Ile<br>370      375      380 | 1152 |
| ttc tca gac cgg cca ggc ctc gag caa ccc ctt tta gtg gag gaa atc<br>Phe Ser Asp Arg Pro Gly Leu Glu Gln Pro Leu Leu Val Glu Glu Ile<br>385      390      395      400 | 1200 |
| cag aga tac tac ttg aag acg ctg cgg gtt tac att tta aat cag cac<br>Gln Arg Tyr Tyr Leu Lys Thr Leu Arg Val Tyr Ile Leu Asn Gln His<br>    405      410      415 | 1248 |
| agc gcg tcg cct cgc tgc gcc gtg ctg ttc ggc aag atc ctc ggc gtg<br>Ser Ala Ser Pro Arg Cys Ala Val Leu Phe Gly Lys Ile Leu Gly Val<br>    420      425      430 | 1296 |
| ctg acg gaa ctg cgc acg ctc ggc acg cag aac tcc aac atg tgc atc<br>Leu Thr Glu Leu Arg Thr Leu Gly Thr Gln Asn Ser Asn Met Cys Ile<br>    435      440      445 | 1344 |
| tcg ctg aag ctg aag aac agg aaa ctt ccg cca ttc ctc gag gag atc<br>Ser Leu Lys Leu Lys Asn Arg Lys Leu Pro Pro Phe Leu Glu Glu Ile<br>450      455      460 | 1392 |
| tgg gac gtg gcc gaa gtg tcg acg acg aag ctt tag<br>Trp Asp Val Ala Glu Val Ser Thr Thr Lys Leu<br>465      470      475 | 1428 |

<210> SEQ ID NO 129
<211> LENGTH: 475
<212> TYPE: PRT
<213> ORGANISM: Synthetic Construct

<400> SEQUENCE: 129

Met Lys Leu Leu Ser Ser Ile Glu Gln Ala Cys Asp Ile Cys Arg Leu
1       5         10         15

Lys Lys Leu Lys Cys Ser Lys Glu Lys Pro Lys Cys Ala Lys Cys Leu
       20         25         30

Lys Asn Asn Trp Glu Cys Arg Tyr Ser Pro Lys Thr Lys Arg Ser Pro
      35         40         45

Leu Thr Arg Ala His Leu Thr Glu Val Glu Ser Arg Leu Glu Arg Leu
  50        55         60

Glu Gln Leu Phe Leu Leu Ile Phe Pro Arg Glu Asp Leu Asp Met Ile
65        70         75         80

Leu Lys Met Asp Ser Leu Gln Asp Ile Lys Ala Leu Leu Thr Gly Leu
       85         90         95

Phe Val Gln Asp Asn Val Asn Lys Asp Ala Val Thr Asp Arg Leu Ala
      100        105        110

Ser Val Glu Thr Asp Met Pro Leu Thr Leu Arg Gln His Arg Ile Ser
    115        120        125

Ala Thr Ser Ser Glu Glu Ser Ser Asn Lys Gly Gln Arg Gln Leu
  130        135        140

```
Thr Val Ser Thr Arg Met Arg Pro Glu Cys Val Pro Glu Ser Thr
145                 150                 155                 160

Cys Lys Asn Lys Arg Arg Glu Lys Glu Ala Gln Arg Glu Lys Asp Lys
                165                 170                 175

Leu Pro Val Ser Thr Thr Val Asp Asp His Met Pro Ala Ile Met
            180                 185                 190

Gln Cys Asp Pro Pro Pro Glu Ala Ala Arg Ile His Glu Val Val
        195                 200                 205

Pro Arg Phe Leu Thr Glu Lys Leu Met Glu Gln Asn Arg Leu Lys Asn
    210                 215                 220

Val Thr Pro Leu Ser Ala Asn Gln Lys Ser Leu Ile Ala Arg Leu Val
225                 230                 235                 240

Trp Tyr Gln Glu Gly Tyr Glu Gln Pro Ser Glu Glu Asp Leu Lys Arg
                245                 250                 255

Val Thr Gln Thr Trp Gln Leu Glu Glu Glu Glu Glu Glu Thr Asp
            260                 265                 270

Met Pro Phe Arg Gln Ile Thr Glu Met Thr Ile Leu Thr Val Gln Leu
        275                 280                 285

Ile Val Glu Phe Ala Lys Gly Leu Pro Gly Phe Ser Lys Ile Ser Gln
    290                 295                 300

Ser Asp Gln Ile Thr Leu Leu Lys Ala Ser Ser Glu Val Met Met
305                 310                 315                 320

Leu Arg Val Ala Arg Arg Tyr Asp Ala Ala Thr Asp Ser Val Leu Phe
                325                 330                 335

Ala Asn Asn Gln Ala Tyr Thr Arg Asp Asn Tyr Arg Lys Ala Gly Met
            340                 345                 350

Ser Tyr Val Ile Glu Asp Leu Leu His Phe Cys Arg Cys Met Tyr Ser
        355                 360                 365

Met Ser Met Asp Asn Val His Tyr Ala Leu Leu Thr Ala Ile Val Ile
370                 375                 380

Phe Ser Asp Arg Pro Gly Leu Glu Gln Pro Leu Leu Val Glu Glu Ile
385                 390                 395                 400

Gln Arg Tyr Tyr Leu Lys Thr Leu Arg Val Tyr Ile Leu Asn Gln His
                405                 410                 415

Ser Ala Ser Pro Arg Cys Ala Val Leu Phe Gly Lys Ile Leu Gly Val
            420                 425                 430

Leu Thr Glu Leu Arg Thr Leu Gly Thr Gln Asn Ser Asn Met Cys Ile
        435                 440                 445

Ser Leu Lys Leu Lys Asn Arg Lys Leu Pro Pro Phe Leu Glu Glu Ile
450                 455                 460

Trp Asp Val Ala Glu Val Ser Thr Thr Lys Leu
465                 470                 475
```

<210> SEQ ID NO 130
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: primer

<400> SEQUENCE: 130
aaaaaaagct tcccaaggcc gtgcggtg                                     28

<210> SEQ ID NO 131

-continued

<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 131
aaaaagagct cttacgcaag ctgcccggcc                              30

<210> SEQ ID NO 132
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer

<400> SEQUENCE: 132
aaaaaagctt gagctcgcca ccgc                                    24

<210> SEQ ID NO 133
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: primer

<400> SEQUENCE: 133
aaaaaggatc ctcacgggag gttgag                                  26

<210> SEQ ID NO 134
<211> LENGTH: 1848
<212> TYPE: DNA
<213> ORGANISM: Synthetic Construct
<220> FEATURE:
<221> NAME/KEY: CDS
<222> LOCATION: (1)..(1848)
<223> OTHER INFORMATION: Ecdysone receptor chimera G(M)MC

<400> SEQUENCE: 134

```
atg cag cag cta tat gtg gat ttt ttt agc cct gcc ttc ata cgc tat      48
Met Gln Gln Leu Tyr Val Asp Phe Phe Ser Pro Ala Phe Ile Arg Tyr
 1               5                  10                  15 tta ttt gct tgg tac tgt ttc ttt tgt cga tgc tca ccc tgt tgt ttg      96
Leu Phe Ala Trp Tyr Cys Phe Phe Cys Arg Cys Ser Pro Cys Cys Leu
            20                  25                  30 gtg tta ctt ctg cag gga tcc gcc acc atg aag cta ctg tct tct atc     144
Val Leu Leu Leu Gln Gly Ser Ala Thr Met Lys Leu Leu Ser Ser Ile
        35                  40                  45 gaa caa gca tgc gat att tgc cga ctt aaa aag ctc aag tgt tcc aaa     192
Glu Gln Ala Cys Asp Ile Cys Arg Leu Lys Lys Leu Lys Cys Ser Lys
    50                  55                  60 gaa aaa ccg aag tgc gcc aag tgt ctg aag aac aac tgg gag tgt cgc     240
Glu Lys Pro Lys Cys Ala Lys Cys Leu Lys Asn Asn Trp Glu Cys Arg
65                  70                  75                  80 tac tct ccc aaa acc aaa agg tct ccg ctg act agg gca cat ctg aca     288
Tyr Ser Pro Lys Thr Lys Arg Ser Pro Leu Thr Arg Ala His Leu Thr
                85                  90                  95 gaa gtg gaa tca agg cta gaa aga ctg gaa cag cta ttt cta ctg att     336
Glu Val Glu Ser Arg Leu Glu Arg Leu Glu Gln Leu Phe Leu Leu Ile
            100                 105                 110
```

-continued

| | |
|---|---|
| ttt cct cga gaa gac ctt gac atg att ttg aaa atg gat tct tta cag<br>Phe Pro Arg Glu Asp Leu Asp Met Ile Leu Lys Met Asp Ser Leu Gln<br>115                         120                      125 | 384 |
| gat ata aaa gca ttg tta aca gga tta ttt gta caa gat aat gtg aat<br>Asp Ile Lys Ala Leu Leu Thr Gly Leu Phe Val Gln Asp Asn Val Asn<br>130                       135                      140 | 432 |
| aaa gat gcc gtc aca gat aga ttg gct tca gtg gag act gat atg cct<br>Lys Asp Ala Val Thr Asp Arg Leu Ala Ser Val Glu Thr Asp Met Pro<br>145                       150                      155                      160 | 480 |
| cta aca ttg aga cag cat aga ata agt gcg aca tca tca tcg gaa gag<br>Leu Thr Leu Arg Gln His Arg Ile Ser Ala Thr Ser Ser Ser Glu Glu<br>                165                      170                      175 | 528 |
| agt agt aac aaa ggt caa aga cag ttg act gta tcg acg cgt atg agg<br>Ser Ser Asn Lys Gly Gln Arg Gln Leu Thr Val Ser Thr Arg Met Arg<br>         180                      185                      190 | 576 |
| ccc gag tgc gtc gtc cca gag tcc acg tgc aag aac aaa aga aga gaa<br>Pro Glu Cys Val Val Pro Glu Ser Thr Cys Lys Asn Lys Arg Arg Glu<br>195                       200                      205 | 624 |
| aag gaa gca cag aga gaa aaa gac aaa ctg cca gtc agt acg acg aca<br>Lys Glu Ala Gln Arg Glu Lys Asp Lys Leu Pro Val Ser Thr Thr Thr<br>210                       215                      220 | 672 |
| gtg gac gat cat atg cct gcc ata atg caa tgt gac cct ccg ccc cca<br>Val Asp Asp His Met Pro Ala Ile Met Gln Cys Asp Pro Pro Pro Pro<br>225                       230                      235                      240 | 720 |
| gag gcg gca agg att cac gaa gtg gtc ccg agg ttc cta acg gag aag<br>Glu Ala Ala Arg Ile His Glu Val Val Pro Arg Phe Leu Thr Glu Lys<br>                245                      250                      255 | 768 |
| cta atg gag cag aac aga ctg aag aat gtg acg ccg ctg tcg gcg aac<br>Leu Met Glu Gln Asn Arg Leu Lys Asn Val Thr Pro Leu Ser Ala Asn<br>         260                      265                      270 | 816 |
| cag aag tcc ctg atc gcg agg ctc gtg tgg tac cag gag ggg tac gag<br>Gln Lys Ser Leu Ile Ala Arg Leu Val Trp Tyr Gln Glu Gly Tyr Glu<br>275                       280                      285 | 864 |
| cag ccg tcg gag gaa gat ctc aag aga gtt aca cag aca tgg cag tta<br>Gln Pro Ser Glu Glu Asp Leu Lys Arg Val Thr Gln Thr Trp Gln Leu<br>290                       295                      300 | 912 |
| gaa gaa gaa gaa gag gag gaa act gac atg ccc ttc cgt cag atc aca<br>Glu Glu Glu Glu Glu Glu Glu Thr Asp Met Pro Phe Arg Gln Ile Thr<br>305                       310                      315                      320 | 960 |
| gag atg acg atc tta aca gtg cag ctt att gta gaa ttc gca aag gga<br>Glu Met Thr Ile Leu Thr Val Gln Leu Ile Val Glu Phe Ala Lys Gly<br>                325                      330                      335 | 1008 |
| cta ccg gga ttc tcc aag ata tct cag tcc gat caa att aca tta tta<br>Leu Pro Gly Phe Ser Lys Ile Ser Gln Ser Asp Gln Ile Thr Leu Leu<br>         340                      345                      350 | 1056 |
| aag gcg tca tca agc gaa gtg atg atg ctg cga gtg gcg cga cgg tac<br>Lys Ala Ser Ser Ser Glu Val Met Met Leu Arg Val Ala Arg Arg Tyr<br>355                       360                      365 | 1104 |
| gac gcg gcg acg gac agc gtg ctg ttc gcg aac aac cag gcg tac acg<br>Asp Ala Ala Thr Asp Ser Val Leu Phe Ala Asn Asn Gln Ala Tyr Thr<br>370                       375                      380 | 1152 |
| cgc gac aac tac cgc aag gcg ggc atg tcc tac gtc atc gag gac ctg<br>Arg Asp Asn Tyr Arg Lys Ala Gly Met Ser Tyr Val Ile Glu Asp Leu<br>385                       390                      395                      400 | 1200 |
| ctg cac ttc tgt cgg tgt atg tac tcc atg agc atg gac aat gtg cac<br>Leu His Phe Cys Arg Cys Met Tyr Ser Met Ser Met Asp Asn Val His<br>                405                      410                      415 | 1248 |
| tac gcg ctg ctc acc gcc atc gtt ata ttc tca gac cgg cca ggc ctc<br>Tyr Ala Leu Leu Thr Ala Ile Val Ile Phe Ser Asp Arg Pro Gly Leu | 1296 |

-continued

| | | | | | | | | | | | | | | |
|---|---|---|---|---|---|---|---|---|---|---|---|---|---|---|
| | | | 420 | | | | 425 | | | | 430 | | | |
| gag | caa | ccc | ctt | tta | gtg | gag | gaa | atc | cag | aga | tac | tac | ttg | aag acg | 1344 |
| Glu | Gln | Pro | Leu | Leu | Val | Glu | Glu | Ile | Gln | Arg | Tyr | Tyr | Leu | Lys Thr | |
| | | 435 | | | | | 440 | | | | 445 | | | | |
| ctg | cgg | gtt | tac | att | tta | aat | cag | cac | agc | gcg | tcg | cct | cgc | tgc gcc | 1392 |
| Leu | Arg | Val | Tyr | Ile | Leu | Asn | Gln | His | Ser | Ala | Ser | Pro | Arg | Cys Ala | |
| | 450 | | | | | 455 | | | | | 460 | | | | |
| gtg | ctg | ttc | ggc | aag | atc | ctc | ggc | gtg | ctg | acg | gaa | ctg | cgc | acg ctc | 1440 |
| Val | Leu | Phe | Gly | Lys | Ile | Leu | Gly | Val | Leu | Thr | Glu | Leu | Arg | Thr Leu | |
| 465 | | | | | 470 | | | | | 475 | | | | 480 | |
| ggc | acg | cag | aac | tcc | aac | atg | tgc | atc | tcg | ctg | aag | ctg | aag | aac agg | 1488 |
| Gly | Thr | Gln | Asn | Ser | Asn | Met | Cys | Ile | Ser | Leu | Lys | Leu | Lys | Asn Arg | |
| | | | | 485 | | | | | 490 | | | | | 495 | |
| aaa | ctt | ccg | cca | ttc | ctc | gag | gag | atc | tgg | gac | gtg | gcc | gaa | gtg tcg | 1536 |
| Lys | Leu | Pro | Pro | Phe | Leu | Glu | Glu | Ile | Trp | Asp | Val | Ala | Glu | Val Ser | |
| | | | | 500 | | | | | 505 | | | | | 510 | |
| acg | acg | aag | ctt | ccc | aag | gcc | gtg | cgg | tgc | acg | ggc | gga | ctc | ttc ttc | 1584 |
| Thr | Thr | Lys | Leu | Pro | Lys | Ala | Val | Arg | Cys | Thr | Gly | Gly | Leu | Phe Phe | |
| | | 515 | | | | | 520 | | | | 525 | | | | |
| ttc | cac | cgg | gac | acg | acg | ccg | gcg | cac | gcg | ggc | gag | acg | gcg | acg cca | 1632 |
| Phe | His | Arg | Asp | Thr | Thr | Pro | Ala | His | Ala | Gly | Glu | Thr | Ala | Thr Pro | |
| | 530 | | | | | 535 | | | | | 540 | | | | |
| atg | gcc | ggt | gga | ggt | gga | gga | gga | gga | gaa | gca | ggg | tcg | tcg | gac | 1680 |
| Met | Ala | Gly | Gly | Gly | Gly | Gly | Gly | Gly | Glu | Ala | Gly | Ser | Ser | Asp | |
| 545 | | | | | 550 | | | | | 555 | | | | 560 | |
| gac | tgc | agc | tcg | gcg | gcg | tcg | gta | tcg | ctt | cgc | gtc | gga | agc | cac gac | 1728 |
| Asp | Cys | Ser | Ser | Ala | Ala | Ser | Val | Ser | Leu | Arg | Val | Gly | Ser | His Asp | |
| | | | | 565 | | | | | 570 | | | | | 575 | |
| gag | ccg | tgc | ttc | tcc | ggc | gac | ggt | gac | ggc | gac | tgg | atg | gac | gac gtg | 1776 |
| Glu | Pro | Cys | Phe | Ser | Gly | Asp | Gly | Asp | Gly | Asp | Trp | Met | Asp | Asp Val | |
| | | | | 580 | | | | | 585 | | | | | 590 | |
| agg | gcc | ctg | gcg | tcg | ttt | ctc | gag | tcc | gac | gag | gac | tgg | ctc | cgc tgt | 1824 |
| Arg | Ala | Leu | Ala | Ser | Phe | Leu | Glu | Ser | Asp | Glu | Asp | Trp | Leu | Arg Cys | |
| | | 595 | | | | | 600 | | | | 605 | | | | |
| cag | acg | gcc | ggg | cag | ctt | gcg | taa | | | | | | | | 1848 |
| Gln | Thr | Ala | Gly | Gln | Leu | Ala | | | | | | | | | |
| | 610 | | | | 615 | | | | | | | | | | |

<210> SEQ ID NO 135
<211> LENGTH: 615
<212> TYPE: PRT
<213> ORGANISM: Synthetic Construct

<400> SEQUENCE: 135

Met Gln Gln Leu Tyr Val Asp Phe Phe Ser Pro Ala Phe Ile Arg Tyr
1               5                   10                  15

Leu Phe Ala Trp Tyr Cys Phe Phe Cys Arg Cys Ser Pro Cys Cys Leu
                20                  25                  30

Val Leu Leu Leu Gln Gly Ser Ala Thr Met Lys Leu Leu Ser Ser Ile
            35                  40                  45

Glu Gln Ala Cys Asp Ile Cys Arg Leu Lys Lys Leu Lys Cys Ser Lys
    50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
            100                 105                 110

-continued

```
Phe Pro Arg Glu Asp Leu Asp Met Ile Leu Lys Met Asp Ser Leu Gln
    115                 120                 125

Asp Ile Lys Ala Leu Leu Thr Gly Leu Phe Val Gln Asp Asn Val Asn
130                 135                 140

Lys Asp Ala Val Thr Asp Arg Leu Ala Ser Val Glu Thr Asp Met Pro
145                 150                 155                 160

Leu Thr Leu Arg Gln His Arg Ile Ser Ala Thr Ser Ser Ser Glu Glu
                165                 170                 175

Ser Ser Asn Lys Gly Gln Arg Gln Leu Thr Val Ser Thr Arg Met Arg
            180                 185                 190

Pro Glu Cys Val Val Pro Glu Ser Thr Cys Lys Asn Lys Arg Arg Glu
        195                 200                 205

Lys Glu Ala Gln Arg Glu Lys Asp Lys Leu Pro Val Ser Thr Thr Thr
210                 215                 220

Val Asp Asp His Met Pro Ala Ile Met Gln Cys Asp Pro Pro Pro
225                 230                 235                 240

Glu Ala Ala Arg Ile His Glu Val Val Pro Arg Phe Leu Thr Glu Lys
                245                 250                 255

Leu Met Glu Gln Asn Arg Leu Lys Asn Val Thr Pro Leu Ser Ala Asn
            260                 265                 270

Gln Lys Ser Leu Ile Ala Arg Leu Val Trp Tyr Gln Glu Gly Tyr Glu
        275                 280                 285

Gln Pro Ser Glu Glu Asp Leu Lys Arg Val Thr Gln Thr Trp Gln Leu
    290                 295                 300

Glu Glu Glu Glu Glu Glu Thr Asp Met Pro Phe Arg Gln Ile Thr
305                 310                 315                 320

Glu Met Thr Ile Leu Thr Val Gln Leu Ile Val Glu Phe Ala Lys Gly
                325                 330                 335

Leu Pro Gly Phe Ser Lys Ile Ser Gln Ser Asp Gln Ile Thr Leu Leu
            340                 345                 350

Lys Ala Ser Ser Ser Glu Val Met Met Leu Arg Val Ala Arg Arg Tyr
        355                 360                 365

Asp Ala Ala Thr Asp Ser Val Leu Phe Ala Asn Asn Gln Ala Tyr Thr
    370                 375                 380

Arg Asp Asn Tyr Arg Lys Ala Gly Met Ser Tyr Val Ile Glu Asp Leu
385                 390                 395                 400

Leu His Phe Cys Arg Cys Met Tyr Ser Met Ser Met Asp Asn Val His
                405                 410                 415

Tyr Ala Leu Leu Thr Ala Ile Val Ile Phe Ser Asp Arg Pro Gly Leu
            420                 425                 430

Glu Gln Pro Leu Leu Val Glu Glu Ile Gln Arg Tyr Tyr Leu Lys Thr
        435                 440                 445

Leu Arg Val Tyr Ile Leu Asn Gln His Ser Ala Ser Pro Arg Cys Ala
    450                 455                 460

Val Leu Phe Gly Lys Ile Leu Gly Val Leu Thr Glu Leu Arg Thr Leu
465                 470                 475                 480

Gly Thr Gln Asn Ser Asn Met Cys Ile Ser Leu Lys Leu Lys Asn Arg
                485                 490                 495

Lys Leu Pro Pro Phe Leu Glu Glu Ile Trp Asp Val Ala Glu Val Ser
            500                 505                 510

Thr Thr Lys Leu Pro Lys Ala Val Arg Cys Thr Gly Gly Leu Phe Phe
        515                 520                 525

Phe His Arg Asp Thr Thr Pro Ala His Ala Gly Glu Thr Ala Thr Pro
```

```
                530             535             540
Met Ala Gly Gly Gly Gly Gly Gly Glu Ala Gly Ser Ser Asp
545                 550                 555                 560

Asp Cys Ser Ser Ala Ala Ser Val Ser Leu Arg Val Gly Ser His Asp
                565                 570                 575

Glu Pro Cys Phe Ser Gly Asp Gly Asp Trp Met Asp Asp Val
                580                 585                 590

Arg Ala Leu Ala Ser Phe Leu Glu Ser Asp Glu Asp Trp Leu Arg Cys
            595                 600                 605

Gln Thr Ala Gly Gln Leu Ala
        610                 615

<210> SEQ ID NO 136
<211> LENGTH: 1863
<212> TYPE: DNA
<213> ORGANISM: Synthetic Construct
<220> FEATURE:
<221> NAME/KEY: CDS
<222> LOCATION: (1)..(1863)
<223> OTHER INFORMATION: Ecdysone receptor chimera G(M)MD

<400> SEQUENCE: 136
```

| | | | | | | | | | | | | | | | | |
|---|---|---|---|---|---|---|---|---|---|---|---|---|---|---|---|---|
| atg | cag | cag | cta | tat | gtg | gat | ttt | ttt | agc | cct | gcc | ttc | ata | cgc | tat | 48 |
| Met | Gln | Gln | Leu | Tyr | Val | Asp | Phe | Phe | Ser | Pro | Ala | Phe | Ile | Arg | Tyr | |
| 1 | | | | 5 | | | | | 10 | | | | | 15 | | |
| tta | ttt | gct | tgg | tac | tgt | ttc | ttt | tgt | cga | tgc | tca | ccc | tgt | tgt | ttg | 96 |
| Leu | Phe | Ala | Trp | Tyr | Cys | Phe | Phe | Cys | Arg | Cys | Ser | Pro | Cys | Cys | Leu | |
| | | | 20 | | | | | 25 | | | | | 30 | | | |
| gtg | tta | ctt | ctg | cag | gga | tcc | gcc | acc | atg | aag | cta | ctg | tct | tct | atc | 144 |
| Val | Leu | Leu | Leu | Gln | Gly | Ser | Ala | Thr | Met | Lys | Leu | Leu | Ser | Ser | Ile | |
| | | 35 | | | | | 40 | | | | | 45 | | | | |
| gaa | caa | gca | tgc | gat | att | tgc | cga | ctt | aaa | aag | ctc | aag | tgc | tcc | aaa | 192 |
| Glu | Gln | Ala | Cys | Asp | Ile | Cys | Arg | Leu | Lys | Lys | Leu | Lys | Cys | Ser | Lys | |
| | 50 | | | | | 55 | | | | | 60 | | | | | |
| gaa | aaa | ccg | aag | tgc | gcc | aag | tgt | ctg | aag | aac | aac | tgg | gag | tgt | cgc | 240 |
| Glu | Lys | Pro | Lys | Cys | Ala | Lys | Cys | Leu | Lys | Asn | Asn | Trp | Glu | Cys | Arg | |
| 65 | | | | | 70 | | | | | 75 | | | | | 80 | |
| tac | tct | ccc | aaa | acc | aaa | agg | tct | ccg | ctg | act | agg | gca | cat | ctg | aca | 288 |
| Tyr | Ser | Pro | Lys | Thr | Lys | Arg | Ser | Pro | Leu | Thr | Arg | Ala | His | Leu | Thr | |
| | | | | 85 | | | | | 90 | | | | | 95 | | |
| gaa | gtg | gaa | tca | agg | cta | gaa | aga | ctg | gaa | cag | cta | ttt | cta | ctg | att | 336 |
| Glu | Val | Glu | Ser | Arg | Leu | Glu | Arg | Leu | Glu | Gln | Leu | Phe | Leu | Leu | Ile | |
| | | | 100 | | | | | 105 | | | | | 110 | | | |
| ttt | cct | cga | gaa | gac | ctt | gac | atg | att | ttg | aaa | atg | gat | tct | tta | cag | 384 |
| Phe | Pro | Arg | Glu | Asp | Leu | Asp | Met | Ile | Leu | Lys | Met | Asp | Ser | Leu | Gln | |
| | | 115 | | | | | 120 | | | | | 125 | | | | |
| gat | ata | aaa | gca | ttg | tta | aca | gga | tta | ttt | gta | caa | gat | aat | gtg | aat | 432 |
| Asp | Ile | Lys | Ala | Leu | Leu | Thr | Gly | Leu | Phe | Val | Gln | Asp | Asn | Val | Asn | |
| | 130 | | | | | 135 | | | | | 140 | | | | | |
| aaa | gat | gcc | gtc | aca | gat | aga | ttg | gct | tca | gtg | gag | act | gat | atg | cct | 480 |
| Lys | Asp | Ala | Val | Thr | Asp | Arg | Leu | Ala | Ser | Val | Glu | Thr | Asp | Met | Pro | |
| 145 | | | | | 150 | | | | | 155 | | | | | 160 | |
| cta | aca | ttg | aga | cag | cat | aga | ata | agt | gcg | aca | tca | tca | tcg | gaa | gag | 528 |
| Leu | Thr | Leu | Arg | Gln | His | Arg | Ile | Ser | Ala | Thr | Ser | Ser | Ser | Glu | Glu | |
| | | | | 165 | | | | | 170 | | | | | 175 | | |
| agt | agt | aac | aaa | ggt | caa | aga | cag | ttg | act | gta | tcg | acg | cgt | atg | agg | 576 |
| Ser | Ser | Asn | Lys | Gly | Gln | Arg | Gln | Leu | Thr | Val | Ser | Thr | Arg | Met | Arg | |
| | | | 180 | | | | | 185 | | | | | 190 | | | |
| ccc | gag | tgc | gtc | gtc | cca | gag | tcc | acg | tgc | aag | aac | aaa | aga | aga | gaa | 624 |
| Pro | Glu | Cys | Val | Val | Pro | Glu | Ser | Thr | Cys | Lys | Asn | Lys | Arg | Arg | Glu | |

-continued

```
             195                 200                 205
aag gaa gca cag aga gaa aaa gac aaa ctg cca gtc agt acg acg aca     672
Lys Glu Ala Gln Arg Glu Lys Asp Lys Leu Pro Val Ser Thr Thr Thr
210                 215                 220 gtg gac gat cat atg cct gcc ata atg caa tgt gac cct ccg ccc cca     720
Val Asp Asp His Met Pro Ala Ile Met Gln Cys Asp Pro Pro Pro Pro
225                 230                 235                 240 gag gcg gca agg att cac gaa gtg gtc ccg agg ttc cta acg gag aag     768
Glu Ala Ala Arg Ile His Glu Val Val Pro Arg Phe Leu Thr Glu Lys
            245                 250                 255 cta atg gag cag aac aga ctg aag aat gtg acg ccg ctg tcg gcg aac     816
Leu Met Glu Gln Asn Arg Leu Lys Asn Val Thr Pro Leu Ser Ala Asn
        260                 265                 270 cag aag tcc ctg atc gcg agg ctc gtg tgg tac cag gag ggg tac gag     864
Gln Lys Ser Leu Ile Ala Arg Leu Val Trp Tyr Gln Glu Gly Tyr Glu
    275                 280                 285 cag ccg tcg gag gaa gat ctc aag aga gtt aca cag aca tgg cag tta     912
Gln Pro Ser Glu Glu Asp Leu Lys Arg Val Thr Gln Thr Trp Gln Leu
290                 295                 300 gaa gaa gaa gaa gag gag gaa act gac atg ccc ttc cgt cag atc aca     960
Glu Glu Glu Glu Glu Glu Glu Thr Asp Met Pro Phe Arg Gln Ile Thr
305                 310                 315                 320 gag atg acg atc tta aca gtg cag ctt att gta gaa ttc gca aag gga    1008
Glu Met Thr Ile Leu Thr Val Gln Leu Ile Val Glu Phe Ala Lys Gly
            325                 330                 335 cta ccg gga ttc tcc aag ata tct cag tcc gat caa att aca tta tta    1056
Leu Pro Gly Phe Ser Lys Ile Ser Gln Ser Asp Gln Ile Thr Leu Leu
        340                 345                 350 aag gcg tca tca agc gaa gtg atg atg ctg cga gtg gcg cga cgg tac    1104
Lys Ala Ser Ser Ser Glu Val Met Met Leu Arg Val Ala Arg Arg Tyr
    355                 360                 365 gac gcg gcg acg gac agc gtg ctg ttc gcg aac aac cag gcg tac acg    1152
Asp Ala Ala Thr Asp Ser Val Leu Phe Ala Asn Asn Gln Ala Tyr Thr
370                 375                 380 cgc gac aac tac cgc aag gcg ggc atg tcc tac gtc atc gag gac ctg    1200
Arg Asp Asn Tyr Arg Lys Ala Gly Met Ser Tyr Val Ile Glu Asp Leu
385                 390                 395                 400 ctg cac ttc tgt cgg tgt atg tac tcc atg agc atg gac aat gtg cac    1248
Leu His Phe Cys Arg Cys Met Tyr Ser Met Ser Met Asp Asn Val His
            405                 410                 415 tac gcg ctg ctc acc gcc atc gtt ata ttc tca gac cgg cca ggc ctc    1296
Tyr Ala Leu Leu Thr Ala Ile Val Ile Phe Ser Asp Arg Pro Gly Leu
        420                 425                 430 gag caa ccc ctt tta gtg gag gaa atc cag aga tac tac ttg aag acg    1344
Glu Gln Pro Leu Leu Val Glu Glu Ile Gln Arg Tyr Tyr Leu Lys Thr
    435                 440                 445 ctg cgg gtt tac att tta aat cag cac agc gcg tcg cct cgc tgc gcc    1392
Leu Arg Val Tyr Ile Leu Asn Gln His Ser Ala Ser Pro Arg Cys Ala
450                 455                 460 gtg ctg ttc ggc aag atc ctc ggc gtg ctg acg gaa ctg cgc acg ctc    1440
Val Leu Phe Gly Lys Ile Leu Gly Val Leu Thr Glu Leu Arg Thr Leu
465                 470                 475                 480 ggc acg cag aac tcc aac atg tgc atc tcg ctg aag ctg aag aac agg    1488
Gly Thr Gln Asn Ser Asn Met Cys Ile Ser Leu Lys Leu Lys Asn Arg
            485                 490                 495 aaa ctt ccg cca ttc ctc gag gag atc tgg gac gtg gcc gaa gtg tcg    1536
Lys Leu Pro Pro Phe Leu Glu Glu Ile Trp Asp Val Ala Glu Val Ser
        500                 505                 510 acg acg aag ctt gag ctc gcc acc gcg gcc gac cca ggc aag acg gcg    1584
Thr Thr Lys Leu Glu Leu Ala Thr Ala Ala Asp Pro Gly Lys Thr Ala
```

```
Thr Thr Lys Leu Glu Leu Ala Thr Ala Ala Asp Pro Gly Lys Thr Ala
            515                 520                 525 acc acc acc acc acg acg acg agc gag atc acc acg gag act ggc gcg       1632
Thr Thr Thr Thr Thr Thr Ser Glu Ile Thr Thr Glu Thr Gly Ala
        530                 535                 540 ctg gag gac tcc gac tcc ctg gcg cac ctg ctg ctg cag ccc ggg aca       1680
Leu Glu Asp Ser Asp Ser Leu Ala His Leu Leu Leu Gln Pro Gly Thr
545                 550                 555                 560 gag gac gcg gag gcc gtc gcg ctc ggg ctc ggc ctc tcc gac ttc ccc       1728
Glu Asp Ala Glu Ala Val Ala Leu Gly Leu Gly Leu Ser Asp Phe Pro
                565                 570                 575 tcc gcc ggg aag gcg gtg ctg gac gac gag gac tcg ttc gtg tgg ccc       1776
Ser Ala Gly Lys Ala Val Leu Asp Asp Glu Asp Ser Phe Val Trp Pro
            580                 585                 590 gcc gcg tcg ttc gac atg ggc gcg tgc tgg gcc ggc gca ggg ttc gcc       1824
Ala Ala Ser Phe Asp Met Gly Ala Cys Trp Ala Gly Ala Gly Phe Ala
        595                 600                 605 gac ccg gac ccc gcc tgc atc ttc ctc aac ctc ccg tga                   1863
Asp Pro Asp Pro Ala Cys Ile Phe Leu Asn Leu Pro
610                 615                 620

<210> SEQ ID NO 137
<211> LENGTH: 620
<212> TYPE: PRT
<213> ORGANISM: Synthetic Construct

<400> SEQUENCE: 137

Met Gln Gln Leu Tyr Val Asp Phe Phe Ser Pro Ala Phe Ile Arg Tyr
1               5                   10                  15

Leu Phe Ala Trp Tyr Cys Phe Phe Cys Arg Cys Ser Pro Cys Cys Leu
            20                  25                  30

Val Leu Leu Leu Gln Gly Ser Ala Thr Met Lys Leu Leu Ser Ser Ile
        35                  40                  45

Glu Gln Ala Cys Asp Ile Cys Arg Leu Lys Lys Leu Lys Cys Ser Lys
    50                  55                  60

Glu Lys Pro Lys Cys Ala Lys Cys Leu Lys Asn Asn Trp Glu Cys Arg
65                  70                  75                  80

Tyr Ser Pro Lys Thr Lys Arg Ser Pro Leu Thr Arg Ala His Leu Thr
                85                  90                  95

Glu Val Glu Ser Arg Leu Glu Arg Leu Glu Gln Leu Phe Leu Leu Ile
            100                 105                 110

Phe Pro Arg Glu Asp Leu Asp Met Ile Leu Lys Met Asp Ser Leu Gln
        115                 120                 125

Asp Ile Lys Ala Leu Leu Thr Gly Leu Phe Val Gln Asp Asn Val Asn
    130                 135                 140

Lys Asp Ala Val Thr Asp Arg Leu Ala Ser Val Glu Thr Asp Met Pro
145                 150                 155                 160

Leu Thr Leu Arg Gln His Arg Ile Ser Ala Thr Ser Ser Ser Glu Glu
                165                 170                 175

Ser Ser Asn Lys Gly Gln Arg Gln Leu Thr Val Ser Thr Arg Met Arg
            180                 185                 190

Pro Glu Cys Val Val Pro Glu Ser Thr Cys Lys Asn Lys Arg Arg Glu
        195                 200                 205

Lys Glu Ala Gln Arg Glu Lys Asp Lys Leu Pro Val Ser Thr Thr Thr
    210                 215                 220

Val Asp Asp His Met Pro Ala Ile Met Gln Cys Asp Pro Pro Pro
225                 230                 235                 240
```

```
Glu Ala Ala Arg Ile His Glu Val Val Pro Arg Phe Leu Thr Glu Lys
                245                 250                 255
Leu Met Glu Gln Asn Arg Leu Lys Asn Val Thr Pro Leu Ser Ala Asn
            260                 265                 270
Gln Lys Ser Leu Ile Ala Arg Leu Val Trp Tyr Gln Glu Gly Tyr Glu
        275                 280                 285
Gln Pro Ser Glu Glu Asp Leu Lys Arg Val Thr Gln Thr Trp Gln Leu
    290                 295                 300
Glu Glu Glu Glu Glu Glu Thr Asp Met Pro Phe Arg Gln Ile Thr
305                 310                 315                 320
Glu Met Thr Ile Leu Thr Val Gln Leu Ile Val Glu Phe Ala Lys Gly
                325                 330                 335
Leu Pro Gly Phe Ser Lys Ile Ser Ser Asp Gln Ile Thr Leu Leu
            340                 345                 350
Lys Ala Ser Ser Ser Glu Val Met Met Leu Arg Val Ala Arg Arg Tyr
        355                 360                 365
Asp Ala Ala Thr Asp Ser Val Leu Phe Ala Asn Asn Gln Ala Tyr Thr
    370                 375                 380
Arg Asp Asn Tyr Arg Lys Ala Gly Met Ser Tyr Val Ile Glu Asp Leu
385                 390                 395                 400
Leu His Phe Cys Arg Cys Met Tyr Ser Met Ser Met Asp Asn Val His
                405                 410                 415
Tyr Ala Leu Leu Thr Ala Ile Val Ile Phe Ser Asp Arg Pro Gly Leu
            420                 425                 430
Glu Gln Pro Leu Leu Val Glu Glu Ile Gln Arg Tyr Tyr Leu Lys Thr
        435                 440                 445
Leu Arg Val Tyr Ile Leu Asn Gln His Ser Ala Ser Pro Arg Cys Ala
    450                 455                 460
Val Leu Phe Gly Lys Ile Leu Gly Val Leu Thr Glu Leu Arg Thr Leu
465                 470                 475                 480
Gly Thr Gln Asn Ser Asn Met Cys Ile Ser Leu Lys Leu Lys Asn Arg
                485                 490                 495
Lys Leu Pro Pro Phe Leu Glu Glu Ile Trp Asp Val Ala Glu Val Ser
            500                 505                 510
Thr Thr Lys Leu Glu Leu Ala Thr Ala Ala Asp Pro Gly Lys Thr Ala
        515                 520                 525
Thr Thr Thr Thr Thr Thr Thr Ser Glu Ile Thr Thr Glu Thr Gly Ala
    530                 535                 540
Leu Glu Asp Ser Asp Ser Leu Ala His Leu Leu Gln Pro Gly Thr
545                 550                 555                 560
Glu Asp Ala Glu Ala Val Ala Leu Gly Leu Gly Leu Ser Asp Phe Pro
                565                 570                 575
Ser Ala Gly Lys Ala Val Leu Asp Asp Glu Asp Ser Phe Val Trp Pro
            580                 585                 590
Ala Ala Ser Phe Asp Met Gly Ala Cys Trp Ala Gly Ala Gly Phe Ala
        595                 600                 605
Asp Pro Asp Pro Ala Cys Ile Phe Leu Asn Leu Pro
    610                 615                 620

<210> SEQ ID NO 138
<211> LENGTH: 29
<212> TYPE: DNA
<213> ORGANISM: Artificial Sequence
<220> FEATURE:
```

-continued

```
<221> NAME/KEY: misc_feature
<222> LOCATION: (1)..(29)
<223> OTHER INFORMATION: primer

<400> SEQUENCE: 138
aaaaactagt aagctactgt cttctatcg                                    29

<210> SEQ ID NO 139
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer

<400> SEQUENCE: 139
ggatcctaaa gcttcgtcgt cgacacttcg                                   30

<210> SEQ ID NO 140
<211> LENGTH: 43
<212> TYPE: DNA
<213> ORGANISM: Artificial Sequence
<220> FEATURE:
<221> NAME/KEY: misc_feature
<222> LOCATION: (1)..(43)
<223> OTHER INFORMATION: primer

<400> SEQUENCE: 140
aaaaaggatc cgccaccatg cacgtgaagc ttgccccccc gac                    43

<210> SEQ ID NO 141
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: primer

<400> SEQUENCE: 141
aaaaaactag tcacgtgccc accgtactcg tcaattcc                          38

<210> SEQ ID NO 142
<211> LENGTH: 1809
<212> TYPE: DNA
<213> ORGANISM: Synthetic Construct
<220> FEATURE:
<221> NAME/KEY: CDS
<222> LOCATION: (1)..(1809)
<223> OTHER INFORMATION: Ecdysone receptor chimera VG(M)M

<400> SEQUENCE: 142
```

| | | | | | | | | | | | | | | | | |
|---|---|---|---|---|---|---|---|---|---|---|---|---|---|---|---|---|
| atg | cag | cag | cta | tat | gtg | gat | ttt | ttt | agc | cct | gcc | ttc | ata | cgc | tat | 48 |
| Met | Gln | Gln | Leu | Tyr | Val | Asp | Phe | Phe | Ser | Pro | Ala | Phe | Ile | Arg | Tyr | |
| 1 | | | | 5 | | | | | 10 | | | | | 15 | | |
| tta | ttt | gct | tgg | tac | tgt | ttc | ttt | tgt | cga | tgc | tca | ccc | tgt | tgt | ttg | 96 |
| Leu | Phe | Ala | Trp | Tyr | Cys | Phe | Phe | Cys | Arg | Cys | Ser | Pro | Cys | Cys | Leu | |
| | | | 20 | | | | | 25 | | | | | 30 | | | |
| gtg | tta | ctt | ctg | cag | gga | tcc | gcc | acc | atg | cac | gtg | aag | ctt | gcc | ccc | 144 |
| Val | Leu | Leu | Leu | Gln | Gly | Ser | Ala | Thr | Met | His | Val | Lys | Leu | Ala | Pro | |
| | | | 35 | | | | | 40 | | | | | 45 | | | |
| ccg | acc | gat | gtc | agc | ctg | ggg | gac | gag | ctc | cac | tta | gac | ggc | gag | gac | 192 |
| Pro | Thr | Asp | Val | Ser | Leu | Gly | Asp | Glu | Leu | His | Leu | Asp | Gly | Glu | Asp | |
| | 50 | | | | | 55 | | | | | 60 | | | | | |
| gtg | gcg | atg | gcg | cat | gcc | gac | gcg | cta | gac | gat | ttc | gat | ctg | gac | atg | 240 |

```
Val Ala Met Ala His Ala Asp Ala Leu Asp Asp Phe Asp Leu Asp Met
 65                  70                  75                  80 ttg ggg gac ggg gat tcc ccg ggt ccg gga ttt acc ccc cac gac tcc      288
Leu Gly Asp Gly Asp Ser Pro Gly Pro Gly Phe Thr Pro His Asp Ser
                 85                  90                  95 gcc ccc tac ggc gct ctg gat atg gcc gac ttc gag ttt gag cag atg      336
Ala Pro Tyr Gly Ala Leu Asp Met Ala Asp Phe Glu Phe Glu Gln Met
            100                 105                 110 ttt acc gat gcc ctt gga att gac gag tac ggt ggg cac gtg act agt      384
Phe Thr Asp Ala Leu Gly Ile Asp Glu Tyr Gly Gly His Val Thr Ser
        115                 120                 125 aag cta ctg tct tct atc gaa caa gca tgc gat att tgc cga ctt aaa      432
Lys Leu Leu Ser Ser Ile Glu Gln Ala Cys Asp Ile Cys Arg Leu Lys
    130                 135                 140 aag ctc aag tgc tcc aaa gaa aaa ccg aag tgc gcc aag tgt ctg aag      480
Lys Leu Lys Cys Ser Lys Glu Lys Pro Lys Cys Ala Lys Cys Leu Lys
145                 150                 155                 160 aac aac tgg gag tgt cgc tac tct ccc aaa acc aaa agg tct ccg ctg      528
Asn Asn Trp Glu Cys Arg Tyr Ser Pro Lys Thr Lys Arg Ser Pro Leu
                165                 170                 175 act agg gca cat ctg aca gaa gtg gaa tca agg cta gaa aga ctg gaa      576
Thr Arg Ala His Leu Thr Glu Val Glu Ser Arg Leu Glu Arg Leu Glu
            180                 185                 190 cag cta ttt cta ctg att ttt cct cga gaa gac ctt gac atg att ttg      624
Gln Leu Phe Leu Leu Ile Phe Pro Arg Glu Asp Leu Asp Met Ile Leu
        195                 200                 205 aaa atg gat tct tta cag gat ata aaa gca ttg tta aca gga tta ttt      672
Lys Met Asp Ser Leu Gln Asp Ile Lys Ala Leu Leu Thr Gly Leu Phe
    210                 215                 220 gta caa gat aat gtg aat aaa gat gcc gtc aca gat aga ttg gct tca      720
Val Gln Asp Asn Val Asn Lys Asp Ala Val Thr Asp Arg Leu Ala Ser
225                 230                 235                 240 gtg gag act gat atg cct cta aca ttg aga cag cat aga ata agt gcg      768
Val Glu Thr Asp Met Pro Leu Thr Leu Arg Gln His Arg Ile Ser Ala
                245                 250                 255 aca tca tca tcg gaa gag agt agt aac aaa ggt caa aga cag ttg act      816
Thr Ser Ser Ser Glu Glu Ser Ser Asn Lys Gly Gln Arg Gln Leu Thr
            260                 265                 270 gta tcg acg cgt atg agg ccc gag tgc gtc gtc cca gag tcc acg tgc      864
Val Ser Thr Arg Met Arg Pro Glu Cys Val Val Pro Glu Ser Thr Cys
        275                 280                 285 aag aac aaa aga aga gaa aag gaa gca cag aga gaa aaa gac aaa ctg      912
Lys Asn Lys Arg Arg Glu Lys Glu Ala Gln Arg Glu Lys Asp Lys Leu
    290                 295                 300 cca gtc agt acg acg aca gtg gac gat cat atg cct gcc ata atg caa      960
Pro Val Ser Thr Thr Thr Val Asp Asp His Met Pro Ala Ile Met Gln
305                 310                 315                 320 tgt gac cct ccg ccc cca gag gcg gca agg att cac gaa gtg gtc ccg     1008
Cys Asp Pro Pro Pro Pro Glu Ala Ala Arg Ile His Glu Val Val Pro
                325                 330                 335 agg ttc cta acg gag aag cta atg gag cag aac aga ctg aag aat gtg     1056
Arg Phe Leu Thr Glu Lys Leu Met Glu Gln Asn Arg Leu Lys Asn Val
            340                 345                 350 acg ccg ctg tcg gcg aac cag aag tcc ctg atc gcg agg ctc gtg tgg     1104
Thr Pro Leu Ser Ala Asn Gln Lys Ser Leu Ile Ala Arg Leu Val Trp
        355                 360                 365 tac cag gag ggg tac gag cag ccg tcg gag gaa gat ctc aag aga gtt     1152
Tyr Gln Glu Gly Tyr Glu Gln Pro Ser Glu Glu Asp Leu Lys Arg Val
    370                 375                 380
```

```
aca cag aca tgg cag tta gaa gaa gaa gag gag gaa act gac atg        1200
Thr Gln Thr Trp Gln Leu Glu Glu Glu Glu Glu Glu Thr Asp Met
385                 390                 395                 400 ccc ttc cgt cag atc aca gag atg acg atc tta aca gtg cag ctt att    1248
Pro Phe Arg Gln Ile Thr Glu Met Thr Ile Leu Thr Val Gln Leu Ile
            405                 410                 415 gta gaa ttc gca aag gga cta ccg gga ttc tcc aag ata tct cag tcc    1296
Val Glu Phe Ala Lys Gly Leu Pro Gly Phe Ser Lys Ile Ser Gln Ser
        420                 425                 430 gat caa att aca tta tta aag gcg tca tca agc gaa gtg atg atg ctg    1344
Asp Gln Ile Thr Leu Leu Lys Ala Ser Ser Ser Glu Val Met Met Leu
    435                 440                 445 cga gtg gcg cga cgg tac gac gcg gcg acg gac agc gtg ctg ttc gcg   1392
Arg Val Ala Arg Arg Tyr Asp Ala Ala Thr Asp Ser Val Leu Phe Ala
450                 455                 460 aac aac cag gcg tac acg cgc gac aac tac cgc aag gcg ggc atg tcc   1440
Asn Asn Gln Ala Tyr Thr Arg Asp Asn Tyr Arg Lys Ala Gly Met Ser
465                 470                 475                 480 tac gtc atc gag gac ctg ctg cac ttc tgt cgg tgt atg tac tcc atg   1488
Tyr Val Ile Glu Asp Leu Leu His Phe Cys Arg Cys Met Tyr Ser Met
            485                 490                 495 agc atg gac aat gtg cac tac gcg ctc ctc acc gcc atc gtt ata ttc   1536
Ser Met Asp Asn Val His Tyr Ala Leu Leu Thr Ala Ile Val Ile Phe
        500                 505                 510 tca gac cgg cca ggc ctc gag caa ccc ctt tta gtg gag gaa atc cag   1584
Ser Asp Arg Pro Gly Leu Glu Gln Pro Leu Leu Val Glu Glu Ile Gln
    515                 520                 525 aga tac tac ttg aag acg ctg cgg gtt tac att tta aat cag cac agc   1632
Arg Tyr Tyr Leu Lys Thr Leu Arg Val Tyr Ile Leu Asn Gln His Ser
530                 535                 540 gcg tcg cct cgc tgc gcc gtg ctg ttc ggc aag atc ctc ggc gtg ctg   1680
Ala Ser Pro Arg Cys Ala Val Leu Phe Gly Lys Ile Leu Gly Val Leu
545                 550                 555                 560 acg gaa ctg cgc acg ctc ggc acg cag aac tcc aac atg tgc atc tcg   1728
Thr Glu Leu Arg Thr Leu Gly Thr Gln Asn Ser Asn Met Cys Ile Ser
            565                 570                 575 ctg aag ctg aag aac agg aaa ctt ccg cca ttc ctc gag gag atc tgg   1776
Leu Lys Leu Lys Asn Arg Lys Leu Pro Pro Phe Leu Glu Glu Ile Trp
        580                 585                 590 gac gtg gcc gaa gtg tcg acg acg aag ctt tag                        1809
Asp Val Ala Glu Val Ser Thr Thr Lys Leu
    595                 600
```

<210> SEQ ID NO 143
<211> LENGTH: 602
<212> TYPE: PRT
<213> ORGANISM: Synthetic Construct

<400> SEQUENCE: 143

```
Met Gln Gln Leu Tyr Val Asp Phe Phe Ser Pro Ala Phe Ile Arg Tyr
1               5                   10                  15

Leu Phe Ala Trp Tyr Cys Phe Phe Cys Arg Cys Ser Pro Cys Cys Leu
            20                  25                  30

Val Leu Leu Leu Gln Gly Ser Ala Thr Met His Val Lys Leu Ala Pro
        35                  40                  45

Pro Thr Asp Val Ser Leu Gly Asp Glu Leu His Leu Asp Gly Glu Asp
    50                  55                  60

Val Ala Met Ala His Ala Asp Ala Leu Asp Asp Phe Asp Leu Asp Met
65                  70                  75                  80
```

-continued

```
Leu Gly Asp Gly Asp Ser Pro Gly Pro Gly Phe Thr Pro His Asp Ser
                85                  90                  95

Ala Pro Tyr Gly Ala Leu Asp Met Ala Asp Phe Glu Phe Glu Gln Met
            100                 105                 110

Phe Thr Asp Ala Leu Gly Ile Asp Glu Tyr Gly Gly His Val Thr Ser
        115                 120                 125

Lys Leu Leu Ser Ser Ile Glu Gln Ala Cys Asp Ile Cys Arg Leu Lys
    130                 135                 140

Lys Leu Lys Cys Ser Lys Glu Lys Pro Lys Cys Ala Lys Cys Leu Lys
145                 150                 155                 160

Asn Asn Trp Glu Cys Arg Tyr Ser Pro Lys Thr Lys Arg Ser Pro Leu
                165                 170                 175

Thr Arg Ala His Leu Thr Glu Val Glu Ser Arg Leu Glu Arg Leu Glu
            180                 185                 190

Gln Leu Phe Leu Leu Ile Phe Pro Arg Glu Asp Leu Asp Met Ile Leu
        195                 200                 205

Lys Met Asp Ser Leu Gln Asp Ile Lys Ala Leu Leu Thr Gly Leu Phe
    210                 215                 220

Val Gln Asp Asn Val Asn Lys Asp Ala Val Thr Asp Arg Leu Ala Ser
225                 230                 235                 240

Val Glu Thr Asp Met Pro Leu Thr Leu Arg Gln His Arg Ile Ser Ala
                245                 250                 255

Thr Ser Ser Ser Glu Glu Ser Ser Asn Lys Gly Gln Arg Gln Leu Thr
            260                 265                 270

Val Ser Thr Arg Met Arg Pro Glu Cys Val Val Pro Glu Ser Thr Cys
        275                 280                 285

Lys Asn Lys Arg Arg Glu Lys Glu Ala Gln Arg Glu Lys Asp Lys Leu
    290                 295                 300

Pro Val Ser Thr Thr Thr Val Asp Asp His Met Pro Ala Ile Met Gln
305                 310                 315                 320

Cys Asp Pro Pro Pro Glu Ala Ala Arg Ile His Glu Val Val Pro
                325                 330                 335

Arg Phe Leu Thr Glu Lys Leu Met Glu Gln Asn Arg Leu Lys Asn Val
            340                 345                 350

Thr Pro Leu Ser Ala Asn Gln Lys Ser Leu Ile Ala Arg Leu Val Trp
        355                 360                 365

Tyr Gln Glu Gly Tyr Glu Gln Pro Ser Glu Glu Asp Leu Lys Arg Val
    370                 375                 380

Thr Gln Thr Trp Gln Leu Glu Glu Glu Glu Glu Thr Asp Met
385                 390                 395                 400

Pro Phe Arg Gln Ile Thr Glu Met Thr Ile Leu Thr Val Gln Leu Ile
                405                 410                 415

Val Glu Phe Ala Lys Gly Leu Pro Gly Phe Ser Lys Ile Ser Gln Ser
            420                 425                 430

Asp Gln Ile Thr Leu Leu Lys Ala Ser Ser Ser Glu Val Met Met Leu
        435                 440                 445

Arg Val Ala Arg Arg Tyr Asp Ala Ala Thr Asp Ser Val Leu Phe Ala
    450                 455                 460

Asn Asn Gln Ala Tyr Thr Arg Asp Asn Tyr Arg Lys Ala Gly Met Ser
465                 470                 475                 480

Tyr Val Ile Glu Asp Leu Leu His Phe Cys Arg Cys Met Tyr Ser Met
                485                 490                 495

Ser Met Asp Asn Val His Tyr Ala Leu Leu Thr Ala Ile Val Ile Phe
```

```
                        500             505             510
Ser Asp Arg Pro Gly Leu Glu Gln Pro Leu Leu Val Glu Glu Ile Gln
        515                 520                 525

Arg Tyr Tyr Leu Lys Thr Leu Arg Val Tyr Ile Leu Asn Gln His Ser
        530                 535                 540

Ala Ser Pro Arg Cys Ala Val Leu Phe Gly Lys Ile Leu Gly Val Leu
545                 550                 555                 560

Thr Glu Leu Arg Thr Leu Gly Thr Gln Asn Ser Asn Met Cys Ile Ser
                565                 570                 575

Leu Lys Leu Lys Asn Arg Lys Leu Pro Pro Phe Leu Glu Glu Ile Trp
        580                 585                 590

Asp Val Ala Glu Val Ser Thr Thr Lys Leu
        595                 600

<210> SEQ ID NO 144
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: primer

<400> SEQUENCE: 144
caaggatccg ccaccatgaa gctactgtct tctatcg                              37

<210> SEQ ID NO 145
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: primer

<400> SEQUENCE: 145
aaaaacacgt gcaagcttgc cccccgac                                        29

<210> SEQ ID NO 146
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: primer

<400> SEQUENCE: 146
aaaaacacgt gttcccaccg tactcgtcaa ttcc                                 34

<210> SEQ ID NO 147
<211> LENGTH: 1800
<212> TYPE: DNA
<213> ORGANISM: Synthetic Construct
<220> FEATURE:
<221> NAME/KEY: CDS
<222> LOCATION: (1)..(1800)
<223> OTHER INFORMATION: Ecdysone receptor chimera GV(M)M

<400> SEQUENCE: 147 atg cag cag cta tat gtg gat ttt ttt agc cct gcc ttc ata cgc tat      48
Met Gln Gln Leu Tyr Val Asp Phe Phe Ser Pro Ala Phe Ile Arg Tyr
1               5                   10                  15 tta ttt gct tgg tac tgt ttc ttt tgt cga tgc tca ccc tgt tgt ttg      96
```

```
                                                                -continued

Leu Phe Ala Trp Tyr Cys Phe Phe Cys Arg Cys Ser Pro Cys Cys Leu
         20                  25                  30 gtg tta ctt ctg cag gga tcc gcc acc atg aag cta ctg tct tct atc    144
Val Leu Leu Leu Gln Gly Ser Ala Thr Met Lys Leu Leu Ser Ser Ile
         35                  40                  45 gaa caa gca tgc gat att tgc cga ctt aaa aag ctc aag tgc tcc aaa    192
Glu Gln Ala Cys Asp Ile Cys Arg Leu Lys Lys Leu Lys Cys Ser Lys
     50                  55                  60 gaa aaa ccg aag tgc gcc aag tgt ctg aag aac aac tgg gag tgt cgc    240
Glu Lys Pro Lys Cys Ala Lys Cys Leu Lys Asn Asn Trp Glu Cys Arg
 65                  70                  75                  80 tac tct ccc aaa acc aaa agg tct ccg ctg act agg gca cat ctg aca    288
Tyr Ser Pro Lys Thr Lys Arg Ser Pro Leu Thr Arg Ala His Leu Thr
                 85                  90                  95 gaa gtg gaa tca agg cta gaa aga ctg gaa cag cta ttt cta ctg att    336
Glu Val Glu Ser Arg Leu Glu Arg Leu Glu Gln Leu Phe Leu Leu Ile
             100                 105                 110 ttt cct cga gaa gac ctt gac atg att ttg aaa atg gat tct tta cag    384
Phe Pro Arg Glu Asp Leu Asp Met Ile Leu Lys Met Asp Ser Leu Gln
         115                 120                 125 gat ata aaa gca ttg tta aca gga tta ttt gta caa gat aat gtg aat    432
Asp Ile Lys Ala Leu Leu Thr Gly Leu Phe Val Gln Asp Asn Val Asn
    130                 135                 140 aaa gat gcc gtc aca gat aga ttg gct tca gtg gag act gat atg cct    480
Lys Asp Ala Val Thr Asp Arg Leu Ala Ser Val Glu Thr Asp Met Pro
145                 150                 155                 160 cta aca ttg aga cag cat aga ata agt gcg aca tca tca tcg gaa gag    528
Leu Thr Leu Arg Gln His Arg Ile Ser Ala Thr Ser Ser Ser Glu Glu
                165                 170                 175 agt agt aac aaa ggt caa aga cag ttg act gta tcg acg cgt atg agg    576
Ser Ser Asn Lys Gly Gln Arg Gln Leu Thr Val Ser Thr Arg Met Arg
            180                 185                 190 ccc gag tgc gtc gtc cca gag tcc acg tgc aag ctt gcc ccc ccg acc    624
Pro Glu Cys Val Val Pro Glu Ser Thr Cys Lys Leu Ala Pro Pro Thr
        195                 200                 205 gat gtc agc ctg ggg gac gag ctc cac tta gac ggc gag gac gtg gcg    672
Asp Val Ser Leu Gly Asp Glu Leu His Leu Asp Gly Glu Asp Val Ala
    210                 215                 220 atg gca cat gcc gac gcg cta gac gat ttc gat ctg gac atg ttg ggg    720
Met Ala His Ala Asp Ala Leu Asp Asp Phe Asp Leu Asp Met Leu Gly
225                 230                 235                 240 gac ggg gat tcc ccg ggt ccg gga ttt acc ccc cac gac tcc gcc ccc    768
Asp Gly Asp Ser Pro Gly Pro Gly Phe Thr Pro His Asp Ser Ala Pro
                245                 250                 255 tac ggc gct ctg gat atg gcc gac ttc gag ttt gag cag atg ttt acc    816
Tyr Gly Ala Leu Asp Met Ala Asp Phe Glu Phe Glu Gln Met Phe Thr
            260                 265                 270 gat gcc ctt gga att gac gag tac ggt ggg aac acg tgc aag aac aaa    864
Asp Ala Leu Gly Ile Asp Glu Tyr Gly Gly Asn Thr Cys Lys Asn Lys
        275                 280                 285 aga aga gaa aag gaa gca cag aga gaa aaa gac aaa ctg cca gtc agt    912
Arg Arg Glu Lys Glu Ala Gln Arg Glu Lys Asp Lys Leu Pro Val Ser
    290                 295                 300 acg acg aca gtg gac gat cat atg cct gcc ata atg caa tgt gac cct    960
Thr Thr Thr Val Asp Asp His Met Pro Ala Ile Met Gln Cys Asp Pro
305                 310                 315                 320 ccg ccc cca gag gcg gca agg att cac gaa gtg gtc ccg agg ttc cta    1008
Pro Pro Pro Glu Ala Ala Arg Ile His Glu Val Val Pro Arg Phe Leu
                325                 330                 335
```

```
acg gag aag cta atg gag cag aac aga ctg aag aat gtg acg ccg ctg      1056
Thr Glu Lys Leu Met Glu Gln Asn Arg Leu Lys Asn Val Thr Pro Leu
            340                 345                 350 tcg gcg aac cag aag tcc ctg atc gcg agg ctc gtg tgg tac cag gag      1104
Ser Ala Asn Gln Lys Ser Leu Ile Ala Arg Leu Val Trp Tyr Gln Glu
        355                 360                 365 ggg tac gag cag ccg tcg gag gaa gat ctc aag aga gtt aca cag aca      1152
Gly Tyr Glu Gln Pro Ser Glu Glu Asp Leu Lys Arg Val Thr Gln Thr
    370                 375                 380 tgg cag tta gaa gaa gaa gaa gag gaa act gac atg ccc ttc cgt          1200
Trp Gln Leu Glu Glu Glu Glu Glu Glu Thr Asp Met Pro Phe Arg
385                 390                 395                 400 cag atc aca gag atg acg atc tta aca gtg cag ctt att gta gaa ttc      1248
Gln Ile Thr Glu Met Thr Ile Leu Thr Val Gln Leu Ile Val Glu Phe
                405                 410                 415 gca aag gga cta ccg gga ttc tcc aag ata tct cag tcc gat caa att      1296
Ala Lys Gly Leu Pro Gly Phe Ser Lys Ile Ser Gln Ser Asp Gln Ile
            420                 425                 430 aca tta tta aag gcg tca tca agc gaa gtg atg atg ctg cga gtg gcg      1344
Thr Leu Leu Lys Ala Ser Ser Ser Glu Val Met Met Leu Arg Val Ala
        435                 440                 445 cga cgg tac gac gcg gcg acg gac agc gtg ctg ttc gcg aac aac cag      1392
Arg Arg Tyr Asp Ala Ala Thr Asp Ser Val Leu Phe Ala Asn Asn Gln
    450                 455                 460 gcg tac acg cgc gac aac tac cgc aag gcg ggc atg tcc tac gtc atc      1440
Ala Tyr Thr Arg Asp Asn Tyr Arg Lys Ala Gly Met Ser Tyr Val Ile
465                 470                 475                 480 gag gac ctg ctg cac ttc tgt cgg tgt atg tac tcc atg agc atg gac      1488
Glu Asp Leu Leu His Phe Cys Arg Cys Met Tyr Ser Met Ser Met Asp
                485                 490                 495 aat gtg cac tac gcg ctg ctc acc gcc atc gtt ata ttc tca gac cgg      1536
Asn Val His Tyr Ala Leu Leu Thr Ala Ile Val Ile Phe Ser Asp Arg
            500                 505                 510 cca ggc ctc gag caa ccc ctt tta gtg gag gaa atc cag aga tac tac      1584
Pro Gly Leu Glu Gln Pro Leu Leu Val Glu Glu Ile Gln Arg Tyr Tyr
        515                 520                 525 ttg aag acg ctg cgg gtt tac att tta aat cag cac agc gcg tcg cct      1632
Leu Lys Thr Leu Arg Val Tyr Ile Leu Asn Gln His Ser Ala Ser Pro
    530                 535                 540 cgc tgc gcc gtg ctg ttc ggc aag atc ctc ggc gtg ctg acg gaa ctg      1680
Arg Cys Ala Val Leu Phe Gly Lys Ile Leu Gly Val Leu Thr Glu Leu
545                 550                 555                 560 cgc acg ctc ggc acg cag aac tcc aac atg tgc atc tcg ctg aag ctg      1728
Arg Thr Leu Gly Thr Gln Asn Ser Asn Met Cys Ile Ser Leu Lys Leu
                565                 570                 575 aag aac agg aaa ctt ccg cca ttc ctc gag gag atc tgg gac gtg gcc      1776
Lys Asn Arg Lys Leu Pro Pro Phe Leu Glu Glu Ile Trp Asp Val Ala
            580                 585                 590 gaa gtg tcg acg acg aag ctt tag                                      1800
Glu Val Ser Thr Thr Lys Leu
        595

<210> SEQ ID NO 148
<211> LENGTH: 599
<212> TYPE: PRT
<213> ORGANISM: Synthetic Construct

<400> SEQUENCE: 148

Met Gln Gln Leu Tyr Val Asp Phe Phe Ser Pro Ala Phe Ile Arg Tyr
1               5                   10                  15
```

-continued

```
Leu Phe Ala Trp Tyr Cys Phe Phe Cys Arg Cys Ser Pro Cys Cys Leu
             20                  25                  30
Val Leu Leu Leu Gln Gly Ser Ala Thr Met Lys Leu Leu Ser Ser Ile
         35                  40                  45
Glu Gln Ala Cys Asp Ile Cys Arg Leu Lys Lys Leu Lys Cys Ser Lys
     50                  55                  60
Glu Lys Pro Lys Cys Ala Lys Cys Leu Lys Asn Asn Trp Glu Cys Arg
65                  70                  75                  80
Tyr Ser Pro Lys Thr Lys Arg Ser Pro Leu Thr Arg Ala His Leu Thr
                 85                  90                  95
Glu Val Glu Ser Arg Leu Glu Arg Leu Glu Gln Leu Phe Leu Leu Ile
             100                 105                 110
Phe Pro Arg Glu Asp Leu Asp Met Ile Leu Lys Met Asp Ser Leu Gln
         115                 120                 125
Asp Ile Lys Ala Leu Leu Thr Gly Leu Phe Val Gln Asp Asn Val Asn
     130                 135                 140
Lys Asp Ala Val Thr Asp Arg Leu Ala Ser Val Glu Thr Asp Met Pro
145                 150                 155                 160
Leu Thr Leu Arg Gln His Arg Ile Ser Ala Thr Ser Ser Ser Glu Glu
                 165                 170                 175
Ser Ser Asn Lys Gly Gln Arg Gln Leu Thr Val Ser Thr Arg Met Arg
             180                 185                 190
Pro Glu Cys Val Val Pro Glu Ser Thr Cys Lys Leu Ala Pro Pro Thr
         195                 200                 205
Asp Val Ser Leu Gly Asp Glu Leu His Leu Asp Gly Glu Asp Val Ala
     210                 215                 220
Met Ala His Ala Asp Ala Leu Asp Asp Phe Asp Leu Asp Met Leu Gly
225                 230                 235                 240
Asp Gly Asp Ser Pro Gly Pro Gly Phe Thr Pro His Asp Ser Ala Pro
                 245                 250                 255
Tyr Gly Ala Leu Asp Met Ala Asp Phe Glu Phe Glu Gln Met Phe Thr
             260                 265                 270
Asp Ala Leu Gly Ile Asp Glu Tyr Gly Gly Asn Thr Cys Lys Asn Lys
         275                 280                 285
Arg Arg Glu Lys Glu Ala Gln Arg Glu Lys Asp Lys Leu Pro Val Ser
     290                 295                 300
Thr Thr Thr Val Asp Asp His Met Pro Ala Ile Met Gln Cys Asp Pro
305                 310                 315                 320
Pro Pro Pro Glu Ala Ala Arg Ile His Glu Val Val Pro Arg Phe Leu
                 325                 330                 335
Thr Glu Lys Leu Met Glu Gln Asn Arg Leu Lys Asn Val Thr Pro Leu
             340                 345                 350
Ser Ala Asn Gln Lys Ser Leu Ile Ala Arg Leu Val Trp Tyr Gln Glu
         355                 360                 365
Gly Tyr Glu Gln Pro Ser Glu Glu Asp Leu Lys Arg Val Thr Gln Thr
     370                 375                 380
Trp Gln Leu Glu Glu Glu Glu Glu Glu Thr Asp Met Pro Phe Arg
385                 390                 395                 400
Gln Ile Thr Glu Met Thr Ile Leu Thr Val Gln Leu Ile Val Glu Phe
                 405                 410                 415
Ala Lys Gly Leu Pro Gly Phe Ser Lys Ile Ser Gln Ser Asp Gln Ile
             420                 425                 430
Thr Leu Leu Lys Ala Ser Ser Ser Glu Val Met Met Leu Arg Val Ala
```

-continued

```
                    435                 440                 445
Arg Arg Tyr Asp Ala Ala Thr Asp Ser Val Leu Phe Ala Asn Asn Gln
    450                 455                 460

Ala Tyr Thr Arg Asp Asn Tyr Arg Lys Ala Gly Met Ser Tyr Val Ile
465                 470                 475                 480

Glu Asp Leu Leu His Phe Cys Arg Cys Met Tyr Ser Met Ser Met Asp
                485                 490                 495

Asn Val His Tyr Ala Leu Leu Thr Ala Ile Val Ile Phe Ser Asp Arg
            500                 505                 510

Pro Gly Leu Glu Gln Pro Leu Leu Val Glu Glu Ile Gln Arg Tyr Tyr
        515                 520                 525

Leu Lys Thr Leu Arg Val Tyr Ile Leu Asn Gln His Ser Ala Ser Pro
    530                 535                 540

Arg Cys Ala Val Leu Phe Gly Lys Ile Leu Gly Val Leu Thr Glu Leu
545                 550                 555                 560

Arg Thr Leu Gly Thr Gln Asn Ser Asn Met Cys Ile Ser Leu Lys Leu
                565                 570                 575

Lys Asn Arg Lys Leu Pro Pro Phe Leu Glu Glu Ile Trp Asp Val Ala
            580                 585                 590

Glu Val Ser Thr Thr Lys Leu
        595
```

CONTROL OF GENE EXPRESSION IN PLANTS

This application claims the benefit of U.S. Provisional Application No. 60/242,969, filed Oct. 24, 2000, incorporated herein by reference in its entirety.

CD-R SEQUENCE LISTING

The Sequence Listing associated with the instant disclosure has been submitted as a 434 KB file on CD-R (in duplicate) instead of on paper. Each CD-R is marked in indelible ink to identify the Applicants, Title, File Name (50018A.ST25.txt), Creation Date (Oct. 23, 2001), Computer System (IBM-PC/MS-DOS/MS-Windows), and Docket No. (50018A). The Sequence Listing submitted on CD-R is hereby incorporated by reference into the instant disclosure.

FIELD OF THE INVENTION

The present invention relates to the exogenous control of gene expression in plants. In particular, the present invention relates to chimeric insect hormone receptors and their use for regulation of expression of target polypeptides in plants in the presence of appropriate chemical ligands.

BACKGROUND OF THE INVENTION

The steroid and thyroid hormone superfamily of nuclear receptors is found in mammals and insects and is composed of over 100 known proteins. These receptors fall into at least two functionally distinct categories known as Class I and Class II (Beato, Cell 56:335–344 (1989); Parker, Sem. Cancer Biol. Ser. 1:81–87(1990)). The best studied examples of Class II receptor proteins are Retinoic Acid Receptor (RAR), Vitamin D Receptor (VDR), and Thyroid Hormone Receptor ($T_3R$) and Retinoic X Receptor (RXR). The receptors bind to the 5' regulatory region of the target gene and, upon binding of a chemical ligand to the receptor, the receptor affects gene expression by interacting with other transcription initiating factors.

In addition to the Class II receptor proteins found in mammals as described above, receptors of similar structure and activity have been identified in insects such as *Drosophila melanogaster* (Koelle et al., Cell 67:59 (1991); Christianson and Kafatos, Biochem. Biophys. Res. Comm. 193:1318 (1993); Henrich et al., Nucleic Acids Res. 18:4143 (1990)). The ecdysone receptor (EcR) binds the steroid hormone 20-hydroxyecdysone (referred to herein as "ecdysone") and, when heterodimerized with the product of the ultraspiracle (USP) gene, transactivates gene expression. USP is most homologous to RXRα, and RXR is capable of forming heterodimers with EcR (Thomas et al., Nature 362:471–475 (1993)).

Class II nuclear receptor polypeptides such as EcR are characterized by the presence of five domains: A/B, C, D, E and F (Evans, R. Science 240:889–895 (1988)), wherein "A/B" refers to the transactivation domain, "C" refers to the DNA binding domain, "D" refers to the hinge/linker domain, "E" refers to the ligand binding domain, and "F" refers to the variable C-terminal domain that is present in some receptor polypeptides.

The "A/B" (transactivation) domain comprises one or more amino acid sequences acting as subdomains that, when combined with the DNA binding domain in a receptor polypeptide, affect the operation of transcription factors during preinitiation and assembly at the TATA box. (See generally, Ptashne, Nature 335:683–689 (1988)). The effect of the transactivation domain is to allow repeated transcription initiation events leading to greater levels of gene expression from a target gene. Different transactivation domains are known to have different degrees of effectiveness in their ability to increase transcription inititiation.

The "C" (DNA binding) domain is a sequence of amino acids having certain functional features that are responsible for binding of the receptor polypeptide to a specific sequence of nucleotides, the response elements, present in the 5' regulatory region of the target gene.

The "D" (hinge/linker) domain is located between the DNA binding domain and the ligand binding domain.

The "E" (ligand binding) domain of the receptor polypeptide provides the means by which the 5' regulatory region of a target gene is activated in response to the presence of a chemical ligand. The ecdysone receptor (EcR) from *Drosophila melanogaster* is one example of a receptor polypeptide where complementary chemical ligands have been identified that bind to the ligand binding domain. The steroid hormone ecdysone triggers coordinate changes in tissue development that results in metamorphosis, and ecdysone has been shown to bind to EcR (Koelle et al. Cell 67:59–77 (1991)). The plant-produced analog of ecdysone, muristerone, also binds to the ligand binding domain of EcR. Other chemicals, such as the non-steroidal ecdysone agonists RH 5849 (Wing, Science 241:467–469 (1988)) and tebufenozide, the latter known as the insecticide MIMIC®, also will act as a chemical ligand for the ligand binding domain of EcR.

In some cases it is desirable to control the time or extent of expression of a phenotypic trait in plants, plant cells or plant tissue. An ideal situation is the regulation of expression of such a trait at will, triggered by a chemical that can be easily applied to field crops, ornamental shrubs, etc. One such system of regulating gene expression that can be used to achieve this ideal situation is the steroid and thyroid hormone superfamily of nuclear receptors, such as EcR/Ultraspiracle heterodimerized receptors.

U.S. Pat. No. 5,880,333, incorporated herein by reference, is drawn to a method of controlling gene expression in plants comprising transforming a plant with at least two receptor expression cassettes and at least one target expression cassette. The first receptor expression cassette comprises a nucleotide sequence for a 5' regulatory region operatively linked to a nucleotide sequence that encodes a first receptor polypeptide operatively linked to a 3' termination region. The second receptor expression cassette comprises a nucleotide sequence for a 5' regulatory region operatively linked to a nucleotide sequence that encodes a second receptor polypeptide operatively linked to a 3' termination region. The first and second receptor polypeptides comprise a first and second ligand binding domain, respectively, which are mutually distinct. The target expression cassette comprises a nucleotide sequence for a 5' regulatory region operatively linked to a nucleotide sequence that encodes a target polypeptide operatively linked to a 3' termination region, wherein the 5' regulatory region of said target expression cassette is activated by said first and second receptor polypeptides in the presence of one or more chemical ligands, whereby expression of said target polypeptide is accomplished. The method is useful for controlling various traits of agronomic importance, such as plant fertility.

However, despite advances such as those described in U.S. Pat. No. 5,880,333, there exists a continuing need to develop new and effective systems for inducible gene expression in plants, including the need to develop novel chimeric insect hormone receptors with increased responsiveness to chemical ligands. Especially desirable would be the development of chimeric class II insect hormone receptors that function in the absence of their normal heterodimerization partners.

SUMMARY OF THE INVENTION

The present invention addresses the aforementioned needs by providing novel chimeric insect hormone receptors and receptor cassettes. The receptor cassettes of the invention are particularly useful for the regulation of expression of target polypeptides in plants in the presence of appropriate chemical ligands. Specifically, each receptor cassette encodes a receptor polypeptide that comprises a DNA binding domain, a hinge region, a ligand binding domain and an activation domain. In a preferred embodiment, the hinge and ligand binding domains are from two different insect ecdysone receptors. In another preferred embodiment, the receptor cassettes are chimeric in that one or more of the DNA binding or activation domains are obtained from a source heterologous with respect to the other domains present in the chimeric receptor cassette.

According to a first aspect, the present invention provides a receptor cassette encoding a chimeric receptor polypeptide comprising: a DNA binding (C) domain; a hinge (D) domain of an ecdysone receptor (EcR) of an insect selected from the group consisting of *Manduca sexta, Agrotis ipsilon, Spodoptera frugipera, Chironomus tentans*, and *Locusta migratoria*; a ligand binding (E) domain that is heterologous with respect to the hinge (D) domain; and an activation domain. Preferably, the ligand binding (E) domain is a ligand binding (E) domain of an ecdysone receptor of an insect selected from the group consisting of *Manduca sexta, Agrotis ipsilon, Spodoptera frugipera, Locusta migratoria, Ostrinia nubilalis*, and *Chironomus tentans*. Also, preferably, the hinge (D) domain is a *Manduca sexta* EcR hinge (D) domain. Preferably, the DNA binding (C) domain is a GAL4 DNA binding domain. According to another preferred embodiment, the DNA binding (C) domain is a *Manduca sexta* EcR DNA binding (C) domain. Preferably, the activation domain is a VP16 activation domain, a maize C1 activation domain, or a maize Dof1 activation domain.

In one embodiment of the receptor cassette described above according to a first aspect of the invention, the hinge (D) domain is a *Manduca sexta* EcR hinge (D) domain, and the ligand binding (E) domain is a *Drosophila melanogaster* EcR ligand binding (E) domain. In a preferred embodiment, the DNA binding (C) domain is a GAL4 DNA binding domain. In another preferred embodiment, the DNA binding (C) domain is a *Manduca sexta* EcR DNA binding (C) domain, the hinge (D) domain is a *Manduca sexta* EcR hinge (D) domain, and the ligand binding (E) domain is a *Drosophila melanogaster* EcR ligand binding (E) domain. Preferably, the C, D, and E domains of the chimeric receptor polypeptide comprise an amino acid sequence at least 90% identical to amino acids 1–421 of SEQ ID NO:64. More preferably, the C, D, and E domains of the chimeric receptor polypeptide comprise amino acids 1–421 of SEQ ID NO:64. In a particularly preferred embodiment, the receptor cassette comprises a nucleic acid sequence of which the complement hybridizes under stringent conditions to nucleotides 1–1263 of SEQ ID NO:63. In an especially preferred embodiment, the receptor cassette comprises nucleotides 1–1263 of SEQ ID NO:63.

In another embodiment of the receptor cassette described above according to a first aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Drosophila melanogaster* EcR ligand binding (E) domain, and the activation domain is a VP16 activation domain. Preferably, the chimeric receptor polypeptide comprises an amino acid sequence at least 90% identical to SEQ ID NO:64. More preferably, the chimeric receptor polypeptide comprises SEQ ID NO:64. In a particularly preferred embodiment, the receptor cassette comprises a nucleic acid sequence of which the complement hybridizes under stringent conditions to SEQ ID NO:63. In an especially preferred embodiment, the receptor cassette comprises SEQ ID NO:63.

In another embodiment of the receptor cassette described above according to a first aspect of the invention, the hinge (D) domain is a *Manduca sexta* EcR hinge (D) domain, and the ligand binding (E) domain is an *Agrotis ipsilon* EcR ligand binding (E) domain. In a preferred embodiment, the DNA binding (C) domain is a *Manduca sexta* EcR DNA binding (C) domain, the hinge (D) domain is a *Manduca sexta* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–422 of SEQ ID NO:66. More preferably, the C, D, and E domains of the chimeric receptor polypeptide comprise amino acids 1–422 of SEQ ID NO:66. In a particularly preferred embodiment, the receptor cassette comprises a nucleic acid sequence of which the complement hybridizes under stringent conditions to nucleotides 1–1266 of SEQ ID NO:65. In an especially preferred embodiment, the receptor cassette comprises nucleotides 1–1266 of SEQ ID NO:65.

In another embodiment of the receptor cassette described above according to a first aspect of the invention, the DNA binding (C) domain is a *Manduca sexta* EcR DNA binding (C) domain, the hinge (D) domain is a *Manduca sexta* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:66. More preferably, the chimeric receptor polypeptide comprises SEQ ID NO:66. In a particularly preferred embodiment, the receptor cassette comprises a nucleic acid sequence of which the complement hybridizes under stringent conditions to SEQ ID NO:65. In an especially preferred embodiment, the receptor cassette comprises SEQ ID NO:65.

In a preferred embodiment of the receptor cassette described above according to a first aspect of the invention, the DNA binding (C) domain is a GAL4 DNA binding domain, the hinge (D) domain is a *Manduca sexta* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–511 of SEQ ID NO:119. More preferably, the C, D, and E domains of the chimeric receptor polypeptide comprise amino acids 1–511 of SEQ ID NO:119. In a particularly preferred embodiment, the receptor cassette comprises a nucleic acid sequence of which the complement hybridizes under stringent conditions to nucleotides 1–1533 of SEQ ID NO:118. In an especially preferred embodiment, the receptor cassette comprises nucleotides 1–1533 of SEQ ID NO:118.

In another preferred embodiment of the receptor cassette described above according to a first aspect of the invention, the DNA binding (C) domain is a GAL4 DNA binding domain, the hinge (D) domain is a *Manduca sexta* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:119. More preferably, the chimeric receptor polypeptide comprises SEQ ID NO:119. In a particularly preferred embodiment, the receptor cassette comprises a nucleic acid sequence of which the complement hybridizes under stringent conditions to SEQ ID NO:118. In an especially preferred embodiment, the receptor cassette comprises SEQ ID NO:118.

In another embodiment of the receptor cassette described above according to a first aspect of the invention, the hinge (D) domain is a *Manduca sexta* EcR hinge (D) domain, and the ligand binding (E) domain is an *Ostrinia nubilalis* EcR ligand binding (E) domain. In a preferred embodiment, the DNA binding (C) domain is a *Manduca sexta* EcR DNA binding (C) domain, the hinge (D) domain is a *Manduca sexta* EcR hinge (D) domain, and the ligand binding (E) domain is an *Ostrinia nubilalis* EcR ligand binding (E) domain. Preferably, the C, D, and E domains of the chimeric receptor polypeptide comprise an amino acid sequence at least 90% identical to amino acids 1–419 of SEQ ID NO:68. More preferably, the C, D, and E domains of the chimeric receptor polypeptide comprise amino acids 1–419 of SEQ ID NO:68. In a particularly preferred embodiment, the receptor cassette comprises a nucleic acid sequence of which the complement hybridizes under stringent conditions to nucleotides 1–1257 of SEQ ID NO:67. In an especially preferred embodiment, the receptor cassette comprises nucleotides 1–1257 of SEQ ID NO:67.

In a preferred embodiment of the receptor cassette described above according to a first aspect of the invention, the DNA binding (C) domain is a GAL4 DNA binding domain, the hinge (D) domain is a *Manduca sexta* EcR hinge (D) domain, and the ligand binding (E) domain is an *Ostrinia nubilalis* EcR ligand binding (E) domain. Preferably, the C, D, and E domains of the chimeric receptor polypeptide comprise an amino acid sequence at least 90% identical to amino acids 1–508 of SEQ ID NO:121. More preferably, the C, D, and E domains of the chimeric receptor polypeptide comprise amino acids 1–508 of SEQ ID NO:121. In a particularly preferred embodiment, the receptor cassette comprises a nucleic acid sequence of which the complement hybridizes under stringent conditions to nucleotides 1–1524 of SEQ ID NO:120. In an especially preferred embodiment, the receptor cassette comprises nucleotides 1–1524 of SEQ ID NO:120. In another preferred embodiment, the DNA binding (C) domain is a GAL4 DNA binding domain, the hinge (D) domain is a *Manduca sexta* EcR hinge (D) domain, the ligand binding (E) domain is an *Ostrinia nubilalis* EcR ligand binding (E) domain, and the activation domain is a VP16 activation domain. According to this embodiment, the chimeric receptor polypeptide comprises an amino acid sequence at least 90% identical to SEQ ID NO:121. More preferably, the chimeric receptor polypeptide comprises SEQ ID NO:121. In a particularly preferred embodiment, the receptor cassette comprises a nucleic acid sequence of which the complement hybridizes under stringent conditions to SEQ ID NO:120. In an especially preferred embodiment, the receptor cassette comprises SEQ ID NO:120.

In another embodiment of the receptor cassette described above according to a first aspect of the invention, the DNA binding (C) domain is a *Manduca sexta* EcR DNA binding (C) domain, the hinge (D) domain is a *Manduca sexta* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:68. More preferably, the chimeric receptor polypeptide comprises SEQ ID NO:68. In a particularly preferred embodiment, the receptor cassette comprises a nucleic acid sequence of which the complement hybridizes under stringent conditions to SEQ ID NO:67. In an especially preferred embodiment, the receptor cassette comprises SEQ ID NO:67.

In another embodiment of the receptor cassette described above according to a first aspect of the invention, the hinge (D) domain is a *Manduca sexta* EcR hinge (D) domain, and the ligand binding (E) domain is a *Spodoptera frugipera* EcR ligand binding (E) domain. In a preferred embodiment, the DNA binding (C) domain is a *Manduca sexta* EcR DNA binding (C) domain, the hinge (D) domain is a *Manduca sexta* EcR hinge (D) domain, and the ligand binding (E) domain is a *Spodoptera frugipera* EcR ligand binding (E) domain. Preferably, the C, D, and E domains of the chimeric receptor polypeptide comprise an amino acid sequence at least 90% identical to amino acids 1–419 of SEQ ID NO:70. More preferably, the C, D, and E domains of the chimeric receptor polypeptide comprise amino acids 1–419 of SEQ ID NO:70. In a particularly preferred embodiment, the receptor cassette comprises a nucleic acid sequence of which the complement hybridizes under stringent conditions to nucleotides 1–1257 of SEQ ID NO:69. In an especially preferred embodiment, the receptor cassette comprises nucleotides 1–1257 of SEQ ID NO:69.

In another embodiment of the receptor cassette described above according to a first aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Spodoptera frugipera* EcR ligand binding (E) domain, and the activation domain is a VP16 activation domain. In a preferred embodiment, the chimeric receptor polypeptide comprises an amino acid sequence at least 90% identical to SEQ ID NO:70. In a more preferred embodiment, the chimeric receptor polypeptide comprises SEQ ID NO:70. In a particularly preferred embodiment, the receptor cassette comprises a nucleic acid sequence of which the complement hybridizes under stringent conditions to SEQ ID NO:69. In an especially preferred embodiment, the receptor cassette comprises SEQ ID NO:69.

In a preferred embodiment of the receptor cassette described above according to a first aspect of the invention, the DNA binding (C) domain is a GAL4 DNA binding domain, the hinge (D) domain is a *Manduca sexta* EcR hinge (D) domain, and the ligand binding (E) domain is a *Spodoptera frugipera* EcR ligand binding (E) domain. Preferably, the C, D, and E domains of the chimeric receptor polypeptide comprise an amino acid sequence at least 90% identical to amino acids 1–508 of SEQ ID NO:123. More preferably, the C, D, and E domains of the chimeric receptor polypeptide comprise amino acids 1–508 of SEQ ID NO:123. In a particularly preferred embodiment, the receptor cassette comprises a nucleic acid sequence of which the complement hybridizes under stringent conditions to nucleotides 1–1524 of SEQ ID NO:122. In an especially preferred embodiment, the receptor cassette comprises nucleotides 1–1524 of SEQ ID NO:122.

In a preferred embodiment of the receptor cassette described above according to a first aspect of the invention, the DNA binding (C) domain is a GAL4 DNA binding domain, the hinge (D) domain is a *Manduca sexta* EcR hinge (D) domain, the ligand binding (E) domain is a *Spodoptera frugipera* EcR ligand binding (E) domain, and the activation domain is a VP16 activation domain. In a preferred embodiment, the chimeric receptor polypeptide comprises an amino acid sequence at least 90% identical to SEQ ID NO:123. In a more preferred embodiment, the chimeric receptor polypeptide comprises SEQ ID NO:123. In a particularly preferred embodiment, the receptor cassette comprises a nucleic acid sequence of which the complement hybridizes under stringent conditions to SEQ ID NO:122. In an especially preferred embodiment, the receptor cassette comprises SEQ ID NO:122.

In another embodiment of the receptor cassette described above according to a first aspect of the invention, the hinge (D) domain is a *Locusta migratoria* EcR hinge (D) domain, and the ligand binding (E) domain is a *Manduca sexta* EcR ligand binding (E) domain. In a preferred embodiment, the DNA binding (C) domain is a GAL4 DNA binding domain. In another preferred embodiment, the DNA binding (C) domain is a *Locusta migratoria* EcR DNA binding (C) domain, the hinge (D) domain is a *Locusta migratoria* EcR hinge (D) domain, and the ligand binding (E) domain is a *Manduca sexta* EcR ligand binding (E) domain. In a preferred embodiment, the C, D, and E domains of the chimeric receptor polypeptide comprise an amino acid sequence at least 90% identical to amino acids 1–407 of SEQ ID NO:84. In a more preferred embodiment, the C, D, and E domains of the chimeric receptor polypeptide comprise amino acids 1–407 of SEQ ID NO:84. In a particularly preferred embodiment, the receptor cassette comprises a nucleic acid sequence of which the complement hybridizes under stringent conditions to nucleotides 1–1221 of SEQ ID NO:83. In an especially preferred embodiment, the receptor cassette comprises nucleotides 1–1221 of SEQ ID NO:83.

In another embodiment of the receptor cassette described above according to a first aspect of the invention, the DNA binding (C) domain is a *Locusta migratoria* EcR DNA binding (C) domain, the hinge (D) domain is a *Locusta migratoria* EcR hinge (D) domain, the ligand binding (E) domain is a *Manduca sexta* EcR ligand binding (E) domain, and the activation domain is a VP16 activation domain. In a preferred embodiment, the chimeric receptor polypeptide comprises an amino acid sequence at least 90% identical to SEQ ID NO:84. In a more preferred embodiment, the chimeric receptor polypeptide comprises SEQ ID NO:84. In a particularly preferred embodiment, the receptor cassette comprises a nucleic acid sequence of which the complement hybridizes under stringent conditions to SEQ ID NO:83. In an especially preferred embodiment, the receptor cassette comprises SEQ ID NO:83.

In another embodiment of the receptor cassette described above according to a first aspect of the invention, the hinge (D) domain is a *Manduca sexta* EcR hinge (D) domain, and the ligand binding (E) domain is a *Locusta migratoria* EcR ligand binding (E) domain. In a preferred embodiment, the DNA binding (C) domain is a GAL4 DNA binding domain. In another preferred embodiment, the DNA binding (C) domain is a *Manduca sexta* EcR DNA binding (C) domain, the hinge (D) domain is a *Manduca sexta* EcR hinge (D) domain, and the ligand binding (E) domain is a *Locusta migratoria* EcR ligand binding (E) domain. In a preferred embodiment, the C, D, and E domains of the chimeric receptor polypeptide comprise an amino acid sequence at least 90% identical to amino acids 1–416 of SEQ ID NO:86. In a more preferred embodiment, the C, D, and E domains of the chimeric receptor polypeptide comprise amino acids 1–416 of SEQ ID NO:86. In a particularly preferred embodiment, the receptor cassette comprises a nucleic acid sequence of which the complement hybridizes under stringent conditions to nucleotides 1–1248 of SEQ ID NO:85. In an especially preferred embodiment, the receptor cassette comprises nucleotides 1–1248 of SEQ ID NO:85.

In another embodiment of the receptor cassette described above according to a first aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Locusta migratoria* EcR ligand binding (E) domain, and the activation domain is a VP16 activation domain. Preferably, the chimeric receptor polypeptide comprises an amino acid sequence at least 90% identical to SEQ ID NO:86. More preferably, the chimeric receptor polypeptide comprises SEQ ID NO:86. In a particularly preferred embodiment, the receptor cassette comprises a nucleic acid sequence of which the complement hybridizes under stringent conditions to SEQ ID NO:85. In an especially preferred embodiment, the receptor cassette comprises SEQ ID NO:85.

In another embodiment of the receptor cassette described above according to a first aspect of the invention, the hinge (D) domain is a *Chironomus tentans* EcR hinge (D) domain, and the ligand binding (E) domain is a *Manduca sexta* EcR ligand binding (E) domain. In a preferred embodiment, the DNA binding (C) domain is a GAL4 DNA binding domain. In another preferred embodiment, the DNA binding (C) domain is a *Chironomus tentans* EcR DNA binding (C) domain, the hinge (D) domain is a *Chironomus tentans* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–441 of SEQ ID NO:90. More preferably, the C, D, and E domains of the chimeric receptor polypeptide comprise amino acids 1–441 of SEQ ID NO:90. In a particularly preferred embodiment, the receptor cassette comprises a nucleic acid sequence of which the complement hybridizes under stringent conditions to nucleotides 1–1323 of SEQ ID NO:89. In an especially preferred embodiment, the receptor cassette comprises nucleotides 1–1323 of SEQ ID NO:89.

In another embodiment of the receptor cassette described above according to a first aspect of the invention, the DNA binding (C) domain is a *Chironomus tentans* EcR DNA binding (C) domain, the hinge (D) domain is a *Chironomus tentans* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:90. More preferably, the chimeric receptor polypeptide comprises SEQ ID NO:90. In a particularly preferred embodiment, the receptor cassette comprises a nucleic acid sequence of which the complement hybridizes under stringent conditions to SEQ ID NO:89. In an especially preferred embodiment, the receptor cassette comprises SEQ ID NO:89.

In another embodiment of the receptor cassette described above according to a first aspect of the invention, the hinge (D) domain is a *Manduca sexta* EcR hinge (D) domain, and the ligand binding (E) domain is a *Chironomus tentans* EcR ligand binding (E) domain. In a preferred embodiment, the DNA binding (C) domain is a GAL4 DNA binding domain. In another preferred embodiment, the DNA binding (C)

domain is a *Manduca sexta* EcR DNA binding (C) domain, the hinge (D) domain is a *Chironomus tentans* EcR hinge (D) domain, and the ligand binding (E) domain is a *Chironomus tentans* EcR ligand binding (E) domain. In a more preferred embodiment, the C, D, and E domains of the chimeric receptor polypeptide comprise an amino acid sequence at least 90% identical to amino acids 1–420 of SEQ ID NO:92. More preferably, the C, D, and E domains of the chimeric receptor polypeptide comprise amino acids 1–420 of SEQ ID NO:92. In a particularly preferred embodiment, the receptor cassette comprises a nucleic acid sequence of which the complement hybridizes under stringent conditions to nucleotides 1–1260 of SEQ ID NO:91. In an especially preferred embodiment, the receptor cassette comprises nucleotides 1–1260 of SEQ ID NO:91.

In another embodiment of the receptor cassette described above according to a first aspect of the invention, the DNA binding (C) domain is a *Manduca sexta* EcR DNA binding (C) domain, the hinge (D) domain is a *Chironomus tentans* EcR hinge (D) domain, the ligand binding (E) domain is a *Chironomus tentans* EcR ligand binding (E) domain, and the activation domain is a VP16 activation domain. In a preferred embodiment, the chimeric receptor polypeptide comprises an amino acid sequence at least 90% identical to SEQ ID NO:92. In another preferred embodiment, the chimeric receptor polypeptide comprises SEQ ID NO:92. In a particularly preferred embodiment, the receptor cassette comprises a nucleic acid sequence of which the complement hybridizes under stringent conditions to SEQ ID NO:91. In an especially preferred embodiment, the receptor cassette comprises SEQ ID NO:91.

According to a second aspect, the present invention provides a receptor cassette encoding a chimeric receptor polypeptide comprising: a DNA binding (C) domain; a hinge (D) domain; a ligand binding (E) domain of an ecdysone receptor (EcR) of an insect selected from the group consisting of *Manduca sexta, Agrotis ipsilon, Spodoptera frugiperda, Chironomus tentans*, and *Locusta migratoria*, wherein the ligand binding (E) domain is heterologous with respect to the hinge (D) domain; and an activation domain. In a preferred embodiment, the hinge (D) domain is a hinge (D) domain of an ecdysone receptor of an insect selected from the group consisting of *Manduca sexta, Agrotis epsilon, Spodoptera frugiperda, Locusta migratoria, Ostrinia nubilalis*, and *Chironomus tentans*. In another preferred embodiment, the DNA binding (C) domain is a GAL4 DNA binding domain. In another preferred embodiment, the ligand binding (E) domain is a *Manduca sexta* EcR ligand binding (E) domain. In another preferred embodiment, the DNA binding (C) domain is a GAL4 DNA binding domain.

In one embodiment of the receptor cassette described above according to a second aspect of the invention, the hinge (D) domain is an *Ostrinia nubilalis* EcR hinge (D) domain, and the ligand binding (E) domain is an *Agrotis ipsilon* EcR ligand binding (E) domain. In a preferred embodiment, the DNA binding (C) domain is a GAL4 DNA binding domain. In another preferred embodiment, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is an *Agrotis ipsilon* EcR ligand binding (E). Preferably, the C, D, and E domains of the chimeric receptor polypeptide comprise an amino acid sequence at least 90% identical to amino acids 1–427 of SEQ ID NO:78. More preferably, the C, D, and E domains of the chimeric receptor polypeptide comprise amino acids 1–427 of SEQ ID NO:78. In a particularly preferred embodiment, the receptor cassette comprises a nucleic acid sequence of which the complement hybridizes under stringent conditions to nucleotides 1–1281 of SEQ ID NO:77. In an especially preferred embodiment, the receptor cassette comprises nucleotides 1–1281 of SEQ ID NO:77.

In another embodiment of the receptor cassette described above according to a second aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:78. More preferably, the chimeric receptor polypeptide comprises SEQ ID NO:78. In a particularly preferred embodiment, the receptor cassette comprises a nucleic acid sequence of which the complement hybridizes under stringent conditions to SEQ ID NO:77. In an especially preferred embodiment, the receptor cassette comprises SEQ ID NO:77.

In another embodiment of the receptor cassette described above according to a second aspect of the invention, the hinge (D) domain is an *Ostrinia nubilalis* EcR hinge (D) domain, and the ligand binding (E) domain is a *Manduca sexta* EcR ligand binding (E) domain. In a preferred embodiment, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is a *Manduca sexta* EcR ligand binding (E) domain. More preferably, the C, D, and E domains of the chimeric receptor polypeptide comprise an amino acid sequence at least 90% identical to amino acids 1–430 of SEQ ID NO:80. More preferably, the C, D, and E domains of the chimeric receptor polypeptide comprise amino acids 1–430 of SEQ ID NO:80. In a particularly preferred embodiment, the receptor cassette comprises a nucleic acid sequence of which the complement hybridizes under stringent conditions to nucleotides 1–1290 of SEQ ID NO:79. In an especially preferred embodiment, the receptor cassette comprises nucleotides 1–1290 of SEQ ID NO:79.

In another embodiment of the receptor cassette described above according to a second aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:80. More preferably, the chimeric receptor polypeptide comprises SEQ ID NO:80. In an especially preferred embodiment, the receptor cassette comprises a nucleic acid sequence of which the complement hybridizes under stringent conditions to SEQ ID NO:79. In an especially preferred embodiment, the receptor cassette comprises SEQ ID NO:79.

In a preferred embodiment of the receptor cassette described above according to a second aspect of the invention, the DNA binding (C) domain is a GAL4 DNA binding domain, the hinge (D) domain is an *Ostrinia nubilalis* EcR hinge (D) domain, and the ligand binding (E) domain is a *Manduca sexta* EcR ligand binding (E) domain. More preferably, the C, D, and E domains of the chimeric receptor polypeptide comprise an amino acid sequence at least 90% identical to amino acids 1–519 of SEQ ID NO:127. More preferably, the C, D, and E domains of the chimeric receptor polypeptide comprise amino acids 1–519 of SEQ ID NO:127. In a particularly preferred embodiment, the receptor cassette comprises a nucleic acid sequence of which the complement hybridizes under stringent conditions to nucleotides 1–1557 of SEQ ID NO:126. In an especially preferred embodiment, the receptor cassette comprises nucleotides 1–1557 of SEQ ID NO:126.

In another preferred embodiment of the receptor cassette described above according to a second aspect of the invention, the DNA binding (C) domain is a GAL4 DNA binding domain, the hinge (D) domain is an *Ostrinia nubilalis* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:127. More preferably, the chimeric receptor polypeptide comprises SEQ ID NO:127. In an especially preferred embodiment, the receptor cassette comprises a nucleic acid sequence of which the complement hybridizes under stringent conditions to SEQ ID NO:126. In an especially preferred embodiment, the receptor cassette comprises SEQ ID NO:126.

In another embodiment of the receptor cassette described above according to a second aspect of the invention, the hinge (D) domain is a *Drosophila melanogaster* EcR hinge (D) domain, and the ligand binding (E) domain is a *Manduca sexta* EcR ligand binding (E) domain. In a preferred embodiment, the DNA binding (C) domain is a GAL4 DNA binding domain. In another preferred embodiment, the DNA binding (C) domain is a *Drosophila melanogaster* EcR DNA binding (C) domain, the hinge (D) domain is a *Drosophila melanogaster* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–436 of SEQ ID NO:72. More preferably, the C, D, and E domains of the chimeric receptor polypeptide comprise amino acids 1–436 of SEQ ID NO:72. In a particularly preferred embodiment, the receptor cassette comprises a nucleic acid sequence of which the complement hybridizes under stringent conditions to nucleotides 1–1308 of SEQ ID NO:71. In an especially preferred embodiment, the receptor cassette comprises nucleotides 1–1308 of SEQ ID NO:71.

In another embodiment of the receptor cassette described above according to a second aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is a *Manduca sexta* EcR ligand binding (E) domain, and the activation domain is a VP16 activation domain. In a preferred embodiment, the chimeric receptor polypeptide comprises an amino acid sequence at least 90% identical to SEQ ID NO:72. In a more preferred embodiment, the chimeric receptor polypeptide comprises SEQ ID NO:72. In a particularly preferred embodiment, the receptor cassette comprises a nucleic acid sequence of which the complement hybridizes under stringent conditions to SEQ ID NO:71. In an especially preferred embodiment, the receptor cassette comprises SEQ ID NO:71.

In another embodiment of the receptor cassette described above according to a second aspect of the invention, the hinge (D) domain is a *Drosophila melanogaster* EcR hinge (D) domain, and the ligand binding (E) domain is an *Agrotis epsilon* EcR ligand binding (E) domain. In a preferred embodiment, the DNA binding (C) domain is a GAL4 DNA binding domain. In another preferred embodiment, the DNA binding (C) domain is a *Drosophila melanogaster* EcR DNA binding (C) domain, the hinge (D) domain is a *Drosophila melanogaster* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–433 of SEQ ID NO:74. More preferably, the C, D, and E domains of the chimeric receptor polypeptide comprise amino acids 1–433 of SEQ ID NO:74. In a particularly preferred embodiment, the receptor cassette comprises a nucleic acid sequence of which the complement hybridizes under stringent conditions to nucleotides 1–1299 of SEQ ID NO:73. In an especially preferred embodiment, the receptor cassette comprises nucleotides 1–1299 of SEQ ID NO:73.

In another embodiment of the receptor cassette described above according to a second aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is an *Agrotis ipsilon* EcR ligand binding (E) domain, and the activation domain is a VP16 activation domain. In a preferred embodiment, the chimeric receptor polypeptide comprises an amino acid sequence at least 90% identical to SEQ ID NO:74. In a more preferred embodiment, the chimeric receptor polypeptide comprises SEQ ID NO:74. In a particularly preferred embodiment, the receptor cassette comprises a nucleic acid sequence of which the complement hybridizes under stringent conditions to SEQ ID NO:73. In an especially preferred embodiment, the receptor cassette comprises SEQ ID NO:73.

According to a third aspect, the present invention provides a receptor cassette encoding a chimeric receptor polypeptide comprising: a GAL4 DNA binding domain or a DNA binding (C) domain of an ecdysone receptor (EcR) of an insect selected from the group consisting of *Ostrinia nubilalis, Locusta migratoria, Chironomus tentans, Manduca sexta*, and *Drosophila melanogaster*; a hinge (D) domain of an ecdysone receptor of an insect selected from the group consisting of *Ostrinia nubilalis, Locusta migratoria, Chironomus tentans, Manduca sexta*, and *Drosophila melanogaster*; a ligand binding (E) domain of an ecdysone receptor of an insect selected from the group consisting of *Ostrinia nubilalis, Locusta migratoria, Chironomus tentans, Manduca sexta*, and *Drosophila melanogaster*; and a heterologous activation domain; wherein the chimeric receptor polypeptide does not include an ecdysone receptor A/B N-terminal domain. In a particularly preferred embodiment, the receptor cassette encodes a chimeric receptor polypeptide that consists essentially of: a GAL4 DNA binding domain or a DNA binding (C) domain of an ecdysone receptor (EcR) of an insect selected from the group consisting of *Ostrinia nubilalis, Locusta migratoria, Chironomus tentans, Manduca sexta*, and *Drosophila melanogaster*; a hinge (D) domain of an ecdysone receptor of an insect selected from the group consisting of *Ostrinia nubilalis, Locusta migratoria, Chironomus tentans, Manduca sexta*, and *Drosophila melanogaster*; a ligand binding (E) domain of an ecdysone receptor of an insect selected from the group consisting of *Ostrinia nubilalis, Locusta migratoria, Chironomus tentans, Manduca sexta*, and *Drosophila melanogaster*; and a heterologous activation domain that is not an ecdysone receptor A/B N-terminal domain. In one preferred embodiment, the DNA binding (C) domain is a GAL4 DNA binding domain. Also, in another preferred embodiment, the activation domain is a VP16 activation domain, a maize C1 activation domain, or a maize Dof1 activation domain.

In one embodiment of the receptor cassette described above according to a third aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a VP16 activation domain. 23. In one configuration, the VP16 activation domain is located at the N-terminus of the chimeric receptor polypeptide. In another configuration, the VP16 activation domain is located internally in the chimeric receptor polypeptide between the GAL4 DNA binding domain and the *Manduca sexta* EcR hinge (D) domain. In yet another configuration, the VP16 activation domain is located at the C-terminus of the chimeric receptor polypeptide. Preferably, the chimeric receptor polypeptide comprises an amino acid sequence at least 90% identical to SEQ ID NO:105. More preferably, the chimeric receptor polypeptide comprises SEQ ID NO:105. In a particularly preferred embodiment, the receptor cassette comprises a nucleic acid sequence of which the complement hybridizes under stringent conditions to nucleotides 2007–3668 of SEQ ID NO:104. In an especially preferred embodiment, the receptor cassette comprises nucleotides 2007–3668 of SEQ ID NO:104.

In another embodiment of the receptor cassette described above according to a third aspect of the invention, the DNA binding (C) domain is a GAL4 DNA binding domain, the hinge (D) domain is an *Ostrinia nubilalis* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:125. More preferably, the chimeric receptor polypeptide comprises SEQ ID NO:125. In a particularly preferred embodiment, the receptor cassette comprises a nucleic acid sequence of which the complement hybridizes under stringent conditions to SEQ ID NO:124. In an especially preferred embodiment, the receptor cassette comprises SEQ ID NO:124.

In another embodiment of the receptor cassette described above according to a third aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a maize C1 activation domain. According to this embodiment, the chimeric receptor polypeptide preferably comprises an amino acid sequence at least 90% identical to SEQ ID NO:135. More preferably, the chimeric receptor polypeptide comprises SEQ ID NO:135. In a particularly preferred embodiment, the receptor cassette comprises a nucleic acid sequence of which the complement hybridizes under stringent conditions to SEQ ID NO:134. In an especially preferred embodiment, the receptor cassette comprises SEQ ID NO:134.

In another embodiment of the receptor cassette described above according to a third aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a maize Dof1 activation domain. According to this embodiment, the chimeric receptor polypeptide preferably comprises an amino acid sequence at least 90% identical to SEQ ID NO:137. More preferably, the chimeric receptor polypeptide comprises SEQ ID NO:137. In a particularly preferred embodiment, the receptor cassette comprises a nucleic acid sequence of which the complement hybridizes under stringent conditions to SEQ ID NO:136. In an especially preferred embodiment, the receptor cassette comprises SEQ ID NO:136.

In another embodiment of the receptor cassette described above according to a third aspect of the invention, the activation domain is an N-terminal VP16 activation domain, the DNA binding (C) domain is a GAL4 DNA binding domain, the hinge (D) domain is a *Manduca sexta* EcR hinge (D) domain, and the ligand binding (E) domain is a *Manduca sexta* EcR ligand binding (E) domain. According to this embodiment, the chimeric receptor polypeptide preferably comprises an amino acid sequence at least 90% identical to SEQ ID NO:143. More preferably, the chimeric receptor polypeptide comprises SEQ ID NO:143. In a particularly preferred embodiment, the receptor cassette comprises a nucleic acid sequence of which the complement hybridizes under stringent conditions to SEQ ID NO:142. In an especially preferred embodiment, the receptor cassette comprises SEQ ID NO:142.

In another embodiment of the receptor cassette described above according to a third aspect of the invention, the DNA binding (C) domain is a GAL4 DNA binding domain, the activation domain is an internally configured VP16 activation domain, the hinge (D) domain is a *Manduca sexta* EcR hinge (D) domain, and the ligand binding (E) domain is a *Manduca sexta* EcR ligand binding (E) domain. According to this embodiment, the chimeric receptor polypeptide preferably comprises an amino acid sequence at least 90% identical to SEQ ID NO:148. More preferably, the chimeric receptor polypeptide comprises SEQ ID NO:148. In a particularly preferred embodiment, the receptor cassette comprises a nucleic acid sequence of which the complement hybridizes under stringent conditions to SEQ ID NO:147. In an especially preferred embodiment, the receptor cassette comprises SEQ ID NO:147.

In another embodiment of the receptor cassette described above according to a third aspect of the invention, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is an *Ostrinia nubilalis* EcR ligand binding (E) domain. More preferably, the C, D, and E domains of the chimeric receptor polypeptide comprise an amino acid sequence at least 90% identical to amino acids 1–424 of SEQ ID NO:76. In a more preferred embodiment, the C, D, and E domains of the chimeric receptor polypeptide comprise amino acids 1–424 of SEQ ID NO:76. In a particularly preferred embodiment, the receptor cassette comprises a nucleic acid sequence of which the complement hybridizes under stringent conditions to nucleotides 1–1272 of SEQ ID NO:75. In an especially preferred embodiment, the receptor cassette comprises nucleotides 1–1272 of SEQ ID NO:75.

In another embodiment of the receptor cassette described above according to a third aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:76. More preferably, the chimeric receptor polypeptide comprises SEQ ID NO:76. In a particularly preferred embodiment, the receptor cassette comprises a nucleic acid sequence of which the complement hybridizes under stringent conditions to SEQ ID NO:75. In an especially preferred embodiment, the receptor cassette comprises SEQ ID NO:75.

In another embodiment of the receptor cassette described above according to a third aspect of the invention, the DNA binding (C) domain is a *Locusta migratoria* EcR DNA binding (C) domain, the hinge (D) domain is a *Locusta migratoria* EcR hinge (D) domain, and the ligand binding (E) domain is a *Locusta migratoria* EcR ligand binding (E) domain. Preferably, the C, D, and E domains of the chimeric receptor polypeptide comprise an amino acid sequence at least 90% identical to amino acids 1–398 of SEQ ID NO:82. More preferably, the C, D, and E domains of the chimeric receptor polypeptide comprise amino acids 1–398 of SEQ ID NO:82. In a particularly preferred embodiment, the receptor cassette comprises a nucleic acid sequence of which the complement hybridizes under stringent conditions to nucleotides 1–1194 of SEQ ID NO:81. In an especially preferred embodiment, the receptor cassette comprises nucleotides 1–1194 of SEQ ID NO:81.

In another embodiment of the receptor cassette described above according to a third aspect of the invention, the DNA binding (C) domain is a *Locusta migratoria* EcR DNA binding (C) domain, the hinge (D) domain is a *Locusta migratoria* EcR hinge (D) domain, the ligand binding (E) domain is a *Locusta migratoria* EcR ligand binding (E) domain, and the activation domain is a VP16 activation domain. Preferably, the chimeric receptor polypeptide comprises an amino acid sequence at least 90% identical to SEQ ID NO:82. More preferably, the chimeric receptor polypeptide comprises SEQ ID NO:82. In a particularly preferred embodiment, the receptor cassette comprises a nucleic acid sequence of which the complement hybridizes under stringent conditions to SEQ ID NO:81. In an especially preferred embodiment, the receptor cassette comprises SEQ ID NO:81.

In another embodiment of the receptor cassette described above according to a third aspect of the invention, the DNA binding (C) domain is a *Chironomus tentans* EcR DNA binding (C) domain, the hinge (D) domain is a *Chironomus tentans* EcR hinge (D) domain, and the ligand binding (E) domain is a *Chironomus tentans* EcR ligand binding (E) domain. In a preferred embodiment, the C, D, and E domains of the chimeric receptor polypeptide comprise an amino acid sequence at least 90% identical to amino acids 1–436 of SEQ ID NO:88. In a more preferred embodiment, the C, D, and E domains of the chimeric receptor polypeptide comprise amino acids 1–436 of SEQ ID NO:88. In a particularly preferred embodiment, the receptor cassette comprises a nucleic acid sequence of which the complement hybridizes under stringent conditions to nucleotides 1–1308 of SEQ ID NO:87. In an especially preferred embodiment, the receptor cassette comprises nucleotides 1–1308 of SEQ ID NO:87.

In another embodiment of the receptor cassette described above according to a third aspect of the invention, the DNA binding (C) domain is a *Chironomus tentans* EcR DNA binding (C) domain, the hinge (D) domain is a *Chironomus tentans* EcR hinge (D) domain, the ligand binding (E) domain is a *Chironomus tentans* EcR ligand binding (E) domain, and the activation domain is a VP16 activation domain. Preferably, the chimeric receptor polypeptide comprises an amino acid sequence at least 90% identical to SEQ ID NO:88. More preferably, the chimeric receptor polypeptide comprises SEQ ID NO:88. In a particularly preferred embodiment, the receptor cassette comprises a nucleic acid sequence of which the complement hybridizes under stringent conditions to SEQ ID NO:87. In an especially preferred embodiment, the receptor cassette comprises SEQ ID NO:87.

In another embodiment of the receptor cassette described above according to a third aspect of the invention, the DNA binding (C) domain is a *Manduca sexta* EcR DNA binding (C) domain, the hinge (D) domain is a *Manduca sexta* EcR hinge (D) domain, and the ligand binding (E) domain is a *Manduca sexta* EcR ligand binding (E) domain. In a preferred embodiment, the C, D, and E domains of the chimeric receptor polypeptide comprise an amino acid sequence at least 90% identical to amino acids 1–425 of SEQ ID NO:94. In a more preferred embodiment, the C, D, and E domains of the chimeric receptor polypeptide comprise amino acids 1–425 of SEQ ID NO:94. In a particularly preferred embodiment, the receptor cassette comprises a nucleic acid sequence of which the complement hybridizes under stringent conditions to nucleotides 1–1275 of SEQ ID NO:93. In an especially preferred embodiment, the receptor cassette comprises nucleotides 1–1275 of SEQ ID NO:93.

In another embodiment of the receptor cassette described above according to a third aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:94. More preferably, the chimeric receptor polypeptide comprises SEQ ID NO:94. In a particularly preferred embodiment, the receptor cassette comprises a nucleic acid sequence of which the complement hybridizes under stringent conditions to SEQ ID NO:93. In an especially preferred embodiment, the receptor cassette comprises SEQ ID NO:93.

In another embodiment of the receptor cassette described above according to a third aspect of the invention, the DNA binding (C) domain is a *Drosophila melanogaster* EcR DNA binding (C) domain, the hinge (D) domain is a *Drosophila melanogaster* EcR hinge (D) domain, and the ligand binding (E) domain is an *Drosophila melanogaster* EcR ligand binding (E) domain. Preferably, the C, D, and E domains of the chimeric receptor polypeptide comprise an amino acid sequence at least 90% identical to amino acids 1–432 of SEQ ID NO:96. More preferably, the C, D, and E domains of the chimeric receptor polypeptide comprise amino acids 1–432 of SEQ ID NO:96. In a particularly preferred embodiment, the receptor cassette comprises a nucleic acid sequence of which the complement hybridizes under stringent conditions to nucleotides 1–1296 of SEQ ID NO:95. In an especially preferred embodiment, the receptor cassette comprises nucleotides 1–1296 of SEQ ID NO:95

In another embodiment of the receptor cassette described above according to a third aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is an *Drosophila melanogaster* EcR ligand binding (E) domain, and the activation domain is a VP16 activation domain. Preferably, the chimeric receptor polypeptide comprises an amino acid sequence at least 90% identical to SEQ ID NO:96. More preferably, the chimeric receptor polypeptide comprises SEQ ID NO:96. In a particularly preferred embodiment, the receptor cassette comprises a nucleic acid sequence of which the complement hybridizes under stringent conditions to SEQ ID NO:95. In an especially preferred embodiment, the receptor cassette comprises SEQ ID NO:95

According to a fourth aspect, the present invention provides a receptor cassette encoding a chimeric receptor polypeptide comprising: at least one DNA binding (C) domain; a hinge (D) domain of an insect ecdysone receptor (EcR); a ligand binding (E) domain of an insect ecdysone receptor, wherein the ligand binding (E) domain is heterologous with respect to the hinge (D) domain; and a heterologous activation domain; wherein the chimeric receptor polypeptide does not include an ecdysone receptor A/B N-terminal domain. In a particularly preferred embodiment, the receptor cassette encodes a chimeric receptor polypeptide that consists essentially of: at least one DNA binding (C) domain; a hinge (D) domain of an insect ecdysone receptor; a ligand binding (E) domain of an insect ecdysone receptor, wherein the ligand binding (E) domain is heterologous with respect to the hinge (D) domain; and a heterologous activation domain that is not an ecdysone receptor A/B N-terminal domain. Preferably, the DNA binding (C) domain is a GAL4 DNA binding domain. Also, preferably, the activation domain is a VP16 activation domain, a maize C1 activation domain, or a maize Dof1 activation domain.

According to a fifth aspect, the present invention provides a receptor cassette encoding a chimeric receptor polypeptide comprising: a DNA binding (C) domain; a hinge (D) domain of an insect ecdysone receptor (EcR); a ligand binding (E) domain of an ecdysone receptor of a lepidopteran insect other than *Bombyx mori*, wherein the ligand binding (E) domain is heterologous with respect to the hinge (D) domain; and an activation domain. Preferably, the DNA binding (C) domain is a GAL4 DNA binding domain. Also, preferably, the activation domain is a VP16 activation domain, a maize C1 activation domain, or a maize Dof1 activation domain. Still further, preferably, the hinge (D) domain is the hinge (D) domain of a lepidopteran insect ecdysone receptor.

According to a sixth aspect, the present invention provides an isolated nucleic acid molecule comprising a nucleotide sequence that encodes an ecdysone receptor of *Spodoptera frugiperda* or *Agrotis ipsilon*. Preferably, the ecdysone receptor comprises an amino acid sequence at least 90% identical to SEQ ID NO:8 or SEQ ID NO:10. More preferably, the ecdysone receptor comprises SEQ I) NO:8 or SEQ ID NO:10. More preferably, the isolated nucleic acid molecule comprises a nucleotide sequence of which the complement hybridizes under stringent conditions to SEQ ID NO:7 or SEQ ID NO:9. Even more preferably, the isolated nucleic acid molecule comprises SEQ ID NO:7 or SEQ ID NO:9.

Additional aspects of the present invention involve a receptor expression cassette comprising a heterologous promoter sequence operatively linked to any of the above-described receptor cassettes of the invention; a recombinant vector comprising a receptor expression cassette according to the invention; and a transgenic host cell comprising a receptor expression cassette according to the invention. Preferably, the transgenic host cell is a plant cell. Yet additional aspects of the present invention involve a transgenic plant comprising such a transgenic plant cell, and seed from such a transgenic plant. Transgenic plants according to the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon (e.g., watermelon), plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis*, and woody plants such as coniferous and deciduous trees.

A twelth aspect of the present invention concerns a method of controlling gene expression in a plant, comprising: transforming the plant with a receptor expression cassette comprising a 5' regulatory region capable of promoting expression in a plant cell operatively linked to a receptor cassette of the invention as described above, and a 3' terminating region; and a target expression cassette comprising a 5' regulatory region operatively linked to a target nucleotide sequence, wherein the 5' regulatory region comprises one or more response elements complementary to the DNA binding (C) domain of the chimeric receptor polypeptide; expressing the chimeric receptor polypeptide in the plant; contacting the plant with a chemical ligand that is complementary to the ligand binding (E) domain of the chimeric receptor polypeptide, whereby the chimeric receptor polypeptide in the presence of the chemical ligand activates expression of the target nucleotide sequence. Preferably, the ligand binding (E) domain of the chimeric receptor polypeptide is a *Manduca sexta* EcR ligand binding (E) domain. Also, preferably, the chemical ligand is tebufenozide or methoxytebufenozide.

In an especially preferred embodiment, the present invention provides a method of controlling gene expression in a plant, comprising: a) transforming the plant with (i) a receptor expression cassette comprising a 5' regulatory region capable of promoting expression in a plant cell operatively linked to a receptor cassette encoding a chimeric receptor polypeptide comprising a DNA binding (C) domain, a hinge (D) domain of a *Manduca sexta* ecdysone receptor, a ligand binding (E) domain of a *Manduca sexta* ecdysone receptor, and an activation domain, and a 3' terminating region; and (ii) a target expression cassette comprising a 5' regulatory region operatively linked to a target nucleotide sequence, wherein the 5' regulatory region comprises one or more response elements complementary to the DNA binding (C) domain of the chimeric receptor polypeptide; b) expressing the chimeric receptor polypeptide in the plant; c) contacting the plant with a chemical ligand that is complementary to the ligand binding (E) domain of the chimeric receptor polypeptide, whereby the chimeric receptor polypeptide in the presence of the chemical ligand activates expression of the target nucleotide sequence. Preferably, the DNA binding (C) domain is a GAL4 DNA binding domain. Also, preferably, the activation domain of the chimeric receptor polypeptide is a VP16 activation domain, a maize C1 activation domain, or a maize Dof1 activation domain. Still further, preferably, the chemical ligand is tebufenozide or methoxytebufenozide.

According to a thirteenth aspect, the present invention provides a chimeric receptor polypeptide comprising: a DNA binding (C) domain; a hinge (D) domain of an ecdysone receptor (EcR) of an insect selected from the group consisting of *Manduca sexta, Agrotis ipsilon, Spodoptera frugipera, Chironomus tentans*, and *Locusta migratoria*; a ligand binding (E) domain that is heterologous with respect to the hinge (D) domain; and an activation domain. In a preferred embodiment, the ligand binding (E) domain is a ligand binding (E) domain of an ecdysone receptor of an insect selected from the group consisting of *Manduca sexta, Agrotis epsilon, Spodoptera frugiperda, Locusta migratoria, Ostrinia nubilalis*, and *Chironomus tentans*. In another preferred embodiment, the hinge (D) domain is a *Manduca sexta* EcR hinge (D) domain. In a preferred embodiment, the DNA binding (C) domain is a GAL4 DNA binding domain. In another preferred embodiment, the DNA binding (C) domain is a *Manduca sexta* EcR DNA binding (C) domain. Preferably, the activation domain is a VP16 activation domain, a maize C1 activation domain, or a maize Dof1 activation domain.

In one embodiment of the chimeric receptor polypeptide described above according to a thirteenth aspect of the invention, the hinge (D) domain is a *Manduca sexta* EcR hinge (D) domain, and the ligand binding (E) domain is a *Drosophila melanogaster* EcR ligand binding (E) domain. In a preferred embodiment, the DNA binding (C) domain is a GAL4 DNA binding domain. In another preferred embodiment, the DNA binding (C) domain is a *Manduca sexta* EcR DNA binding (C) domain, the hinge (D) domain is a *Manduca sexta* EcR hinge (D) domain, and the ligand binding (E) domain is a *Drosophila melanogaster* EcR ligand binding (E) domain. Preferably, the C, D, and E domains of the chimeric receptor polypeptide comprise an amino acid sequence at least 90% identical to amino acids 1–421 of SEQ ID NO:64. More preferably, the C, D, and E domains of the chimeric receptor polypeptide comprise amino acids 1–421 of SEQ ID NO:64.

In another embodiment of the chimeric receptor polypeptide described above according to a thirteenth aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Drosophila melanogaster* EcR ligand binding (E) domain, and the activation domain is a VP16 activation domain. In a preferred embodiment, the chimeric receptor polypeptide comprises an amino acid sequence at least 90% identical to SEQ ID NO:64. In a more preferred embodiment, the chimeric receptor polypeptide comprises SEQ ID NO:64.

In another embodiment of the chimeric receptor polypeptide described above according to a thirteenth aspect of the invention, the hinge (D) domain is a *Manduca sexta* EcR hinge (D) domain, and the ligand binding (E) domain is an *Agrotis ipsilon* EcR ligand binding (E) domain. In a preferred embodiment, the DNA binding (C) domain is a *Manduca sexta* EcR DNA binding (C) domain, the hinge (D) domain is a *Manduca sexta* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–422 of SEQ ID NO:66. More preferably, the C, D, and E domains of the chimeric receptor polypeptide comprise amino acids 1–422 of SEQ ID NO:66.

In another embodiment of the chimeric receptor polypeptide described above according to a thirteenth aspect of the invention, the DNA binding (C) domain is a *Manduca sexta* EcR DNA binding (C) domain, the hinge (D) domain is a *Manduca sexta* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:66. More preferably, the chimeric receptor polypeptide comprises SEQ ID NO:66.

In a preferred embodiment of the chimeric receptor polypeptide described above according to a thirteenth aspect of the invention, the DNA binding (C) domain is a GAL4 DNA binding domain, the hinge (D) domain is a *Manduca sexta* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–511 of SEQ ID NO:119. More preferably, the C, D, and E domains of the chimeric receptor polypeptide comprise amino acids 1–511 of SEQ ID NO:119.

In another preferred embodiment of the chimeric receptor polypeptide described above according to a thirteenth aspect of the invention, the DNA binding domain is a GAL4 DNA binding domain, the hinge (D) domain is a *Manduca sexta* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:119. More preferably, the chimeric receptor polypeptide comprises SEQ ID NO:119.

In another embodiment of the chimeric receptor polypeptide described above according to a thirteenth aspect of the invention, the hinge (D) domain is a *Manduca sexta* EcR hinge (D) domain, and the ligand binding (E) domain is an *Ostrinia nubilalis* EcR ligand binding (E) domain. In a preferred embodiment, the DNA binding (C) domain is a *Manduca sexta* EcR DNA binding (C) domain, the hinge (D) domain is a *Manduca sexta* EcR hinge (D) domain, and the ligand binding (E) domain is an *Ostrinia nubilalis* EcR ligand binding (E) domain. Preferably, the C, D, and E domains of the chimeric receptor polypeptide comprise an amino acid sequence at least 90% identical to amino acids 1–419 of SEQ ID NO:68. More preferably, the C, D, and E domains of the chimeric receptor polypeptide comprise amino acids 1–419 of SEQ ID NO:68.

In another embodiment of the chimeric receptor polypeptide described above according to a thirteenth aspect of the invention, the DNA binding (C) domain is a *Manduca sexta* EcR DNA binding (C) domain, the hinge (D) domain is a *Manduca sexta* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:68. More preferably, the chimeric receptor polypeptide comprises SEQ ID NO:68.

In another embodiment of the chimeric receptor polypeptide described above according to a thirteenth aspect of the invention, the DNA binding (C) domain is a GAL4 DNA binding domain, the hinge (D) domain is a *Manduca sexta* EcR hinge (D) domain, and the ligand binding (E) domain is an *Ostrinia nubilalis* EcR ligand binding (E) domain. Preferably, the C, D, and E domains of the chimeric receptor polypeptide comprise an amino acid sequence at least 90% identical to amino acids 1–508 of SEQ ID NO:121. More preferably, the C, D, and E domains of the chimeric receptor polypeptide comprise amino acids 1–508 of SEQ ID NO:121.

In another embodiment of the chimeric receptor polypeptide described above according to a thirteenth aspect of the invention, the DNA binding (C) domain is a GAL4 DNA binding domain, the hinge (D) domain is a *Manduca sexta* EcR hinge (D) domain, the ligand binding (E) domain is an *Ostrinia nubilalis* EcR ligand binding (E) domain, and the activation domain is a VP16 activation domain. According to this embodiment, the chimeric receptor polypeptide comprises an amino acid sequence at least 90% identical to SEQ ID NO:121. More preferably, the chimeric receptor polypeptide comprises SEQ ID NO:121.

In another embodiment of the chimeric receptor polypeptide described above according to a thirteenth aspect of the invention, the hinge (D) domain is a *Manduca sexta* EcR hinge (D) domain, and the ligand binding (E) domain is a *Spodoptera frugipera* EcR ligand binding (E) domain. In a preferred embodiment, the DNA binding (C) domain is a Manduca sexta EcR DNA binding (C) domain, the hinge (D) domain is a Manduca sexta EcR hinge (D) domain, and the ligand binding (E) domain is a Spodoptera frugipera EcR ligand binding (E) domain. Preferably, the C, D, and E domains of the chimeric receptor polypeptide comprise an amino acid sequence at least 90% identical to amino acids 1–419 of SEQ ID NO:70. More preferably, the C, D, and E domains of the chimeric receptor polypeptide comprise amino acids 1–419 of SEQ ID NO:70.

In another embodiment of the chimeric receptor polypeptide described above according to a thirteenth aspect of the invention, the DNA binding (C) domain is a Manduca sexta EcR DNA binding (C) domain, the hinge (D) domain is a Manduca sexta EcR hinge (D) domain, the ligand binding (E) domain is a Spodoptera frugipera EcR ligand binding (E) domain, and the activation domain is a VP16 activation domain. In a preferred embodiment, the chimeric receptor polypeptide comprises an amino acid sequence at least 90% identical to SEQ ID NO:70. In a more preferred embodiment, the chimeric receptor polypeptide comprises SEQ ID NO:70.

In a preferred embodiment of the chimeric receptor polypeptide described above according to a thirteenth aspect of the invention, the DNA binding (C) domain is a GAL4 DNA binding domain, the hinge (D) domain is a Manduca sexta EcR hinge (D) domain, and the ligand binding (E) domain is a Spodoptera frugipera EcR ligand binding (E) domain. Preferably, the C, D, and E domains of the chimeric receptor polypeptide comprise an amino acid sequence at least 90% identical to amino acids 1–508 of SEQ ID NO:123. More preferably, the C, D, and E domains of the chimeric receptor polypeptide comprise amino acids 1–508 of SEQ ID NO:123.

In another preferred embodiment of the chimeric receptor polypeptide described above according to a thirteenth aspect of the invention, the DNA binding (C) domain is a GAL4 DNA binding domain, the hinge (D) domain is a Manduca sexta EcR hinge (D) domain, the ligand binding (E) domain is a Spodoptera frugipera EcR ligand binding (E) domain, and the activation domain is a VP16 activation domain. In a preferred embodiment, the chimeric receptor polypeptide comprises an amino acid sequence at least 90% identical to SEQ ID NO:123. In a more preferred embodiment, the chimeric receptor polypeptide comprises SEQ ID NO:123.

In another embodiment of the chimeric receptor polypeptide described above according to a thirteenth aspect of the invention, the hinge (D) domain is a Locusta migratoria EcR hinge (D) domain, and the ligand binding (E) domain is a Manduca sexta EcR ligand binding (E) domain. In a preferred embodiment, the DNA binding (C) domain is a GAL4 DNA binding domain. In another preferred embodiment, the DNA binding (C) domain is a Locusta migratoria EcR DNA binding (C) domain, the hinge (D) domain is a Locusta migratoria EcR hinge (D) domain, and the ligand binding (E) domain is a Manduca sexta EcR ligand binding (E) domain. Preferably, the C, D, and E domains of the chimeric receptor polypeptide comprise More preferably, the C, D, and E domains of the chimeric receptor polypeptide comprise amino acids 1–407 of SEQ ID NO:84.

In another embodiment of the chimeric receptor polypeptide described above according to a thirteenth aspect of the invention, the DNA binding (C) domain is a Locusta migratoria EcR DNA binding (C) domain, the hinge (D) domain is a Locusta migratoria EcR hinge (D) domain, the ligand binding (E) domain is a Manduca sexta EcR ligand binding (E) domain, and the activation domain is a VP16 activation domain. In a preferred embodiment, the chimeric receptor polypeptide comprises an amino acid sequence at least 90% identical to SEQ ID NO:84. In another preferred embodiment, the chimeric receptor polypeptide comprises SEQ ID NO:84.

In another embodiment of the chimeric receptor polypeptide described above according to a thirteenth aspect of the invention, the hinge (D) domain is a Manduca sexta EcR hinge (D) domain, and the ligand binding (E) domain is a Locusta migratoria EcR ligand binding (E) domain. In a preferred embodiment, the DNA binding (C) domain is a GAL4 DNA binding domain. In another preferred embodiment, the DNA binding (C) domain is a Manduca sexta EcR DNA binding (C) domain, the hinge (D) domain is a Manduca sexta EcR hinge (D) domain, and the ligand binding (E) domain is a Locusta migratoria EcR ligand binding (E) domain. Preferably, the C, D, and E domains of the chimeric receptor polypeptide comprise an amino acid sequence at least 90% identical to amino acids 1–416 of SEQ ID NO:86. More preferably, the C, D, and E domains of the chimeric receptor polypeptide comprise an amino acid sequence at least 90% identical to amino acids 1–416 of SEQ ID NO:86.

In another embodiment of the chimeric receptor polypeptide described above according to a thirteenth aspect of the invention, the DNA binding (C) domain is a Manduca sexta EcR DNA binding (C) domain, the hinge (D) domain is a Manduca sexta EcR hinge (D) domain, the ligand binding (E) domain is a Locusta migratoria EcR ligand binding (E) domain, and the activation domain is a VP16 activation domain. Preferably, the chimeric receptor polypeptide comprises an amino acid sequence at least 90% identical to SEQ ID NO:86. More preferably, the chimeric receptor polypeptide comprises SEQ ID NO:86.

In another embodiment of the chimeric receptor polypeptide described above according to a thirteenth aspect of the invention, the hinge (D) domain is a Chironomus tentans EcR hinge (D) domain, and the ligand binding (E) domain is a Manduca sexta EcR ligand binding (E) domain. In a preferred embodiment, the DNA binding (C) domain is a GAL4 DNA binding domain. In another preferred embodiment, the DNA binding (C) domain is a Chironomus tentans EcR DNA binding (C) domain, the hinge (D) domain is a Chironomus tentans EcR hinge (D) domain, and the ligand binding (E) domain is a Manduca sexta EcR ligand binding (E) domain. Preferably, the C, D, and E domains of the chimeric receptor polypeptide comprise an amino acid sequence at least 90% identical to amino acids 1–441 of SEQ ID NO:90. More preferably, the C, D, and E domains of the chimeric receptor polypeptide comprise amino acids 1–441 of SEQ ID NO:90.

In another embodiment of the chimeric receptor polypeptide described above according to a thirteenth aspect of the invention, the DNA binding (C) domain is a Chironomus tentans EcR DNA binding (C) domain, the hinge (D) domain is a Chironomus tentans EcR hinge (D) domain, the ligand binding (E) domain is a Manduca sexta EcR ligand binding (E) domain, and the activation domain is a VP16 activation domain. In a preferred embodiment, the chimeric receptor polypeptide comprises an amino acid sequence at least 90% identical to SEQ ID NO:90. In a more preferred embodiment, the chimeric receptor polypeptide comprises SEQ ID NO:90.

In another embodiment of the chimeric receptor polypeptide described above according to a thirteenth aspect of the invention, the hinge (D) domain is a Manduca sexta EcR hinge (D) domain, and the ligand binding (E) domain is a *Chironomus tentans* EcR ligand binding (E) domain. In a preferred embodiment, the DNA binding (C) domain is a GAL4 DNA binding domain. In another preferred embodiment, the DNA binding (C) domain is a *Manduca sexta* EcR DNA binding (C) domain, the hinge (D) domain is a *Chironomus tentans* EcR hinge (D) domain, and the ligand binding (E) domain is a *Chironomus tentans* EcR ligand binding (E) domain. Preferably, the C, D, and E domains of the chimeric receptor polypeptide comprise an amino acid sequence at least 90% identical to amino acids 1–420 of SEQ ID NO:92. More preferably, the C, D, and E domains of the chimeric receptor polypeptide comprise amino acids 1–420 of SEQ ID NO:92.

In another embodiment of the chimeric receptor polypeptide described above according to a thirteenth aspect of the invention, the DNA binding (C) domain is a *Manduca sexta* EcR DNA binding (C) domain, the hinge (D) domain is a *Chironomus tentans* EcR hinge (D) domain, the ligand binding (E) domain is a *Chironomus tentans* EcR ligand binding (E) domain, and the activation domain is a VP16 activation domain. In a preferred embodiment, the chimeric receptor polypeptide comprises an amino acid sequence at least 90% identical to SEQ ID NO:92. In a more preferred embodiment, the chimeric receptor polypeptide comprises SEQ ID NO:92.

According to a fourteenth aspect, the present invention provides a chimeric receptor polypeptide comprising: a DNA binding (C) domain; a hinge (D) domain; a ligand binding (E) domain of an ecdysone receptor (EcR) of an insect selected from the group consisting of *Manduca sexta, Agrotis ipsilon, Spodoptera frugipera, Chironomus tentans,* and *Locusta migratoria,* wherein the ligand binding (E) domain is heterologous with respect to the hinge (D) domain; and an activation domain.

In one embodiment of the chimeric receptor polypeptide described above according to a fourteenth aspect of the invention, the hinge (D) domain is a hinge (D) domain of an ecdysone receptor of an insect selected from the group consisting of *Manduca sexta, Agrotis ipsilon, Spodoptera frugiperda, Locusta migratoria, Ostrinia nubilalis,* and *Chironomus tentans*. In a preferred embodiment, the DNA binding (C) domain is a GAL4 DNA binding domain. In another preferred embodiment, the ligand binding (E) domain is a *Manduca sexta* ligand binding (E) domain. In another preferred embodiment, the activation domain is a VP16 activation domain, a maize C1 activation domain, or a maize Dof1 activation domain.

In another embodiment of the chimeric receptor polypeptide described above according to a fourteenth aspect of the invention, the hinge (D) domain is an *Ostrinia nubilalis* EcR hinge (D) domain, and the ligand binding (E) domain is an *Agrotis ipsilon* EcR ligand binding (E) domain. In a preferred embodiment, the DNA binding (C) domain is a GAL4 DNA binding domain. In another preferred embodiment, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–427 of SEQ ID NO:78. More preferably, the C, D, and E domains of the chimeric receptor polypeptide comprise amino acids 1–427 of SEQ ID NO:78.

In another embodiment of the chimeric receptor polypeptide described above according to a fourteenth aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is an *Agrotis ipsilon* EcR ligand binding (E) domain, and the activation domain is a VP16 activation domain. In a preferred embodiment, the chimeric receptor polypeptide comprises an amino acid sequence at least 90% identical to SEQ ID NO:78. In a more preferred embodiment, the chimeric receptor polypeptide comprises SEQ ID NO:78.

In another embodiment of the chimeric receptor polypeptide described above according to a fourteenth aspect of the invention, the hinge (D) domain is an *Ostrinia nubilalis* EcR hinge (D) domain, and the ligand binding (E) domain is a *Manduca sexta* EcR ligand binding (E) domain. In a preferred embodiment, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–430 of SEQ ID NO:80. More preferably, the C, D, and E domains of the chimeric receptor polypeptide comprise amino acids 1–430 of SEQ ID NO:80.

In another embodiment of the chimeric receptor polypeptide described above according to a fourteenth aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:80. More preferably, the chimeric receptor polypeptide comprises SEQ ID NO:80.

In a preferred embodiment of the chimeric receptor polypeptide described above according to a fourteenth aspect of the invention, the DNA binding (C) domain is a GAL4 DNA binding domain, the hinge (D) domain is an *Ostrinia nubilalis* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–519 of SEQ ID NO:127. More preferably, the C, D, and E domains of the chimeric receptor polypeptide comprise amino acids 1–519 of SEQ ID NO:127.

In another preferred embodiment of the chimeric receptor polypeptide described above according to a fourteenth aspect of the invention, the DNA binding (C) domain is a GAL4 DNA binding domain, the hinge (D) domain is an *Ostrinia nubilalis* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:127. More preferably, the chimeric receptor polypeptide comprises SEQ ID NO:127.

In another embodiment of the chimeric receptor polypeptide described above according to a fourteenth aspect of the invention, the hinge (D) domain is a *Drosophila melanogaster* EcR hinge (D) domain, and the ligand binding (E) domain is a *Manduca sexta* EcR ligand binding (E) domain. In a preferred embodiment, the DNA binding (C) domain is a GAL4 DNA binding domain. In another preferred embodiment, the DNA binding (C) domain is a *Drosophila melanogaster* EcR DNA binding (C) domain, the hinge (D) domain is a *Drosophila melanogaster* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–436 of SEQ ID NO:72. More preferably, the C, D, and E domains of the chimeric receptor polypeptide comprise amino acids 1–436 of SEQ ID NO:72.

In another embodiment of the chimeric receptor polypeptide described above according to a fourteenth aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is a *Manduca sexta* EcR ligand binding (E) domain, and the activation domain is a VP16 activation domain. In a preferred embodiment, the chimeric receptor polypeptide comprises an amino acid sequence at least 90% identical to SEQ ID NO:72. In a more preferred embodiment, the chimeric receptor polypeptide comprises SEQ ID NO:72.

In another embodiment of the chimeric receptor polypeptide described above according to a fourteenth aspect of the invention, the hinge (D) domain is a *Drosophila melanogaster* EcR hinge (D) domain, and the ligand binding (E) domain is an *Agrotis ipsilon* EcR ligand binding (E) domain. In a preferred embodiment, the DNA binding (C) domain is a GAL4 DNA binding domain. In another preferred embodiment, the DNA binding (C) domain is a *Drosophila melanogaster* EcR DNA binding (C) domain, the hinge (D) domain is a *Drosophila melanogaster* EcR hinge (D) domain, and the ligand binding (E) domain is an *Agrotis ipsilon* EcR ligand binding (E) domain. Preferably, the C, D, and E domains of the chimeric receptor polypeptide comprise an amino acid sequence at least 90% identical to amino acids 1–433 of SEQ ID NO:74. More preferably, the C, D, and E domains of the chimeric receptor polypeptide comprise amino acids 1–433 of SEQ ID NO:74.

In another embodiment of the chimeric receptor polypeptide described above according to a fourteenth aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is an *Agrotis ipsilon* EcR ligand binding (E) domain, and the activation domain is a VP16 activation domain. Preferably, the chimeric receptor polypeptide comprises an amino acid sequence at least 90% identical to SEQ ID NO:74. More preferably, the chimeric receptor polypeptide comprises SEQ ID NO:74.

According to an fifteenth aspect, the present invention provides a chimeric receptor polypeptide comprising: a GAL4 DNA binding domain or a DNA binding (C) domain of an ecdysone receptor (EcR) of an insect selected from the group consisting of *Ostrinia nubilalis, Locusta migratoria, Chironomus tentans, Manduca sexta*, and *Drosophila melanogaster*; a hinge (D) domain of an ecdysone receptor of an insect selected from the group consisting of *Ostrinia nubilalis, Locusta migratoria, Chironomus tentans, Manduca sexta*, and *Drosophila melanogaster*; a ligand binding (E) domain of an ecdysone receptor of an insect selected from the group consisting of *Ostrinia nubilalis, Locusta migratoria, Chironomus tentans, Manduca sexta*, and *Drosophila melanogaster*; and a heterologous activation domain; wherein the chimeric receptor polypeptide does not include an ecdysone receptor A/B N-terminal domain. In a particularly preferred embodiment, the chimeric receptor polypeptide consists essentially of: a GAL4 DNA binding domain or a DNA binding (C) domain of an ecdysone receptor (EcR) of an insect selected from the group consisting of *Ostrinia nubilalis, Locusta migratoria, Chironomus tentans, Manduca sexta*, and *Drosophila melanogaster*; a hinge (D) domain of an ecdysone receptor of an insect selected from the group consisting of *Ostrinia nubilalis, Locusta migratoria, Chironomus tentans, Manduca sexta*, and *Drosophila melanogaster*; a ligand binding (E) domain of an ecdysone receptor of an insect selected from the group consisting of *Ostrinia nubilalis, Locusta migratoria, Chironomus tentans, Manduca sexta*, and *Drosophila melanogaster*; and a heterologous activation domain that is not an ecdysone receptor A/B N-terminal domain. In one preferred embodiment, the DNA binding (C) domain is a GAL4 DNA binding domain. Also, in another preferred embodiment, the activation domain is a VP16 activation domain, a maize C1 activation domain, or a maize Dof1 activation domain.

In one embodiment of the chimeric receptor polypeptide described above according to a fifteenth aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a VP16 activation domain. In one configuration, the VP16 activation domain is located at the N-terminus of the chimeric receptor polypeptide. In another configuration, the VP16 activation domain is located internally in the chimeric receptor polypeptide between the GAL4 DNA binding domain and the *Manduca sexta* EcR hinge (D) domain. In yet another configuration, the VP16 activation domain is located at the C-terminus of the chimeric receptor polypeptide. Preferably, the chimeric receptor polypeptide comprises an amino acid sequence at least 90% identical to SEQ ID NO:105. More preferably, the chimeric receptor polypeptide comprises SEQ ID NO:105.

In another embodiment of the chimeric receptor polypeptide described above according to a fifteenth aspect of the invention, the DNA binding (C) domain is a GAL4 DNA binding domain, the hinge (D) domain is an *Ostrinia nubilalis* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:125. More preferably, the chimeric receptor polypeptide comprises SEQ ID NO:125.

In another embodiment of the chimeric receptor polypeptide described above according to a fifteenth aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a maize C1 activation domain. According to this embodiment, the chimeric receptor polypeptide preferably comprises an amino acid sequence at least 90% identical to SEQ ID NO:135. More preferably, the chimeric receptor polypeptide comprises SEQ ID NO:135.

In another embodiment of the chimeric receptor polypeptide described above according to a fifteenth aspect of the invention, the DNA binding (C) domain is a GAL4 DNA binding domain, the hinge (D) domain is a *Manduca sexta* EcR hinge (D) domain, the ligand binding (E) domain is a *Manduca sexta* EcR ligand binding (E) domain, and the activation domain is a maize Dof1 activation domain. According to this embodiment, the chimeric receptor polypeptide preferably comprises an amino acid sequence at least 90% identical to SEQ ID NO:137. More preferably, the chimeric receptor polypeptide comprises SEQ ID NO:137.

In another embodiment of the chimeric receptor polypeptide described above according to a fifteenth aspect of the invention, the activation domain is an N-terminal VP16 activation domain, the DNA binding (C) domain is a GAL4 DNA binding domain, the hinge (D) domain is a *Manduca sexta* EcR hinge (D) domain, and the ligand binding (E) domain is a *Manduca sexta* EcR ligand binding (E) domain. According to this embodiment, the chimeric receptor polypeptide preferably comprises an amino acid sequence at least 90% identical to SEQ ID NO:143. More preferably, the chimeric receptor polypeptide comprises SEQ ID NO:143.

In another embodiment of the chimeric receptor polypeptide described above according to a fifteenth aspect of the invention, the DNA binding (C) domain is a GAL4 DNA binding domain, the activation domain is an internally configured VP16 activation domain, the hinge (D) domain is a *Manduca sexta* EcR hinge (D) domain, and the ligand binding (E) domain is a *Manduca sexta* EcR ligand binding (E) domain. According to this embodiment, the chimeric receptor polypeptide preferably comprises an amino acid sequence at least 90% identical to SEQ ID NO:148. More preferably, the chimeric receptor polypeptide comprises SEQ ID NO:148.

In one embodiment of the chimeric receptor polypeptide described above according to an fifteenth aspect of the invention, the DNA binding (C) domain is an *Ostrinia nubilalis* EcR DNA binding (C) domain, the hinge (D) domain is an *Ostrinia nubilalis* EcR hinge (D) domain, and the ligand binding (E) domain is an *Ostrinia nubilalis* EcR ligand binding (E) domain. In a preferred embodiment, the C, D, and E domains of the chimeric receptor polypeptide comprise an amino acid sequence at least 90% identical to amino acids 1–424 of SEQ ID NO:76. In a more preferred embodiment, the C, D, and E domains of the chimeric receptor polypeptide comprise amino acids 1–424 of SEQ ID NO:76.

In another embodiment of the chimeric receptor polypeptide described above according to an fifteenth aspect of the invention, the DNA binding (C) domain is an *Ostrinia nubilalis* EcR DNA binding (C) domain, the hinge (D) domain is an *Ostrinia nubilalis* EcR hinge (D) domain, the ligand binding (E) domain is an *Ostrinia nubilalis* EcR ligand binding (E) domain, and the activation domain is a VP16 activation domain. Preferably, the chimeric receptor polypeptide comprises an amino acid sequence at least 90% identical to SEQ ID NO:76. More preferably, the chimeric receptor polypeptide comprises SEQ ID NO:76.

In another embodiment of the chimeric receptor polypeptide described above according to an fifteenth aspect of the invention, the DNA binding (C) domain is a *Locusta migratoria* EcR DNA binding (C) domain, the hinge (D) domain is a *Locusta migratoria* EcR hinge (D) domain, and the ligand binding (E) domain is a *Locusta migratoria* EcR ligand binding (E) domain. Preferably, the C, D, and E domains of the chimeric receptor polypeptide comprise an amino acid sequence at least 90% identical to amino acids 1–398 of SEQ ID NO:82. More preferably, the C, D, and E domains of the chimeric receptor polypeptide comprise amino acids 1–398 of SEQ ID NO:82.

In another embodiment of the chimeric receptor polypeptide described above according to an fifteenth aspect of the invention, the DNA binding (C) domain is a *Locusta migratoria* EcR DNA binding (C) domain, the hinge (D) domain is a *Locusta migratoria* EcR hinge (D) domain, the ligand binding (E) domain is a *Locusta migratoria* EcR ligand binding (E) domain, and the activation domain is a VP16 activation domain. In a preferred embodiment, the chimeric receptor polypeptide comprises an amino acid sequence at least 90% identical to SEQ ID NO:82. In a more preferred embodiment, the chimeric receptor polypeptide comprises SEQ ID NO:82.

In another embodiment of the chimeric receptor polypeptide described above according to an fifteenth aspect of the invention, the DNA binding (C) domain is a *Chironomus tentans* EcR DNA binding (C) domain, the hinge (D) domain is a *Chironomus tentans* EcR hinge (D) domain, and the ligand binding (E) domain is a *Chironomus tentans* EcR ligand binding (E) domain. Preferably, the C, D, and E domains of the chimeric receptor polypeptide comprise an amino acid sequence at least 90% identical to amino acids 1–436 of SEQ ID NO:88. More preferably, the C, D, and E domains of the chimeric receptor polypeptide comprise amino acids 1–436 of SEQ ID NO:88.

In another embodiment of the chimeric receptor polypeptide described above according to an fifteenth aspect of the invention, the DNA binding (C) domain is a *Chironomus tentans* EcR DNA binding (C) domain, the hinge (D) domain is a *Chironomus tentans* EcR hinge (D) domain, the ligand binding (E) domain is a *Chironomus tentans* EcR ligand binding (E) domain, and the activation domain is a VP16 activation domain. Preferably, the chimeric receptor polypeptide comprises an amino acid sequence at least 90% identical to SEQ ID NO:88. More preferably, the chimeric receptor polypeptide comprises SEQ ID NO:88.

In another embodiment of the chimeric receptor polypeptide described above according to an fifteenth aspect of the invention, the DNA binding (C) domain is a *Manduca sexta* EcR DNA binding (C) domain, the hinge (D) domain is a *Manduca sexta* EcR hinge (D) domain, and the ligand binding (E) domain is a *Manduca sexta* EcR ligand binding (E) domain. Preferably, the C, D, and E domains of the chimeric receptor polypeptide comprise an amino acid sequence at least 90% identical to amino acids 1–425 of SEQ ID NO:94. More preferably, the C, D, and E domains of the chimeric receptor polypeptide comprise amino acids 1–425 of SEQ ID NO:94.

In another embodiment of the chimeric receptor polypeptide described above according to an fifteenth aspect of the invention, the DNA binding (C) domain is a *Manduca sexta* EcR DNA binding (C) domain, the hinge (D) domain is a *Manduca sexta* EcR hinge (D) domain, the ligand binding (E) domain is a *Manduca sexta* EcR ligand binding (E) domain, and the activation domain is a VP16 activation domain. Preferably, the chimeric receptor polypeptide comprises an amino acid sequence at least 90% identical to SEQ ID NO:94. More preferably, the chimeric receptor polypeptide comprises SEQ ID NO:94.

In another embodiment of the chimeric receptor polypeptide described above according to an fifteenth aspect of the invention, the DNA binding (C) domain is a *Drosophila melanogaster* EcR DNA binding (C) domain, the hinge (D) domain is a *Drosophila melanogaster* EcR hinge (D) domain, and the ligand binding (E) domain is an *Drosophila melanogaster* EcR ligand binding (E) domain. Preferably, the C, D, and E domains of the chimeric receptor polypeptide comprise an amino acid sequence at least 90% identical to amino acids 1–432 of SEQ ID NO:96. More preferably, the C, D, and E domains of the chimeric receptor polypeptide comprise amino acids 1–432 of SEQ ID NO:96.

In another embodiment of the chimeric receptor polypeptide described above according to an fifteenth aspect of the invention, the DNA binding (C) domain is a *Drosophila melanogaster* EcR DNA binding (C) domain, the hinge (D) domain is a *Drosophila melanogaster* EcR hinge (D) domain, the ligand binding (E) domain is an *Drosophila melanogaster* EcR ligand binding (E) domain, and the activation domain is a VP16 activation domain. Preferably, the chimeric receptor polypeptide comprises an amino acid sequence at least 90% identical to SEQ ID NO:96. Preferably, the chimeric receptor polypeptide comprises SEQ ID NO:96.

According to a sixteenth aspect, the present invention provides a chimeric receptor polypeptide comprising: at least one DNA binding (C) domain; a hinge (D) domain of an insect ecdysone receptor (EcR); a ligand binding (E) domain of an insect ecdysone receptor, wherein the ligand binding (E) domain is heterologous with respect to the hinge (D) domain; and a heterologous activation domain; wherein the chimeric receptor polypeptide does not include an ecdysone receptor A/B N-terminal domain. In a particulary preferred embodiment, the chimeric receptor polypeptide consists essentially of: at least one DNA binding (C) domain; a hinge (D) domain of an insect ecdysone receptor; a ligand binding (E) domain of an insect ecdysone receptor, wherein the ligand binding (E) domain is heterologous with respect to the hinge (D) domain; and a heterologous activation domain that is not an ecdysone receptor A/B N-terminal domain. Preferably, the DNA binding (C) domain is a GAL4 DNA binding domain. Also, preferably, the activation domain is a VP16 activation domain, a maize C1 activation domain, or a maize Dof1 activation domain.

According to a seventeenth aspect, the present invention provides a chimeric receptor polypeptide comprising: a DNA binding (C) domain; a hinge (D) domain of an insect ecdysone receptor (EcR); a ligand binding (E) domain of an ecdysone receptor of a lepidopteran insect other than *Bombyx mori*, wherein the ligand binding (E) domain is heterologous with respect to the hinge (D) domain; and an activation domain. Preferably, the DNA binding (C) domain is a GAL4 DNA binding domain. Preferably, the activation domain is a VP16 activation domain, a maize C1 activation domain, or a maize Dof1 activation domain. In a preferred embodiment, the hinge (D) domain is the hinge (D) domain of a lepidopteran insect ecdysone receptor.

According to a eighteenth aspect, the present invention provides an isolated ecdysone receptor of *Spodoptera frugiperda* or *Agrotis ipsilon*. Preferably, such a receptor comprises an amino acid sequence at least 90% identical to SEQ ID NO:8 or SEQ ID NO:10. More preferably, such a receptor SEQ ID NO:8 or SEQ ID NO:10.

According to a nineteenth aspect, the present invention provides a method of controlling gene expression in a transgenic plant, comprising: expressing in the transgenic plant a chimeric receptor polypeptide of the invention, as described above, and a target expression cassette comprising a 5' regulatory region operatively linked to a target nucleotide sequence, wherein the 5' regulatory region comprises one or more response elements complementary to the DNA binding (C) domain of the chimeric receptor polypeptide; and contacting the transgenic plant with a chemical ligand that is complementary to the ligand binding (E) domain of the chimeric receptor polypeptide, whereby the chimeric receptor polypeptide in the presence of the chemical ligand activates expression of the target nucleotide sequence. Preferably, the ligand binding (E) domain of the chimeric receptor polypeptide is a *Manduca sexta* EcR ligand binding (E) domain. Also, preferably, the chemical ligand is tebufenozide or methoxytebufenozide.

In an especially preferred embodiment, the present invention provides a method of controlling gene expression in a transgenic plant, comprising: expressing in the transgenic plant (i) a chimeric receptor polypeptide comprising a DNA binding (C) domain, a hinge (D) domain of a *Manduca sexta* ecdysone receptor, a ligand binding (E) domain of a *Manduca sexta* ecdysone receptor, and an activation domain; and (ii) a target expression cassette comprising a 5' regulatory region operatively linked to a target nucleotide sequence, wherein the 5' regulatory region comprises one or more response elements complementary to the DNA binding (C) domain of the chimeric receptor polypeptide; and contacting the transgenic plant with a chemical ligand that is complementary to the ligand binding (E) domain of the chimeric receptor polypeptide, whereby the chimeric receptor polypeptide in the presence of the chemical ligand activates expression of the target nucleotide sequence. Preferably, the DNA binding (C) domain is a GAL4 DNA binding domain. Also, preferably, the activation domain of the chimeric receptor polypeptide is a VP16 activation domain, a maize C1 activation domain, or a maize Dof1 activation domain. Further, preferably, the chemical ligand is tebufenozide or methoxytebufenozide.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO:1 shows a nucleotide sequence that encodes the ecdysone receptor of *Manduca sexta* (tobacco hornworm).

SEQ ID NO:2 shows the amino acid sequence of the *Manduca sexta* ecdysone receptor encoded by SEQ ID NO:1.

SEQ ID NO:3 shows the 5' end of a nucleotide sequence that encodes the ecdysone receptor of *Ostrinia nubilalis* (European cornborer).

SEQ ID NO:4 shows the amino acid sequence of the N-terminus of the *Ostrinia nubilalis* ecdysone receptor encoded by SEQ ID NO:3.

SEQ ID NO:5 shows the 3' end of a nucleotide sequence that encodes the ecdysone receptor of *Ostrinia nubilalis* (European cornborer).

SEQ ID NO:6 shows the amino acid sequence of the C-terminus of the *Ostrinia nubilalis* ecdysone receptor encoded by SEQ ID NO:5. SEQ ID NO:4 and SEQ ID NO:6 collectively comprise the A/B, C, D, and E domains of the *Ostrinia nubilalis* ecdysone receptor.

SEQ ID NO:7 shows the 3' end of a nucleotide sequence that encodes the ecdysone receptor of *Spodoptera frugipera* (Fall armyworm).

SEQ ID NO:8 shows the amino acid sequence of the C-terminus (a portion of the D domain and the full E domain) of the *Spodoptera frugipera* ecdysone receptor encoded by SEQ ID NO:7.

SEQ ID NO:9 shows the 3' end of a nucleotide sequence that encodes the ecdysone receptor of *Agrotis ipsilon* (Black cutworm).

SEQ ID NO:10 shows the amino acid sequence of the C-terminus (a portion of the D domain and the full E domain) of the *Agrotis ipsilon* ecdysone receptor encoded by SEQ ID NO:9.

SEQ ID NO:11 shows a nucleotide sequence that encodes the ecdysone receptor of *Locusta migratoria* (migratory locust).

SEQ ID NO:12 shows the amino acid sequence of the *Locusta migratoria* ecdysone receptor encoded by SEQ ID NO:11.

SEQ ID NO:13 shows a nucleotide sequence that encodes the ecdysone receptor of *Chironomus tentans*.

SEQ ID NO:14 shows the amino acid sequence of the *Chironomus tentans* ecdysone receptor encoded by SEQ ID NO:13.

SEQ ID NO:15 through SEQ ID NO:41 are oligonucleotide primers.

SEQ ID NO:42 shows the nucleotide sequence of the inserted region in pCGS154.

SEQ ID NO:43 through SEQ ID NO:60 are oligonucleotide primers.

SEQ ID NO:61 and SEQ ID NO:62 collectively show a double stranded oligonucleotide used to create a multiple cloning site (MCS), which has the recognition sequences for restriction enzymes SmaI, SalI, EcoRI, BspEI, HindIII, and XbaI.

SEQ ID NO:63 shows the nucleotide sequence that encodes the ecdysone receptor chimera MDV, which comprises the *Manduca sexta* C and D domains, the *Drosophila melanogaster* E domain, and the VP16 Activation domain. Nucleotides 1–1263 code for the EcR C, D, and E domains, whereas nucleotides 1264–1506 code for the VP16 Activation domain.

SEQ ID NO:64 shows the amino acid sequence of the ecdysone receptor chimera MDV encoded by SEQ ID NO:63. Amino acids 1–421 constitute the C, D, and E domains of the receptor chimera.

SEQ ID NO:65 shows the nucleotide sequence that encodes the ecdysone receptor chimera MBV, which comprises the *Manduca sexta* C and D domains, the black cutworm (*Agrotis ipsilon*) E domain, and the VP16 Activation domain. Nucleotides 1–1266 code for the EcR C, D, and E domains, whereas nucleotides 1267–1509 code for the VP16 Activation domain.

SEQ ID NO:66 shows the amino acid sequence of the ecdysone receptor chimera MBV encoded by SEQ ID NO:65. Amino acids 1–422 constitute the C, D, and E domains of the receptor chimera.

SEQ ID NO:67 shows the nucleotide sequence that encodes the ecdysone receptor chimera MEV, which comprises the *Manduca sexta* C and D domains, the European corn borer (*Ostrinia nubilalis*) E domain, and the VP16 Activation domain. Nucleotides 1–1257 code for the EcR C, D, and E domains, whereas nucleotides 1258–1500 code for the VP16 Activation domain.

SEQ ID NO:68 shows the amino acid sequence of the ecdysone receptor chimera MEV encoded by SEQ ID NO:67. Amino acids 1–419 constitute the C, D, and E domains of the receptor chimera.

SEQ ID NO:69 shows the nucleotide sequence that encodes the ecdysone receptor chimera MFV, which comprises the *Manduca sexta* C and D domains, the fall armyworm (*Spodoptera frugipera*) E domain, and the VP16 Activation domain. Nucleotides 1–1257 code for the EcR C, D, and E domains, whereas nucleotides 1258–1500 code for the VP16 Activation domain.

SEQ ID NO:70 shows the amino acid sequence of the ecdysone receptor chimera MFV encoded by SEQ ID NO:69. Amino acids 1–419 constitute the C, D, and E domains of the receptor chimera.

SEQ ID NO:71 shows the nucleotide sequence that encodes the ecdysone receptor chimera DMV, which comprises the *Drosophila melanogaster* C and D domains, the *Manduca sexta* E domain, and the VP16 Activation domain. Nucleotides 1–1308 code for the EcR C, D, and E domains, whereas nucleotides 1309–1551 code for the VP16 Activation domain.

SEQ ID NO:72 shows the amino acid sequence of the ecdysone receptor chimera DMV encoded by SEQ ID NO:71. Amino acids 1–436 constitute the C, D, and E domains of the receptor chimera.

SEQ ID NO:73 shows the nucleotide sequence that encodes the ecdysone receptor chimera DBV, which comprises the *Drosophila melanogaster* C and D domains, the black cutworm (*Agrotis ipsilon*) E domain, and the VP16 Activation domain. Nucleotides 1–1299 code for the EcR C, D, and E domains, whereas nucleotides 1300–1542 code for the VP16 Activation domain.

SEQ ID NO:74 shows the amino acid sequence of the ecdysone receptor chimera DBV encoded by SEQ ID NO:73. Amino acids 1–433 constitute the C, D, and E domains of the receptor chimera.

SEQ ID NO:75 shows the nucleotide sequence that encodes the ecdysone receptor chimera EEV, which comprises the European corn borer (*Ostrinia nubilalis*) C and D domains, the European corn borer E domain, and the VP16 Activation domain. Nucleotides 1–1272 code for the EcR C, D, and E domains, whereas nucleotides 1273–1515 code for the VP16 Activation domain.

SEQ ID NO:76 shows the amino acid sequence of the ecdysone receptor chimera EEV encoded by SEQ ID NO:75. Amino acids 1–424 constitute the C, D, and E domains of the receptor chimera.

SEQ ID NO:77 shows the nucleotide sequence that encodes the ecdysone receptor chimera EBV, which comprises the European corn borer (*Ostrinia nubilalis*) C and D domains, the black cutworm (*Agrotis ipsilon*) E domain, and the VP16 Activation domain. Nucleotides 1–1281 code for the EcR C, D, and E domains, whereas nucleotides 1282–1524 code for the VP16 Activation domain.

SEQ ID NO:78 shows the amino acid sequence of the ecdysone receptor chimera EBV encoded by SEQ ID NO:77. Amino acids 1–427 constitute the C, D, and E domains of the receptor chimera.

SEQ ID NO:79 shows the nucleotide sequence that encodes the ecdysone receptor chimera EMV, which comprises the European corn borer (*Ostrinia nubilalis*) C and D domains, the *Manduca sexta* E domain, and the VP16 Activation domain. Nucleotides 1–1290 code for the EcR C, D, and E domains, whereas nucleotides 1291–1533 code for the VP16 Activation domain.

SEQ ID NO:80 shows the amino acid sequence of the ecdysone receptor chimera EMV encoded by SEQ ID NO:79. Amino acids 1–430 constitute the C, D, and E domains of the receptor chimera.

SEQ ID NO:81 shows the nucleotide sequence that encodes the ecdysone receptor chimera LLV, which comprises the *Locusta migratoria* C and D domains, the *Locusta migratoria* E domain, and the VP16 Activation domain. Nucleotides 1–1194 code for the EcR C, D, and E domains, whereas nucleotides 1195–1437 code for the VP16 Activation domain.

SEQ ID NO:82 shows the amino acid sequence of the ecdysone receptor chimera LLV encoded by SEQ ID NO:81. Amino acids 1–398 constitute the C, D, and E domains of the receptor chimera.

SEQ ID NO:83 shows the nucleotide sequence that encodes the ecdysone receptor chimera LMV, which comprises the *Locusta migratoria* C and D domains, the *Manduca sexta* E domain, and the VP16 Activation domain. Nucleotides 1–1221 code for the EcR C, D, and E domains, whereas nucleotides 1222–1464 code for the VP16 Activation domain.

SEQ ID NO:84 shows the amino acid sequence of the ecdysone receptor chimera LMV encoded by SEQ ID NO:83. Amino acids 1–407 constitute the C, D, and E domains of the receptor chimera.

SEQ ID NO:85 shows the nucleotide sequence that encodes the ecdysone receptor chimera MLV, which comprises the *Manduca sexta* C and D domains, the *Locusta migratoria* E domain, and the VP16 Activation domain. Nucleotides 1–1248 code for the EcR C, D, and E domains, whereas nucleotides 1249–1491 code for the VP16 Activation domain.

SEQ ID NO:86 shows the amino acid sequence of the ecdysone receptor chimera MLV encoded by SEQ ID NO:85. Amino acids 1–416 constitute the C, D, and E domains of the receptor chimera.

SEQ ID NO:87 shows the nucleotide sequence that encodes the ecdysone receptor chimera CCV, which comprises the *Chironomus tentans* C and D domains, the *Chironomus tentans* E domain, and the VP16 Activation domain. Nucleotides 1–1308 code for the EcR C, D, and E domains, whereas nucleotides 1309–1551 code for the VP16 Activation domain.

SEQ ID NO:88 shows the amino acid sequence of the ecdysone receptor chimera CCV encoded by SEQ ID NO:87. Amino acids 1–436 constitute the C, D, and E domains of the receptor chimera.

SEQ ID NO:89 shows the nucleotide sequence that encodes the ecdysone receptor chimera CMV, which comprises the *Chironomus tentans* C and D domains, the *Manduca sexta* E domain, and the VP16 Activation domain. Nucleotides 1–1323 code for the EcR C, D, and E domains, whereas nucleotides 1324–1566 code for the VP16 Activation domain.

SEQ ID NO:90 shows the amino acid sequence of the ecdysone receptor chimera CMV encoded by SEQ ID NO:89. Amino acids 1–441 constitute the C, D, and E domains of the receptor chimera.

SEQ ID NO:91 shows the nucleotide sequence that encodes the ecdysone receptor chimera MCV, which comprises the *Manduca sexta* C and D domains, the *Chironomus tentans* E domain, and the VP16 Activation domain. Nucleotides 1–1260 code for the EcR C, D, and E domains, whereas nucleotides 1261–1503 code for the VP16 Activation domain.

SEQ ID NO:92 shows the amino acid sequence of the ecdysone receptor chimera MCV encoded by SEQ ID NO:91. Amino acids 1–420 constitute the C, D, and E domains of the receptor chimera.

SEQ ID NO:93 shows the nucleotide sequence that encodes the ecdysone receptor chimera MMV, which comprises the *Manduca sexta* C and D domains, the *Manduca sexta* E domain, and the VP16 Activation domain. Nucleotides 1–1275 code for the EcR C, D, and E domains, whereas nucleotides 1276–1518 code for the VP16 Activation domain.

SEQ ID NO:94 shows the amino acid sequence of the ecdysone receptor chimera MMV encoded by SEQ ID NO:93. Amino acids 1–425 constitute the C, D, and E domains of the receptor chimera.

SEQ ID NO:95 shows the nucleotide sequence that encodes the ecdysone receptor chimera DDV, which comprises the *Drosophila melanogaster* C and D domains, the *Drosophila melanogaster* E domain, and the VP16 Activation domain. Nucleotides 1–1296 code for the EcR C, D, and E domains, whereas nucleotides 1297–1539 code for the VP16 Activation domain.

SEQ ID NO:96 shows the amino acid sequence of the ecdysone receptor chimera DDV encoded by SEQ ID NO:95. Amino acids 1–432 constitute the C, D, and E domains of the receptor chimera.

SEQ ID NO:97 through SEQ ID NO:102 are oligonucleotide primers.

SEQ ID NO:103 shows the nucleotide sequence of the reporter fragment cloned into pCGS601.

SEQ ID NO:104 shows the nucleotide sequence (nucleotides 2007–3668) that encodes the ecdysone receptor chimera G(M)MV, which comprises the GAL4 DNA Binding Domain, the *Manduca* D and E Domains, and the VP16 Activation Domain, as contained in pCGS202.

SEQ ID NO:105 shows the amino acid sequence of the ecdysone receptor chimera G(M)MV encoded by nucleotides 2007–3668 of SEQ ID NO:104. Amino acids 1–147 constitute the GAL4 DNA Binding Domain, amino acids 148–473 constitute the *Manduca* D and E Domains, and amino acids 474–553 constitute the VP16 Activation domain.

SEQ ID NO:106 shows the nucleotide sequence of the maize Adh intron number 1.

SEQ ID NO:107 shows the nucleotide sequence of the maize shrunken (Sh) intron number 1.

SEQ ID NO:108 shows the nucleotide sequence of the maize ubiquitin intron number 1 SEQ ID NO:109 shows the nucleotide sequence of the rice actin intron.

SEQ ID NO:110 through SEQ ID NO:117 are oligonucleotide primers.

SEQ ID NO:118 shows the nucleotide sequence that encodes the ecdysone receptor chimera G(M)BV, which comprises the GAL4 DNA Binding Domain, the *Manduca* D and E Domains, and the VP16 Activation Domain. Nucleotides 1–564 code for the GAL4 DNA Binding Domain; nucleotides 565–848 code for the *Manduca* hinge (D) domain; nucleotides 849–1533 code for the BCW (*Agrotis ipsilon*) ligand binding (E) domain; and nucleotides 1534–1776 code for the VP16 Activation Domain.

SEQ ID NO:119 shows the amino acid sequence of the ecdysone receptor chimera G(M)BV encoded by SEQ ID NO:118.

SEQ ID NO:120 shows the nucleotide sequence that encodes the ecdysone receptor chimera G(M)EV, which comprises the GAL4 DNA Binding Domain, the *Manduca* D Domain, the ECB (*Ostrinia nubilalis*) Ligand Binding (E) Domain, and the VP16 Activation Domain. Nucleotides 1–564 code for the GAL4 DNA Binding Domain; nucleotides 565–848 code for the *Manduca* hinge (D) domain; nucleotides 849–1524 code for the ECB (*Ostrinia nubilalis*) ligand binding (E) domain; and nucleotides 1525–1767 code for the VP16 Activation Domain.

SEQ ID NO:121 shows the amino acid sequence of the ecdysone receptor chimera G(M)EV encoded by SEQ ID NO:120.

SEQ ID NO:122 shows the nucleotide sequence that encodes the ecdysone receptor chimera G(M)FV, which comprises the GAL4 DNA Binding Domain, the *Manduca* D Domain, the FAW (*Spodoptera frugipera*) Ligand Binding (E) Domain, and the VP16 Activation Domain. Nucleotides 1–564 code for the GAL4 DNA Binding Domain; nucleotides 565–848 code for the *Manduca* hinge (D) domain; nucleotides 849–1524 code for the FAW (*Spodoptera frugipera*) ligand binding (E) domain; and nucleotides 1525–1767 code for the VP16 Activation Domain.

SEQ ID NO:123 shows the amino acid sequence of the ecdysone receptor chimera G(M)FV encoded by SEQ ID NO:122.

SEQ ID NO:124 shows the nucleotide sequence that encodes the ecdysone receptor chimera G(E)EV, which comprises the GAL4 DNA Binding Domain, the ECB (*Ostrinia nubilalis*) D Domain, the ECB (*Ostrinia nubilalis*) Ligand Binding (E) Domain, and the VP16 Activation Domain. Nucleotides 1–564 code for the GAL4 DNA Binding Domain; nucleotides 565–863 code for the ECB (*Ostrinia nubilalis*) hinge (D) domain; nucleotides 864–1539 code for the ECB (*Ostrinia nubilalis*) ligand binding (E) domain; and nucleotides 1540–1782 code for the VP16 Activation Domain.

SEQ ID NO:125 shows the amino acid sequence of the ecdysone receptor chimera G(E)EV encoded by SEQ ID NO:124.

SEQ ID NO:126 shows the nucleotide sequence that encodes the ecdysone receptor chimera G(E)MV, which comprises the GAL4 DNA Binding Domain, the ECB (*Ostrinia nubilalis*) D Domain, the *Manduca* Ligand Binding (E) Domain, and the VP16 Activation Domain. Nucleotides 1–564 code for the GAL4 DNA Binding Domain; nucleotides 565–863 code for the ECB (*Ostrinia nubilalis*) hinge (D) domain; nucleotides 864–1557 code for the *Manduca* ligand binding (E) domain; and nucleotides 1558–1800 code for the VP16 Activation Domain.

SEQ ID NO:127 shows the amino acid sequence of the ecdysone receptor chimera G(E)MV encoded by SEQ ID NO:126.

SEQ ID NO:128 shows the G(M)M (GAL4 DNA Binding Domain fused to the *Manduca* EcR Hinge and Ligand Binding Domain) chimeric receptor nucleotide coding sequence.

SEQ ID NO:129 shows the amino acid sequence of the GAL4 DNA Binding Domain fused to the *Manduca* EcR Hinge and Ligand Binding Domain encoded by SEQ ID NO:128.

SEQ ID NO:130 through SEQ ID NO:133 are oligonucleotide primers.

SEQ ID NO:134 shows the nucleotide sequence that encodes the ecdysone receptor chimera G(M)MC, which comprises the GAL4 DNA Binding Domain, the *Manduca* D Domain, the *Manduca* Ligand Binding (E) Domain, and the maize C1 Activation Domain.

SEQ ID NO:135 shows the amino acid sequence of the ecdysone receptor chimera G(M)MC encoded by SEQ ID NO:134.

SEQ ID NO:136 shows the nucleotide sequence that encodes the ecdysone receptor chimera G(M)MD, which comprises the GAL4 DNA Binding Domain, the *Manduca* D Domain, the *Manduca* Ligand Binding (E) Domain, and the maize Dof1 Activation Domain.

SEQ ID NO:137 shows the amino acid sequence of the ecdysone receptor chimera G(M)MD encoded by SEQ ID NO:136.

SEQ ID NO:138 through SEQ ID NO:141 are oligonucleotide primers.

SEQ ID NO:142 shows the nucleotide sequence that encodes the ecdysone receptor chimera VG(M)M, which comprises the VP16 Activation Domain, the GAL4 DNA Binding Domain, the *Manduca* D Domain, and the *Manduca* Ligand Binding (E) Domain.

SEQ ID NO:143 shows the amino acid sequence of the ecdysone receptor chimera VG(M)M encoded by SEQ ID NO:142.

SEQ ID NO:144 through SEQ ID NO:146 are oligonucleotide primers.

SEQ ID NO:147 shows the nucleotide sequence that encodes the ecdysone receptor chimera GV(M)M, which comprises the GAL4 DNA Binding Domain, the VP16 Activation Domain, the *Manduca* D Domain, and the *Manduca* Ligand Binding (E) Domain.

SEQ ID NO:148 shows the amino acid sequence of the ecdysone receptor chimera GV(M)M encoded by SEQ ID NO:147.

DEFINITIONS

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric" gene is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

In the context of the present invention, the term "chimeric" is also used to indicate that the receptor polypeptide is comprised of domains, at least one of which has an origin that is heterologous with respect to the other domains present. These chimeric receptor polypeptides are encoded by nucleotide sequences that have been fused or ligated together resulting in a coding sequence that does not occur naturally.

Chimeric receptor polypeptides of the present invention are referenced by a linear nomenclature from N-terminal to C-terminal portion of the polypeptide. Using this nomenclature, a chimeric receptor polypeptide having the transactivation domain from VP16 fused to the N-terminal end of the EcR receptor would be designated as VP16-EcR. Conversely, if VP16 is fused to the C-terminus of the EcR receptor, the chimeric receptor polypeptide would be designated EcR-VP16.

Chimeric receptor polypeptides of the present invention are alternately referenced by a linear triplet or linear quartet nomenclature to indicate which domains are present in the construct in N-terminal to C-terminal orientation. In the case of triplet nomenclature, the first letter of the triplet corresponds to the origin of the DNA binding and hinge domains; the second letter of the triplet indicates the origin of the ligand binding domain; and the last letter of the triplet indicates the activation domain. In this manner, the chimeric receptors are designated in the table set forth in Example 5. For example, the MDV EcR chimera comprises the DNA binding and hinge domains from *Manduca sexta*, the ligand binding domain from *Drosophila melanogaster* and the activation domain of VP16; and the MBV EcR chimera comprises the DNA binding and hinge domains from *Manduca sexta*, the ligand binding domain from *Agrotis ipsilon* (Black cutworm) and the activation domain of VP16.

In the case of quartet nomenclature, the first letter of the quartet corresponds to the origin of the DNA binding domain; the second letter of the quartet (which is in brackets) corresponds to the origin of the hinge domain; the third letter of the quartet indicates the origin of the ligand binding domain; and the last letter of the quartet indicates the activation domain. In this manner, the chimeric receptors are designated in the table set forth in Example 23. For example, the G(M)EV EcR chimera comprises the yeast GAL4 DNA binding domain, the hinge domain from *Manduca sexta*, the ligand binding domain from European corn borer (*Ostrinia nubilalis*), and the VP16 activation domain; and the G(M)MV EcR chimera comprises the yeast GAL4 DNA binding domain, the hinge domain from *Manduca sexta*, the ligand binding domain from *Manduca sexta*, and the VP16 activation domain.

Gene constructions are denominated in terms of a 5' regulatory region and its operably-linked coding sequence, where the 5' regulatory region is designated before a slash mark (/) and the coding sequence designated after the slash mark. For example, the gene construction ubi/EcR-VP16 designates the ubiquitin promoter (of e.g. *Zea mays*) fused to the chimeric receptor EcR-VP16, where the transactivation domain of VP16 is fused to the C-terminal end of EcR.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins*, W. H. Freeman and Company. In addition, individual substitutions, deletions or additions which alter, add or delete a single amino acid or a small percentage of amino acids in an encoded sequence are also "conservatively modified variations."

A "DNA binding domain" (a.k.a. "C domain") is the portion of a receptor polypeptide that comprises a sequence of amino acids that binds non-covalently a specific nucleotide sequence known as a response element (RE). In nuclear receptors, response elements are located in the 5' regulatory region of a target expression cassette and comprise a pair of half-sites, each half-site having a 6 base pair core wherein a single DNA binding domain recognizes a single half-site. The half-sites may be arranged in relative linear orientation to each other as either direct repeats, palindromic repeats, or inverted repeats. A response element binds either a homodimer or heterodimer of receptor polypeptides. The nucleotide sequence and linear orientation of the half-sites determines which DNA binding domain or domains will form a complementary binding pair with said response element, as well as the ability of receptor polypeptides to interact with each other in a dimer.

"Ecdysone receptor" ("EcR") refers to the receptors found in certain insects that are known to bind ecdysone as their ligand or that have high homology with previously isolated ecdysone receptors from other insects. Ecdysone receptors have been isolated from a number of insects including dipteran, coleopteran, and lepidopteran insects.

"Expression cassette" as used herein means a nucleic acid sequence capable of directing expression of a particular nucleotide sequence in an appropriate host cell, comprising a promoter operatively linked to the nucleotide sequence of interest, which is operatively linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and has been introduced into the host cell or an ancestor of the host cell by a transformation event. The expression of the nucleotide sequence in the expression cassette may be under the control of either a constitutive promoter or an inducible promoter that initiates transcription only when the host cell is exposed to some particular external stimulus. In the case of a multicellular organism, such as a plant, the promoter can also be specific to a particular tissue, or organ, or stage of development.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. "Gene of interest" refers to any gene which, when transferred to a host organism, confers upon the host a desired characteristic. In the case of plant hosts, desired characteristics include antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to a host organism, e.g. a plant, for the production of commercially valuable enzymes or metabolites in the host.

Heterologous/exogenous: The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of codon optimization. The terms also includes non-naturally occurring multiple copies of a naturally occurring sequence. Thus, the terms refer to a nucleic acid segment that is foreign or heterologous to the cell, or homologous to the cell but in a position within the host cell nucleic acid in which the element is not ordinarily found. Exogenous nucleic acid segments are expressed to yield exogenous polypeptides. For example, in the context of the present invention, "heterologous" is used to indicate that a receptor polypeptide has a different natural origin with respect to its current host. For example, if the ecdysone receptor (EcR) from an insect species is expressed in a plant cell, then the EcR is described as being heterologous with respect to its current host, which is the plant cell. "Heterologous" is also used to indicate that one or more of the domains present in a receptor polypeptide differ in their natural origin with respect to other domains present. For example, if the transactivation domain from the herpes simplex VP16 protein is fused to the ecdysone receptor from *Manduca sexta*, then the VP16 transactivation domain is heterologous with respect to the EcR-moiety. Furthermore, if a domain from *Manduca sexta* EcR is fused to a domain from *Agrotis epsilon* EcR to make a functional receptor, then the chimeric fusion would have domains that are heterologous with respect to each other. In addition, a heterologous receptor polypeptide comprising the fusion of the VP16 protein to the *Manduca sexta* ecdysone receptor, when expressed in a plant, would also be considered heterologous with respect to the plant host.

A "hinge domain" (a.k.a. "D domain") is the portion of a receptor polypeptide that comprises the amino acids between the DNA binding (C) domain and ligand binding (E) domain. The hinge domain may participate in the interaction of the receptor polypeptide with another receptor polypeptide to form either a homodimer or heterodimer.

A "homologous" nucleic acid (e.g. DNA) sequence is a nucleic acid (e.g. DNA) sequence naturally associated with a host cell into which it is introduced. For example, in the context of the present invention, "homologous" is used to indicate that a receptor polypeptide has the same natural origin with respect to its current host. For example, the ecdysone receptor is found in certain insect species and is said to be homologous with respect to the insect species in which it originates. "Homologous" is also used to indicate that one or more of the domains present in a receptor polypeptide have the same natural origin with respect to each other. For example, the DNA binding domain and the ligand binding domain of *Manduca sexta* EcR are considered to be of a homologous origin with respect to each other.

"Homologous recombination" is the reciprocal exchange of nucleic acid fragments between homologous nucleic acid molecules.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described below or by visual inspection.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "ligand binding domain" (a.k.a. "E domain") is the portion of a receptor polypeptide that comprises a sequence of amino acids whose structure binds non-covalently a chemical ligand. Hence, a ligand binding domain and its chemical ligand form a binding pair.

Mature Protein: protein that is normally targeted to a cellular organelle and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

A "moiety" refers to that share or portion of a receptor polypeptide that is derived from the indicated source. For example, "EcR-moiety" refers to that portion of the receptor polypeptide that was derived from a native ecdysone receptor. A "moiety" as used herein may comprise one or more domains.

Native: refers to a gene that is present in the genome of an untransformed cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" may also be used interchangeably with gene, cDNA, and mRNA encoded by a gene.

"ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

A "receptor cassette" as used herein comprises a nucleotide sequence that encodes a receptor polypeptide.

A "receptor expression cassette" as used herein comprises a nucleotide sequence for a 5' regulatory region, e.g. a promoter that permits expression in plant tissues, operatively linked to a nucleotide sequence that encodes a receptor polypeptide and an untranslated 3' termination region (stop codon and polyadenylation sequence).

"Receptor polypeptide" as used herein refers to a polypeptide that activates the expression of a target gene of interest or target expression cassette in response to an applied chemical ligand. The receptor polypeptide is comprised of a ligand binding domain, a DNA binding domain and a transactivation domain.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination. "Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Substantially identical: the phrase "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al.,

*J. Mol. Biol.* 215: 403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

A "subsequence" refers to a sequence of nucleic acids or amino acids that comprise a part of a longer sequence of nucleic acids or amino acids (e.g., protein) respectively.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

A "target expression cassette" comprises a nucleotide sequence for a 5' regulatory region operatively linked to a target nucleotide sequence, the expression of which is activated by a receptor polypeptide in the presence of a chemical ligand. The 5' regulatory region of the target gene comprises a core promoter sequence, an initiation of transcription sequence and the one or more response elements necessary for complementary binding of the DNA binding domain of the receptor polypeptide. The promoter sequence may be a minimal promoter. The target expression cassette also possesses a 3' termination region (stop codon and polyadenylation sequence). The target nucleotide sequence may encode a polypeptide or expression of the target nucleotide sequence may result in an RNA species that itself is active, such as an antisense RNA or a double-stranded RNA molecule.

A "transcriptional activation domain" or "transactivation domain" or "activation domain" (a.k.a. "A/B domain") is the portion of a receptor polypeptide that comprises one or more sequences of amino acids acting as subdomains that affect the operation of transcription factors during preinitiation and assembly at the TATA box. The effect of the transactivation domain is to allow repeated transcription initiation events, leading to greater levels of gene expression.

"Transformation" is a process for introducing heterologous nucleic acid into a host cell or organism. In particular, "transformation" means the stable integration of a DNA molecule into the genome of an organism of interest. Transformed cells, tissues, or insects are understood to encompass not only the end product of a transformation process, but also transgenic progeny thereof.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DETAILED DESCRIPTION OF THE INVENTION

I. Native and Chimeric Receptor Polypeptides

The present invention comprises a receptor cassette encoding a receptor polypeptide. In a preferred embodiment, the receptor polypeptide is composed of a hinge region, a ligand binding domain, a DNA binding domain, and a transactivation domain. The DNA binding domain binds the receptor polypeptide to the 5' regulatory region of a target expression cassette at the site of its response element. The hinge domain of the receptor polypeptide resides between the DNA binding and ligand binding domains and influences the activity of the ligand binding domain. The ligand binding domain of the receptor polypeptide binds, when present, a complementary chemical ligand. Binding of the chemical ligand causes a conformational change in the receptor polypeptide and allows the transactivation domain to affect transcription of the target nucleotide sequence, resulting in production of, e.g., an encoded polypeptide, an antisense RNA, or a double-stranded RNA molecule.

The chimeric receptor polypeptides used in the present invention may have one or more domains obtained from a heterologous source. The use of chimeric receptor polypeptides has the benefit of combining domains from different sources, thus providing a receptor polypeptide activated by a choice of chemical ligands and possessing desirable ligand binding, DNA binding and transactivation characteristics.

Chimeric receptor polypeptides may be used in the present invention to activate expression of a target nucleotide sequence that, e.g., encodes a target polypeptide. One or more of the four domains of a receptor polypeptide may be chosen from a heterologous source based upon their effectiveness for transactivation, DNA binding, or chemical ligand binding. The DNA binding (C) and transactivation (A/B) domains of the chimeric receptor polypeptide may also be obtained from any organism, such as plants, insects and mammals, which has similar transcriptional regulating functions. The hinge (D) and ligand binding (E) domains of the chimeric receptor polypeptide are preferably chosen from insect ecdysone receptors. In one embodiment of the invention, the hinge (D) and ligand binding (E) domains are each selected from the ecdysone receptor of a different insect. Chimeric receptor polypeptides as provided herein offer the advantage of combining optimum transactivating activity, complementary binding of a selected chemical ligand, and recognition of a specific response element. Thus, a chimeric polypeptide may be constructed that is tailored for a specific purpose. These chimeric receptor polypeptides also provide improved functionality.

It is also considered a part of the present invention that the transactivation (A/B), ligand-binding (E), and DNA-binding (C) domains may be assembled in the chimeric receptor polypeptide in any functional arrangement. For example, where one subdomain of a transactivation domain is found at the N-terminal portion of a naturally-occuring receptor, the chimeric receptor polypeptide of the present invention may include a transactivation domain at the C-terminus in place of, or in addition to, a transactivation domain at the N-terminus. Chimeric receptor polypeptides as disclosed herein may also have multiple domains of the same type, for example, more than one transactivation domain per receptor polypeptide.

Chimeric receptor casettes and chimeric receptor polypeptides may be constructed from domains available from ecdysone receptors of the natural insect population. Numerous ecdysone receptors are available and can be used with the present invention. These ecdysone receptors include but are not limited to ecdysone receptors from *Drosophila melanogaster* (genbank accession M74078; Koelle et al. (1991) *Cell* 67: 59–77), *Manduca sexta* (genbank accession U19812; Fujiwara et al. (1995) *Insect Biochem Mol Biol.* 25: 845–856), *Bombyx mori* (genbank accessions L35266 and D43943; Swevers et al. (1995) *Insect Biochem Mol Biol* 25: 857–866), *Ostrinia nubilalis* (WO 00/15791A1), *Chironomus tentans* (genbank accession S60739), *Spodoptera exigua* (WO 96/37609), *Locusta migratoria* (genbank accession AF049136; Saleh et al. (1998) *Mol Cell Endocrinol* 143: 91–99), *Choristoneura fumiferana* (genbank accession U29531; Kothapalli et al. (1995) *Dev. Genet.* 17: 319–330) and *Heliothis virescens* (WO 96/37609). In an additional embodiment of the present invention, novel ecdysone receptor domains are cloned from the insect ecdysone receptors of *Agrotis ipsilon* and *Spodoptera frugiperda*.

A. The Ligand Binding Domain

The ligand binding (E) domain of the receptor polypeptide provides the means by which the 5' regulatory region of the target expression cassette is activated in response to the presence of a chemical ligand. The ecdysone receptor (EcR) from *Drosophila* is one example of a receptor polypeptide where complementary chemical ligands have been identified that bind to the ligand binding domain. The steroid hormone ecdysone triggers coordinate changes in tissue development that results in metamorphosis, and ecdysone has been shown to bind to EcR. (Koelle et al., *Cell* 67: 59–77 (1991)). The plant-produced analog of ecdysone, muristerone, also binds to the ligand binding domain of EcR. Other chemicals, such as the non-steroidal ecdysone agonists RH 5849 (Wing, *Science* 241: 467–469 (1988)), RH-2485 (methoxyfenozide, Dhadialla et al. (1998) Annu Rev Entom 43: 545–569) and RH 5992 (tebufenozide), the latter known as the insecticide MIMIC®, also will act as a chemical ligand for the ligand binding domain of EcR. See also, Dhadialla et al., *Annu. Rev. Entomol.* 43:545–569 (1998), incorporated herein by reference, which describes several insecticides with ecdysteroidal and juvenile hormone activity.

The ecdysone receptors from different insects generally have homology among their amino acid sequences. The ligand binding domain of EcR's from closely related insects shows high homology whereas EcR's from less closely related species are more divergent in their amino acid sequences. In one embodiment of the present invention, the ligand binding domain of the chimeric receptor polypeptide is from the ecdysone receptor of an insect selected from the group consisting of *Manduca sexta, Agrotis ipsilon, Ostrinia nubilalis, Spodoptera frugiperda, Locusta migratoria*, and *Chironomus tentans*. In a preferred embodiment, the ligand binding domain is from the ecdysone receptor of *Manduca sexta, Agrotis ipsilon, Ostrinia nubilalis, Spodoptera frugiperda*, or *Chironomus tentans*. These ligand binding domains confer high level activity upon the chimeric receptor polypeptide when the receptor polypeptide is expressed in a cell along with a target expression cassette and exposed to a ligand.

The choice of chemical ligand will depend on which ligand binding domains are present in the receptor polypeptide. Any chemical compound will suffice as long as it is shown to form a complementary binding pair with the chosen ligand binding domain. When a naturally-occuring compound is known to form a complementary binding pair with a particular ligand binding domain, these known compounds also find use in the present invention. Particularly useful chemicals include but are not limited to insecticides that form a complementary binding pair with the ligand binding domain. Such chemicals include but are not limited to hormones, hormone agonists, and hormone antagonists whose function as insecticides can be acscribed to their binding to native receptor proteins in insects. In addition, chemicals with these hormone or hormone-related properties which are known as insecticides have the additional benefit of already having been examined for agricultural production, making such chemicals "ready-to-use" for field application to crops. Useful chemicals with these properties include but are not limited to RH 5849, RH-2485 (methoxyfenozide), and RH 5992 (tebufenozide), B. The Hinge Domain The hinge (D) domain is defined as amino acids of the receptor polypeptide between the DNA binding (C) and ligand binding (E) domains. The activities ascribed to this region are the abilities of the receptor polypeptide to interact with itself in a homodimer or with a second heterologous receptor polypeptide in a heterodimer. Mutations in the hinge region have been shown to alter the ability of the ecdysone receptor to interact with the ultraspiracle receptor and the RXR receptor. In the present invention, the hinge domain is used to modulate the activity of the chimeric receptor polypeptide. In one embodiment of the present invention, the hinge domain of the chimeric receptor polypeptide is from the ecdysone receptor of an insect selected from the group consisting of *Manduca sexta, Agrotis ipsilon, Ostrinia nubilalis, Spodoptera frugiperda, Locusta migratoria*, and *Chironomus tentans*. In a preferred embodiment, the hinge domain is from the ecdysone receptor of *Manduca sexta, Agrotis ipsilon, Ostrinia nubilalis, Spodoptera frugiperda*, or *Locusta migratoria*.

A preferred embodiment of the present invention provides chimeric receptor polypeptides wherein the hinge and ligand binding domains are, with respect to one another, selected from different insect ecdysone receptors. The combination of hinge and ligand binding domains in chimeric receptor polypeptides results in receptor polypeptides with novel activities in response to ligands.

C. The DNA Binding Domain and its Response Elements

The DNA binding (C) domain is a sequence of amino acids having certain functional features that are responsible for binding of the receptor polypeptide to a specific sequence of nucleotides, the response elements, which are present in the 5' regulatory region of the target expression cassette. In one embodiment of the invention, the DNA binding domain is obtained from an insect ecdysone receptor and contains cysteine residues arranged in such a way that, when coordinated by zinc ions, forms the so-called "zinc-finger" motif. The structure of DNA binding domains for the insect ecdysone receptors is highly conserved from one insect species to another, and consequently there is limited variation in the response elements used to form a complementary binding pair (Evans, *Science* 240: 889–895 (1988)). Nevertheless, considerable flexibility can be introduced into the method of controlling gene expression by using these conserved response elements in other ways. In a preferred embodiment of the invention, multiple copies of the appropriate response element are placed in the 5' regulatory region, which allows multiple sites for binding of receptor polypeptide resulting in a greater degree of activation.

Additional flexibility in controlling gene expression by the present invention may be obtained by using DNA binding domains and response elements from other transcriptional activators, which include but are not limited to the LexA or GAL4 proteins. The DNA binding domain from the LexA protein encoded by the lexA gene from *E. coli* and its complementary binding site (Brent and Ptashne, *Cell* 43: 729–736 (1985), which describes a LexA/GAL4 transcriptional activator) can be utilized. Another useful source is from the GAL4 protein of yeast (Sadowski et al., *Nature* 335: 563–564 (1988), which describes a GAL4-VP16 transcriptional activator). In one preferred embodiment of the invention, a chimeric receptor polypeptide is constructed by fusing the GAL4 DNA binding domain to a moiety containing the hinge and ligand binding domains from *Manduca* EcR, which can control expression of a target expression cassette.

An additional degree of flexibility in controlling gene expression can be obtained by using synthetic DNA binding domains and response elements. Protein engineering experiments have shown that it is possible to rationally alter the DNA binding characteristics of zinc finger domains to bind to a DNA target sequence of choice (Liu et al., *Proc. Natl. Acad. Sci.* 94: 5525–5530 (1997); Desjarlais and Berg, *Proc. Natl. Acad. Sci.* 90: 2256–2260 (1993)). The use of a synthetic zinc finger binding domain allows the chimeric receptor polypeptide to recognize a target sequence of choice. This target sequence may be part of a target cassette transformed into a plant or may be a target sequence in the genome of a plant, to control expression of a native plant gene.

D. The Transactivation Domain

Transactivation (A/B) domains can be defined as amino acid sequences that, when combined with the DNA binding domain in a receptor polypeptide, increase productive transcription initiation by RNA polymerases. (See generally, Ptashne, *Nature* 335: 683–689 (1988); Meshi, *Plant Cell Physiol* 36: 1405–1420 (1995)). Different transactivation domains are known to have different degrees of effectiveness in their abilities to increase transcription initiation. In the present invention, it is desirable to use transactivation domains that have superior transactivating effectiveness in plant cells in order to create a high level of target expression cassette expression in response to the presence of chemical ligand. Transactivation domains that have been shown to be particularly effective in the method of the present invention include but are not limited to VP16 (Triezenberg, et al., *Genes and Dev.* 2(6): 718–729 (1988)—isolated from the herpes simplex virus) and C1 (Goff et al., *Genes and Dev.* 5:298–309 (1991)—isolated from maize), AP1 (isolated from *Arabidopsis*), and Dof1 (isolated from maize). In one preferred embodiment of the present invention, the transactivation domain from VP16 is fused to an EcR moiety for controlling target polypeptide expression in plants. Other transactivation domains may also be effective.

II. Repression of Gene Expression

As described above, the method of the present invention can be used to increase gene expression over a minimal, basal level. One of the outstanding benefits of the present method, however, is that it can also be used for decreasing or inhibiting gene expression, i.e., gene repression. A means of controlling gene expression through repression can be accomplished by using a repression domain in place of the transactivation domain. Repression domains can be defined as amino acid sequences that, when combined with the DNA binding domain in a receptor polypeptide, decrease the productive transcription initiation by RNA polymerases (Ng, *Trends Biochem. Sci.* 25:121–126 (2000)). Repression domains that can be used with the present invention to decrease expression of a target cassette include but are not limited to the repression domains of AtHD2A (Wu, *Plant J.* 22:19–27(2000)), Oshox1, and Oshox3 (Meijer, *Mol. Gen. Genet.* 263: 12–21 (2000)).

III. Controlling Gene Expression in Transgenic Plants

The invention further comprises a method of controlling plant gene expression comprising transforming a plant with the insect ecdysone receptor cassette encoding a chimeric receptor polypeptide, and at least one target expression cassette. The insect ecdysone receptor cassette is operatively linked with a 5' regulatory region capable of promoting expression in a plant cell, and a 3' terminating region. The target expression cassette comprises a 5' regulatory region operatively linked to a target nucleotide sequence, wherein the 5' regulatory region comprises one or more response elements complementary to the DNA binding domain of the receptor polypeptide. The target expression cassette is activated by the chimeric receptor polypeptide in the presence of one or more chemical ligands and the expression of the target nucleotide sequence is accomplished.

In accordance with a preferred embodiment of the invention, it has been discovered that a chimeric receptor polypeptide comprising the *Manduca* ecdysone receptor hinge and ligand binding domains activates high levels of expression of a target expression cassette in the presence of ligand. Thus a preferred embodiment of the present invention is a method of controlling gene expression in a plant comprising transforming a plant with a target expression cassette and a receptor expression cassette comprising a 5' regulatory region capable of promoting expression in a plant cell, a receptor cassette comprising a DNA binding domain, a hinge domain from the *Manduca sexta* ecdysone receptor, a ligand binding domain from the *Manduca sexta* ecdysone receptor, a transactivation domain, and a 3' terminating region. The target expression cassette is activated by the receptor polypeptide in the presence of one or more chemical ligands and the expression of the target nucleotide sequence is accomplished.

The chimeric receptor polypeptide encoded by the receptor cassette may be expressed in plants when it is operatively linked to a promoter that permits expression in plant tissues and cells. Appropriate promoters are chosen for the receptor expression cassettes so that expression of the receptor polypeptides may be constitutive, developmentally regulated, tissue specific, cell specific or cell compartment specific. Promoters may also be chosen so that expression of the receptor polypeptides themselves can be chemically-induced in the plant, thereby increasing the level of promoter induction by ligand. By combining promoter elements that confer specific expression with those conferring chemically-induced expression, the receptor polypeptides may be expressed or activated within specific cells or tissues of the plant in response to chemical application. The nucleotide sequence that encodes the receptor polypeptide may be modified for improved expression in plants, improved functionality, or both. Such modifications include, but are not limited to, altering codon usage, insertion of introns or creation of mutations.

Target polypeptides whose expression is activated by the receptor polypeptides in the presence of a chemical ligand are also disclosed. The expression of any coding sequence may be controlled by the present invention, provided that the promoter operatively linked to said coding sequence has been engineered to contain the response element or response elements that are complementary to the DNA binding domain of the receptor polypeptides used. For example, target polypeptides that are useful for controlling plant fertility are activated by the receptor polypeptides in the presence of a chemical ligand.

A. Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754–756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

Position Before the Initiating ATG in 14 Maize Genes

|   | -10 | -9 | -8 | -7 | -6 | -5 | -4 | -3 | -2 | -1 |
|---|-----|----|----|----|----|----|----|----|----|----|
| C | 3   | 8  | 4  | 6  | 2  | 5  | 6  | 0  | 10 | 7  |
| T | 3   | 0  | 3  | 4  | 3  | 2  | 1  | 1  | 1  | 0  |
| A | 2   | 3  | 1  | 4  | 3  | 2  | 3  | 7  | 2  | 3  |
| G | 6   | 3  | 6  | 0  | 6  | 5  | 4  | 6  | 1  | 5  |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

B. Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Callis et al., J. Biol. Chem. 265:12486–12493 (1990) and Norris et al., Plant Mol. Biol. 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., *Plant J.* 16:223–233 (1998) may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., *Plant Cell* 4: 645–656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4 minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103–106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wuni gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop*. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126–6130 (1989)); potyvirus leaders, for example, TEV leader (Tobacco Etch Virus) (Allison et al., 1986); MDMV leader (Maize Dwarf Mosaic Virus); *Virology* 154:9–20); human immunoglobulin heavy-chain binding protein (BiP) leader, (Macejak, D. G., and Sarnow, P., *Nature* 353: 90–94 (1991); untranslated leader from the coat protein mRNA of alfalfa mosaic virus (AMV RNA 4), (Jobling, S. A., and Gehrke, L., *Nature* 325:622–625 (1987); tobacco mosaic virus leader (TMV), (Gallie, D. R. et al., *Molecular Biology of RNA*, pages 237–256 (1989)); and Maize Chlorotic Mottle Virus leader (MCMV) (Lommel, S. A. et al., *Virology* 81:382–385 (1991). See also, Della-Cioppa et al., *Plant Physiology* 84:965–968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., *Plant Cell* 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) *Plant Mol Biol* 23: 995–1003; Green (2000) *Trends Biochem Sci* 25: 59–63)

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. *J. Biol. Chem.* 263: 15104–15109 (1988)). These signal sequences can be fused to heterologous gene products to effect the import of heterologous products into the chloroplast (van den Broeck, et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

C. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

a. pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB 10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

D. Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using *Agrobacterium* has also been described. See, WO 94/00977 and U.S. Pat. No. 5,591,616, both of which are incorporated herein by reference. See also, Negrotto et al., *Plant Cell Reports* 19: 798–803 (2000), incorporated herein by reference.

3. Transformation of Plastids

Seeds of *Nicotiana tabacum* c.v. 'Xanthi nc' are germinated seven per plate in a 1" circular array on T agar medium and bombarded 12–14 days after sowing with 1 $\mu$m tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 $\mu$mol photons/m$^2$/s) on plates of RMOP medium (Svab, Z., Hajdukiewicz, P. and Maliga, P. (1990) *PNAS* 87, 8526–8530) containing 500 $\mu$g/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

IV. Breeding and Seed Production

A. Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

B. Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual*, 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Cloning of Insect Ecdysone Receptors

PCR primers are designed based on the published sequence for *Manduca sexta* ecdysone receptor (EcR) (genbank accession number U19812 (SEQ ID NOs:1 and 2)) to clone the gene in two halves. RNA is prepared from prepupae larva of *Manduca sexta* using the LiCl/phenol method (Current protocols in molecular biology vol 1, unit 4.3, 1987, John Wiley and sons, publishers) and 1 µg of total RNA is used to prepare cDNA using MMLV reverse transcriptase (Promega). The cDNA is used in a PCR reaction with the primers described above to generate two PCR products for the 5' and 3' halves of the gene. These are subcloned into the pGEM-TA vector (Promega) and sequenced. The two fragments are joined at a unique NdeI site within each fragment and ligated into pBS-KS (Stratagene) to create a full length *Manduca sexta* EcR clone named pBSFLMa.

To clone additional lepidopteran ecdysone receptor domains, primers are designed based on homology between insect ecdysone receptors using the Align and Sequencher programs. The primers preferably used are 5'-gtgaagtgaaagcctacgtc-3' (SEQ ID NO:15) (upstream of the ATG) and 5'-tgacgcgctcttcgacatgagac-3' (SEQ ID NO:16) (starting before and including the ATG), and a degenerate primer 5'-ggytgytcrtabccbtcctggta-3' (SEQ ID NO:17) (where y=c/t, r=g/a and b=g/t/c) for the 5' half of each gene and primers 5'-ccbscsathatgcartgtgahc-3' (SEQ ID NO:18) and 5'-ccacrtcccagatctcctcga-3' (SEQ ID NO:19) (where b=g/t/c, h=a/t/c, r=a/g) for the 3' end of the genes. Total RNA is prepared from prepupae larva from black cutworm (BCW, *Agrotis ipsilon*), European corn borer (ECB, *Ostrinia nubilalis*) and fall army worm (FAW, *Spodoptera frugipera*) and used for reverse transcriptase and PCR reactions as described above. Products are cloned into pGEM-TA and sequenced. The following partial clones from the ecdysone receptors are obtained: ECB 5' end (SEQ ID NOs:3 and 4) and 3' end (SEQ ID NOs:5 and 6) (collectively comprising A/B, C, D and E domains); FAW 3' end (SEQ ID NOs:7 and 8) (comprising a portion of the D domain and the full E domain); and BCW 3' end (SEQ ID NOs:9 and 10) (comprising a portion of the D domain and the full E domain).

The ecdysone receptors of *Locusta migratoria* and *Chironomus tentans* are cloned using the published genbank sequence AF049136 (SEQ ID NOs:11 and 12), and S60739 (SEQ ID NOs:13 and 14), respectively, to design PCR primers. Partial cDNAs (comprising the C, D and E domains) are isolated, cloned in pGEM-TA and confirmed by sequencing.

Example 2

Construction of VP16 Transactivation Domain Fusions to Ecdysone Receptors (EcR's) and Cloning Into Insect Cell Expression Vectors A fragment containing the herpes simplex VP16 transactivation domain is cloned from plasmid 35S/USP-VP16 (U.S. Pat. No. 5,880,333) using the PCR primers 5'-aagcttgcccccccgaccg-3' (SEQ ID NO:20) (placing a HindIII site at the 5' end of the domain) and 5'-tctagaggatcctacccaccgtact-3' (SEQ ID NO:21) (placing an inframe stop codon followed by BamHI and XbaI sites at the 3' end of the domain).

A HindIII site followed by an inframe stop codon and BamHI site is placed at the 3' end of the E domain (ligand binding domain) of each cloned lepidopteran receptor using the oligonucleotides: 5'-ggatcctaaagcttcgtcgtcgacacttcg-3' (SEQ ID NO:22) (for *Manduca sexta* EcR), 5'-ggatcctaaagcttcccgcgggattccacg-3' (SEQ ID NO:23) (for black cutworm EcR); 5'-ggatcctaaagcttcacgtcccagatctcctc-3' (SEQ ID NO:24) (for fall armyworm EcR); 5'-ggatcctaaagcttcacgtcccagatctcctccag-3' (SEQ ID NO:25) (for European cornborer EcR); 5'-ggatcctaaagctttgggatc-acatcccag-3' (SEQ ID NO:26 ) (for *Locusta migratoria* EcR); 5'-ggatcctaaagctttggcgggatggcatga-3' (SEQ ID NO:27) (for *Drosophila melanogaster* EcR); and 5'-ggatcctaaagcttgacatcgccgacatcccagac-3' (SEQ ID NO:28) (for *Chironomus tentans* EcR) in a PCR reaction.

For EcR-VP16 chimeras, the VP16 domain is fused in frame to the 3' end of the E domain of all the cloned ecdysone receptors using the HindIII site 3' to each EcR clone and the HindIII site engineered at the 5' end of VP16.

For the *Manduca* EcR clone from pBSFLMa (Example 1), a BamHI site is engineered adjacent to the ATG of EcR using the oligonucleotide 5'-ctgcaggatccagacgccgctggtcaa-ac-3' (SEQ ID NO:29) in a PCR reaction. The *Drosophila* EcR clone from 35S/EcR (Example 1 of U.S. Pat. No. 5,880,333) is modified by placing a BamHI site immediately upstream of the ATG with the oligonuclotide 5' ggcaggatccatgaagcggcgctggtc-3' (SEQ ID NO:30) and a BglII site placed at the 3' end of the *Drosophila* ecdysone receptor ligand binding (E) domain using the oligonucleotide 5'-cggaagatctcgtgcatggccagcgtg-3' (SEQ ID NO:31) in a PCR reaction.

The plasmid pPacU (Courey A J and Tjian R (1988) *Cell* 55, 887–898) is used as the starting vector for expression constructs. The *Manduca* EcR clone is ligated into pPacU using the BamHI sites flanking the *Manduca* EcR coding region. This expression cassette is referred to as MaFL The *Drosophila* EcR is ligated into the BamHI site of pPacU using the BamHI and BglII sites. This expression cassette is referred to as DrosFL.

To create a *Drosophila* EcR-VP16 fusion containing only domains C, D and E fused to VP16, a fragment is taken from plasmid 35S/EcR$^{227-825}$-C1 (Example 5 of U.S. Pat. No. 5,880,333) using the BamHI site just upstream of the C domain and the KpnI site just upstream of the E domain and fusing it with the *Drosophila* E-domain-VP16 fusion KpnI-BamHI fragment from above. This fusion (SEQ ID NO:95) is ligated into pPacU using the BamHI sites to create the construct referred to as DDV.

A truncated *Manduca* EcR containing domains C, D and E is fused to VP16. A BamHI site and inframe ATG is engineered just 5' to the C domain using the degenerate primers 5'-ggatccatgggycgagaagaattrtcaccr-3' (SEQ ID NO:32) and 5'-ccacrtcccagatctcctcga-3' (SEQ ID NO:33). This fragment is then joined using the Nde site to the 3' end of *Manduca* EcR, which has an engineered HindIII site at the 3' end as described above. The reconstructed *Manduca* C, D and E domains are then fused inframe to VP16 with the HindIII site and the entire fusion (SEQ ID NO:93) is ligated into pPacU at the BamHI site to create the construct referred to as MMV. Similarly, a BamHI site and inframe ATG is engineered just 5' to the C domain of European corn borer EcR using the degenerate primers 5'-ggatccatgggycgagaag-aattrtcaccr-3' (SEQ ID NO:34) and 5'-ggytgytcrtabccbtcct-ggta-3' (SEQ ID NO:35). A BamHI site is also engineered at the 5' end of the C domain for *Locusta* EcR using the primers 5'-ggatccatgggccgggaggacctctcgccg-3' (SEQ ID NO:36) and 5'-ggatcctaaagctttgggatcacatcccag-3' (SEQ ID NO:37).

Example 3

Construction of Reporter Plasmids

A minimal promoter vector is made by ligating a synthetic TATA box sequence oligonucleotide pair, 5'-agcttgagggtataatg-3' (SEQ ID NO:38) and 3'-actcccatattactcga-5' (SEQ ID NO:39), into the HindIII site of vector pGL3-basic (Promega) so that the HindIII site is recreated 5' to the inserted oligonucleotide and destroyed between the oligonucleotide and the downstream luciferase gene. This vector is designated TATA5.

The binding site from the hsp27 gene (Koelle et al., *Cell* 67(1): 59–77 (1991)) is made with the oligonucleotide pair, 5'-gatccgagacaaggggttcaatgcacttgtccaatga-3' (SEQ ID NO:40) and 3'-gctctgttcccaagttacgtgaacaggttactctag-5' (SEQ ID NO:41). This site is multimerized and ligated into the BglII site of vector TATA-5. One isolate, pCGS154, contains the sequence below in the inserted region, having 2 pairs of sites in inverted orientations. One site has a deletion of a single base from the consensus sequence. The sequence of the inserted region in pCGS154 is shown below:

1 gatccgagac aagggttcaa tgcacttgtc caatgagatc
41 cgagacaagg gttcaatgca cttgtccaat gagatctcat
81 tggacaagtg cattgaacct tgtctcggat ctcattggac
121 aagtgcattg aaccttgtc tcggatc (SEQ ID NO:42).

Example 4

Comparison of *Manduca* and *Drosophila* EcR Activities

An in vivo cell based assay is designed to measure transcriptional activation by the receptors of a reporter plasmid. S2 *Drosophila* cells (ATCC CRL-1963) are transiently transfected with luciferase reporter and receptor expression plasmids using the calcium phosphate precipitation procedure (Di Nocera and David (1983) *PNAS* 80, 7095–7098). S2 cells are plated in 96 well format at a density of $2 \times 10^5$ in 166.6 µl of Schneider's *Drosophila* media supplemented with antibiotics and 10% heat inactivated fetal bovine serum (GIBO-BRL). The following day, 33.4 µl of a calcium phosphate precipitate containing 3–6 ng of pCGS154 reporter plasmid, 3–6 ng of EcR receptor plasmid along with salmon sperm DNA to a total of 400 ng DNA per well is added. Chemical ligands are added 16–24 hours after DNA addition to the cells. Cells are then harvested and extracted 24 hours after chemistry addition following the procedures for the luciferase assay by centrifuging and resuspending the cell pellets in 100 µl of cell culture lysis reagent (Promega). Luciferase activity is quantitated using chemiluminescence (Promega) using an analytical luminescence model 2001 luminometer.

S2 cells contain *Drosophila* EcR and USP. The endogenous USP can be used as the heterodimerization partner for EcR or exogenous USP expression plasmid can be added to the assay.

To compare the activities of *Manduca* and *Drosophila* EcR, S2 cells are transiently transfected using the above procedure with the reporter plasmid pCGS 154 and either full-length *Drosophila* EcR, DDV, full-length *Manduca* EcR, or MMV. Tebufenozide at 0.2 82 M and 2 µM is used as the chemical ligand. Luciferase assays are performed as described above. All of the results are normalized as a ratio of activity to the light unit value for the pCGS154 reporter without chemistry.

| Reporter | EcR vector | No Chemistry | 0.2 µM tebufenozide | 2 µM tebufenozide |
|---|---|---|---|---|
| CGS154 | DrosFL | 1 | 1 | 16 |
| CGS154 | DDV | 1 | 3 | 253 |
| CGS154 | MaFL | 1 | 100 | 198 |
| CGS154 | MMV | 1 | 1625 | 1424 |
| CGS154 | none | 1 | 1 | 17 |

These results demonstrate that the *Drosophila* and *Manduca* receptors have different responses to tebufenozide. The *Manduca* EcR is capable of activating the reporter construct at lower levels of compound (0.2 µM) than is the *Drosophila* EcR. Additionally, the truncated *Manduca* receptor fused to VP16 (MMV) exhibits higher activity than the full-length *Manduca* receptor and the similar truncated *Drosophila* EcR fused to VP16 (DDV).

Example 5

Construction of Chimeric EcR Expression Vectors

The existence of a conserved KpnI site in the *Drosophila* and lepidopteran EcR's just 5' to the E domain allows the domains to be exchanged between the different receptors. For the *Locusta migratoria* and *Chironomus tentans* EcR's, a KpnI site is created in an equivalent position by using the oligonucleotides 5'-ggatccatgaaacttgatgatggcaatatg-3' (SEQ ID NO:43), 5'-tggtaccagataagcttataaataacg-3' (SEQ ID NO:44), 5'-tggtaccaagacggttatgaacagccg-3' (SEQ ID NO:45) and 5'-ggatcctaaagcttgacatcgccgacatcccagac-3' (SEQ ID NO:46) for *Chironomus* and 5'-ggatccatgggccgggaggacctctcgccg-3' (SEQ ID NO:47), 5'-ggatccacacaagcctatgtataag-3' (SEQ ID NO:48), 5'-tgtggtaccagaatgaatatgagtctc-3' (SEQ ID NO:49) and 5'-ggatcctaaagctttgggatcacatcccag-3' (SEQ ID NO:50) for *Locusta* in PCR reactions.

Expression constructs are created in pPacU, containing the C and D domains of one species' EcR fused to the E domain-VP16 fusion from a different species' EcR. These constructs are generated using a BamHI-KpnI fragment from the EcR clones (C and D domain) and a KpnI-BamHI fragment from the EcR-VP16 fusions (E domain-VP16).

| EcR chimera | C + D domains | E domain | Activation domain | SEQ ID NO: |
|---|---|---|---|---|
| MDV | *Manduca sexta* | *Drosophila melanogaster* | VP16 | 63–64 |
| MBV | *Manduca sexta* | Black cutworm (*Agrotis ipsilon*) | VP16 | 65–66 |
| MEV | *Manduca sexta* | European corn borer (*Ostrinia nubilalis*) | VP16 | 67–68 |
| MFV | *Manduca sexta* | Fall armyworm (*Spodoptera frugiperda*) | VP16 | 69–70 |
| DMV | *Drosophila melanogaster* | *Manduca sexta* | VP16 | 71–72 |
| DBV | *Drosophila melanogaster* | Black cutworm (*Agrotis ipsilon*) | VP16 | 73–74 |
| EEV | European corn borer (*Ostrinia nubilalis*) | European corn borer (*Ostrinia nubilalis*) | VP16 | 75–76 |
| EBV | European corn borer (*Ostrinia nubilalis*) | Black cutworm (*Agrotis ipsilon*) | VP16 | 77–78 |
| EMV | European corn borer (*Ostrinia nubilalis*) | *Manduca sexta* | VP16 | 79–80 |
| LLV | *Locusta migratoria* | *Locusta migratoria* | VP16 | 81–82 |
| LMV | *Locusta migratoria* | *Manduca sexta* | VP16 | 83–84 |
| MLV | *Manduca sexta* | *Locusta migratoria* | VP16 | 85–86 |

-continued

| EcR chimera | C + D domains | E domain | Activation domain | SEQ ID NO: |
|---|---|---|---|---|
| CCV | Chironomus tentans | Chironomus tentans | VP16 | 87–88 |
| CMV | Chironomus tentans | Manduca sexta | VP16 | 89–90 |
| MCV | Manduca sexta | Chironomus tentans | VP16 | 91–92 |
| MMV | Manduca sexta | Manduca sexta | VP16 | 93–94 |
| DDV | Drosophila melanogaster | Drosophila melanogaster | VP16 | 95–96 |

Example 6

Comparison of EcR Chimera Activities with Manduca and Drosophila C+D (Hinge+DNA Binding) Domains The activities of the EcR-VP16 chimeras are compared by transiently transfecting S2 cells as described in Example 3. Tebufenozide is added to the cells at 0.2 μM concentration. Results are expressed as fold activation, a ratio of the activity of the constructs with chemistry added as compared to activity of the constructs without chemistry. All results are normalized to the luciferase activity of the pCGS154 reporter without receptor addition.

| Construct | Assay # 1 Fold Activation With Chemistry | Assay # 2 Fold Activation With Chemistry | Fold Activation With Chemistry |
|---|---|---|---|
| DDV | 1.01 | 0.68 | |
| DMV | 8.67 | 3.72 | |
| MDV | 1.20 | 1.18 | |
| MMV | 87.65 | 151.06 | |
| No receptor | 1.0 | 1.0 | |
| LLV | | | 0.47 |
| LMV | | | 48.8 |
| No receptor | | | 1.0 |

These results demonstrate that the Manduca EcR E domain confers a higher activity in response to tebufenozide as compared with the E domain of Drosophila or Locusta. The activity of the Manduca E domain is further increased when the C and D domains of Manduca EcR are added.

Example 7

Comparison of EcR Chimera Activities with Different E (Ligand Binding) Domains

The activities of the EcR-VP16 chimeras are compared by transiently transfecting S2 cells as in Example 3. Tebufenozide is added to the cells at 0.2 μM concentration. Results are expressed as fold activation of constructs with chemistry as compared to without chemistry. All results are normalized to the luciferase activity of the pCGS154 reporter without receptor.

| Construct | Fold Activation With Chemistry Assay #1 | Fold Activation With Chemistry Assay #2 |
|---|---|---|
| No receptor | 1.0 | 1.0 |
| MDV | 1.1 | 1.1 |
| MLV | 1.7 | 1.0 |
| MMV | 719.2 | 595.1 |
| MBV | 215.7 | 211.1 |
| MEV | 363.7 | 131.5 |
| MFV | 159.9 | 175.4 |

These results demonstrate that constructs containing the E domains of lepidopteran EcR's have a higher response to tebufenozide as compared to E domains from other insect EcR's such as Drosophila and Locusta.

Example 8

Comparison of EcR Chimeras with Lepidopteran C, D and E Domains

The activities of the EcR-VP16 chimeras are compared by transiently transfecting S2 cells as in Example 3. Tebufenozide is added to the cells at 0.2 μM concentration. Results are expressed as fold activation of constructs with chemistry as compared to without chemistry. All results are normalized to the luciferase activity of the pCGS154 reporter without receptor.

| Construct | Fold Activation With Chemistry Assay #1 | Fold Activation With Chemistry Assay #2 |
|---|---|---|
| No receptor | 1.0 | 1.0 |
| DBV | 17.37 | 3.94 |
| EBV | 975.0 | 273.7 |
| MBV | 559.1 | 866.7 |

These results demonstrate that the addition of the C and D domains from lepidopteran insects increase the response of the receptor to tebufenozide as compared with the chimera containing the C and D domains from Drosophila.

Example 9

Increased Activity of Chimeric EcR's

The activities of the EcR-VP16 chimeras are compared by transiently transfecting S2 cells as in Example 3. Tebufenozide is added to the cells at 0.2 μM concentration. Results are expressed as fold activation of constructs with chemistry as compared to without chemistry addition. All results are normalized to the luciferase activity of the pCGS154 reporter without receptor.

| Construct | Fold Activation With Chemistry |
|---|---|
| CCV | 2.0 |
| MCV | 553.3 |
| No receptor | 1.0 |

This example demonstrates that specific domains from Manduca EcR such as the E domain can be fused with other EcR's to create chimeric EcR's with increased response to tebufenozide.

Example 10

Construction of a Monocot-Expressible Target Expression Cassette Comprising the Firefly Luciferase Reporter Gene and Having Response Elements for the GAL4 DNA Binding Domain A monocot plant expressible reporter construct comprising the firefly luciferase reporter gene having response elements for the GAL4 DNA binding domain is constructed in the following manner. The luciferase gene is removed from pGL3-basic (Promega) using HindIII, followed by filling in of the 5' overhang to create a blunt end using Klenow DNA polymerase, and is subsequently cut with XbaI. The luciferase fragment is subcloned into pBluescript (Stratagene) at the XbaI and SmaI sites. This construct is named pBS-luc. The NOS 3' transcriptional termination region is cloned into pBS-luc and the resulting construct is named pBS-lucNOS.

The minimal bronze 1 (bz1) promoter (Roth et al., *Plant Cell* 3: 317 (1991)) is cloned into pBS-lucNOS in two parts; one is the TATA region and the other is the intron. The TATA region of the bz1 promoter is cloned by ligating together two sets of annealed oligos, bztata1 (5'-agcttcgcacgcgtggtc-gcgcggaataaagcggacacgttgcgccccag-3' (SEQ ID NO:51))+ bztata2 (5'-ttcgctgggggcgcaacgtgtccgctttattccgcgcgaccacgc-gtgcga-3' (SEQ ID NO:52)) annealed to bztata3 (5'-cgaagcccgcacgcatcgcattcgcatcgcatcgcaggtcgcatccgacgctag-aag-3' (SEQ ID NO:53))+bztata4 (5'-aattcttctagcgtcggatg-cgacctgcgatgcgatgcgaatgcgatgcgtgcgggc-3' (SEQ ID NO:54)). The annealed set bztata1/2 contains a complementary overhang to the annealed set bztata3/4. The final DNA fragment contains HindIII (5') and EcoRI (3') adapter overhangs. This region is ligated to pBS-lucNOS to form pbz1TATALUC.

The bz1 intron region is cloned by PCR and is designed to have EcoRI restriction sites on both the 5' and 3' ends using primers bzintron1 (5'-ccgaattccgggaggacgttggcga-ccagggt-3' (SEQ ID NO:55)) and bzintron2 (5'-ccgaattcggtgggagatcagtagcccgtcca-3' (SEQ ID NO:56)).

The two annealed bz1 TATA DNA fragments are mixed with the bz1 intron that is obtained by PCR and digested with EcoRI, and the 3 DNA fragments are ligated to pBluescript that is digested with HindIII and EcoRI. The resulting plasmid containing both the bz1 TATA and intron is named pBS-TATA/intron. The bz1 TATA/intron fragment is obtained from pBS-TATA/intron by digesting with HindIII and a partial EcoRI digest and this fragment is ligated to pBS-lucNOS at the HindIII/EcoRI site to form pBS-bz1TATA/intronLUC.

The final step in making the reporter is to insert 10 GAL4 DNA binding sites into pBS-bz1TATALUC and pBS-bz1TATA/intronLUC. The 10 GAL4 elements (Guyer et al. (1998) *Genetics* 149:633–9) are inserted into pBS-bz1TATALUC and pBS-bz1TATA/intronLUC at the KpnI/XhoI sites. The resulting vectors are named pCGS228 and pCGS206.

Four additional reporter constructs containing the firefly luciferase reporter gene and having response elements for the GAL4 DNA binding domain are created. These constructs differ in the intron that is inserted in place of the bz1 intron, downstream of the bronze1 TATA region of the promoter. Four additional introns are used: the Adh intron number 1 (SEQ ID NO:106), the Sh intron number 1 (SEQ ID NO:107), the maize ubiquitin intron number 1 (SEQ ID NO:108), and the rice actin intron (SEQ ID NO:109).

For the maize ubi intron (SEQ ID NO:108), the intron is amplified from an expression vector containing the maize ubiquitin promoter with a NOS (nopaline synthase) terminator, using taq DNA polymerase and primers ubi5pst (5'-ggcctgcagggcgttccggtccatggttagggc-3' (SEQ ID NO:110)) and ubi3pst (5'-tccctgcagaagtaacaccaaacaaca-3' (SEQ ID NO:111)). The amplified intron is digested with PstI and ligated to pCGS228 that is digested with PstI to form pCGS215.

The Adh intron 1 (SEQ ID NO:106), containing blunt ends on both ends, is ligated to pCGS228 that is digested with EcoRI and blunt ended with Klenow DNA polymerase. The resulting vector is named pCGS216.

The Sh intron 1 (SEQ ID NO:107), containing blunt ends on both ends, is ligated to pCGS228 that is digested with EcoRI and blunt ended with Klenow DNA polymerase. The resulting vector is named pCGS217.

The rice actin intron (SEQ ID NO:109) is amplified from an expression vector containing the rice actin promoter with a NOS (nopaline synthase) terminator using taq DNA polymerase and PCR primers act5-ecori (5'-ggcgaattcccggtaaccaccccgccctc-3' (SEQ ID NO:112)) and act3-ecori (5'-cgcgaattctccctgcagcttctacctacaaaa-3' (SEQ ID NO:113)). The amplified intron is digested with EcoRI and ligated to pCGS228 that is digested with EcoRI. The resulting plasmid is named pCGS218.

Example 11

Construction of Expression Vector G(M)MV Containing the Yeast GAL4 DNA Binding Domain, the *Manduca* Ecdysone Receptor Hinge (D) and Ligand Binding (E) Domains, and the Herpes Simplex Virus Protein 16 (VP16) Transcription Activation Domain Driven by the Maize Ubiquitin Promoter An expression vector containing the maize ubiquitin promoter driving chimeric protein "G(M)MV" comprised of the yeast GAL4 DNA binding domain, the *Manduca* hinge (D) and ligand binding (E) domains, and the herpes simplex VP16 transcriptional activation domain is constructed in the following manner. The GAL4 DNA binding domain is amplified by PCR using the following primers and the plasmid pBD-GAL4 Cam (Stratagene) as template:

GAL4BDforward (5'-aggatccgccaccatgaagctactgtcttc-3' (SEQ ID NO:57)) and GAL4BDreverse (5'-aacgcgtcgatacagtcaactgtctttgacc-3' (SEQ ID NO:58)). The resulting PCR fragment is cloned into pT-Adv (Clonetech) by TA cloning and is referred to as pT-Adv-gal4bd.

The hinge and ligand binding domains (D and E domains) of the *Manduca* EcR with a VP16 activation domain at the C-terminus is amplified by PCR using the following primers and MMV (Example 2) as template: MV forward (5'-aacgcgtatgaggcccgagtgcg-3' (SEQ ID NO:59)) and MV reverse (5'-aaatccggaaatacgactcactatagggcgaat-3' (SEQ ID NO:60)). The resulting PCR fragment is cloned into pT-Adv (Clonetech) by TA cloning and is referred to as pT-Adv-MV.

The GAL4 DNA binding domain is isolated from pT-Adv-gal4bd by digesting with MluI and BamHI. The *Manduca* D and E domains with the VP16 activation domain are isolated from pT-Adv-MV by digesting with SacII, followed by blunt ending with T4 DNA polymerase, and a subsequent digestion with MluI. An expression vector containing the maize ubiquitin promoter with a NOS (nopaline synthase) terminator is digested with SacI, followed by blunt ending with T4 DNA polymerase and a subsequent BamHI digestion. The GAL4 DNA binding domain, *Manduca* D and E domains with the VP16 activation domain, and vector fragments are ligated together and the resulting plasmid encoding G(M)MV is named pCGS203. The DNA sequence encoding chimeric receptor G(M)MV is shown as nucleotides 2007–3668 of SEQ ID NO:104 and the amino acid sequence of the encoded receptor is shown as SEQ ID NO:105.

Example 12

Transformation of Maize Suspension Culture Cells with Vectors Encoding *Manduca* EcR Polypeptides Controls Expression of Reporter Polypeptides in the Presence of Chemical Ligands Maize BMS (Black Mexican Sweet) cultured cells are transfected with pCGS206 and pCGS208 by high velocity microprojectile bombardment. In addition, an expression plasmid containing the maize ubiquitin promoter driving the expression of β-glucuronidase (GUS) is added to the transfection to serve as an internal control to normalize against variations among the samples.

Transfections are treated and cell lysates are made essentially as described in U.S. Pat. No. 5,880,333. Tebufenozide (Teb) is added to the cells at a final concentration of 10 μM. Both luciferase and GUS assays are performed with 20 μl of cell lysate for each assay using the Promega Luciferase Kit (Promega cat #E1500) and GUS-Light Kit (Tropix) respectively. Relative light units are determined using a Turner Designs TD 20/20 luminometer. The normalized values (using the GUS reporter control) are listed in the following table.

| Constructs | Assay #1 Luciferase | Fold Induction | Assay #2 Luciferase | Fold Induction | Assay #3 Luciferase | Fold Induction |
|---|---|---|---|---|---|---|
| pCGS206 | 2.32 | — | — | — | 0.12 | 1 |
| pCGS206 + Teb | 1.49 | 0.64 | 0.79 | 1 | — | — |
| pCGS206 + pCGS208 | 0.78 | — | 1.51 | — | 3.87 | — |
| pCGS206 + pCGS208 + Teb | 28.26 | 36.2 | 50.11 | 33.2 | 150.89 | 39.0 |

The "G(M)MV" *Manduca* EcR (ubi/GAL4-MV) is able to achieve an average of 36-fold induction with tebufenozide.

In addition to tebufenozide, methoxytebufenozide ("MethoxyTeb") is also capable of inducing gene expression in maize BMS cells. Both pCGS206 and pCGS208 are transfected as described above and methoxytebufenozide is added in place of tebufenozide at 25 μM and 10 μM.

| Constructs | Assay #1 Luciferase | Fold Activation | Assay #2 Luciferase | Fold Activation |
|---|---|---|---|---|
| pCGS206 | 0.81 | — | — | — |
| pCGS206 + MethoxyTeb | 0.86 | 1.06 | 1.27 | — |
| pCGS206 + pCGS208 | 15.65 | — | 11.86 | — |
| pCGS206 + pCGS208 + MethoxyTeb | 310.89 | 19.9 | 345.5 | 29.1 |

Thus, methoxytebufenozide activates the *Manduca* "G(M)MV"EcR (ubi/GAL4-MV) on average 25 fold.

The overall expression level of tebufenozide induction on pCGS203 is dependent on the promoter/intron of the reporter in cultured maize cells. Maize BMS cells are transfected and assayed as described above.

| Constructs | Luciferase | Fold Induction |
|---|---|---|
| pCGS228 + pCGS203 | 2.6 | — |
| pCGS228 + pCGS203 + 10 μM Teb | 6.7 | 2.6 |
| pCGS206 + pCGS203 | 0.99 | — |
| pCGS206 + pCGS203 + 10 μM teb | 69.71 | 70.3 |
| pCGS215 + pCGS203 | 1.5 | — |
| pCGS215 + pCGS203 + 10 μM teb | 27.4 | 18.8 |
| pCGS216 + pCGS203 | 4.2 | — |
| pCGS216 + pCGS203 + 10 μM teb | 87.9 | 20.9 |
| pCGS217 + pCGS203 | 1.31 | — |

-continued

| Constructs | Luciferase | Fold Induction |
|---|---|---|
| pCGS217 + pCGS203 + 10 μM teb | 18.7 | 14.3 |
| pCGS218 + pCGS203 | 3.7 | — |
| pCGS218 + pCGS203 + 10 μM teb | 20.1 | 5.4 |

The addition of various introns changes the overall activation level of tebufenozide induction. Addition of the Adh intron 1 increases the expression level to 87.9 RLU, while the addition of the Sh intron 1 has a moderate expression level of 18.7. Therefore, using different introns regulates the expression level of a desired trait produced from the switch system.

Example 13

Construction of a Vector for Expression of Foreign Genes in Dicot Plants

A dicot expression vector containing the *Arabidopsis* ubiquitin promoter and 5' UTR, a multiple cloning site (MCS), and the nopaline synthase 3' transcriptional termination region (NOS) is generated, and named pCGS417. A cassette containing the *Arabidopsis* ubiquitin promoter and 5' untranslated region (UTR) and the NOS terminator is cloned into pBluescript using XhoI and NotI. The MCS is created at the BamHI site between the ubiquitin 5' UTR and the NOS terminator by ligating in the following double stranded oligonucleotide, which has the recognition sequences for restriction enzymes SmaI, SalI, EcoRI, BspEI, HindIII, and XbaI:

luciferase expression levels using the Promega Luciferase Kit (Promega cat #E1500) using a Turner Designs TD 20/20 luminometer. GUS expression levels are determined using the GUS-Light kit (Tropix). GUS activity is used to normalize luciferase levels to compensate for differences in DNA delivery to each sample.

|           | Assay #1 | | Assay #2 | | Assay #3 | |
|-----------|----------|----|----------|----|----------|----|
| Receptors | Luciferase | Fold Induction | Luciferase | Fold Induction | Luciferase | Fold Induction |
| None | 0.853 | | | | | |
| None + Teb. | 0.808 | 0.95 | | | | |
| pCGS432 | 1.980 | | 0.297 | | 3.395 | |
| pCGS432 + Teb. | 11.93 | 6.0 | 4.269 | 14.4 | 20.49 | 6.0 |

(SEQ ID NO:61)
5'-gatcccgggtcgacgaattctccggaagcttctaga-3'

(SEQ ID NO:62)
3'-gggcccagctgcttaagaggccttcgaagatctctag-5'.

These results demonstrate that the luciferase reporter is activated only in the presence of both the GAL4-MV construct and the ligand tebufenozide. Tebufenozide does not activate the reporter in the absence of the EcR receptor.

Example 14

Construction of a Dicot Expressible Receptor Expression Cassette Encoding the DNA Binding Domain from GAL4 and the Ligand Binding Domain from *Manduca* EcR The chimeric receptor fusion GAL4-MV, containing the DNA binding domain from GAL4, the ligand binding (E) domain from *Manduca* EcR, and the viral transactivation domain from VP16, is removed from the monocot expression vector pCGS208 and cloned into pCGS417 using the BamHI restriction sites. This construct is named pCGS431. The VP16 activation domain is removed from the chimeric protein by restriction with XbaI and HindIII. The 5' overhangs generated in by this digest are filled in using the large (Klenow) fragment of DNA polymerase I, and the vector is recircularized by self-ligation. The resulting vector contains an in-frame transcriptional termination codon immediately downstream of the filled-in HindIII sequence. This vector, encoding a GAL4 DNA binding domain-*Manduca* EcR E domain-VP16 fusion protein, is named pCGS432.

Example 15

Transformation of Tobacco Cells with the Reporter and Receptor Constructs Produces a Chemically Inducible Plant Cell System The GAL4-MV expression vector pCGS432 and the GAL4×10-Luciferase vector pCGS206 are simultaneously delivered into BY2 suspension cells (*Nicotania tobacum* L. cv. Bright Yellow 2) by high velocity microprojectile bombardment. A β-glucuronidase (GUS) vector is included as an internal control for transfection efficiency between samples. Transfected cells are incubated overnight in the presence and absence of the appropriate chemical ligand (tebufenozide (Teb), RH5889) in BY2 liquid culture media. After incubation, the cells are harvested and lysed by mechanical disruption. Cellular debris is removed by centrifugation at 20,800 g at 4° C. for 10 minutes. Cell lysates are assayed for Example 16

Construction of Dicot Expressible Receptor Expression Cassettes Encoding the DNA Binding Domain from GAL4, the Ligand Binding Domain from *Manduca* EcR, and the C1 Transcriptional Activation Domain Chimeric receptor fusion proteins are constructed containing the GAL4 DNA binding domain (DBD) and *Manduca* EcR (MecR) ligand binding (E) domain, fused to the C1 transcriptional activation domain in either an N-terminal configuration (C1-GAL4-MEcR), an internal configuration (GAL4-C1-MEcR), or a C-terminal configuration (GAL4-MEcR-C1). The GAL4-MEcR-C1 receptor is designed using the dicot GAL4-MEcR-VP16 expression vector, pCGS431 (Example 14). pCGS431 is digested with XbaI and HindIII to remove the VP16 activation domain. The C1 activation domain is PCR amplified using the primers 5'-ggcaagcttcccaaggccgtgcgg-3' (SEQ ID NO:97), and 5'-ggctctagactacgcaagctgcccggc-3' (SEQ ID NO:98), which include an in-frame HindIII site at the 5'end of C1 and a translational stop codon and XbaI site at the 3' end of C1. The PCR product is digested with both HindIII and XbaI and cloned into the digested pCGS431. This dicot expression vector encoding the fusion receptor GAL4-MEcR-C1 is named pCGS443.

The GAL4-C1-MEcR chimeric receptor is designed using the GAL4-MEcR expression vector, pCGS432 (Example 14). pCGS432 is digested with MluI. The C1 activation domain is PCR amplified using primers that include in-frame MluI sites on both the 5' and 3' ends of C1, 5'-ggcacgcgtcccaaggccgtgcgg-3' (SEQ ID NO:99) and 5'-gccacgcgtcgcaagctgcccggc-3' (SEQ ID NO:100). The PCR product is digested with MluI and cloned between the GAL4 DBD and the *Manduca* EcR E domain in the MluI digested pCGS432. This dicot expression vector encoding the fusion receptor GAL4-C1-MEcR is named pCGS442.

The C1-GAL4-MEcR chimeric receptor is also designed using the GAL4-MEcR expression vector, pCGS432. pCGS432 is digested with BamHI, which cuts at the junction between the GAL4 DBD and the *Manduca* EcR E domain. The C1 activation domain is PCR amplified using primers that include in frame BamHI sites on both the 5' and 3' ends of C1, 5'-ccgggatccgccaccatgcccaaggccgtgcgg-3' (SEQ ID NO:101), and 5'-ccgggatcccgcaagctgcccggc-3' (SEQ ID NO:102). The PCR product is digested with BamHI and cloned into the digested pCGS432. This dicot expression vector encoding the fusion receptor C1-GAL4-MEcR is named pCGS441.

Example 17

Transformation of Tobacco Cells with reporter and GAL4-MEcR-C1 Receptor Constructs Produces a Chemically Inducible Plant Cell System The GAL4-*Manduca* EcR-C1 expression vectors (pCGS441, pCGS442, and pCGS443) and the GAL4×10-Luciferase vector pCGS206 (Example 10) are simultaneously delivered into BY2 suspension cells (*Nicotiana tobaccum* L. cv. Bright Yellow 2) by high velocity microprojectile bombardment. A β-glucuronidase (GUS) vector is included as an internal control for transfection efficiency between samples. Transfected cells are incubated overnight in the presence and absence of the appropriate chemical ligand (tebufenozide (teb), RH5992) in BY2 liquid culture media. After incubation, the cells are harvested and lysed by mechanical disruption. Cellular debris is removed by centrifugation at 20,800 g at 4° C. for 10 minutes. Cell lysates are assayed for luciferase expression levels using the Promega Luciferase Kit (cat #E1500) using a Turner Designs TD 20/20 luminometer. β-glucuronidase expression levels are determined using the GUS-Light kit (Tropix). GUS activity is used to normalize luciferase levels to compensate for differences in DNA delivery to each sample.

|  | Assay #1 | | Assay #2 | |
| --- | --- | --- | --- | --- |
| Receptors | Luciferase | Fold Induction | Luciferase | Fold Induction |
| None |  |  | 3.113 |  |
| None + Teb |  |  | 3.394 | 1.1 |
| pCGS441 | 3.548 |  | 3.752 |  |
| pCGS441 + Teb | 68.05 | 19.2 | 28.77 | 7.7 |
| pCGS442 | 9.287 |  | 4.572 |  |
| pCGS442 + Teb | 50.24 | 5.4 | 19.1 | 4.2 |
| pCGS443 | 10.84 |  | 7.233 |  |
| pCGS443 + Teb | 161.6 | 14.9 | 80.43 | 11.1 |

These results demonstrate that all three chimeric receptors (pCGS441, pCGS442, and pCGS443) are able to specifically activate the luciferase reporter upon treatment with the ligand tebufenozide. The GAL4-MEcR-C1 (pCGS443) construct is able to direct a higher level of reporter expression upon ligand induction than are the GAL4-C1-MEcR (pCGS442) or the C1-GAL4-MEcR (pCGS441) chimeric receptors.

Example 18

Construction of a Monocot Reporter Construct for use in *Agrobacterium* Transformation A vector for use in *Agrobacterium* transformation of maize containing 10 GAL4 DNA binding elements upstream of the bronze1 TATA containing minimal promoter fused with a fragment of the bronze1 first intron sequence driving luciferase expression is constructed in the following manner. The reporter fragment is excised from pCGS206 (Example 10) using KpnI and BglII. A modified pBluescript vector containing a BglII site is digested with KpnI and BglII and the reporter fragment is ligated into modified pBluescript. Using KpnI and SmaI, the reporter fragment (SEQ ID NO:103) is then removed from the modified pBluescript vector and directionally cloned into an *Agrobacterium* monocot transformation vector that contains the PMI gene under control of the maize ubiquitin promoter. This plasmid is named pCGS601.

Example 19

Construction of a Monocot Expression Vector Containing the Yeast GAL4 DNA Binding Domain, the *Manduca* EcR Ligand Binding Domain, and the VP16 Transcription Activation Domain for use in *Agrobacterium* Transformation A vector for use in *Agrobacterium* transformation of maize containing the maize ubiquitin promoter driving a chimeric protein comprised of the GAL4 DNA binding domain, the *Manduca* Ligand binding (E) domain, and the herpes simplex viral protein 16 transcriptional activation domain is constructed in the following manner. The GAL4-*Manduca* EcR-VP16 chimeric receptor is excised from plasmid pCGS208 using AscI and SfoI. A plasmid containing a herbicide tolerant *Arabidopsis* protox gene encoding a protox enzyme having a Tyr to Met mutation at AA 426 and a Ser to Leu mutation at AA 305 (sub-sequences 7 and 13 in Table 1B of U.S. Pat. No. 6,084,155) downstream of the maize ubiquitin promoter is digested with HindIII followed by blunt ending using Klenow DNA polymerase. The plasmid is subsequently digested with AscI and the GAL4-*Manduca* EcR-VP16 DNA fragment (SEQ ID NO:104) is ligated into the plasmid to form pCGS202. Both the ubiquitin-protox cassette and the ubiquitin-GAL4-EcR-VP16 chimera are between the left and right border fragments for *Agrobacterium* transformation.

Example 20

*Agrobacterium*-Mediated Transformation of Maize

Transformation of immature maize embryos is performed essentially as described in Negrotto et al., *Plant Cell Reports* 19: 798–803 (2000). For this example, all media constituents are as described in Negrotto et al., 2000, supra. However, various media constituents described in the literature may be substituted.

A. Transformation Plasmids and Selectable Marker

The genes used for transformation are cloned into a vector suitable for maize transformation. Vectors used contain either the phosphomannose isomerase (PMI) gene (Negrotto et al., 2000) or a herbicide-tolerant protoporphyrin oxidase (protox) gene (e.g. that encoding a protox enzyme having a Tyr to Met mutation at AA 426 and a Ser to Leu mutation at AA 305 (sub-sequences 7 and 13 in Table 1B of U.S. Pat. No. 6,084,155)), which allows for selection of transgenic cells with either mannose or herbicide supplemented media respectively. In the case of single genes—e.g. a reporter construct or an induction system—one strain of *Agrobacterium* is utilized in an experiment. For transfer of both genes, they are either cloned into a single T-region on one plasmid, or they are cloned onto separate plasmids and the two *Agrobacterium* strains harboring these separate plasmids are mixed 1:1 before inoculation followed by selection for both marker genes. Alternatively, the genes are cloned separately onto plasmids with compatible origins of replication and transformed into a single *Agrobacterium* strain that is used for transformation, or transformed plants from single transgenes are crossed to produce progeny with both traits.

B. Preparation of *Agrobacterium tumefaciens*

*Agrobacterium* strain LBA4404 (pSB1) containing the plant transformation plasmid is grown on YEP (yeast extract (5 g/L), peptone (10 g/L), NaCl (5 g/L), 15 g/l agar, pH 6.8) solid medium for 2–4 days at 28° C. Approximately $0.8 \times 10^9$ Agrobacteria are suspended in LS-inf media supplemented with 100 μM As (Negrotto, et al., 2000). Bacteria are pre-induced in this medium for 30–60 minutes.

C. Inoculation

Immature embryos from A188 or other suitable maize genotype are excised from 8–12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark at 28° C. for 10 days.

D. Selection of Transformed Cells and Regeneration of Transformed Plants

PMI selection: Immature embryos, producing embryogenic callus, are transferred to LSD1M0.5S medium. The cultures are selected on this medium for 6 weeks with a subculture step at 3 weeks. Surviving calli are transferred either to LSD1M0.5S medium to be bulked-up or to Reg1 medium supplemented with mannose. Following culturing in the light (16 hour light/8 hour dark regimen), green tissues are then transferred to Reg2 medium without growth regulators and incubated for 1–2 weeks. Plantlets are transferred to Magenta GA-7 boxes (Magenta Corp, Chicago Ill.) containing Reg3 medium and grown in the light. After 2–3 weeks, plants are tested for the presence of the PMI genes and other genes of interest by PCR. Positive plants from the PCR assay are transferred to the greenhouse.

Herbicide selection: Selection conditions are essentially performed as described for PMI selection and regeneration with the following media modifications. Silver nitrate is used in both initiation and selection media and sucrose is used at 30 g/L. A protox inhibitory herbicide (U.S. Pat. No. 6,084,155) is added to the media at 5nM for initiation and primary selection, 500 nM for second selection and 750 nM for the final selection. Regeneration 1 is carried out on media supplemented with 50 nM herbicide with no herbicide selection in subsequent regeneration media.

Combined selection: When mixed infections are used, selection and regeneration are accomplished with both mannose and herbicide containing media.

Example 21

Chemical Induction of Transgenic Maize Plants Containing both the GAL4-*Manduca* EcR Chimeric Protein and a Luciferase Reporter Transgenic maize plants containing pCGS601 and pCGS202 from Examples 18 and 19, respectively, are chemically induced with tebufenozide (teb, RH5992). A formulation mixture containing 10% of a 2.0 mM tebufenozide solution in ethanol and 1% surfactant is applied directly to the leaves of the transgenic maize plants. The solution is left on the leaves between 18 and 40 hours. Leaves are then frozen in liquid nitrogen and ground to a powder. Subsequently, leaves are homogenized in cell culture lysis reagent (CCLR; 25 mM Tris-phosphate pH 7.8, 2 mM DTT, 2 mM 1,2-diaminoclyclohexane-N,N,N',N'-tetraacetic acid, 10% glycerol, and 1% triton X-100). After spinning for 7 minutes at 14,000 g to pellet the cell debris, 20 μl of the supernatant is assayed for luciferase activity by the standard method (as described in the preceding examples).

Six plants are treated with chemistry: three with ethanol as control and three with tebufenozide. After 40 hours, plants are assayed for luciferase activity.

| Plant Number | Treatment | Activity |
|---|---|---|
| 1 | Ethanol | 280.05 |
| 2 | Ethanol | 6.149 |
| 3 | Ethanol | 119.4 |
| 4 | Tebufenozide | 2729 |
| 5 | Tebufenozide | 745.3 |
| 6 | Tebufenozide | 2373 |

The transgenic maize plants containing the luciferase reporter and the GAL4-*Manduca* EcR-VP16 chimeric protein demonstrate a significant induction with tebufenozide above the ethanol controls.

To determine fold induction with tebufenozide, leaves of individual plants are compared for activity. Using the same plant, one leaf is treated with ethanol and another with tebufenozide. The plants are incubated for 18 hours and assayed for luciferase activity as described above.

| Plant Number | Treatment | Activity | Fold Induction |
|---|---|---|---|
| 1 | Tebufenozide | 118.1 | 11 |
| 2 | Ethanol | 29.35 | |
| 2 | Tebufenozide | 180 | 6 |
| 3 | Ethanol | 9.98 | |
| 3 | Tebufenozide | 369.1 | 37 |

These results demonstrate approximately 10 to 40 fold induction after treatment with tebufenozide.

Example 22

Chemical Induction by Tebufenozide on Various Tissues of Transgenic Plants Containing pCGS202 and pCGS601

Transgenic plants harboring DNA from the plasmids pCGS202 and pCGS601 are chemically induced with tebufenozide as in Example 21, using 2.0 mM RH5992 formulated in 1% surfactant. This mixture is applied directly to one leaf of a plant while a control formulation mixture containing ethanol instead of tebufenozide is applied to another leaf. Treatments are left on the leaves between 24–48 hours. Plants are then treated by spraying the leaves with a mixture containing 7.5 mM luciferin and 1% surfactant and incubating for 5 minutes. Either whole plants or tissues are placed into a dark box and photon emission is monitored using a digital camera and software that counts the accumulated photons that are emitted. Both the image of the tissue and the total photon count is recorded.

Plants at V5 stage are treated as above. The plants treated with tebufenozide emit substantial amounts of light compared with those treated with ethanol only. The table below contains actual counts of leaf samples from maize plants transformed with pCGS601 and pCGS202.

| Treatment on Leaf | Total Photons Counted |
|---|---|
| Ethanol | 1612 |
| Tebufenozide | 187,784 |
| Fold Induction | 116 Fold |

Late stage post pollinated maize plants are also treated as above. Leaves are analyzed as above and the total photon counts are recorded in the table below.

| Treatment on Leaf | Total Photons Counted |
|---|---|
| Ethanol | 3,681 |
| Tebufenozide | 110,766 |
| Fold Induction | 30 Fold |

Similar treatment and results are obtained with the following tissue: roots, tassel, anther, stalk, embryo, and seed.

Example 23

Construction of Expression Vectors Containing the Yeast GAL4 DNA Binding Domain, Combinations of D+E domains (hinge+ligand binding domains), and the Herpes Simplex Virus Protein 16 (VP16) Transcription Activation Domain Driven by the Maize Ubiquitin Promoter Constructs are cloned by insertion of receptor domains (MluI, PvuII or EcoRV) and the yeast GAL4 DNA Binding Domain (BamHI, MluI) into an expression vector containing the maize ubiquitin promoter with a NOS (nopaline synthase) terminator (SacI blunt, BamHI) via three-way ligation. Receptor domains are cloned by PCR amplification of D (hinge), E (ligand binding domain), and VP16 from constructs described in Example 5 (MBV (SEQ ID NOs:65–66); MFV (SEQ ID NOs:69–70); MEV (SEQ ID NO:67–68); EEV (SEQ ID NOs:75–76); and EMV (SEQ ID NOs:79–80)). Forward primers Manduca_Hinge-f (5'-gctcgacgcgtatgaggcccgagtgcgtcgtcccagag-3' (SEQ ID NO:114)) and ECB_Hinge-f (5'-gctcgacgcgtatgaggcccga-gtgcgtggtgccag-3' (SEQ ID NO:115)) place a MluI restriction site at the 5' end of the D domain. Reverse primers VP16-r (PvuII) (5'-tgccagctgctagaggatcctacccaccgtactcg-3' (SEQ ID NO:116)) and VP16-r (EcoRV) (5'-tgcgatatcggatcctacccaccgtactcgtcaattcc-3' (SEQ ID NO:117)) place either a PvuII or EcoRV site as indicated at the 3' end of the E domain. PCR reactions (50 μl volume) contain 1× buffer, 0.1 μg DNA template, 200 μM dNTPs, 400 nM of both a forward and a reverse primer, and 2.5 U DNA Polymerase. PCR reaction conditions are as follows: 5 minutes at 94° C., 30 cycles of 1 minute at 94° C., 1 minute at 65° C., 1 minute at 72° C., then 10 minutes at 72° C. Amplified cDNA fragments include: 1) (M)BV (1215 bp), consisting of the Manduca D domain, the BCW E domain, and VP16; 2) (M)EV (1206 bp), consisting of the Manduca D domain, the ECB E domain, and VP16; 3) (M)FV (1211 bp), consisting of the Manduca D domain, the FAW E domain, and VP16; 4) (E)EV (1221 bp), consisting of the ECB D domain, the ECB E domain, and VP16; 5) (E)MV (1244 bp), consisting of the ECB D domain, the Manduca E domain, and VP16. The yeast GAL4 DNA Binding Domain is obtained by digestion with BamHI and MluI then isolation of a 453 bp product. An expression vector containing the maize ubiquitin promoter with a NOS (nopaline synthase) terminator (SacI blunt, BamHI) backbone is prepared by digestion with SacI, removal of 3' overhangs with T4 DNA Polymerase, and then digestion with BamHI to yield a 4969 bp product.

| EcR chimera | DNA Binding Domain | D domain | E domain | Activation domain | SEQ ID NO: |
|---|---|---|---|---|---|
| G(M)MV | GAL4 | Manduca sexta | Manduca sexta | VP16 | 104–105 |
| G(M)BV | GAL4 | Manduca sexta | Black cutworm (Agrotis ipsilon) | VP16 | 118–119 |
| G(M)EV | GAL4 | Manduca sexta | European corn borer (Ostrinia nubilalis) | VP16 | 120–121 |
| G(M)FV | GAL4 | Manduca sexta | Fall armyworm (Spodoptera frugiperda) | VP16 | 122–123 |
| G(E)EV | GAL4 | European corn borer (Ostrinia nubilalis) | European corn borer (Ostrinia nubilalis) | VP16 | 124–125 |
| G(E)MV | GAL4 | European corn borer (Ostrinia nubilalis) | Manduca sexta | VP16 | 126–127 |

Example 24

Combinations of D+E Domains (Hinge+Ligand Binding Domains) Alter the Level of Unliganded Background and Overall Expression Upon Tebufenozide Induction Maize BMS cells are transfected and assayed as in Example 12.

| | Normalized Average (EtOH) | Normalized Average (20 μM Teb) | Fold Induction with Teb Relative to Reporter with EtOH | Fold Induction with Teb Relative to Receptor with EtOH |
|---|---|---|---|---|
| Experiment 1 | | | | |
| Reporter | 3.671 | 2.916 | 1 | 1 |
| G(M)MV | 6.889 | 305.622 | 83 | 44 |
| G(M)BV | 8.701 | 298.862 | 81 | 34 |
| G(M)EV | 6.965 | 436.532 | 119 | 63 |
| G(M)FV | 3.766 | 192.440 | 52 | 51 |

-continued

|  | Normalized Average (EtOH) | Normalized Average (20 μM Teb) | Fold Induction with Teb Relative to Reporter with EtOH | Fold Induction with Teb Relative to Receptor with EtOH |
|---|---|---|---|---|
| G(E)EV | 7.601 | 436.430 | 119 | 57 |
| G(E)MV | 14.499 | 496.184 | 135 | 34 |
| Experiment 2 |  |  |  |  |
| Reporter | .418 | .102 | 1 | 1 |
| G(M)MV | 1.721 | 25.604 | 61 | 15 |
| G(M)BV | 1.539 | 39.677 | 95 | 26 |
| G(M)EV | 0.028 | 58.166 | 139 | 58 |
| G(M)FV | 0.484 | 23.896 | 57 | 24 |
| G(E)EV | 2.394 | 41.446 | 99 | 17 |
| G(E)MV | 2.537 | 39.716 | 95 | 16 |

Depending on the combination, D+E domains (hinge+ ligand binding domain) affect the level of unliganded background and the level of tebufenozide induction. Such variation provides the opportunity to establish specific conditions of gene expression output by altering receptor domains. The highest fold induction is obtained from EcR chimera G(M) EV having a *Manduca* D (hinge) domain and a European Corn Borer E (ligand binding) domain.

Example 25

Construction of Expression Vectors Containing the Yeast GAL4 DNA Binding Domain, the *Manduca* Hinge (D) and Ligand Binding (E) Domains, and Alternative Activation Domains Derived from Plant Transcription Factors An expression vector containing the maize ubiquitin promoter with a NOS (nopaline synthase) terminator is used as a vector backbone. The G(M)M (GAL4 DNA Binding Domain fused to the *Manduca* EcR Hinge and Ligand Binding Domain) chimeric receptor nucleotide coding sequence (SEQ ID NOs:128–129) is generated by digesting the dicot expression vector pCGS443 (Example 16) with HindIII and BamHI. These reagents are used for cloning-in of additional transcriptional activation domains in frame with the G(M)M chimeric receptor, as detailed below.

The maize C1 activation domain is PCR amplified using the following primers to engineer a HindIII site and a SacI site on the 5' and 3' ends respectively of the C1 activation domain: HindIII C1 5' (5'-aaaaaaagcttcccaaggccgtgcggtg-3' (SEQ ID NO:130)) and SacI C1 3' (5'-aaaaagagctcttacgcaagctgcccggcc-3' (SEQ ID NO:131)).

Expression vector pUbi-G(M)MC (pCGS672) is obtained via a three-way ligation between the C1 PCR product digested with HindIII and SacI, an expression vector containing the maize ubiquitin promoter with a NOS (nopaline synthase) terminator digested with BamHI and SacI, and the G(M)M BamHI/HindIII fragment.

The maize Dof1 transcriptional activation domain is cloned via RT-PCR from total maize RNA using the following primers: HindIII Dof1 5' (5'-aaaaaagcttgagctcgccaccgc-3' (SEQ ID NO:132)) and BamHI Dof1 3' (5'-aaaaaggatcctcacgggaggttgag-3' (SEQ ID NO:133)).

Expression vector pUbi-G(M)MD (pCGS678) is obtained via a three-way ligation between the Dof1 PCR product digested with HindIII and BamHI, an expression vector containing the maize ubiquitin promoter with a NOS (nopaline synthase) terminator digested with BamHI, and the G(M)M BamHI/HindIII fragment.

| EcR chimera | DNA Binding Domain | D domain | E domain | Activation domain | SEQ ID NO: |
|---|---|---|---|---|---|
| G(M)MV | GAL4 | *Manduca sexta* | *Manduca sexta* | VP16 | 104–105 |
| G(M)MC | GAL4 | *Manduca sexta* | *Manduca sexta* | C1 | 134–135 |
| G(M)MD | GAL4 | *Manduca sexta* | *Manduca sexta* | Dof1 | 136–137 |

Example 26

Transformation of Maize Suspension Culture Cells with Vectors Encoding the G(M)MV, G(M)MC, and G(M)MD Chimeric Receptors in Addition to a Luciferase Reporter Gene Vector Transformation of maize suspension cells, chemical treatment, and reporter activity assays are performed as described in Example 12. Maize BMS (Black Mexican Sweet) cultured cells are transfected with pCGS206 (pBS-bz1TATA/intronLUC), pCGS203 (G(M)MV), pCGS672 (G(M)MC), and pCGS678 (G(M)MD) by high velocity microprojectile bombardment. In addition, an expression plasmid containing the maize ubiquitin promoter driving the expression of β-glucuronidase (GUS) is added to the transfection to serve as an internal control to normalize against variations among the samples.

Transfections are treated and cell lysates are made essentially as described in U.S. Pat. No. 5,880,333. Tebufenozide (Teb) is added to the cells at a final concentration of 10 μM. Both luciferase and GUS assays are performed with 20 μl of cell lysate for each assay using the Promega Luciferase Kit (Promega cat #E1500) and GUS-Light Kit (Tropix) respectively. Relative light units are determined using a Turner Designs TD 20/20 luminometer. The normalized values (using the GUS reporter control) are listed in the following table.

| Constructs | Experiment #1 Luciferase | Fold Induction | Experiment #2 Luciferase | Fold Induction |
|---|---|---|---|---|
| Reporter alone | 1.00 | — | 1.00 | — |
| G(M)MV | 5.97 | — | 3.89 | — |
| G(M) | 99.49 | 16.7 | 136.41 | 35.1 |

-continued

| Constructs | Experiment #1 Luciferase | Fold Induction | Experiment #2 Luciferase | Fold Induction |
|---|---|---|---|---|
| MV + Teb | | | | |
| G(M)MC | 2.05 | — | 1.58 | — |
| G(M) MC + Teb | 53.20 | 26.0 | 28.05 | 17.8 |
| G(M)MD | 2.14 | — | 1.18 | — |
| G(M) MD + Teb | 6.37 | 3.0 | 9.14 | 7.8 |

Example 27

Construction of Monocot Receptor Expression Cassettes Encoding the GAL4 DNA Binding Domain, the Hinge and Ligand Binding Domains from *Manduca* EcR, and the VP16 Transcriptional Activation Domain in Various Configurations Chimeric receptor fusion proteins are constructed containing the GAL4 DNA Binding Domain (DBD) and *Manduca* EcR Hinge (D) and Ligand Binding (E) domains (MEcR), fused to the VP16 transcriptional activation domain in either an N-terminal configuration (VP16-GAL4-MEcR), an internal configuration (GAL4-VP16-MEcR) or a C-terminal configuration (GAL4-MEcR-VP16). The monocot G(M)MV expression construct (GAL4-MEcR-VP16) is described (pCGS203, Example II).

For construct VG(M)M (VP16-GAL4-MEcR), the following primers are used to generate GAL4-MEcR-Stop: Gal4 DBD 5' (5'-aaaaactagtaagctactgtcttctatcg-3' (SEQ ID NO:138)) and MEcR 3' w/stop (5'-ggatcctaaagcttcgtcgtcgacacttcg-3' (SEQ ID NO:139)). The ATG/Kozak VP16 activation domain cassette is amplified from pCGS203 using the following primers: VP16 5' ATG/Kozak (5'-aaaaaggatccgccaccatgcacgtgaagcttgccccccgac-3' (SEQ ID NO:140)) and VP16 3' no stop (5'-aaaaaactagtcacgtgcccaccgtactcgtcaattcc-3' (SEQ ID NO:141)). The monocot expression vector is generated by performing a three-way ligation between an expression vector containing the maize ubiquitin promoter with a NOS (nopaline synthase) terminator digested with BamHI, Gal4-MEcR-Stop digested with SpeI and BamHI, and ATG/Kozak VP16 digested with SpeI and BamHI, resulting in pUbi:VP16-Gal4 DBD-MEcR LBD (VG(M)M; pCGS686). The DNA sequence encoding chimeric receptor VG(M)M is shown as SEQ ID NO:142 and the amino acid sequence of the encoded receptor is shown as SEQ ID NO:143.

For construct GV(M)M (GAL4-VP16-MEcR), the following primer is used in conjuction with primer MEcR 3' w/stop (SEQ ID NO:139) to generate ATG/Kozak Gal4 DBD-MEcR-Stop: Gal4 DBD 5' ATG/Kozak (5'-caaggatccgccaccatgaagctactgtcttctatcg-3' (SEQ ID NO:144)). This Gal4 DBD-MEcR product is TA cloned into pT-Adv, and digested out with BamHI. This is then cloned into an expression vector containing the maize ubiquitin promoter with a NOS (nopaline synthase) terminator that has been cut with BamHI to produce pUbi-Gal4 DBD-MEcR. The VP16 activation domain is generated by PCR amplification from pCGS203 using the following primers: VP16 PmlI 5' (5'-aaaaacacgtgcaagcttgccccccgac-3' (SEQ ID NO:145)) and VP16 PmlI 3' (5'-aaaaacacgtgttcccaccgtactcgtcaattcc-3' (SEQ ID NO:146)). The resulting PCR product is digested with PmlI and cloned into pUbi-Gal4 DBD-MEcR that has also been digested with PmlI. The resulting GV(M)M construct has the Zm Ubi promoter driving expression of the Gal4 DBD-VP16-MEcR chimeric receptor (pCGS687). The DNA sequence encoding chimeric receptor GV(M)M is shown as SEQ ID NO:147 and the amino acid sequence of the encoded receptor is shown as SEQ ID NO:148.

Example 28

Transformation of Maize Suspension Culture Cells with G(M)MV, GV(M)M, and VG(M)M Receptors Controls Expression of a Reporter in the Presence of a Chemical Ligand Maize BMS cells are bombarded with reporter vector pCGS206 and chimeric receptors and treated with tebufenozide essentially as described in Example 12. Transfections are treated and cell lysates are made essentially as described in U.S. Pat. No. 5,880,333. Tebufenozide (Teb) is added to the cells at a final concentration of 10 $\mu$M. Both luciferase and GUS assays are performed with 20 $\mu$l of cell lysate for each assay using the Promega Luciferase Kit (Promega cat #E1500) and GUS-Light Kit (Tropix) respectively. Relative light units (RLU) are determined using a Turner Designs TD 20/20 luminometer. The normalized values (using the GUS reporter control) are listed in the following table.

| Receptors | Experiment #1 RLU | Fold Induction | Experiment #2 RLU | Fold Induction |
|---|---|---|---|---|
| None | 1.0 | — | 1.0 | — |
| None + Teb | 1.0 | 1.0 | 1.0 | 1.0 |
| G(M)MV | 3.73 | — | 3.17 | — |
| G(M)MV + Teb | 37.56 | 10.1 | 66.96 | 21.1 |
| GV(M)M | 1.71 | — | 1.77 | — |
| GV(M)M + Teb | 13.33 | 7.8 | 14.15 | 8.0 |
| VG(M)M | 2.21 | — | 2.52 | — |
| VG(M)M + Teb | 58.02 | 26.3 | 33.69 | 13.4 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the present invention.

What is claimed is:

1. A receptor cassette encoding a chimeric receptor polypeptide comprising:
   1) a DNA binding (C) domain;
   2) a hinge (D) domain of an ecdysone receptor (EcR) of an insect selected from the group consisting of *Manduca sexta, Chironomus tentans*, and *Locusta migratoria*;
   3) a ligand binding (E) domain that is heterologous with respect to said hinge (D) domain; and
   4) an activation domain; wherein
   a) said DNA binding (C) domain is a *Manduca sexta* EcR DNA binding (C) domain, said hinge (D) domain is a *Manduca sexta* EcR hinge (D) domain, and said ligand binding (E) domain is a *Drosophila melanogaster* EcR ligand binding (E) domain;
   b) said DNA binding (C) domain is a *Manduca sexta* EcR DNA binding (C) domain, said hinge (D) domain is a *Manduca sexta* EcR hinge (D) domain, and said ligand binding (E) domain is an *Agrotis ipsilon* EcR ligand binding (E) domain;
   c) said DNA binding (C) domain is a GAL4 DNA binding domain, said hinge (D) domain is a *Manduca sexta* EcR hinge (D) domain, and said ligand binding (E) domain is an *Agrotis ipsilon* EcR ligand binding (E) domain;
   d) said DNA binding (C) domain is a *Manduca sexta* EcR DNA binding (C) domain, said hinge (D) domain is a *Manduca sexta* EcR hinge (D) domain, and said ligand binding (E) domain is an *Ostrinia nubilalis* EcR ligand binding (E) domain;
   e) said DNA binding (C) domain is a GAL4 DNA binding domain, said hinge (D) domain is a *Manduca sexta* EcR hinge (D) domain, and said ligand binding (E) domain is an *Ostrinia nubilalis* EcR ligand binding (E) domain;
   f) said DNA binding (C) domain is a *Manduca sexta* EcR DNA binding (C) domain, said hinge (D) domain is a *Manduca sexta* EcR hinge (D) domain, and said ligand binding (E) domain is a *Spodopterda frugipera* EcR ligand binding (E) domain;
   g) said DNA binding (C) domain is a GAL4 DNA binding domain, said hinge (D) domain is a *Manduca sexta* EcR hinge (D) domain, and said ligand binding (E) domain is a *Spodopterda frugipera* EcR ligand binding (E) domain;
   h) said DNA binding (C) domain is a *Locusta migratoria* EcR DNA binding (C) domain, said hinge (D) domain is a *Locusta migratoria* EcR hinge (D) domain, and said ligand binding (E) domain is a *Manduca sexta* EcR ligand binding (E) domain;
   i) said DNA binding (C) domain is a *Manduca sexta* EcR DNA binding (C) domain, said hinge (D) domain is a *Manduca sexta* EcR hinge (D) domain, and said ligand binding (E) domain is a *Locusta migratoria* EcR ligand binding (E) domain;
   j) said DNA binding (C) domain is a *Chironomus tentans* EcR DNA binding (C) domain, said hinge (D) domain is a *Chironomus tentans* EcR hinge (D) domain, and said ligand binding (E) domain is a *Manduca sexta* EcR ligand binding (E) domain; or
   k) said DNA binding (C) domain is a *Manduca sexta* EcR DNA binding (C) domain, said hinge (D) domain is a *Chironomus tentans* EcR hinge (D) domain, and said ligand binding (E) domain is a *Chironomus tentans* EcR ligand binding (E) domain.

2. A receptor cassette according to claim 1, wherein said activation domain is a VP16 activation domain.

3. A receptor cassette encoding a chimeric receptor polypeptide comprising:
   1) a DNA binding (C) domain;
   2) a hinge (D) domain of an ecdysone receptor (EcR) of an insect, wherein said hinge (D) domain is a *Manduca sexta* EcR hinge (D) domain;

3) a ligand binding (E) domain that is heterologous with respect to said hinge (D) domain wherein said ligand binding (E) domain is an *Ostrinia nubilalis* EcR ligand binding (E) domain; and 4) an activation domain.

4. A receptor cassette according to claim 3, wherein said DNA binding (C) domain is a GAL4 DNA binding domain.

5. A receptor cassette according to claim 4, wherein the C, D, and E domains of said chimeric receptor polypeptide comprise an amino acid sequence at least 90% identical to amino acids 1–508 of SEQ ID NO:121.

6. A receptor cassette according to claim 5, wherein the C, D, and E domains of said chimeric receptor polypeptide comprise amino acids 1–508 of SEQ ID NO:121.

7. A receptor cassette according to claim 4, comprising nucleotides 1–1524 of SEQ ID NO:120.

8. A receptor cassette according to claim 4, wherein said DNA binding (C) domain is a GAL4 DNA binding domain, wherein said hinge (D) domain is a *Manduca sexta* EcR hinge (D) domain, wherein said ligand binding (E) domain is an *Ostrinia nubilalis* EcR ligand binding (E) domain, and wherein said activation domain is a VP16 activation domain.

9. A receptor cassette according to claim 8, wherein said chimeric receptor polypeptide comprises an amino acid sequence at least 90% identical to SEQ ID NO:121.

10. A receptor cassette according to claim 9, wherein said chimeric receptor polypeptide comprises SEQ ID NO:121.

11. A receptor cassette according to claim 8, comprising SEQ ID NO:120.

12. A receptor cassette encoding a chimeric receptor polypeptide comprising:

a) a DNA binding (C) domain;

b) a hinge (D) domain;

c) a ligand binding (E) domain of an ecdysone receptor (EcR) of an insect selected from the group consisting of *Manduca sexta, Agrotis ipsilon, Spodoptera frugiperda, Chironomus tentans*, and *Locusta migratoria*, wherein said ligand binding (E) domain is heterologous with respect to said hinge (D) domain; and d) an activation domain.

13. A receptor cassette according to claim 12, wherein:

a) said DNA binding (C) domain is an *Ostrinia nubilalis* EcR DNA binding (C) domain, said hinge (D) domain is an *Ostrinia nubilalis* EcR hinge (D) domain, and said ligand binding (E) domain is an *Agrotis ipsilon* EcR ligand binding (E) domain;

b) said DNA binding (C) domain is an *Ostrinia nubilalis* EcR DNA binding (C) domain, said hinge (D) domain is an *Ostrinia nubilalis* EcR hinge (D) domain, and said ligand binding (E) domain is a *Manduca sexta* EcR ligand binding (E) domain;

c) said DNA binding (C) domain is a GAL4 DNA binding domain, said hinge (D) domain is an *Ostrinia nubilalis* EcR hinge (D) domain, and said ligand binding (E) domain is a *Manduca sexta* EcR ligand binding (E) domain;

d) said DNA binding (C) domain is a *Drosophila melanogaster* EcR DNA binding (C) domain, said hinge (D) domain is a *Drosophila melanogaster* EcR hinge (D) domain, and said ligand binding (E) domain is a *Manduca sexta* EcR ligand binding (E) domain; or e) said DNA binding (C) domain is a *Drosophila melanogaster* EcR DNA binding (C) domain, said hinge (D) domain is a *Drosophila melanogaster* EcR hinge (D) domain, and said ligand binding (E) domain is an *Agrotis ipsilon* EcR ligand binding (E) domain.

14. A receptor cassette according to claim 13, wherein said activation domain is a VP16 activation domain.

15. A receptor expression cassette comprising a heterologous promoter sequence operatively linked to a receptor cassette according to claim 12.

16. A recombinant vector comprising a receptor expression cassette according to claim 15.

17. A receptor expression cassette comprising a heterologous promoter sequence operatively linked to a receptor cassette according to claim 13.

18. A recombinant vector comprising a receptor expression cassette according to claim 17.

19. A receptor expression cassette comprising a heterologous promoter sequence operatively linked to a receptor cassette according to claim 14.

20. A recombinant vector comprising a receptor expression cassette according to claim 19.

21. A receptor cassette encoding a chimeric receptor polypeptide comprising: said DNA binding (C) domain is a GAL4 DNA binding domain, wherein said hinge (D) domain is a *Manduca sexta* EcR hinge (D) domain, wherein said ligand binding (E) domain is a *Manduca sexta* EcR ligand binding (E) domain, and wherein said activation domain is a VP16 activation domain.

22. A receptor cassette according to claim 21, wherein said VP16 activation domain is located internally in said chimeric receptor polypeptide between said GAL4 DNA binding domain and said *Manduca sexta* EcR hinge (D) domain.

23. A receptor cassette according to claim 21, wherein said VP16 activation domain is located at the C-terminus of said chimeric receptor polypeptide.

24. A receptor cassette according to claim 23, wherein said chimeric receptor polypeptide comprises an amino acid sequence at least 90% identical to SEQ ID NO:105.

25. A receptor cassette according to claim 24, wherein said chimeric receptor polypeptide comprises SEQ ID NO:105.

26. A receptor cassette according to claim 23, comprising nucleotides 2007–3668 of SEQ ID NO:104.

* * * * *